US011059907B2

(12) United States Patent
Brommage, Jr. et al.

(10) Patent No.: US 11,059,907 B2
(45) Date of Patent: Jul. 13, 2021

(54) ANTIBODIES THAT BIND NOTUM PECTINACETYLESTERASE

(71) Applicant: Lexicon Pharmaceuticals, Inc., The Woodlands, TX (US)

(72) Inventors: Robert Joseph Brommage, Jr., The Woodlands, TX (US); Xiao Feng, The Woodlands, TX (US); Seokjoo Hong, The Woodlands, TX (US); Gregory Landes, San Bruno, CA (US); Jeff Liu, The Woodlands, TX (US); David George Potter, The Woodlands, TX (US); David Reed Powell, Houston, TX (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 0 days.

(21) Appl. No.: 16/277,466

(22) Filed: Feb. 15, 2019

(65) Prior Publication Data
US 2019/0241677 A1   Aug. 8, 2019

Related U.S. Application Data

(60) Division of application No. 14/952,264, filed on Nov. 25, 2015, now abandoned, which is a continuation of application No. 13/885,815, filed as application No. PCT/US2011/061785 on Nov. 22, 2011, now abandoned.

(60) Provisional application No. 61/416,927, filed on Nov. 24, 2010.

(51) Int. Cl.
*A61K 39/395* (2006.01)
*C07K 16/40* (2006.01)
*A61K 39/00* (2006.01)

(52) U.S. Cl.
CPC .......... *C07K 16/40* (2013.01); *A61K 39/3955* (2013.01); *A61K 2039/505* (2013.01); *C07K 2317/14* (2013.01); *C07K 2317/24* (2013.01); *C07K 2317/33* (2013.01); *C07K 2317/51* (2013.01); *C07K 2317/515* (2013.01); *C07K 2317/565* (2013.01); *C07K 2317/76* (2013.01); *C07K 2317/92* (2013.01)

(58) Field of Classification Search
CPC .............................. A61K 39/395; C07K 16/40
See application file for complete search history.

(56) References Cited

U.S. PATENT DOCUMENTS

2004/0063924 A1*  4/2004  Tang ...................... C07K 14/47
                                                536/23.5
2016/0152731 A1    6/2016  Brommage et al.

FOREIGN PATENT DOCUMENTS

| EP | 1652923 | 10/2011 |
|---|---|---|
| WO | WO 2003/062410 | 7/2003 |
| WO | WO 2005/014818 | 2/2005 |
| WO | WO 2012/027723 | 1/2012 |
| WO | WO 2012/071381 | 5/2012 |

OTHER PUBLICATIONS

Knappik et al., J. Mol. Biol., 2000, vol. 296(1):57-86.*
Allen et al., "Emerging targets in osteoporosis disease modification," J Med Chem, 2010, 53:4332-4353.
Boder et al., "Directed evolution of antibody fragments with monovalent femtomolar antigen-binding affinity," PNAS, 2000, 97:10701-10705.
Borrebaeck et al., "Human monoclonal antibodies produced by primary in vitro immunization of peripheral blood lymphocytes," PNAS, 1988, 85:3995-3999.
Brommage and Vafai, "Rapid Embedding Protocol for Visualizing Bone Mineral and Matrix" Calcified Tissue Int'l 67: 479-480 (2000).
Cavard et al., "Gene expression profiling provides insights into the pathways involved in solid pseudopapillary neoplasm of the pancreas," J Pathol., 2009, 218:201-209.
Eppstein et al., "Biological activity of liposome-encapsulated murine interferon gamma is mediated by a cell membrane receptor," PNAS, 1985, 82:3688-3692.
Extended European Search Report for EP 11843652.6, dated Nov. 27, 2014, 8 pages.
File history for U.S. Appl. No. 13/885,815, filed Jul. 31, 2013.
Guo et al., "Substituted benzothiophene or benzofuran derivatives as a novel class of bone morphogenetic protein-2 up-regulators: synthesis, structure-activity relationships, and preventive bone loss efficacies in senescence accelerated mice (SAMP6) and ovariectomized rats," J Med Chem., 2010, 53:1819-1829.
International Search Report and Written Opinion for PCT/US2011/061785, dated Mar. 23, 2012, 9 pages.
Kang et al., "Antibody redesign by chain shuffling from random combinatorial immunoglobulin libraries," PNAS, 1991, 88:11120-11123.
Kido et al, "Antibody Therapy for Osteoporosis," Osteoporosis Therapy, 2009, vol. 8, No. 4, pp. 345-348.
Krishnan et al. (2006) "Regulation of bone mass by Wnt signaling." Journal of Clinical Investigation. 116:1202-1209.
Morrison et al., "Chimeric human antibody molecules: mouse antigen-binding domains with human constant region domains," PNAS, 1984, 81:6851-6855.

(Continued)

*Primary Examiner* — Xiaozhen Xie

(74) *Attorney, Agent, or Firm* — McNeill Baur PLLC

(57) ABSTRACT

Antibodies that neutralize Notum Pectinacetylesterase are described, as well as compositions comprising them, and methods of their use to treat diseases and disorders affecting the bone.

13 Claims, 15 Drawing Sheets

Figure 1:
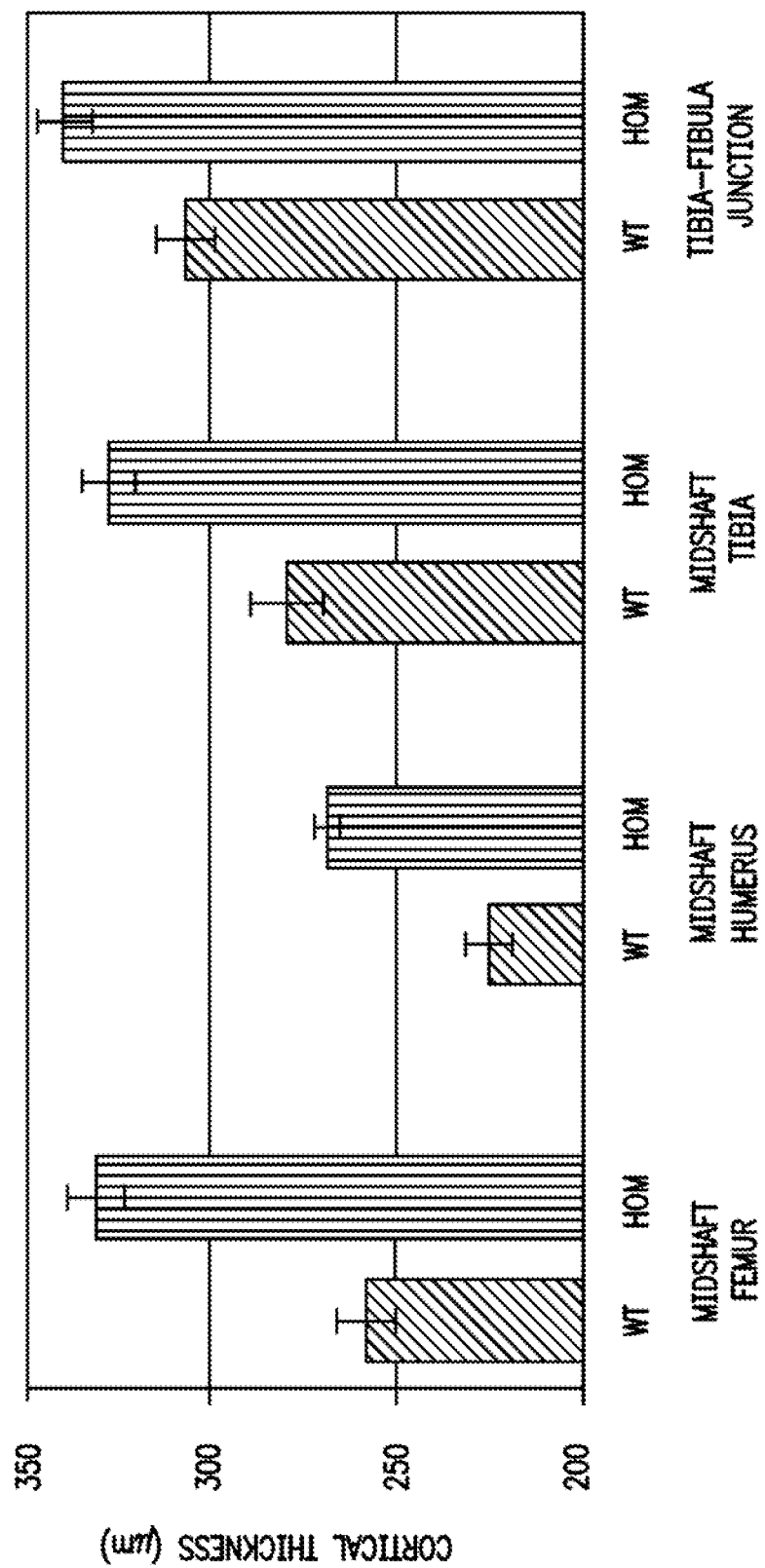

Specification includes a Sequence Listing.

(56) References Cited

OTHER PUBLICATIONS

Queen et al., "A humanized antibody that binds to the interleukin 2 receptor," PNAS, 1989, 86:10029-10033.
Roux et al., "New Treatment Targets in Osteporosis," Joint Bone Spine, 2010, 77:222-228.
Tomizuka et al., "Double trans-chromosomic mice: maintenance of two individual human chromosome fragments containing Ig heavy and kappa loci and expression of fully human antibodies," PNAS, 2000, 97:722-727.
Torisu et al., "Human homolog of Notum, overexpressed in hepatocellular carcinoma, is regulated transcriptionally by beta-catenin/TCF," Cancer Sci., 2008, 99:1139-1146.
Traister et al., "Mammalian Notum induces the release of glypicans and other GPI-anchored proteins from the cell surface," Biochemical Journal, 2007, 410:503-511.
Wiren et al., (2010) "Signaling pathways implicated in androgen regulation of endocortical bone." Bone. 46:710-723.

\* cited by examiner

SEQUENCE LISTING

<160> NUMBER OF SEQ ID NOS: 131

<210> SEQ ID NO 1
<211> LENGTH: 496
<212> TYPE: PRT
<213> ORGANISM: Homo sapiens
<220> FEATURE:
<221> NAME/KEY: misc_feature
<222> LOCATION: (1)..(496)
<223> OTHER INFORMATION: Human NOTUM

<400> SEQUENCE: 1

Met Gly Arg Gly Val Arg Val Leu Leu Leu Ser Leu Leu His Cys
1               5                   10                  15

Ala Gly Gly Ser Glu Gly Arg Lys Thr Trp Arg Arg Gly Gln Gln
                20                  25                  30

Pro Pro Pro Pro Pro Arg Thr Glu Ala Ala Pro Ala Ala Gly Gln Pro
            35                  40                  45

Val Glu Ser Phe Pro Leu Asp Phe Thr Ala Val Glu Gly Asn Met Asp
50                  55                  60

Ser Phe Met Ala Gln Val Lys Ser Leu Ala Gln Ser Leu Tyr Pro Cys
65                  70                  75                  80

Ser Ala Gln Gln Leu Asn Glu Asp Leu Arg Leu His Leu Leu Leu Asn
                85                  90                  95

Thr Ser Val Thr Cys Asn Asp Gly Ser Pro Ala Gly Tyr Tyr Leu Lys
                100                 105                 110

Glu Ser Arg Gly Ser Arg Arg Trp Leu Leu Phe Leu Glu Gly Gly Trp
            115                 120                 125

Tyr Cys Phe Asn Arg Glu Asn Cys Asp Ser Arg Tyr Asp Thr Met Arg
        130                 135                 140

Arg Leu Met Ser Ser Arg Asp Trp Pro Arg Thr Arg Thr Gly Thr Gly
145                 150                 155                 160

Ile Leu Ser Ser Gln Pro Glu Glu Asn Pro Tyr Trp Trp Asn Ala Asn
                165                 170                 175

Met Val Phe Ile Pro Tyr Cys Ser Ser Asp Val Trp Ser Gly Ala Ser
            180                 185                 190

Ser Lys Ser Glu Lys Asn Glu Tyr Ala Phe Met Gly Ala Leu Ile Ile
        195                 200                 205

Gln Glu Val Val Arg Glu Leu Leu Gly Arg Gly Leu Ser Gly Ala Lys
    210                 215                 220

Val Leu Leu Leu Ala Gly Ser Ser Ala Gly Gly Thr Gly Val Leu Leu
225                 230                 235                 240

Asn Val Asp Arg Val Ala Glu Gln Leu Glu Lys Leu Gly Tyr Pro Ala
                245                 250                 255

Ile Gln Val Arg Gly Leu Ala Asp Ser Gly Trp Phe Leu Asp Asn Lys
            260                 265                 270

```
Gln Tyr Arg His Thr Asp Cys Val Asp Thr Ile Thr Cys Ala Pro Thr
            275                 280                 285

Glu Ala Ile Arg Arg Gly Ile Arg Tyr Trp Asn Gly Val Val Pro Glu
290                 295                 300

Arg Cys Arg Arg Gln Phe Gln Glu Gly Glu Trp Asn Cys Phe Phe
305                 310                 315                 320

Gly Tyr Lys Val Tyr Pro Thr Leu Arg Cys Pro Val Phe Val Gln
            325                 330                 335

Trp Leu Phe Asp Glu Ala Gln Leu Thr Val Asp Asn Val His Leu Thr
                340                 345                 350

Gly Gln Pro Val Gln Glu Gly Leu Arg Leu Tyr Ile Gln Asn Leu Gly
            355                 360                 365

Arg Glu Leu Arg His Thr Leu Lys Asp Val Pro Ala Ser Phe Ala Pro
370                 375                 380

Ala Cys Leu Ser His Glu Ile Ile Ile Arg Ser His Trp Thr Asp Val
385                 390                 395                 400

Gln Val Lys Gly Thr Ser Leu Pro Arg Ala Leu His Cys Trp Asp Arg
            405                 410                 415

Ser Leu His Asp Ser His Lys Ala Ser Lys Thr Pro Leu Lys Gly Cys
                420                 425                 430

Pro Val His Leu Val Asp Ser Cys Pro Trp Pro His Cys Asn Pro Ser
            435                 440                 445

Cys Pro Thr Val Arg Asp Gln Phe Thr Gly Gln Glu Met Asn Val Ala
            450                 455                 460

Gln Phe Leu Met His Met Gly Phe Asp Met Gln Thr Val Ala Gln Pro
465                 470                 475                 480

Gln Gly Leu Glu Pro Ser Glu Leu Leu Gly Met Leu Ser Asn Gly Ser
            485                 490                 495

<210> SEQ ID NO 2
<211> LENGTH: 503
<212> TYPE: PRT
<213> ORGANISM: Mus musculus
<220> FEATURE:
<221> NAME/KEY: misc_feature
<222> LOCATION: (1)..(503)
<223> OTHER INFORMATION: Mouse NOTUM

<400> SEQUENCE: 2

Met Gly Gly Glu Val Arg Val Leu Leu Leu Gly Leu Leu His Trp
1               5                   10                  15

Val Gly Gly Ser Glu Gly Arg Lys Thr Trp Arg Arg Gly Gln Gln
            20                  25                  30

Pro Pro Gln Pro Pro Pro Pro Leu Pro Gln Arg Ala Glu Val
            35                  40                  45

Glu Pro Gly Ala Gly Gln Pro Val Glu Ser Phe Pro Leu Asp Phe Thr
50                  55                  60

Ala Val Glu Gly Asn Met Asp Ser Phe Met Ala Gln Val Lys Ser Leu
65                  70                  75                  80

Ala Gln Ser Leu Tyr Pro Cys Ser Ala Gln Gln Leu Asn Glu Asp Leu
                85                  90                  95

Arg Leu His Leu Leu Asn Thr Ser Val Thr Cys Asn Asp Gly Ser
            100                 105                 110

Pro Ala Gly Tyr Tyr Leu Lys Glu Ser Lys Gly Ser Arg Arg Trp Leu
            115                 120                 125

Leu Phe Leu Glu Gly Gly Trp Tyr Cys Phe Asn Arg Glu Asn Cys Asp
```

130                 135                 140
Ser Arg Tyr Ser Thr Met Arg Arg Leu Met Ser Ser Lys Asp Trp Pro
145                 150                 155                 160

His Thr Arg Thr Gly Thr Gly Ile Leu Ser Ser Gln Pro Glu Glu Asn
                165                 170                 175

Pro His Trp Trp Asn Ala Asn Met Val Phe Ile Pro Tyr Cys Ser Ser
            180                 185                 190

Asp Val Trp Ser Gly Ala Ser Pro Lys Ser Asp Lys Asn Glu Tyr Ala
        195                 200                 205

Phe Met Gly Ser Leu Ile Ile Gln Glu Val Val Arg Glu Leu Leu Gly
    210                 215                 220

Lys Gly Leu Ser Gly Ala Lys Val Leu Leu Leu Ala Gly Ser Ser Ala
225                 230                 235                 240

Gly Gly Thr Gly Val Leu Leu Asn Val Asp Arg Val Ala Glu Leu Leu
                245                 250                 255

Glu Glu Leu Gly Tyr Pro Ser Ile Gln Val Arg Gly Leu Ala Asp Ser
            260                 265                 270

Gly Trp Phe Leu Asp Asn Lys Gln Tyr Arg Arg Ser Asp Cys Ile Asp
        275                 280                 285

Thr Ile Asn Cys Ala Pro Thr Asp Ala Ile Arg Arg Gly Ile Arg Tyr
    290                 295                 300

Trp Ser Gly Met Val Pro Glu Arg Cys Gln Arg Gln Phe Lys Glu Gly
305                 310                 315                 320

Glu Glu Trp Asn Cys Phe Phe Gly Tyr Lys Val Tyr Pro Thr Leu Arg
                325                 330                 335

Cys Pro Val Phe Val Val Gln Trp Leu Phe Asp Glu Ala Gln Leu Thr
            340                 345                 350

Val Asp Asn Val His Leu Thr Gly Gln Pro Val Gln Gly Gln Trp
        355                 360                 365

Leu Tyr Ile Gln Asn Leu Gly Arg Glu Leu Arg Gly Thr Leu Lys Asp
    370                 375                 380

Val Gln Ala Ser Phe Ala Pro Ala Cys Leu Ser His Glu Ile Ile Ile
385                 390                 395                 400

Arg Ser Tyr Trp Thr Asp Val Gln Val Lys Gly Thr Ser Leu Pro Arg
                405                 410                 415

Ala Leu His Cys Trp Asp Arg Ser Phe His Asp Ser His Lys Ala Ser
            420                 425                 430

Lys Thr Pro Met Lys Gly Cys Pro Phe His Leu Val Asp Ser Cys Pro
        435                 440                 445

Trp Pro His Cys Asn Pro Ser Cys Pro Thr Ile Arg Asp Gln Phe Thr
    450                 455                 460

Gly Gln Glu Met Asn Val Ala Gln Phe Leu Met His Met Gly Phe Asp
465                 470                 475                 480

Val Gln Thr Val Ala Gln Gln Gly Met Glu Pro Ser Lys Leu Leu
                485                 490                 495

Gly Met Leu Ser Asn Gly Asn
            500

<210> SEQ ID NO 3
<211> LENGTH: 496
<212> TYPE: PRT
<213> ORGANISM: Homo sapiens
<220> FEATURE:
<221> NAME/KEY: misc_feature
<222> LOCATION: (1)..(496)

<223> OTHER INFORMATION: Human NOTUM S232A

<400> SEQUENCE: 3

```
Met Gly Arg Gly Val Arg Val Leu Leu Leu Ser Leu Leu His Cys
1               5                   10                  15

Ala Gly Gly Ser Glu Gly Arg Lys Thr Trp Arg Arg Gly Gln Gln
            20                  25                  30

Pro Pro Pro Pro Arg Thr Glu Ala Ala Pro Ala Ala Gly Gln Pro
            35                  40                  45

Val Glu Ser Phe Pro Leu Asp Phe Thr Ala Val Glu Gly Asn Met Asp
 50                  55                  60

Ser Phe Met Ala Gln Val Lys Ser Leu Ala Gln Ser Leu Tyr Pro Cys
65                   70                  75                  80

Ser Ala Gln Gln Leu Asn Glu Asp Leu Arg Leu His Leu Leu Asn
                85                  90                  95

Thr Ser Val Thr Cys Asn Asp Gly Ser Pro Ala Gly Tyr Tyr Leu Lys
                100                 105                 110

Glu Ser Arg Gly Ser Arg Arg Trp Leu Leu Phe Leu Glu Gly Gly Trp
                115                 120                 125

Tyr Cys Phe Asn Arg Glu Asn Cys Asp Ser Arg Tyr Asp Thr Met Arg
130                 135                 140

Arg Leu Met Ser Ser Arg Asp Trp Pro Arg Thr Arg Thr Gly Thr Gly
145                 150                 155                 160

Ile Leu Ser Ser Gln Pro Glu Glu Asn Pro Tyr Trp Trp Asn Ala Asn
                165                 170                 175

Met Val Phe Ile Pro Tyr Cys Ser Ser Asp Val Trp Ser Gly Ala Ser
                180                 185                 190

Ser Lys Ser Glu Lys Asn Glu Tyr Ala Phe Met Gly Ala Leu Ile Ile
            195                 200                 205

Gln Glu Val Val Arg Glu Leu Leu Gly Arg Gly Leu Ser Gly Ala Lys
210                 215                 220

Val Leu Leu Leu Ala Gly Ser Ala Ala Gly Gly Thr Gly Val Leu Leu
225                 230                 235                 240

Asn Val Asp Arg Val Ala Glu Gln Leu Glu Lys Leu Gly Tyr Pro Ala
                245                 250                 255

Ile Gln Val Arg Gly Leu Ala Asp Ser Gly Trp Phe Leu Asp Asn Lys
            260                 265                 270

Gln Tyr Arg His Thr Asp Cys Val Asp Thr Ile Thr Cys Ala Pro Thr
            275                 280                 285

Glu Ala Ile Arg Arg Gly Ile Arg Tyr Trp Asn Gly Val Val Pro Glu
            290                 295                 300

Arg Cys Arg Arg Gln Phe Gln Glu Gly Glu Glu Trp Asn Cys Phe Phe
305                 310                 315                 320

Gly Tyr Lys Val Tyr Pro Thr Leu Arg Cys Pro Val Phe Val Val Gln
                325                 330                 335

Trp Leu Phe Asp Glu Ala Gln Leu Thr Val Asp Asn Val His Leu Thr
                340                 345                 350

Gly Gln Pro Val Gln Glu Gly Leu Arg Leu Tyr Ile Gln Asn Leu Gly
            355                 360                 365

Arg Glu Leu Arg His Thr Leu Lys Asp Val Pro Ala Ser Phe Ala Pro
370                 375                 380

Ala Cys Leu Ser His Glu Ile Ile Ile Arg Ser His Trp Thr Asp Val
385                 390                 395                 400
```

-continued

```
Gln Val Lys Gly Thr Ser Leu Pro Arg Ala Leu His Cys Trp Asp Arg
                405                 410                 415

Ser Leu His Asp Ser His Lys Ala Ser Lys Thr Pro Leu Lys Gly Cys
            420                 425                 430

Pro Val His Leu Val Asp Ser Cys Pro Trp Pro His Cys Asn Pro Ser
        435                 440                 445

Cys Pro Thr Val Arg Asp Gln Phe Thr Gly Gln Glu Met Asn Val Ala
    450                 455                 460

Gln Phe Leu Met His Met Gly Phe Asp Met Gln Thr Val Ala Gln Pro
465                 470                 475                 480

Gln Gly Leu Glu Pro Ser Glu Leu Leu Gly Met Leu Ser Asn Gly Ser
                485                 490                 495
```

<210> SEQ ID NO 4
<211> LENGTH: 503
<212> TYPE: PRT
<213> ORGANISM: Mus musculus
<220> FEATURE:
<221> NAME/KEY: misc_feature
<222> LOCATION: (1)..(503)
<223> OTHER INFORMATION: Mouse NOTUM S239A mutant

<400> SEQUENCE: 4

```
Met Gly Gly Glu Val Arg Val Leu Leu Leu Gly Leu Leu His Trp
1               5                   10                  15

Val Gly Gly Ser Glu Gly Arg Lys Thr Trp Arg Arg Gly Gln Gln
                20                  25                  30

Pro Pro Gln Pro Pro Pro Pro Leu Pro Gln Arg Ala Glu Val
                35                  40                  45

Glu Pro Gly Ala Gly Gln Pro Val Glu Ser Phe Pro Leu Asp Phe Thr
    50                  55                  60

Ala Val Glu Gly Asn Met Asp Ser Phe Met Ala Gln Val Lys Ser Leu
65                  70                  75                  80

Ala Gln Ser Leu Tyr Pro Cys Ser Ala Gln Gln Leu Asn Glu Asp Leu
                85                  90                  95

Arg Leu His Leu Leu Asn Thr Ser Val Thr Cys Asn Asp Gly Ser
                100                 105                 110

Pro Ala Gly Tyr Tyr Leu Lys Glu Ser Lys Gly Ser Arg Arg Trp Leu
            115                 120                 125

Leu Phe Leu Glu Gly Gly Trp Tyr Cys Phe Asn Arg Glu Asn Cys Asp
        130                 135                 140

Ser Arg Tyr Ser Thr Met Arg Arg Leu Met Ser Ser Lys Asp Trp Pro
145                 150                 155                 160

His Thr Arg Thr Gly Thr Gly Ile Leu Ser Ser Gln Pro Glu Glu Asn
                165                 170                 175

Pro His Trp Trp Asn Ala Asn Met Val Phe Ile Pro Tyr Cys Ser Ser
                180                 185                 190

Asp Val Trp Ser Gly Ala Ser Pro Lys Ser Asp Lys Asn Glu Tyr Ala
            195                 200                 205

Phe Met Gly Ser Leu Ile Ile Gln Glu Val Val Arg Glu Leu Leu Gly
        210                 215                 220

Lys Gly Leu Ser Gly Ala Lys Val Leu Leu Ala Gly Ser Ala Ala
225                 230                 235                 240

Gly Gly Thr Gly Val Leu Leu Asn Val Asp Arg Val Ala Glu Leu Leu
                245                 250                 255

Glu Glu Leu Gly Tyr Pro Ser Ile Gln Val Arg Gly Leu Ala Asp Ser
```

```
            260                 265                 270
Gly Trp Phe Leu Asp Asn Lys Gln Tyr Arg Arg Ser Asp Cys Ile Asp
            275                 280                 285

Thr Ile Asn Cys Ala Pro Thr Asp Ala Ile Arg Arg Gly Ile Arg Tyr
        290                 295                 300

Trp Ser Gly Met Val Pro Glu Arg Cys Gln Arg Gln Phe Lys Glu Gly
305                 310                 315                 320

Glu Glu Trp Asn Cys Phe Phe Gly Tyr Lys Val Tyr Pro Thr Leu Arg
                325                 330                 335

Cys Pro Val Phe Val Val Gln Trp Leu Phe Asp Glu Ala Gln Leu Thr
            340                 345                 350

Val Asp Asn Val His Leu Thr Gly Gln Pro Val Gln Glu Gly Gln Trp
        355                 360                 365

Leu Tyr Ile Gln Asn Leu Gly Arg Glu Leu Arg Gly Thr Leu Lys Asp
    370                 375                 380

Val Gln Ala Ser Phe Ala Pro Ala Cys Leu Ser His Glu Ile Ile Ile
385                 390                 395                 400

Arg Ser Tyr Trp Thr Asp Val Gln Val Lys Gly Thr Ser Leu Pro Arg
                405                 410                 415

Ala Leu His Cys Trp Asp Arg Ser Phe His Asp Ser His Lys Ala Ser
            420                 425                 430

Lys Thr Pro Met Lys Gly Cys Pro Phe His Leu Val Asp Ser Cys Pro
        435                 440                 445

Trp Pro His Cys Asn Pro Ser Cys Pro Thr Ile Arg Asp Gln Phe Thr
    450                 455                 460

Gly Gln Glu Met Asn Val Ala Gln Phe Leu Met His Met Gly Phe Asp
465                 470                 475                 480

Val Gln Thr Val Ala Gln Gln Gly Met Glu Pro Ser Lys Leu Leu
                485                 490                 495

Gly Met Leu Ser Asn Gly Asn
            500

<210> SEQ ID NO 5
<211> LENGTH: 500
<212> TYPE: PRT
<213> ORGANISM: Cavia porcellus
<220> FEATURE:
<221> NAME/KEY: misc_feature
<222> LOCATION: (1)..(500)
<223> OTHER INFORMATION: Guinea pig NOTUM

<400> SEQUENCE: 5

Met Gly Arg Gly Val Arg Val Leu Phe Leu Leu Gly Leu Leu His Trp
1               5                   10                  15

Ala Gly Gly Gly Glu Gly Arg Lys Thr Trp Arg Arg Gly Gln Gln
            20                  25                  30

Pro Ala Pro Ala Pro Leu Pro Pro Gln Arg Thr Glu Ala Ala Pro Gly
        35                  40                  45

Thr Gly Gln Pro Val Glu Ser Phe Pro Leu Asp Phe Thr Ala Val Glu
    50                  55                  60

Gly Asn Met Asp Ser Phe Met Ala Gln Val Lys Ser Leu Ala Gln Ser
65                  70                  75                  80

Leu Tyr Pro Cys Ser Ala Gln Gln Leu Asn Glu Asp Leu Arg Leu His
                85                  90                  95

Leu Leu Leu Asn Thr Ser Val Thr Cys Asn Asp Gly Ser Pro Ala Gly
            100                 105                 110
```

-continued

Tyr Tyr Leu Lys Glu Ser Lys Gly Ser Arg Arg Trp Leu Leu Phe Leu
         115                 120                 125

Glu Gly Gly Trp Tyr Cys Phe Ser Arg Glu Asn Cys Asp Ser Arg Tyr
130                 135                 140

Asp Thr Met Arg Arg Leu Met Ser Ser Lys Asp Trp Pro Gln Thr Arg
145                 150                 155                 160

Thr Gly Thr Gly Ile Leu Ser Ser Gln Pro Glu Glu Asn Pro Tyr Trp
                165                 170                 175

Trp Asn Ala Asn Met Val Phe Ile Pro Tyr Cys Ser Ser Asp Val Trp
                180                 185                 190

Ser Gly Ala Ser Ser Lys Ser Glu Lys Asn Glu Tyr Val Phe Met Gly
                195                 200                 205

Ala Leu Ile Ile Arg Glu Val Val Gln Glu Leu Leu Gly Arg Gly Leu
                210                 215                 220

Ser Gly Ala Lys Val Leu Leu Leu Ala Gly Ser Ser Ala Gly Gly Thr
225                 230                 235                 240

Gly Val Leu Leu Asn Val Asp Arg Val Ala Glu Gln Leu Glu Gln Leu
                245                 250                 255

Gly Tyr Pro Ala Ile Gln Val Arg Gly Leu Ala Asp Ser Gly Trp Phe
                260                 265                 270

Leu Asp Asn Lys Gln Tyr Arg Arg Thr Asp Cys Val Asp Thr Val Thr
                275                 280                 285

Cys Ala Pro Thr Glu Ala Ile Arg Arg Gly Ile Arg Tyr Trp Asn Gly
290                 295                 300

Met Val Pro Glu Arg Cys Arg Ser Gln Phe Lys Glu Gly Glu Glu Trp
305                 310                 315                 320

Asn Cys Phe Leu Gly Tyr Lys Val Tyr Pro Thr Leu Arg Cys Pro Val
                325                 330                 335

Phe Val Val Gln Trp Leu Phe Asp Glu Ala Gln Leu Thr Ala Asp Asn
                340                 345                 350

Ala His Leu Thr Gly Gln Pro Val Gln Glu Gly Gln Trp Leu Tyr Ile
                355                 360                 365

Gln Asn Leu Gly His Glu Leu Arg Asn Thr Leu Lys Asp Val Pro Ala
370                 375                 380

Ser Phe Ala Pro Ala Cys Leu Ser His Glu Ile Ile Arg Ser His
385                 390                 395                 400

Trp Thr Asp Val Gln Val Lys Gly Thr Ser Leu Pro Arg Ala Leu His
                405                 410                 415

Cys Trp Asp Arg Ser Leu His Asp Ser His Lys Ala Ser Lys Thr Pro
                420                 425                 430

Leu Lys Gly Cys Pro Ile His Leu Val Asp Ser Cys Pro Trp Pro His
                435                 440                 445

Cys Asn Pro Ser Cys Pro Thr Ile Arg Asp Gln Phe Thr Gly Gln Glu
450                 455                 460

Met Asn Val Ala Gln Phe Leu Met His Met Gly Phe Asp Val Gln Thr
465                 470                 475                 480

Val Ala Gln Gln Gln Gly Leu Glu Pro Ser Lys Leu Leu Gly Met Leu
                485                 490                 495

Ser Ser Gly Ser
            500

<210> SEQ ID NO 6
<211> LENGTH: 496

```
<212> TYPE: PRT
<213> ORGANISM: Macaca mulatta
<220> FEATURE:
<221> NAME/KEY: misc_feature
<222> LOCATION: (1)..(496)
<223> OTHER INFORMATION: Rhesus macaque NOTUM

<400> SEQUENCE: 6
```

Met Gly Arg Gly Val Arg Val Leu Leu Leu Gly Leu Leu His Cys
1               5                   10                  15

Ala Gly Gly Ser Glu Gly Arg Lys Thr Trp Arg Arg Gly Gln Gln
                20                  25                  30

Pro Pro Pro Pro Pro Arg Thr Glu Ala Ala Pro Ala Ala Gly Gln Pro
            35                  40                  45

Val Glu Ser Phe Pro Leu Asp Phe Thr Ala Val Glu Gly Asn Met Asp
50                  55                  60

Ser Phe Met Ala Gln Val Lys Ser Leu Ala Gln Ser Leu Tyr Pro Cys
65                  70                  75                  80

Ser Ala Gln Gln Leu Asn Glu Asp Leu Arg Leu His Leu Leu Asn
                85                  90                  95

Thr Ser Val Thr Cys Asn Asp Gly Ser Pro Ala Gly Tyr Tyr Leu Lys
                100                 105                 110

Glu Ser Arg Gly Ser Arg Arg Trp Leu Leu Phe Leu Glu Gly Gly Trp
            115                 120                 125

Tyr Cys Phe Asn Arg Glu Asn Cys Asp Ser Arg Tyr Asn Thr Met Arg
            130                 135                 140

Arg Leu Met Ser Ser Arg Asp Trp Pro Arg Thr Arg Thr Gly Thr Gly
145                 150                 155                 160

Ile Leu Ser Ser Gln Pro Glu Glu Asn Pro Tyr Trp Trp Asn Ala Asn
                165                 170                 175

Met Val Phe Ile Pro Tyr Cys Ser Ser Asp Val Trp Ser Gly Ala Ser
                180                 185                 190

Ser Lys Ser Glu Lys Asn Glu Tyr Ala Phe Met Gly Ala Leu Ile Ile
            195                 200                 205

Gln Glu Val Val Arg Glu Leu Leu Gly Arg Gly Leu Ser Gly Ala Lys
210                 215                 220

Val Leu Leu Leu Ala Gly Ser Ser Ala Gly Gly Thr Gly Val Leu Leu
225                 230                 235                 240

Asn Val Asp Arg Val Ala Glu Gln Leu Glu Glu Leu Gly Tyr Pro Ala
                245                 250                 255

Ile Gln Val Arg Gly Leu Ala Asp Ser Gly Trp Phe Leu Asp Asn Lys
                260                 265                 270

Gln Tyr Arg His Thr Asp Cys Val Asp Thr Ile Thr Cys Ala Pro Thr
            275                 280                 285

Glu Ala Ile Arg Arg Gly Ile Arg Tyr Trp Asn Gly Val Val Pro Glu
290                 295                 300

Arg Cys Arg Arg Gln Phe Gln Glu Gly Glu Glu Trp Asn Cys Phe Phe
305                 310                 315                 320

Gly Tyr Lys Ile Tyr Pro Thr Leu Arg Cys Pro Val Phe Val Val Gln
                325                 330                 335

Trp Leu Phe Asp Glu Ala Gln Leu Thr Val Asp Asn Val His Leu Thr
                340                 345                 350

Gly Gln Pro Val Gln Glu Ser Gln Arg Leu Tyr Ile Gln Asn Leu Gly
            355                 360                 365

Arg Glu Leu Arg His Thr Leu Lys Asp Val Pro Ala Ser Phe Ala Pro

```
                    370                 375                 380
Ala Cys Leu Ser His Glu Ile Ile Arg Ser His Trp Thr Asp Val
385                 390                 395                 400

Gln Val Lys Gly Thr Ser Leu Pro Arg Ala Leu His Cys Trp Asp Arg
                    405                 410                 415

Ser Leu His Asp Ser His Lys Asn Ser Lys Thr Pro Leu Lys Gly Cys
                420                 425                 430

Pro Val His Leu Val Asp Ser Cys Pro Trp Pro His Cys Asn Pro Ser
            435                 440                 445

Cys Pro Thr Val Arg Asp Gln Phe Thr Gly Gln Glu Met Asn Val Ala
            450                 455                 460

Gln Phe Leu Met His Met Gly Phe Asp Val Gln Thr Val Ala Gln Gln
465                 470                 475                 480

Gln Gly Pro Glu Pro Ser Lys Leu Leu Gly Leu Pro Ser Asp Gly Ser
                    485                 490                 495
```

<210> SEQ ID NO 7
<211> LENGTH: 125
<212> TYPE: PRT
<213> ORGANISM: Artificial Sequence
<220> FEATURE:
<223> OTHER INFORMATION: Synthetic: MAb 1.731 heavy chain variable
      region

<400> SEQUENCE: 7

```
Glu Val Gln Leu Gln Gln Ser Gly Pro Glu Leu Val Lys Pro Gly Ala
1               5                   10                  15

Ser Val Lys Val Ser Cys Lys Ala Ser Gly Tyr Pro Phe Thr Asp Tyr
                20                  25                  30

Phe Ile His Trp Val Lys Gln Thr His Gly Lys Ser Leu Glu Trp Ile
            35                  40                  45

Gly Tyr Phe Phe Pro Lys Asn Gly Ala Asn Gly Tyr Asn Gln Lys Phe
        50                  55                  60

Glu Gly Lys Val Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Arg Tyr Gly Asn Tyr Tyr Ser Met Asp Tyr Trp Gly Gln Gly
            100                 105                 110

Thr Ser Val Thr Val Ser Ser Ala Lys Thr Thr Pro Pro
        115                 120                 125
```

<210> SEQ ID NO 8
<211> LENGTH: 113
<212> TYPE: PRT
<213> ORGANISM: Artificial Sequence
<220> FEATURE:
<223> OTHER INFORMATION: Synthetic: MAb 1.731 light chain variable
      region

<400> SEQUENCE: 8

```
Ser Phe Val Met Thr Gln Thr Pro Lys Phe Leu Leu Val Ser Ala Gly
1               5                   10                  15

Asp Arg Val Thr Ile Thr Cys Lys Ala Ser Gln Ser Val Gly Asp Asp
                20                  25                  30

Val Ala Trp Tyr Gln Gln Lys Pro Gly Gln Ser Pro Thr Leu Leu Ile
            35                  40                  45

Tyr Arg Val Ser Asn Arg Tyr Thr Gly Val Pro Asp Arg Phe Thr Gly
```

```
                  50                  55                  60
Ser Gly Tyr Gly Thr Asp Phe Thr Phe Thr Ile Asn Thr Val Gln Ala
 65                  70                  75                  80

Glu Asp Leu Ala Val Tyr Phe Cys Gln Gln Asp Tyr Ser Ser Pro Tyr
                 85                  90                  95

Thr Phe Gly Gly Gly Thr Gln Leu Glu Val Lys Arg Ala Asp Ala Ala
            100                 105                 110

Pro

<210> SEQ ID NO 9
<211> LENGTH: 10
<212> TYPE: PRT
<213> ORGANISM: Artificial Sequence
<220> FEATURE:
<223> OTHER INFORMATION: Synthetic: MAb 1.731 heavy chain CDR1

<400> SEQUENCE: 9

Gly Tyr Pro Phe Thr Asp Tyr Phe Ile His
 1               5                  10

<210> SEQ ID NO 10
<211> LENGTH: 10
<212> TYPE: PRT
<213> ORGANISM: Artificial Sequence
<220> FEATURE:
<223> OTHER INFORMATION: Synthetic: MAb 1.731 heavy chain CDR2

<400> SEQUENCE: 10

Tyr Phe Phe Pro Lys Asn Gly Ala Asn Gly
 1               5                  10

<210> SEQ ID NO 11
<211> LENGTH: 10
<212> TYPE: PRT
<213> ORGANISM: Artificial Sequence
<220> FEATURE:
<223> OTHER INFORMATION: Synthetic: MAb 1.731 heavy chain CDR3

<400> SEQUENCE: 11

Arg Tyr Gly Asn Tyr Tyr Ser Met Asp Tyr
 1               5                  10

<210> SEQ ID NO 12
<211> LENGTH: 11
<212> TYPE: PRT
<213> ORGANISM: Artificial Sequence
<220> FEATURE:
<223> OTHER INFORMATION: Synthetic: MAb 1.731 light chain CDR1

<400> SEQUENCE: 12

Lys Ala Ser Gln Ser Val Gly Asp Asp Val Ala
 1               5                  10

<210> SEQ ID NO 13
<211> LENGTH: 7
<212> TYPE: PRT
<213> ORGANISM: Artificial Sequence
<220> FEATURE:
<223> OTHER INFORMATION: Synthetic: MAb 1.731 light chain CDR2

<400> SEQUENCE: 13

Arg Val Ser Asn Arg Tyr Thr
 1               5
```

```
<210> SEQ ID NO 14
<211> LENGTH: 9
<212> TYPE: PRT
<213> ORGANISM: Artificial Sequence
<220> FEATURE:
<223> OTHER INFORMATION: Synthetic: MAb 1.731 light chain CDR3

<400> SEQUENCE: 14

Gln Gln Asp Tyr Ser Ser Pro Tyr Thr
1               5

<210> SEQ ID NO 15
<211> LENGTH: 124
<212> TYPE: PRT
<213> ORGANISM: Artificial Sequence
<220> FEATURE:
<223> OTHER INFORMATION: Synthetic: MAb 1.802 heavy chain variable
      region

<400> SEQUENCE: 15

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Phe Arg Gln Ala Pro Glu Lys Gly Leu Glu Trp Val
        35                  40                  45

Ala Tyr Ile Ser Ser Gly Ser Arg Thr Val Tyr Ala Asp Thr Val
    50                  55                  60

Lys Gly Arg Phe Thr Ile Ser Arg Asp Asn Ala Lys Asn Thr Leu Ser
65                  70                  75                  80

Leu Gln Met Thr Ser Leu Arg Ser Glu Asp Thr Ala Met Tyr Tyr Cys
                85                  90                  95

Ala Arg Lys His Tyr Asn Gly Gly Tyr Phe Asp Val Trp Gly Thr Gly
            100                 105                 110

Thr Thr Val Thr Val Ser Ser Ala Lys Thr Thr Pro
        115                 120

<210> SEQ ID NO 16
<211> LENGTH: 117
<212> TYPE: PRT
<213> ORGANISM: Artificial Sequence
<220> FEATURE:
<223> OTHER INFORMATION: Synthetic: MAb 1.802 light chain variable
      region

<400> SEQUENCE: 16

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ile Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Pro Thr Phe Gly Ser Gly Thr Lys Leu Glu Ile Lys Arg
            100                 105                 110
```

Ala Asp Ala Ala Pro
        115

<210> SEQ ID NO 17
<211> LENGTH: 10
<212> TYPE: PRT
<213> ORGANISM: Artificial Sequence
<220> FEATURE:
<223> OTHER INFORMATION: Synthetic: MAb 1.802 heavy chain CDR1

<400> SEQUENCE: 17

Gly Phe Thr Phe Ser Asp Tyr Gly Met His
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic: MAb 1.802 heavy chain CDR2

<400> SEQUENCE: 18

Tyr Ile Ser Ser Gly Ser Arg Thr Val Tyr
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic: MAb 1.802 heavy chain CDR3

<400> SEQUENCE: 19

Lys His Tyr Asn Gly Gly Tyr Phe Asp Val
1               5                   10

<210> SEQ ID NO 20
<211> LENGTH: 15
<212> TYPE: PRT
<213> ORGANISM: Artificial Sequence
<220> FEATURE:
<223> OTHER INFORMATION: Synthetic: MAb 1.802 light chain CDR1

<400> SEQUENCE: 20

Arg Ala Ser Lys Ile Val Ser Thr Ser Gly Tyr Ser Tyr Met His
1               5                   10                  15

<210> SEQ ID NO 21
<211> LENGTH: 7
<212> TYPE: PRT
<213> ORGANISM: Artificial Sequence
<220> FEATURE:
<223> OTHER INFORMATION: Synthetic: MAb 1.802 light chain CDR2

<400> SEQUENCE: 21

Leu Ala Ser Asn Leu Glu Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic: MAb 1.802 light chain CDR3

<400> SEQUENCE: 22

Gln His Ser Arg Glu Leu Pro Pro Thr

```
1               5
```

<210> SEQ ID NO 23
<211> LENGTH: 125
<212> TYPE: PRT
<213> ORGANISM: Artificial Sequence
<220> FEATURE:
<223> OTHER INFORMATION: Synthetic: MAb 1.815 heavy chain variable
      region

<400> SEQUENCE: 23

```
Asp Val Gln Leu Leu Glu Ser Gly Gly Gly Leu Val Gln Pro Gly Gly
1               5                   10                  15

Ser Arg Lys Leu Ser Cys Ala Ala Ser Gly Phe Thr Phe Ser Asp Phe
            20                  25                  30

Gly Met His Trp Val Arg Gln Ala Pro Glu Lys Gly Leu Glu Trp Val
        35                  40                  45

Ala Tyr Ser Ser Ser Gly Gly Thr Thr Val Tyr Tyr Ala Asp Thr Val
    50                  55                  60

Lys Gly Arg Leu Thr Leu Ser Arg Asp Asn Ser Lys Asn Thr Leu Phe
65                  70                  75                  80

Leu Glu Met Thr Ser Leu Arg Ser Glu Asp Thr Ala Met Tyr Tyr Cys
                85                  90                  95

Ala Arg Ala Ser Tyr Asp Gly Gly Tyr Phe Asp Cys Trp Gly Gln Gly
            100                 105                 110

Thr Ser Leu Thr Val Ser Ser Ala Lys Thr Thr Pro Pro
        115                 120                 125
```

<210> SEQ ID NO 24
<211> LENGTH: 117
<212> TYPE: PRT
<213> ORGANISM: Artificial Sequence
<220> FEATURE:
<223> OTHER INFORMATION: Synthetic: MAb 1.815 light chain variable
      region

<400> SEQUENCE: 24

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Ile His Trp Tyr Gln Gln Lys Pro Gly Gln Pro Pro
        35                  40                  45

Lys Leu Leu Ile Tyr Leu Ala Ser Asp Leu Glu Ser Gly Val Pro Ala
    50                  55                  60

Arg Phe Ser Gly Ser Gly Ser Gly Ala Ala Phe Thr Leu Asn Ile His
65                  70                  75                  80

Pro Val Glu Glu Glu Asp Ala Ala Thr Tyr Tyr Cys His His Ser Arg
                85                  90                  95

Glu Leu Pro Phe Thr Phe Gly Ser Gly Thr Lys Leu Glu Ile Lys Arg
            100                 105                 110

Ala Asp Ala Ala Pro
        115
```

<210> SEQ ID NO 25
<211> LENGTH: 10
<212> TYPE: PRT
<213> ORGANISM: Artificial Sequence
<220> FEATURE:
<223> OTHER INFORMATION: Synthetic: MAb 1.815 heavy chain CDR1

```
<400> SEQUENCE: 25

Gly Phe Thr Phe Ser Asp Phe Gly Met His
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic: MAb 1.815 heavy chain CDR2

<400> SEQUENCE: 26

Tyr Ser Ser Ser Gly Gly Thr Thr Val Tyr
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic: MAb 1.815 heavy chain CDR3

<400> SEQUENCE: 27

Ala Ser Tyr Asp Gly Gly Tyr Phe Asp Cys
1               5                   10

<210> SEQ ID NO 28
<211> LENGTH: 15
<212> TYPE: PRT
<213> ORGANISM: Artificial Sequence
<220> FEATURE:
<223> OTHER INFORMATION: Synthetic: MAb 1.815 light chain CDR1

<400> SEQUENCE: 28

Arg Ala Ser Lys Ser Val Ser Thr Ser Gly Tyr Ser Tyr Ile His
1               5                   10                  15

<210> SEQ ID NO 29
<211> LENGTH: 7
<212> TYPE: PRT
<213> ORGANISM: Artificial Sequence
<220> FEATURE:
<223> OTHER INFORMATION: Synthetic: MAb 1.815 light chain CDR2

<400> SEQUENCE: 29

Leu Ala Ser Asp Leu Glu Ser
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic: MAb 1.815 light chain CDR3

<400> SEQUENCE: 30

His His Ser Arg Glu Leu Pro Phe Thr
1               5

<210> SEQ ID NO 31
<211> LENGTH: 125
<212> TYPE: PRT
<213> ORGANISM: Artificial Sequence
<220> FEATURE:
<223> OTHER INFORMATION: Synthetic: MAb 1.846 heavy chain variable
      region
```

<400> SEQUENCE: 31

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Leu Arg Gln Ala Pro Glu Lys Gly Leu Glu Trp Val
        35                  40                  45

Ala Tyr Ile Ser Ser Gly Ser Thr Thr Leu Ser Tyr Ala Asn Thr Met
    50                  55                  60

Lys Gly Arg Phe Thr Ile Ser Arg Asp Asn Ala Lys Lys Thr Leu Ser
65                  70                  75                  80

Leu Gln Met Thr Ser Leu Arg Ser Glu Asp Thr Ala Ile Tyr Tyr Cys
                85                  90                  95

Ala Arg Lys Asn Tyr Asn Gly Gly Tyr Phe Asp Val Trp Gly Thr Gly
            100                 105                 110

Thr Thr Val Thr Val Ser Ser Ala Lys Thr Pro Pro
        115                 120                 125

<210> SEQ ID NO 32
<211> LENGTH: 117
<212> TYPE: PRT
<213> ORGANISM: Artificial Sequence
<220> FEATURE:
<223> OTHER INFORMATION: Synthetic: MAb 1.846 light chain variable
      region

<400> SEQUENCE: 32

Asp Ile Val Leu Thr Gln Ser Pro Ala Ser Leu Val Val Ser Leu Gly
1               5                   10                  15

Gln Arg Ala Thr Ile Ser Cys Arg Ala Ser Lys Ser Val Ser Glu Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Gly Asp Ala Thr Thr Tyr Tyr Cys Gln His Ser Arg
                85                  90                  95

Val Leu Pro Pro Thr Phe Gly Ser Gly Thr Lys Leu Glu Ile Lys Arg
            100                 105                 110

Ala Asp Ala Ala Pro
        115

<210> SEQ ID NO 33
<211> LENGTH: 10
<212> TYPE: PRT
<213> ORGANISM: Artificial Sequence
<220> FEATURE:
<223> OTHER INFORMATION: Synthetic: MAb 1.846 heavy chain CDR1

<400> SEQUENCE: 33

Gly Phe Thr Phe Ser Asp Tyr Gly Met His
1               5                   10

<210> SEQ ID NO 34
<211> LENGTH: 10
<212> TYPE: PRT

<213> ORGANISM: Artificial Sequence
<220> FEATURE:
<223> OTHER INFORMATION: Synthetic: MAb 1.846 heavy chain CDR2

<400> SEQUENCE: 34

Tyr Ile Ser Ser Gly Ser Thr Thr Leu Ser
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic: MAb 1.846 heavy chain CDR3

<400> SEQUENCE: 35

Lys Asn Tyr Asn Gly Gly Tyr Phe Asp Val
1               5                   10

<210> SEQ ID NO 36
<211> LENGTH: 15
<212> TYPE: PRT
<213> ORGANISM: Artificial Sequence
<220> FEATURE:
<223> OTHER INFORMATION: Synthetic: MAb 1.846 light chain CDR1

<400> SEQUENCE: 36

Arg Ala Ser Lys Ser Val Ser Glu Ser Gly Tyr Ser Tyr Met His
1               5                   10                  15

<210> SEQ ID NO 37
<211> LENGTH: 7
<212> TYPE: PRT
<213> ORGANISM: Artificial Sequence
<220> FEATURE:
<223> OTHER INFORMATION: Synthetic: MAb 1.846 light chain CDR2

<400> SEQUENCE: 37

Leu Ala Ser Asn Leu Glu Ser
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic: MAb 1.846 light chain CDR3

<400> SEQUENCE: 38

Gln His Ser Arg Val Leu Pro Pro Thr
1               5

<210> SEQ ID NO 39
<211> LENGTH: 127
<212> TYPE: PRT
<213> ORGANISM: Artificial Sequence
<220> FEATURE:
<223> OTHER INFORMATION: Synthetic: MAb 2.1029 heavy chain variable
      region

<400> SEQUENCE: 39

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu

```
                35                  40                  45

Gly Val Ile Trp Ala Gly Gly Ser Thr Asn Tyr Asn Ser Ala Leu Met
         50                  55                  60

Ser Arg Leu Ser Ile Ser Lys Asp Asn Ser Lys Ser Gln Val Phe Leu
 65                  70                  75                  80

Lys Met Asn Ser Leu Gln Thr Asp Asp Thr Ala Ile Tyr Phe Cys Ala
                 85                  90                  95

Arg Asp Gly Asp Tyr Gly Thr Ile Tyr Ala Met Asp Tyr Trp Gly Gln
                100                 105                 110

Gly Thr Ser Val Thr Val Ser Ser Ala Lys Thr Thr Ala Pro Ser
            115                 120                 125

<210> SEQ ID NO 40
<211> LENGTH: 113
<212> TYPE: PRT
<213> ORGANISM: Artificial Sequence
<220> FEATURE:
<223> OTHER INFORMATION: Synthetic: MAb 2.1029 light chain variable
      region

<400> SEQUENCE: 40

Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Ser Asn Tyr
             20                  25                  30

Leu Asn Trp Tyr Gln Gln Lys Pro Asp Gly Thr Val Lys Leu Leu Ile
         35                  40                  45

Tyr Tyr Thr Ser Arg Leu His Ser Gly Val Pro Ser Arg Phe Thr Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Lys Thr Leu Pro Arg
                 85                  90                  95

Thr Phe Gly Gly Gly Thr Met Leu Glu Ile Lys Arg Ala Asp Ala Ala
                100                 105                 110

Pro

<210> SEQ ID NO 41
<211> LENGTH: 10
<212> TYPE: PRT
<213> ORGANISM: Artificial Sequence
<220> FEATURE:
<223> OTHER INFORMATION: Synthetic: MAb 2.1029 heavy chain CDR1

<400> SEQUENCE: 41

Gly Phe Ser Leu Thr Ser Tyr Gly Val His
 1               5                  10

<210> SEQ ID NO 42
<211> LENGTH: 9
<212> TYPE: PRT
<213> ORGANISM: Artificial Sequence
<220> FEATURE:
<223> OTHER INFORMATION: Synthetic: MAb 2.1029 heavy chain CDR2

<400> SEQUENCE: 42

Val Ile Trp Ala Gly Gly Ser Thr Asn
 1               5

<210> SEQ ID NO 43
```

```
<211> LENGTH: 12
<212> TYPE: PRT
<213> ORGANISM: Artificial Sequence
<220> FEATURE:
<223> OTHER INFORMATION: Synthetic: MAb 2.1029 heavy chain CDR3

<400> SEQUENCE: 43

Asp Gly Asp Tyr Gly Thr Ile Tyr Ala Met Asp Tyr
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic: MAb 2.1029 light chain CDR1

<400> SEQUENCE: 44

Arg Ala Ser Gln Asp Ile Ser Asn Tyr Leu Asn
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Synthetic: MAb 2.1029 light chain CDR2

<400> SEQUENCE: 45

Tyr Thr Ser Arg Leu His Ser
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic: MAb 2.1029 light chain CDR3

<400> SEQUENCE: 46

Gln Gln Gly Lys Thr Leu Pro Arg Thr
1               5

<210> SEQ ID NO 47
<211> LENGTH: 126
<212> TYPE: PRT
<213> ORGANISM: Artificial Sequence
<220> FEATURE:
<223> OTHER INFORMATION: Synthetic: MAb 2.55 heavy chain variable region

<400> SEQUENCE: 47

Glu Val Gln Leu Gln Gln Ser Gly Thr Val Leu Ala Arg Pro Gly Ala
1               5                   10                  15

Leu Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Ala Ile Tyr Pro Gly Lys Ser Asp Thr Arg Tyr Asn Gln Lys Phe
    50                  55                  60

Lys Asp Lys Ala Lys Leu Thr Ala Val Thr Ser Thr Thr Ala Tyr
65                  70                  75                  80

Met Asp Leu Ser Ser Leu Thr Asp Glu Asp Ser Ala Val Tyr Tyr Cys
                85                  90                  95

Ser Arg Arg Tyr Gly Asn Phe Tyr Ala Met Asp Tyr Trp Gly Gln Gly
```

```
                100             105             110
Thr Ser Val Thr Val Ser Ser Ala Lys Thr Thr Ala Pro Ser
        115             120             125

<210> SEQ ID NO 48
<211> LENGTH: 113
<212> TYPE: PRT
<213> ORGANISM: Artificial Sequence
<220> FEATURE:
<223> OTHER INFORMATION: Synthetic: MAb 2.55 light chain variable region

<400> SEQUENCE: 48

Ser Ile Val Met Thr Gln Thr Pro Lys Phe Leu Leu Val Ser Ala Gly
1               5                   10                  15

Asp Arg Val Thr Met Thr Cys Lys Ala Ser Gln Ser Val Ser Asn Asp
            20                  25                  30

Val Ala Trp Tyr Gln Gln Lys Pro Gly Gln Ser Pro Glu Leu Leu Ile
        35                  40                  45

Tyr Tyr Ala Ser Asp Arg Tyr Thr Gly Val Pro Asp Arg Phe Thr Gly
    50                  55                  60

Ser Gly Tyr Gly Thr Asp Phe Thr Leu Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Thr Lys Arg Ala Asp Ala Ala
            100                 105                 110

Pro

<210> SEQ ID NO 49
<211> LENGTH: 10
<212> TYPE: PRT
<213> ORGANISM: Artificial Sequence
<220> FEATURE:
<223> OTHER INFORMATION: Synthetic: MAb 2.55 heavy chain CDR1

<400> SEQUENCE: 49

Gly Tyr Thr Phe Thr Ser Tyr Trp Met His
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthetic: MAb 2.55 heavy chain CDR2

<400> SEQUENCE: 50

Ala Ile Tyr Pro Gly Lys Ser Asp Thr Arg
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic: MAb 2.55 heavy chain CDR3

<400> SEQUENCE: 51

Arg Tyr Gly Asn Phe Tyr Ala Met Asp Tyr
1               5                   10

<210> SEQ ID NO 52
```

```
<211> LENGTH: 11
<212> TYPE: PRT
<213> ORGANISM: Artificial Sequence
<220> FEATURE:
<223> OTHER INFORMATION: Synthetic: MAb 2.55 light chain CDR1

<400> SEQUENCE: 52

Lys Ala Ser Gln Ser Val Ser Asn Asp Val Ala
1               5                   10

<210> SEQ ID NO 53
<211> LENGTH: 7
<212> TYPE: PRT
<213> ORGANISM: Artificial Sequence
<220> FEATURE:
<223> OTHER INFORMATION: Synthetic: MAb 2.55 light chain CDR2

<400> SEQUENCE: 53

Tyr Ala Ser Asp Arg Tyr Thr
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic: MAb 2.55 light chain CDR3

<400> SEQUENCE: 54

Gln Gln Asp Tyr Ser Ser Pro Tyr Thr
1               5

<210> SEQ ID NO 55
<211> LENGTH: 123
<212> TYPE: PRT
<213> ORGANISM: Artificial Sequence
<220> FEATURE:
<223> OTHER INFORMATION: Synthetic: MAb 2.78 heavy chain variable region

<400> SEQUENCE: 55

Asp Val Gln Leu Val Glu Ser Gly Gly Leu Val Gln Pro Gly Gly
1               5                   10                  15

Ser Arg Lys Leu Ser Cys Ala Ala Ser Gly Phe Thr Phe Ser Ser Phe
                20                  25                  30

Gly Met His Trp Val Arg Gln Ala Pro Glu Lys Gly Leu Glu Trp Val
            35                  40                  45

Ala Tyr Ile Thr Ser Gly Ser Gly Ala Ile Tyr Tyr Ala Asp Thr Val
        50                  55                  60

Arg Gly Arg Phe Thr Ile Ser Arg Asp Thr Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Ser Ala Asp Gly Leu Asp Tyr Trp Gly Gln Gly Thr Ser Val
            100                 105                 110

Thr Val Ser Ser Ala Lys Thr Thr Pro Pro Ser
        115                 120

<210> SEQ ID NO 56
<211> LENGTH: 113
<212> TYPE: PRT
<213> ORGANISM: Artificial Sequence
<220> FEATURE:
<223> OTHER INFORMATION: Synthetic: MAb 2.78 light chain variable region
```

```
<400> SEQUENCE: 56

Asp Ile Gln Met Thr Gln Ser Pro Ala Ser Leu Tyr Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Gly Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Lys Ser
65                  70                  75                  80

Glu Asp Phe Gly Ser Tyr Tyr Cys Gln His Phe Trp Gly Thr Pro Phe
                85                  90                  95

Thr Phe Gly Ser Gly Thr Lys Leu Glu Ile Lys Arg Ala Asp Ala Ala
            100                 105                 110

Pro

<210> SEQ ID NO 57
<211> LENGTH: 10
<212> TYPE: PRT
<213> ORGANISM: Artificial Sequence
<220> FEATURE:
<223> OTHER INFORMATION: Synthetic: MAb 2.78 heavy chain CDR1

<400> SEQUENCE: 57

Gly Phe Thr Phe Ser Ser Phe Gly Met His
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Synthetic: MAb 2.78 heavy chain CDR2

<400> SEQUENCE: 58

Tyr Ile Thr Ser Gly Ser Gly Ala Ile Tyr
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Synthetic: MAb 2.78 heavy chain CDR3

<400> SEQUENCE: 59

Ser Ala Asp Gly Leu Asp Tyr
1               5

<210> SEQ ID NO 60
<211> LENGTH: 11
<212> TYPE: PRT
<213> ORGANISM: Artificial Sequence
<220> FEATURE:
<223> OTHER INFORMATION: Synthetic: MAb 2.78 light chain CDR1

<400> SEQUENCE: 60

Arg Ala Ser Glu Asn Ile Tyr Ser Asn Leu Ala
1               5                   10

<210> SEQ ID NO 61
```

```
<211> LENGTH: 7
<212> TYPE: PRT
<213> ORGANISM: Artificial Sequence
<220> FEATURE:
<223> OTHER INFORMATION: Synthetic: MAb 2.78 light chain CDR2

<400> SEQUENCE: 61

Gly Ala Thr Asn Leu Ala Asp
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic: MAb 2.78 light chain CDR3

<400> SEQUENCE: 62

Gln His Phe Trp Gly Thr Pro Phe Thr
1               5

<210> SEQ ID NO 63
<211> LENGTH: 116
<212> TYPE: PRT
<213> ORGANISM: Artificial Sequence
<220> FEATURE:
<223> OTHER INFORMATION: Synthetic: Humanized Ab (HumAb) 2.78 heavy
      chain variable region

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ser Tyr Ile Thr Ser Gly Ser Gly Ala Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Ala Asp Gly Leu Asp Tyr Trp Gly Gln Gly Thr Thr Val
            100                 105                 110

Thr Val Ser Ser
        115

<210> SEQ ID NO 64
<211> LENGTH: 455
<212> TYPE: PRT
<213> ORGANISM: Artificial Sequence
<220> FEATURE:
<223> OTHER INFORMATION: Synthetic: HumAb 2.78 heavy chain

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ser Tyr Ile Thr Ser Gly Ser Gly Ala Ile Tyr Tyr Ala Asp Ser Val
```

```
                50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Ala Asp Gly Leu Asp Tyr Trp Gly Gln Gly Thr Thr Val
                100                 105                 110

Thr Val Ser Ser Asp Val Trp Gly Gln Gly Thr Thr Val Thr Val Ser
                115                 120                 125

Ser Ala Ser Thr Lys Gly Pro Ser Val Phe Pro Leu Ala Pro Cys Ser
                130                 135                 140

Arg Ser Thr Ser Glu Ser Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
                180                 185                 190

Ser Leu Ser Ser Val Val Thr Val Thr Ser Ser Asn Phe Gly Thr Gln
                195                 200                 205

Thr Tyr Thr Cys Asn Val Asp His Lys Pro Ser Asn Thr Lys Val Asp
210                 215                 220

Lys Thr Val Glu Arg Lys Cys Cys Val Glu Cys Pro Pro Cys Pro Ala
225                 230                 235                 240

Pro Pro Val Ala Gly Pro Ser Val Phe Leu Phe Pro Pro Lys Pro Lys
                245                 250                 255

Asp Thr Leu Met Ile Ser Arg Thr Pro Glu Val Thr Cys Val Val Val
                260                 265                 270

Asp Val Ser His Glu Asp Pro Glu Val Gln Phe Asn Trp Tyr Val Asp
                275                 280                 285

Gly Met Glu Val His Asn Ala Lys Thr Lys Pro Arg Glu Glu Gln Phe
                290                 295                 300

Asn Ser Thr Phe Arg Val Val Ser Val Leu Thr Val Val His Gln Asp
305                 310                 315                 320

Trp Leu Asn Gly Lys Glu Tyr Lys Cys Lys Val Ser Asn Lys Gly Leu
                325                 330                 335

Pro Ala Pro Ile Glu Lys Thr Ile Ser Lys Thr Lys Gly Gln Pro Arg
                340                 345                 350

Glu Pro Gln Val Tyr Thr Leu Pro Pro Ser Arg Glu Glu Met Thr Lys
                355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Met Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
                435                 440                 445

Leu Ser Leu Ser Pro Gly Lys
450                 455

<210> SEQ ID NO 65
```

<211> LENGTH: 106
<212> TYPE: PRT
<213> ORGANISM: Artificial Sequence
<220> FEATURE:
<223> OTHER INFORMATION: Synthetic: HumAb 2.78 light chain variable
      region

<400> SEQUENCE: 65

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Gly Thr Pro Phe
                85                  90                  95

Thr Phe Gly Gln Gly Thr Lys Val Glu Ile
            100                 105
```

<210> SEQ ID NO 66
<211> LENGTH: 214
<212> TYPE: PRT
<213> ORGANISM: Artificial Sequence
<220> FEATURE:
<223> OTHER INFORMATION: Synthetic: HumAb 2.78 light chain

<400> SEQUENCE: 66

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Gly Thr Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
<210> SEQ ID NO 67
<211> LENGTH: 120
<212> TYPE: PRT
<213> ORGANISM: Artificial Sequence
<220> FEATURE:
<223> OTHER INFORMATION: Synthetic: HumAb 2.1029 heavy chain variable
      region

<400> SEQUENCE: 67

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Asp Tyr Gly Thr Ile Tyr Ala Met Asp Tyr Trp Gly Gln
            100                 105                 110

Gly Thr Leu Val Thr Val Ser Ser
        115                 120

<210> SEQ ID NO 68
<211> LENGTH: 459
<212> TYPE: PRT
<213> ORGANISM: Artificial Sequence
<220> FEATURE:
<223> OTHER INFORMATION: Synthetic: HumAb 2.1029 heavy chain

<400> SEQUENCE: 68

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Asp Tyr Gly Thr Ile Tyr Ala Met Asp Tyr Trp Gly Gln
            100                 105                 110

Gly Thr Leu Val Thr Val Ser Ser Asp Val Trp Gly Gln Gly Thr Thr
        115                 120                 125

Val Thr Val Ser Ser Ala Ser Thr Lys Gly Pro Ser Val Phe Pro Leu
    130                 135                 140

Ala Pro Cys Ser Arg Ser Thr Ser Glu Ser Thr Ala Ala Leu Gly Cys
145                 150                 155                 160

Leu Val Lys Asp Tyr Phe Pro Glu Pro Val Thr Val Ser Trp Asn Ser
```

Phe Asn Arg Gly Glu Cys
    210

```
                165                 170                 175
Gly Ala Leu Thr Ser Gly Val His Thr Phe Pro Ala Val Leu Gln Ser
                180                 185                 190

Ser Gly Leu Tyr Ser Leu Ser Ser Val Val Thr Val Thr Ser Ser Asn
                195                 200                 205

Phe Gly Thr Gln Thr Tyr Thr Cys Asn Val Asp His Lys Pro Ser Asn
            210                 215                 220

Thr Lys Val Asp Lys Thr Val Glu Arg Lys Cys Cys Val Glu Cys Pro
225                 230                 235                 240

Pro Cys Pro Ala Pro Pro Val Ala Gly Pro Ser Val Phe Leu Phe Pro
                245                 250                 255

Pro Lys Pro Lys Asp Thr Leu Met Ile Ser Arg Thr Pro Glu Val Thr
                260                 265                 270

Cys Val Val Val Asp Val Ser His Glu Asp Pro Glu Val Gln Phe Asn
            275                 280                 285

Trp Tyr Val Asp Gly Met Glu Val His Asn Ala Lys Thr Lys Pro Arg
        290                 295                 300

Glu Glu Gln Phe Asn Ser Thr Phe Arg Val Val Ser Val Leu Thr Val
305                 310                 315                 320

Val His Gln Asp Trp Leu Asn Gly Lys Glu Tyr Lys Cys Lys Val Ser
                325                 330                 335

Asn Lys Gly Leu Pro Ala Pro Ile Glu Lys Thr Ile Ser Lys Thr Lys
                340                 345                 350

Gly Gln Pro Arg Glu Pro Gln Val Tyr Thr Leu Pro Pro Ser Arg Glu
            355                 360                 365

Glu Met Thr Lys Asn Gln Val Ser Leu Thr Cys Leu Val Lys Gly Phe
        370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Met Leu Asp Ser Asp Gly Ser Phe
                405                 410                 415

Phe Leu Tyr Ser Lys Leu Thr Val Asp Lys Ser Arg Trp Gln Gln Gly
                420                 425                 430

Asn Val Phe Ser Cys Ser Val Met His Glu Ala Leu His Asn His Tyr
            435                 440                 445

Thr Gln Lys Ser Leu Ser Leu Ser Pro Gly Lys
        450                 455

<210> SEQ ID NO 69
<211> LENGTH: 106
<212> TYPE: PRT
<213> ORGANISM: Artificial Sequence
<220> FEATURE:
<223> OTHER INFORMATION: Synthetic: HumAb 2.1029 light chain variable
      region

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60
```

```
Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Gly Lys Thr Leu Pro Arg
                 85                  90                  95

Thr Phe Gly Gly Gly Thr Lys Val Glu Ile
                100                 105

<210> SEQ ID NO 70
<211> LENGTH: 214
<212> TYPE: PRT
<213> ORGANISM: Artificial Sequence
<220> FEATURE:
<223> OTHER INFORMATION: Synthetic: HumAb 2.1029 light chain

<400> SEQUENCE: 70

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Tyr Thr Ser Arg Leu His Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Gly Lys Thr Leu Pro Arg
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 71
<211> LENGTH: 119
<212> TYPE: PRT
<213> ORGANISM: Artificial Sequence
<220> FEATURE:
<223> OTHER INFORMATION: Synthetic: HumAb 1.802 heavy chain variable
      region

<400> SEQUENCE: 71

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
                 20                  25                  30

Gly Met His Trp Val Arg Gln Ala Pro Gly Lys Gly Leu Glu Trp Val
```

```
                35                  40                  45
Ser Tyr Ile Ser Ser Gly Ser Arg Thr Val Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Arg Lys His Tyr Asn Gly Gly Tyr Phe Asp Val Trp Gly Gln Gly
                100                 105                 110

Thr Leu Val Thr Val Ser Ser
            115

<210> SEQ ID NO 72
<211> LENGTH: 458
<212> TYPE: PRT
<213> ORGANISM: Artificial Sequence
<220> FEATURE:
<223> OTHER INFORMATION: Synthetic: HumAb 1.802 heavy chain

<400> SEQUENCE: 72

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
                 20                  25                  30

Gly Met His Trp Val Arg Gln Ala Pro Gly Lys Gly Leu Glu Trp Val
             35                  40                  45

Ser Tyr Ile Ser Ser Gly Ser Arg Thr Val Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Arg Lys His Tyr Asn Gly Gly Tyr Phe Asp Val Trp Gly Gln Gly
                100                 105                 110

Thr Leu Val Thr Val Ser Ser Asp Val Trp Gly Gln Gly Thr Thr Val
            115                 120                 125

Thr Val Ser Ser Ala Ser Thr Lys Gly Pro Ser Val Phe Pro Leu Ala
130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Thr Ser Ser Asn Phe
        195                 200                 205

Gly Thr Gln Thr Tyr Thr Cys Asn Val Asp His Lys Pro Ser Asn Thr
    210                 215                 220

Lys Val Asp Lys Thr Val Glu Arg Lys Cys Cys Val Glu Cys Pro Pro
225                 230                 235                 240

Cys Pro Ala Pro Pro Val Ala Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Gln Phe Asn Trp
```

```
                275                 280                 285
Tyr Val Asp Gly Met Glu Val His Asn Ala Lys Thr Lys Pro Arg Glu
    290                 295                 300
Glu Gln Phe Asn Ser Thr Phe Arg Val Val Ser Val Leu Thr Val Val
305                 310                 315                 320
His Gln Asp Trp Leu Asn Gly Lys Glu Tyr Lys Cys Lys Val Ser Asn
                325                 330                 335
Lys Gly Leu Pro Ala Pro Ile Glu Lys Thr Ile Ser Lys Thr Lys Gly
            340                 345                 350
Gln Pro Arg Glu Pro Gln Val Tyr Thr Leu Pro Pro Ser Arg Glu Glu
        355                 360                 365
Met Thr Lys Asn Gln Val Ser Leu Thr Cys Leu Val Lys Gly Phe Tyr
    370                 375                 380
Pro Ser Asp Ile Ala Val Glu Trp Glu Ser Asn Gly Gln Pro Glu Asn
385                 390                 395                 400
Asn Tyr Lys Thr Thr Pro Pro Met Leu Asp Ser Asp Gly Ser Phe Phe
                405                 410                 415
Leu Tyr Ser Lys Leu Thr Val Asp Lys Ser Arg Trp Gln Gln Gly Asn
            420                 425                 430
Val Phe Ser Cys Ser Val Met His Glu Ala Leu His Asn His Tyr Thr
        435                 440                 445
Gln Lys Ser Leu Ser Leu Ser Pro Gly Lys
    450                 455

<210> SEQ ID NO 73
<211> LENGTH: 110
<212> TYPE: PRT
<213> ORGANISM: Artificial Sequence
<220> FEATURE:
<223> OTHER INFORMATION: Synthetic: HumAb 1.802 light chain variable
      region

<400> SEQUENCE: 73

Asp Ile Val Met Thr Gln Ser Pro Asp Ser Leu Ala Val Ser Leu Gly
1               5                   10                  15
Glu Arg Ala Thr Ile Asn Cys Arg Ala Ser Lys Ile Val Ser Thr Ser
            20                  25                  30
Gly Tyr Ser Tyr Met His Trp Tyr Gln Gln Lys Pro Gly Gln Pro Pro
        35                  40                  45
Lys Leu Leu Ile Tyr Leu Ala Ser Asn Leu Glu Ser Gly Val Pro Asp
    50                  55                  60
Arg Phe Ser Gly Ser Gly Ser Gly Thr Asp Phe Thr Leu Thr Ile Ser
65                  70                  75                  80
Ser Leu Gln Ala Glu Asp Val Ala Val Tyr Tyr Cys Gln His Ser Arg
                85                  90                  95
Glu Leu Pro Pro Thr Phe Gly Gln Gly Thr Lys Leu Glu Ile
            100                 105                 110

<210> SEQ ID NO 74
<211> LENGTH: 218
<212> TYPE: PRT
<213> ORGANISM: Artificial Sequence
<220> FEATURE:
<223> OTHER INFORMATION: Synthetic: HumAb 1.802 light chain

<400> SEQUENCE: 74

Asp Ile Val Met Thr Gln Ser Pro Asp Ser Leu Ala Val Ser Leu Gly
1               5                   10                  15
```

```
Glu Arg Ala Thr Ile Asn Cys Arg Ala Ser Lys Ile Val Ser Thr Ser
                20                  25                  30

Gly Tyr Ser Tyr Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln His Ser Arg
                 85                  90                  95

Glu Leu Pro Pro Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 75
<211> LENGTH: 119
<212> TYPE: PRT
<213> ORGANISM: Artificial Sequence
<220> FEATURE:
<223> OTHER INFORMATION: Synthetic: HumAb 1.815 heavy chain variable
      region

<400> SEQUENCE: 75

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Phe
                20                  25                  30

Gly Met His Trp Ile Arg Gln Ala Pro Gly Lys Gly Leu Glu Trp Val
            35                  40                  45

Ser Tyr Ser Ser Gly Gly Thr Thr Val Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ala Ser Tyr Asp Gly Gly Tyr Phe Asp Cys Trp Gly Gln Gly
            100                 105                 110

Thr Thr Val Thr Val Ser Ser
            115

<210> SEQ ID NO 76
<211> LENGTH: 458
<212> TYPE: PRT
```

<213> ORGANISM: Artificial Sequence
<220> FEATURE:
<223> OTHER INFORMATION: Synthetic: HumAb 1.815 heavy chain

<400> SEQUENCE: 76

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Phe
            20                  25                  30

Gly Met His Trp Ile Arg Gln Ala Pro Gly Lys Gly Leu Glu Trp Val
        35                  40                  45

Ser Tyr Ser Ser Gly Gly Thr Thr Val Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Ser Tyr Asp Gly Gly Tyr Phe Asp Cys Trp Gly Gln Gly
            100                 105                 110

Thr Thr Val Thr Val Ser Ser Asp Val Trp Gly Gln Gly Thr Thr Val
        115                 120                 125

Thr Val Ser Ser Ala Ser Thr Lys Gly Pro Ser Val Phe Pro Leu Ala
130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Thr Ser Ser Asn Phe
        195                 200                 205

Gly Thr Gln Thr Tyr Thr Cys Asn Val Asp His Lys Pro Ser Asn Thr
    210                 215                 220

Lys Val Asp Lys Thr Val Glu Arg Lys Cys Cys Val Glu Cys Pro Pro
225                 230                 235                 240

Cys Pro Ala Pro Pro Val Ala Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Gln Phe Asn Trp
        275                 280                 285

Tyr Val Asp Gly Met Glu Val His Asn Ala Lys Thr Lys Pro Arg Glu
    290                 295                 300

Glu Gln Phe Asn Ser Thr Phe Arg Val Val Ser Val Leu Thr Val Val
305                 310                 315                 320

His Gln Asp Trp Leu Asn Gly Lys Glu Tyr Lys Cys Lys Val Ser Asn
                325                 330                 335

Lys Gly Leu Pro Ala Pro Ile Glu Lys Thr Ile Ser Lys Thr Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
```

```
385                 390                 395                 400
Asn Tyr Lys Thr Thr Pro Pro Met Leu Asp Ser Asp Gly Ser Phe Phe
            405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
            435                 440                 445

Gln Lys Ser Leu Ser Leu Ser Pro Gly Lys
            450                 455

<210> SEQ ID NO 77
<211> LENGTH: 110
<212> TYPE: PRT
<213> ORGANISM: Artificial Sequence
<220> FEATURE:
<223> OTHER INFORMATION: Synthetic: HumAb 1.815 light chain variable
      region

<400> SEQUENCE: 77

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Tyr Ile His Trp Tyr Gln Gln Lys Pro Gly Gln Pro Pro
        35                  40                  45

Lys Leu Leu Ile Tyr Leu Ala Ser Asp Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys His His Ser Arg
                85                  90                  95

Glu Leu Pro Phe Thr Phe Gly Gln Gly Thr Lys Leu Glu Ile
            100                 105                 110

<210> SEQ ID NO 78
<211> LENGTH: 218
<212> TYPE: PRT
<213> ORGANISM: Artificial Sequence
<220> FEATURE:
<223> OTHER INFORMATION: Synthetic: HumAb 1.815 light chain

<400> SEQUENCE: 78

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Ser
            20                  25                  30

Gly Tyr Ser Tyr Ile His Trp Tyr Gln Gln Lys Pro Gly Gln Pro Pro
        35                  40                  45

Lys Leu Leu Ile Tyr Leu Ala Ser Asp Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys His His Ser Arg
                85                  90                  95

Glu Leu Pro Phe Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125
```

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
        210                 215

<210> SEQ ID NO 79
<211> LENGTH: 119
<212> TYPE: PRT
<213> ORGANISM: Artificial Sequence
<220> FEATURE:
<223> OTHER INFORMATION: Synthetic: HumAb 1.846 heavy chain variable
      region

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ser Tyr Ile Ser Ser Gly Ser Thr Thr Leu Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Lys Asn Tyr Asn Gly Gly Tyr Phe Asp Val Trp Gly Gln Gly
            100                 105                 110

Thr Leu Val Thr Val Ser Ser
        115

<210> SEQ ID NO 80
<211> LENGTH: 458
<212> TYPE: PRT
<213> ORGANISM: Artificial Sequence
<220> FEATURE:
<223> OTHER INFORMATION: Synthetic: HumAb 1.846 heavy chain

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ser Tyr Ile Ser Ser Gly Ser Thr Thr Leu Tyr Ala Asp Ser Val
    50                  55                  60

Lys Gly Arg Phe Thr Ile Ser Arg Asp Asn Ala Lys Asn Ser Leu Tyr
65                  70                  75                  80

```
Leu Gln Met Asn Ser Leu Arg Asp Glu Asp Thr Ala Val Tyr Tyr Cys
                 85                  90                  95

Ala Arg Lys Asn Tyr Asn Gly Gly Tyr Phe Asp Val Trp Gly Gln Gly
            100                 105                 110

Thr Leu Val Thr Val Ser Ser Asp Val Trp Gly Gln Gly Thr Thr Val
        115                 120                 125

Thr Val Ser Ser Ala Ser Thr Lys Gly Pro Ser Val Phe Pro Leu Ala
130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Thr Ser Ser Asn Phe
        195                 200                 205

Gly Thr Gln Thr Tyr Thr Cys Asn Val Asp His Lys Pro Ser Asn Thr
    210                 215                 220

Lys Val Asp Lys Thr Val Glu Arg Lys Cys Cys Val Glu Cys Pro Pro
225                 230                 235                 240

Cys Pro Ala Pro Pro Val Ala Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Gln Phe Asn Trp
        275                 280                 285

Tyr Val Asp Gly Met Glu Val His Asn Ala Lys Thr Lys Pro Arg Glu
    290                 295                 300

Glu Gln Phe Asn Ser Thr Phe Arg Val Val Ser Val Leu Thr Val Val
305                 310                 315                 320

His Gln Asp Trp Leu Asn Gly Lys Glu Tyr Lys Cys Lys Val Ser Asn
                325                 330                 335

Lys Gly Leu Pro Ala Pro Ile Glu Lys Thr Ile Ser Lys Thr Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Met Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 81
<211> LENGTH: 110
<212> TYPE: PRT
<213> ORGANISM: Artificial Sequence
<220> FEATURE:
<223> OTHER INFORMATION: Synthetic: HumAb 1.846 light chain variable
```

-continued region

<400> SEQUENCE: 81

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Glu Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Val Leu Pro Pro Thr Phe Gly Gln Gly Thr Lys Leu Glu Ile
            100                 105                 110

<210> SEQ ID NO 82
<211> LENGTH: 218
<212> TYPE: PRT
<213> ORGANISM: Artificial Sequence
<220> FEATURE:
<223> OTHER INFORMATION: Synthetic: HumAb 1.846 light chain

<400> SEQUENCE: 82

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Glu Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Val Leu Pro Pro Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 83

```
<211> LENGTH: 496
<212> TYPE: PRT
<213> ORGANISM: Artificial Sequence
<220> FEATURE:
<223> OTHER INFORMATION: Synthetic: Human-mouse chimeric NOTUM

<400> SEQUENCE: 83

Met Gly Arg Gly Val Arg Val Leu Leu Leu Ser Leu Leu His Cys
1               5                   10                  15

Ala Gly Gly Ser Glu Gly Arg Lys Thr Trp Arg Arg Gly Gln Gln
                20                  25                  30

Pro Pro Pro Pro Arg Thr Glu Ala Ala Pro Ala Ala Gly Gln Pro
                35                  40                  45

Val Glu Ser Phe Pro Leu Asp Phe Thr Ala Val Glu Gly Asn Met Asp
50                  55                  60

Ser Phe Met Ala Gln Val Lys Ser Leu Ala Gln Ser Leu Tyr Pro Cys
65                  70                  75                  80

Ser Ala Gln Gln Leu Asn Glu Asp Leu Arg Leu His Leu Leu Leu Asn
                85                  90                  95

Thr Ser Val Thr Cys Asn Asp Gly Ser Pro Ala Gly Tyr Tyr Leu Lys
                100                 105                 110

Glu Ser Arg Gly Ser Arg Arg Trp Leu Leu Phe Leu Glu Gly Gly Trp
                115                 120                 125

Tyr Cys Phe Asn Arg Glu Asn Cys Asp Ser Arg Tyr Asp Thr Met Arg
130                 135                 140

Arg Leu Met Ser Ser Arg Asp Trp Pro Arg Thr Arg Thr Gly Thr Gly
145                 150                 155                 160

Ile Leu Ser Ser Gln Pro Glu Glu Asn Pro Tyr Trp Trp Asn Ala Asn
                165                 170                 175

Met Val Phe Ile Pro Tyr Cys Ser Ser Asp Val Trp Ser Gly Ala Ser
                180                 185                 190

Ser Lys Ser Glu Lys Asn Glu Tyr Ala Phe Met Gly Ala Leu Ile Ile
                195                 200                 205

Gln Glu Val Val Arg Glu Leu Leu Gly Arg Gly Leu Ser Gly Ala Lys
                210                 215                 220

Val Leu Leu Leu Ala Gly Ser Ser Ala Gly Gly Thr Gly Val Leu Leu
225                 230                 235                 240

Asn Val Asp Arg Val Ala Glu Gln Leu Glu Lys Leu Gly Tyr Pro Ala
                245                 250                 255

Ile Gln Val Arg Gly Leu Ala Asp Ser Gly Trp Phe Leu Asp Asn Lys
                260                 265                 270

Gln Tyr Arg Arg Ser Asp Cys Ile Asp Thr Ile Asn Cys Ala Pro Thr
                275                 280                 285

Asp Ala Ile Arg Arg Gly Ile Arg Tyr Trp Ser Gly Met Val Pro Glu
                290                 295                 300

Arg Cys Gln Arg Gln Phe Lys Glu Gly Glu Glu Trp Asn Cys Phe Phe
305                 310                 315                 320

Gly Tyr Lys Val Tyr Pro Thr Leu Arg Cys Pro Val Phe Val Val Gln
                325                 330                 335

Trp Leu Phe Asp Glu Ala Gln Leu Thr Val Asp Asn Val His Leu Thr
                340                 345                 350

Gly Gln Pro Val Gln Glu Gly Gln Trp Leu Tyr Ile Gln Asn Leu Gly
                355                 360                 365

Arg Glu Leu Arg Gly Thr Leu Lys Asp Val Gln Ala Ser Phe Ala Pro
                370                 375                 380
```

```
Ala Cys Leu Ser His Glu Ile Ile Arg Ser Tyr Trp Thr Asp Val
385                 390                 395                 400

Gln Val Lys Gly Thr Ser Leu Pro Arg Ala Leu His Cys Trp Asp Arg
            405                 410                 415

Ser Phe His Asp Ser His Lys Ala Ser Lys Thr Pro Met Lys Gly Cys
            420                 425                 430

Pro Phe His Leu Val Asp Ser Cys Pro Trp Pro His Cys Asn Pro Ser
            435                 440                 445

Cys Pro Thr Ile Arg Asp Gln Phe Thr Gly Gln Glu Met Asn Val Ala
    450                 455                 460

Gln Phe Leu Met His Met Gly Phe Asp Val Gln Thr Val Ala Gln Gln
465                 470                 475                 480

Gln Gly Met Glu Pro Ser Lys Leu Leu Gly Met Leu Ser Asn Gly Asn
                485                 490                 495
```

<210> SEQ ID NO 84
<211> LENGTH: 503
<212> TYPE: PRT
<213> ORGANISM: Artificial Sequence
<220> FEATURE:
<223> OTHER INFORMATION: Synthetic: Mouse-human chimeric NOTUM

<400> SEQUENCE: 84

```
Met Gly Gly Glu Val Arg Val Leu Leu Leu Gly Leu Leu His Trp
1               5                   10                  15

Val Gly Gly Ser Glu Gly Arg Lys Thr Trp Arg Arg Gly Gln Gln
            20                  25                  30

Pro Pro Gln Pro Pro Pro Pro Pro Leu Pro Gln Arg Ala Glu Val
            35                  40                  45

Glu Pro Gly Ala Gly Gln Pro Val Glu Ser Phe Pro Leu Asp Phe Thr
    50                  55                  60

Ala Val Glu Gly Asn Met Asp Ser Phe Met Ala Gln Val Lys Ser Leu
65                  70                  75                  80

Ala Gln Ser Leu Tyr Pro Cys Ser Ala Gln Gln Leu Asn Glu Asp Leu
                85                  90                  95

Arg Leu His Leu Leu Asn Thr Ser Val Thr Cys Asn Asp Gly Ser
                100                 105                 110

Pro Ala Gly Tyr Tyr Leu Lys Glu Ser Lys Gly Ser Arg Arg Trp Leu
            115                 120                 125

Leu Phe Leu Glu Gly Gly Trp Tyr Cys Phe Asn Arg Glu Asn Cys Asp
130                 135                 140

Ser Arg Tyr Ser Thr Met Arg Arg Leu Met Ser Ser Lys Asp Trp Pro
145                 150                 155                 160

His Thr Arg Thr Gly Thr Gly Ile Leu Ser Ser Gln Pro Glu Glu Asn
                165                 170                 175

Pro His Trp Trp Asn Ala Asn Met Val Phe Ile Pro Tyr Cys Ser Ser
            180                 185                 190

Asp Val Trp Ser Gly Ala Ser Pro Lys Ser Asp Lys Asn Glu Tyr Ala
            195                 200                 205

Phe Met Gly Ser Leu Ile Ile Gln Glu Val Val Arg Glu Leu Leu Gly
    210                 215                 220

Lys Gly Leu Ser Gly Ala Lys Val Leu Leu Leu Ala Gly Ser Ser Ala
225                 230                 235                 240

Gly Gly Thr Gly Val Leu Leu Asn Val Asp Arg Val Ala Glu Leu Leu
                245                 250                 255
```

```
Glu Glu Leu Gly Tyr Pro Ser Ile Gln Val Arg Gly Leu Ala Asp Ser
            260                 265                 270

Gly Trp Phe Leu Asp Asn Lys Gln Tyr Arg His Thr Asp Cys Val Asp
        275                 280                 285

Thr Ile Thr Cys Ala Pro Thr Glu Ala Ile Arg Arg Gly Ile Arg Tyr
    290                 295                 300

Trp Asn Gly Val Val Pro Glu Arg Cys Arg Arg Gln Phe Gln Glu Gly
305                 310                 315                 320

Glu Glu Trp Asn Cys Phe Phe Gly Tyr Lys Val Tyr Pro Thr Leu Arg
                325                 330                 335

Cys Pro Val Phe Val Val Gln Trp Leu Phe Asp Glu Ala Gln Leu Thr
            340                 345                 350

Val Asp Asn Val His Leu Thr Gly Gln Pro Val Gln Glu Gly Leu Arg
        355                 360                 365

Leu Tyr Ile Gln Asn Leu Gly Arg Glu Leu Arg His Thr Leu Lys Asp
    370                 375                 380

Val Pro Ala Ser Phe Ala Pro Ala Cys Leu Ser His Glu Ile Ile Ile
385                 390                 395                 400

Arg Ser His Trp Thr Asp Val Gln Val Lys Gly Thr Ser Leu Pro Arg
                405                 410                 415

Ala Leu His Cys Trp Asp Arg Ser Leu His Asp Ser His Lys Ala Ser
            420                 425                 430

Lys Thr Pro Leu Lys Gly Cys Pro Val His Leu Val Asp Ser Cys Pro
        435                 440                 445

Trp Pro His Cys Asn Pro Ser Cys Pro Thr Val Arg Asp Gln Phe Thr
    450                 455                 460

Gly Gln Glu Met Asn Val Ala Gln Phe Leu Met His Met Gly Phe Asp
465                 470                 475                 480

Met Gln Thr Val Ala Gln Pro Gln Gly Leu Glu Pro Ser Glu Leu Leu
                485                 490                 495

Gly Met Leu Ser Asn Gly Ser
            500

<210> SEQ ID NO 85
<211> LENGTH: 496
<212> TYPE: PRT
<213> ORGANISM: Artificial Sequence
<220> FEATURE:
<223> OTHER INFORMATION: Synthetic: Human-mouse-human chimeric NOTUM

<400> SEQUENCE: 85

Met Gly Arg Gly Val Arg Val Leu Leu Leu Ser Leu Leu His Cys
1               5                   10                  15

Ala Gly Gly Ser Glu Gly Arg Lys Thr Trp Arg Arg Gly Gln Gln
                20                  25                  30

Pro Pro Pro Pro Pro Arg Thr Glu Ala Ala Pro Ala Ala Gly Gln Pro
            35                  40                  45

Val Glu Ser Phe Pro Leu Asp Phe Thr Ala Val Glu Gly Asn Met Asp
        50                  55                  60

Ser Phe Met Ala Gln Val Lys Ser Leu Ala Gln Ser Tyr Pro Cys
65                  70                  75                  80

Ser Ala Gln Gln Leu Asn Glu Asp Leu Arg Leu His Leu Leu Leu Asn
                85                  90                  95

Thr Ser Val Thr Cys Asn Asp Gly Ser Pro Ala Gly Tyr Tyr Leu Lys
            100                 105                 110
```

Glu Ser Arg Gly Ser Arg Arg Trp Leu Leu Phe Leu Glu Gly Gly Trp
            115                 120                 125

Tyr Cys Phe Asn Arg Glu Asn Cys Asp Ser Arg Tyr Asp Thr Met Arg
        130                 135                 140

Arg Leu Met Ser Ser Arg Asp Trp Pro Arg Thr Arg Thr Gly Thr Gly
145                 150                 155                 160

Ile Leu Ser Ser Gln Pro Glu Glu Asn Pro Tyr Trp Trp Asn Ala Asn
                165                 170                 175

Met Val Phe Ile Pro Tyr Cys Ser Ser Asp Val Trp Ser Gly Ala Ser
            180                 185                 190

Pro Lys Ser Asp Lys Asn Glu Tyr Ala Phe Met Gly Ser Leu Ile Ile
        195                 200                 205

Gln Glu Val Val Arg Glu Leu Leu Gly Lys Gly Leu Ser Gly Ala Lys
        210                 215                 220

Val Leu Leu Leu Ala Gly Ser Ser Ala Gly Gly Thr Gly Val Leu Leu
225                 230                 235                 240

Asn Val Asp Arg Val Ala Glu Leu Leu Glu Glu Leu Gly Tyr Pro Ser
                245                 250                 255

Ile Gln Val Arg Gly Leu Ala Asp Ser Gly Trp Phe Leu Asp Asn Lys
            260                 265                 270

Gln Tyr Arg Arg Ser Asp Cys Ile Asp Thr Ile Asn Cys Ala Pro Thr
        275                 280                 285

Asp Ala Ile Arg Arg Gly Ile Arg Tyr Trp Ser Gly Met Val Pro Glu
        290                 295                 300

Arg Cys Gln Arg Gln Phe Lys Glu Gly Glu Trp Asn Cys Phe Phe
305                 310                 315                 320

Gly Tyr Lys Val Tyr Pro Thr Leu Arg Cys Pro Val Phe Val Val Gln
                325                 330                 335

Trp Leu Phe Asp Glu Ala Gln Leu Thr Val Asp Asn Val His Leu Thr
            340                 345                 350

Gly Gln Pro Val Gln Glu Gly Leu Arg Leu Tyr Ile Gln Asn Leu Gly
        355                 360                 365

Arg Glu Leu Arg His Thr Leu Lys Asp Val Pro Ala Ser Phe Ala Pro
        370                 375                 380

Ala Cys Leu Ser His Glu Ile Ile Ile Arg Ser His Trp Thr Asp Val
385                 390                 395                 400

Gln Val Lys Gly Thr Ser Leu Pro Arg Ala Leu His Cys Trp Asp Arg
                405                 410                 415

Ser Leu His Asp Ser His Lys Ala Ser Lys Thr Pro Leu Lys Gly Cys
            420                 425                 430

Pro Val His Leu Val Asp Ser Cys Pro Trp Pro His Cys Asn Pro Ser
        435                 440                 445

Cys Pro Thr Val Arg Asp Gln Phe Thr Gly Gln Glu Met Asn Val Ala
450                 455                 460

Gln Phe Leu Met His Met Gly Phe Asp Met Gln Thr Val Ala Gln Pro
465                 470                 475                 480

Gln Gly Leu Glu Pro Ser Glu Leu Leu Gly Met Leu Ser Asn Gly Ser
                485                 490                 495

<210> SEQ ID NO 86
<211> LENGTH: 503
<212> TYPE: PRT
<213> ORGANISM: Artificial Sequence
<220> FEATURE:

<223> OTHER INFORMATION: Synthetic: Mouse-human-mouse chimeric NOTUM

<400> SEQUENCE: 86

```
Met Gly Gly Glu Val Arg Val Leu Leu Leu Gly Leu Leu His Trp
 1               5                  10                  15

Val Gly Gly Ser Glu Gly Arg Lys Thr Trp Arg Arg Gly Gln Gln
                20                  25                  30

Pro Pro Gln Pro Pro Pro Pro Leu Pro Gln Arg Ala Glu Val
                35                  40                  45

Glu Pro Gly Ala Gly Gln Pro Val Glu Ser Phe Pro Leu Asp Phe Thr
 50                  55                  60

Ala Val Glu Gly Asn Met Asp Ser Phe Met Ala Gln Val Lys Ser Leu
 65                  70                  75                  80

Ala Gln Ser Leu Tyr Pro Cys Ser Ala Gln Gln Leu Asn Glu Asp Leu
                85                  90                  95

Arg Leu His Leu Leu Asn Thr Ser Val Thr Cys Asn Asp Gly Ser
                100                 105                 110

Pro Ala Gly Tyr Tyr Leu Lys Glu Ser Lys Gly Ser Arg Arg Trp Leu
                115                 120                 125

Leu Phe Leu Glu Gly Gly Trp Tyr Cys Phe Asn Arg Glu Asn Cys Asp
    130                 135                 140

Ser Arg Tyr Ser Thr Met Arg Arg Leu Met Ser Ser Lys Asp Trp Pro
145                 150                 155                 160

His Thr Arg Thr Gly Thr Gly Ile Leu Ser Ser Gln Pro Glu Glu Asn
                165                 170                 175

Pro His Trp Trp Asn Ala Asn Met Val Phe Ile Pro Tyr Cys Ser Ser
                180                 185                 190

Asp Val Trp Ser Gly Ala Ser Ser Lys Ser Glu Lys Asn Glu Tyr Ala
                195                 200                 205

Phe Met Gly Ala Leu Ile Ile Gln Glu Val Val Arg Glu Leu Leu Gly
    210                 215                 220

Arg Gly Leu Ser Gly Ala Lys Val Leu Leu Leu Ala Gly Ser Ser Ala
225                 230                 235                 240

Gly Gly Thr Gly Val Leu Leu Asn Val Asp Arg Val Ala Glu Gln Leu
                245                 250                 255

Glu Lys Leu Gly Tyr Pro Ala Ile Gln Val Arg Gly Leu Ala Asp Ser
                260                 265                 270

Gly Trp Phe Leu Asp Asn Lys Gln Tyr Arg His Thr Asp Cys Val Asp
    275                 280                 285

Thr Ile Thr Cys Ala Pro Thr Glu Ala Ile Arg Arg Gly Ile Arg Tyr
290                 295                 300

Trp Asn Gly Val Val Pro Glu Arg Cys Arg Arg Gln Phe Gln Glu Gly
305                 310                 315                 320

Glu Glu Trp Asn Cys Phe Phe Gly Tyr Lys Val Tyr Pro Thr Leu Arg
                325                 330                 335

Cys Pro Val Phe Val Val Gln Trp Leu Phe Asp Glu Ala Gln Leu Thr
                340                 345                 350

Val Asp Asn Val His Leu Thr Gly Gln Pro Val Gln Glu Gly Gln Trp
                355                 360                 365

Leu Tyr Ile Gln Asn Leu Gly Arg Glu Leu Arg Gly Thr Leu Lys Asp
    370                 375                 380

Val Gln Ala Ser Phe Ala Pro Ala Cys Leu Ser His Glu Ile Ile Ile
385                 390                 395                 400
```

```
Arg Ser Tyr Trp Thr Asp Val Gln Val Lys Gly Thr Ser Leu Pro Arg
                405                 410                 415

Ala Leu His Cys Trp Asp Arg Ser Phe His Asp Ser His Lys Ala Ser
            420                 425                 430

Lys Thr Pro Met Lys Gly Cys Pro Phe His Leu Val Asp Ser Cys Pro
        435                 440                 445

Trp Pro His Cys Asn Pro Ser Cys Pro Thr Ile Arg Asp Gln Phe Thr
    450                 455                 460

Gly Gln Glu Met Asn Val Ala Gln Phe Leu Met His Met Gly Phe Asp
465                 470                 475                 480

Val Gln Thr Val Ala Gln Gln Gly Met Glu Pro Ser Lys Leu Leu
                485                 490                 495

Gly Met Leu Ser Asn Gly Asn
            500
```

<210> SEQ ID NO 87
<211> LENGTH: 466
<212> TYPE: PRT
<213> ORGANISM: Homo sapiens
<220> FEATURE:
<221> NAME/KEY: misc_feature
<222> LOCATION: (1)..(466)
<223> OTHER INFORMATION: Human NOTUM (Delta1-46)

<400> SEQUENCE: 87

```
Met Pro Leu Leu Leu Leu Pro Leu Leu Trp Ala Gly Ala Leu Ala
1               5                   10                  15

Gln Pro Val Glu Ser Phe Pro Leu Asp Phe Thr Ala Val Glu Gly Asn
                20                  25                  30

Met Asp Ser Phe Met Ala Gln Val Lys Ser Leu Ala Gln Ser Leu Tyr
            35                  40                  45

Pro Cys Ser Ala Gln Gln Leu Asn Glu Asp Leu Arg Leu His Leu Leu
    50                  55                  60

Leu Asn Thr Ser Val Thr Cys Asn Asp Gly Ser Pro Ala Gly Tyr Tyr
65                  70                  75                  80

Leu Lys Glu Ser Arg Gly Ser Arg Arg Trp Leu Leu Phe Leu Glu Gly
                85                  90                  95

Gly Trp Tyr Cys Phe Asn Arg Glu Asn Cys Asp Ser Arg Tyr Asp Thr
            100                 105                 110

Met Arg Arg Leu Met Ser Ser Arg Asp Trp Pro Arg Thr Arg Thr Gly
        115                 120                 125

Thr Gly Ile Leu Ser Ser Gln Pro Glu Glu Asn Pro Tyr Trp Trp Asn
    130                 135                 140

Ala Asn Met Val Phe Ile Pro Tyr Cys Ser Ser Asp Val Trp Ser Gly
145                 150                 155                 160

Ala Ser Ser Lys Ser Glu Lys Asn Glu Tyr Ala Phe Met Gly Ala Leu
                165                 170                 175

Ile Ile Gln Glu Val Val Arg Glu Leu Leu Gly Arg Gly Leu Ser Gly
            180                 185                 190

Ala Lys Val Leu Leu Leu Ala Gly Ser Ser Ala Gly Gly Thr Gly Val
        195                 200                 205

Leu Leu Asn Val Asp Arg Val Ala Glu Gln Leu Glu Lys Leu Gly Tyr
    210                 215                 220

Pro Ala Ile Gln Val Arg Gly Leu Ala Asp Ser Gly Trp Phe Leu Asp
225                 230                 235                 240

Asn Lys Gln Tyr Arg His Thr Asp Cys Val Asp Thr Ile Thr Cys Ala
```

```
                245                 250                 255
Pro Thr Glu Ala Ile Arg Arg Gly Ile Arg Tyr Trp Asn Gly Val Val
            260                 265                 270

Pro Glu Arg Cys Arg Arg Gln Phe Gln Glu Gly Glu Trp Asn Cys
            275                 280             285

Phe Phe Gly Tyr Lys Val Tyr Pro Thr Leu Arg Cys Pro Val Phe Val
290                 295                 300

Val Gln Trp Leu Phe Asp Glu Ala Gln Leu Thr Val Asp Asn Val His
305                 310                 315                 320

Leu Thr Gly Gln Pro Val Gln Glu Gly Leu Arg Leu Tyr Ile Gln Asn
                325                 330                 335

Leu Gly Arg Glu Leu Arg His Thr Leu Lys Asp Val Pro Ala Ser Phe
            340                 345             350

Ala Pro Ala Cys Leu Ser His Glu Ile Ile Arg Ser His Trp Thr
            355                 360                 365

Asp Val Gln Val Lys Gly Thr Ser Leu Pro Arg Ala Leu His Cys Trp
370                 375                 380

Asp Arg Ser Leu His Asp Ser His Lys Ala Ser Lys Thr Pro Leu Lys
385                 390                 395                 400

Gly Cys Pro Val His Leu Val Asp Ser Cys Pro Trp Pro His Cys Asn
                405                 410                 415

Pro Ser Cys Pro Thr Val Arg Asp Gln Phe Thr Gly Gln Glu Met Asn
            420                 425             430

Val Ala Gln Phe Leu Met His Met Gly Phe Asp Met Gln Thr Val Ala
                435                 440                 445

Gln Pro Gln Gly Leu Glu Pro Ser Glu Leu Leu Gly Met Leu Ser Asn
    450                 455                 460

Gly Ser
465

<210> SEQ ID NO 88
<211> LENGTH: 496
<212> TYPE: PRT
<213> ORGANISM: Homo sapiens
<220> FEATURE:
<221> NAME/KEY: misc_feature
<222> LOCATION: (1)..(496)
<223> OTHER INFORMATION: Human NOTUM N96D

<400> SEQUENCE: 88

Met Gly Arg Gly Val Arg Val Leu Leu Leu Ser Leu Leu His Cys
1               5                   10                  15

Ala Gly Gly Ser Glu Gly Arg Lys Thr Trp Arg Arg Gly Gln Gln
                20                  25                  30

Pro Pro Pro Pro Arg Thr Glu Ala Ala Pro Ala Gly Gln Pro
            35                  40                  45

Val Glu Ser Phe Pro Leu Asp Phe Thr Ala Val Glu Gly Asn Met Asp
    50                  55                  60

Ser Phe Met Ala Gln Val Lys Ser Leu Ala Gln Ser Leu Tyr Pro Cys
65                  70                  75                  80

Ser Ala Gln Gln Leu Asn Glu Asp Leu Arg Leu His Leu Leu Asp
                85                  90                  95

Thr Ser Val Thr Cys Asn Asp Gly Ser Pro Ala Gly Tyr Tyr Leu Lys
            100                 105                 110

Glu Ser Arg Gly Ser Arg Arg Trp Leu Leu Phe Leu Glu Gly Gly Trp
        115                 120                 125
```

```
Tyr Cys Phe Asn Arg Glu Asn Cys Asp Ser Arg Tyr Asp Thr Met Arg
            130                 135                 140

Arg Leu Met Ser Ser Arg Asp Trp Pro Arg Thr Arg Thr Gly Thr Gly
145                 150                 155                 160

Ile Leu Ser Ser Gln Pro Glu Glu Asn Pro Tyr Trp Trp Asn Ala Asn
                165                 170                 175

Met Val Phe Ile Pro Tyr Cys Ser Ser Asp Val Trp Ser Gly Ala Ser
            180                 185                 190

Ser Lys Ser Glu Lys Asn Glu Tyr Ala Phe Met Gly Ala Leu Ile Ile
        195                 200                 205

Gln Glu Val Val Arg Glu Leu Gly Arg Gly Leu Ser Gly Ala Lys
    210                 215                 220

Val Leu Leu Leu Ala Gly Ser Ser Ala Gly Gly Thr Gly Val Leu Leu
225                 230                 235                 240

Asn Val Asp Arg Val Ala Glu Gln Leu Glu Lys Leu Gly Tyr Pro Ala
                245                 250                 255

Ile Gln Val Arg Gly Leu Ala Asp Ser Gly Trp Phe Leu Asp Asn Lys
            260                 265                 270

Gln Tyr Arg His Thr Asp Cys Val Asp Thr Ile Thr Cys Ala Pro Thr
        275                 280                 285

Glu Ala Ile Arg Arg Gly Ile Arg Tyr Trp Asn Gly Val Val Pro Glu
    290                 295                 300

Arg Cys Arg Arg Gln Phe Gln Glu Gly Glu Glu Trp Asn Cys Phe Phe
305                 310                 315                 320

Gly Tyr Lys Val Tyr Pro Thr Leu Arg Cys Pro Val Phe Val Val Gln
                325                 330                 335

Trp Leu Phe Asp Glu Ala Gln Leu Thr Val Asp Asn Val His Leu Thr
            340                 345                 350

Gly Gln Pro Val Gln Glu Gly Leu Arg Leu Tyr Ile Gln Asn Leu Gly
        355                 360                 365

Arg Glu Leu Arg His Thr Leu Lys Asp Val Pro Ala Ser Phe Ala Pro
    370                 375                 380

Ala Cys Leu Ser His Glu Ile Ile Ile Arg Ser His Trp Thr Asp Val
385                 390                 395                 400

Gln Val Lys Gly Thr Ser Leu Pro Arg Ala Leu His Cys Trp Asp Arg
                405                 410                 415

Ser Leu His Asp Ser His Lys Ala Ser Lys Thr Pro Leu Lys Gly Cys
            420                 425                 430

Pro Val His Leu Val Asp Ser Cys Pro Trp Pro His Cys Asn Pro Ser
        435                 440                 445

Cys Pro Thr Val Arg Asp Gln Phe Thr Gly Gln Glu Met Asn Val Ala
    450                 455                 460

Gln Phe Leu Met His Met Gly Phe Asp Met Gln Thr Val Ala Gln Pro
465                 470                 475                 480

Gln Gly Leu Glu Pro Ser Glu Leu Leu Gly Met Leu Ser Asn Gly Ser
                485                 490                 495

<210> SEQ ID NO 89
<211> LENGTH: 131
<212> TYPE: PRT
<213> ORGANISM: Homo sapiens
<220> FEATURE:
<221> NAME/KEY: misc_feature
<222> LOCATION: (1)..(131)
<223> OTHER INFORMATION: Human NOTUM Q47-M177
```

<400> SEQUENCE: 89

Gln Pro Val Glu Ser Phe Pro Leu Asp Phe Thr Ala Val Glu Gly Asn
1               5                   10                  15

Met Asp Ser Phe Met Ala Gln Val Lys Ser Leu Ala Gln Ser Leu Tyr
            20                  25                  30

Pro Cys Ser Ala Gln Gln Leu Asn Glu Asp Leu Arg Leu His Leu Leu
        35                  40                  45

Leu Asn Thr Ser Val Thr Cys Asn Asp Gly Ser Pro Ala Gly Tyr Tyr
    50                  55                  60

Leu Lys Glu Ser Arg Gly Ser Arg Arg Trp Leu Leu Phe Leu Glu Gly
65                  70                  75                  80

Gly Trp Tyr Cys Phe Asn Arg Glu Asn Cys Asp Ser Arg Tyr Asp Thr
                85                  90                  95

Met Arg Arg Leu Met Ser Ser Arg Asp Trp Pro Arg Thr Arg Thr Gly
            100                 105                 110

Thr Gly Ile Leu Ser Ser Gln Pro Glu Glu Asn Pro Tyr Trp Trp Asn
        115                 120                 125

Ala Asn Met
    130

<210> SEQ ID NO 90
<211> LENGTH: 10
<212> TYPE: PRT
<213> ORGANISM: Artificial Sequence
<220> FEATURE:
<223> OTHER INFORMATION: Synthetic: Campaign 1 heavy chain CDR1
      consensus
<220> FEATURE:
<221> NAME/KEY: misc_feature
<222> LOCATION: (7)..(7)
<223> OTHER INFORMATION: X is Y or F

<400> SEQUENCE: 90

Gly Phe Thr Phe Ser Asp Xaa Gly Met His
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Synthetic: Campaign 1 heavy chain CDR3
      consensus
<220> FEATURE:
<221> NAME/KEY: misc_feature
<222> LOCATION: (2)..(2)
<223> OTHER INFORMATION: X is H or N

<400> SEQUENCE: 91

Lys Xaa Tyr Asn Gly Gly Tyr Phe Asp Val
1               5                   10

<210> SEQ ID NO 92
<211> LENGTH: 15
<212> TYPE: PRT
<213> ORGANISM: Artificial Sequence
<220> FEATURE:
<223> OTHER INFORMATION: Synthetic: Campaign 1 light chain CDR1
      consensus
<220> FEATURE:
<221> NAME/KEY: misc_feature
<222> LOCATION: (5)..(5)
<223> OTHER INFORMATION: X is I or S
<220> FEATURE:

```
<221> NAME/KEY: misc_feature
<222> LOCATION: (8)..(8)
<223> OTHER INFORMATION: X is T or E
<220> FEATURE:
<221> NAME/KEY: misc_feature
<222> LOCATION: (14)..(14)
<223> OTHER INFORMATION: X is M or I

<400> SEQUENCE: 92

Arg Ala Ser Lys Xaa Val Ser Xaa Ser Gly Tyr Ser Tyr Xaa His
1               5                   10                  15

<210> SEQ ID NO 93
<211> LENGTH: 7
<212> TYPE: PRT
<213> ORGANISM: Artificial Sequence
<220> FEATURE:
<223> OTHER INFORMATION: Synthetic: Campaign 1 light chain CDR2
      consensus
<220> FEATURE:
<221> NAME/KEY: misc_feature
<222> LOCATION: (4)..(4)
<223> OTHER INFORMATION: X is D or N

<400> SEQUENCE: 93

Leu Ala Ser Xaa Leu Glu Ser
1               5

<210> SEQ ID NO 94
<211> LENGTH: 496
<212> TYPE: PRT
<213> ORGANISM: Homo sapiens
<220> FEATURE:
<221> NAME/KEY: misc_feature
<222> LOCATION: (1)..(496)
<223> OTHER INFORMATION: Human NOTUM D141S

<400> SEQUENCE: 94

Met Gly Arg Gly Val Arg Val Leu Leu Leu Ser Leu Leu His Cys
1               5                   10                  15

Ala Gly Gly Ser Glu Gly Arg Lys Thr Trp Arg Arg Gly Gln Gln
                20                  25                  30

Pro Pro Pro Pro Pro Arg Thr Glu Ala Ala Pro Ala Ala Gly Gln Pro
            35                  40                  45

Val Glu Ser Phe Pro Leu Asp Phe Thr Ala Val Glu Gly Asn Met Asp
    50                  55                  60

Ser Phe Met Ala Gln Val Lys Ser Leu Ala Gln Ser Leu Tyr Pro Cys
65                  70                  75                  80

Ser Ala Gln Gln Leu Asn Glu Asp Leu Arg Leu His Leu Leu Leu Asn
                85                  90                  95

Thr Ser Val Thr Cys Asn Asp Gly Ser Pro Ala Gly Tyr Tyr Leu Lys
                100                 105                 110

Glu Ser Arg Gly Ser Arg Arg Trp Leu Leu Phe Leu Glu Gly Gly Trp
                115                 120                 125

Tyr Cys Phe Asn Arg Glu Asn Cys Asp Ser Arg Tyr Ser Thr Met Arg
            130                 135                 140

Arg Leu Met Ser Ser Arg Asp Trp Pro Arg Thr Arg Thr Gly Thr Gly
145                 150                 155                 160

Ile Leu Ser Ser Gln Pro Glu Glu Asn Pro Tyr Trp Trp Asn Ala Asn
                165                 170                 175

Met Val Phe Ile Pro Tyr Cys Ser Ser Asp Val Trp Ser Gly Ala Ser
                180                 185                 190
```

```
Ser Lys Ser Glu Lys Asn Glu Tyr Ala Phe Met Gly Ala Leu Ile Ile
            195                 200                 205

Gln Glu Val Val Arg Glu Leu Leu Gly Arg Gly Leu Ser Gly Ala Lys
    210                 215                 220

Val Leu Leu Leu Ala Gly Ser Ala Gly Thr Gly Val Leu Leu
225                 230                 235                 240

Asn Val Asp Arg Val Ala Glu Gln Leu Glu Lys Leu Gly Tyr Pro Ala
                245                 250                 255

Ile Gln Val Arg Gly Leu Ala Asp Ser Gly Trp Phe Leu Asp Asn Lys
            260                 265                 270

Gln Tyr Arg His Thr Asp Cys Val Asp Thr Ile Thr Cys Ala Pro Thr
    275                 280                 285

Glu Ala Ile Arg Arg Gly Ile Arg Tyr Trp Asn Gly Val Pro Glu
290                 295                 300

Arg Cys Arg Arg Gln Phe Gln Glu Gly Glu Trp Asn Cys Phe Phe
305                 310                 315                 320

Gly Tyr Lys Val Tyr Pro Thr Leu Arg Cys Pro Val Phe Val Gln
                325                 330                 335

Trp Leu Phe Asp Glu Ala Gln Leu Thr Val Asp Asn Val His Leu Thr
            340                 345                 350

Gly Gln Pro Val Gln Glu Gly Leu Arg Leu Tyr Ile Gln Asn Leu Gly
    355                 360                 365

Arg Glu Leu Arg His Thr Leu Lys Asp Val Pro Ala Ser Phe Ala Pro
370                 375                 380

Ala Cys Leu Ser His Glu Ile Ile Ile Arg Ser His Trp Thr Asp Val
385                 390                 395                 400

Gln Val Lys Gly Thr Ser Leu Pro Arg Ala Leu His Cys Trp Asp Arg
                405                 410                 415

Ser Leu His Asp Ser His Lys Ala Ser Lys Thr Pro Leu Lys Gly Cys
            420                 425                 430

Pro Val His Leu Val Asp Ser Cys Pro Trp Pro His Cys Asn Pro Ser
    435                 440                 445

Cys Pro Thr Val Arg Asp Gln Phe Thr Gly Gln Glu Met Asn Val Ala
450                 455                 460

Gln Phe Leu Met His Met Gly Phe Asp Met Gln Thr Val Ala Gln Pro
465                 470                 475                 480

Gln Gly Leu Glu Pro Ser Glu Leu Leu Gly Met Leu Ser Asn Gly Ser
                485                 490                 495

<210> SEQ ID NO 95
<211> LENGTH: 503
<212> TYPE: PRT
<213> ORGANISM: Mouse
<220> FEATURE:
<221> NAME/KEY: misc_feature
<222> LOCATION: (1)..(503)
<223> OTHER INFORMATION: Mouse NOTUM S148D

<400> SEQUENCE: 95

Met Gly Gly Glu Val Arg Val Leu Leu Leu Gly Leu Leu His Trp
1               5                   10                  15

Val Gly Gly Ser Glu Gly Arg Lys Thr Trp Arg Arg Gly Gln Gln
                20                  25                  30

Pro Pro Gln Pro Pro Pro Pro Leu Pro Gln Arg Ala Glu Val
            35                  40                  45

Glu Pro Gly Ala Gly Gln Pro Val Glu Ser Phe Pro Leu Asp Phe Thr
```

```
              50                  55                  60
Ala Val Glu Gly Asn Met Asp Ser Phe Met Ala Gln Val Lys Ser Leu
 65                  70                  75                  80

Ala Gln Ser Leu Tyr Pro Cys Ser Ala Gln Gln Leu Asn Glu Asp Leu
                 85                  90                  95

Arg Leu His Leu Leu Leu Asn Thr Ser Val Thr Cys Asn Asp Gly Ser
            100                 105                 110

Pro Ala Gly Tyr Tyr Leu Lys Glu Ser Lys Gly Ser Arg Arg Trp Leu
        115                 120                 125

Leu Phe Leu Glu Gly Gly Trp Tyr Cys Phe Asn Arg Glu Asn Cys Asp
    130                 135                 140

Ser Arg Tyr Asp Thr Met Arg Arg Leu Met Ser Ser Lys Asp Trp Pro
145                 150                 155                 160

His Thr Arg Thr Gly Thr Gly Ile Leu Ser Ser Gln Pro Glu Glu Asn
                165                 170                 175

Pro His Trp Trp Asn Ala Asn Met Val Phe Ile Pro Tyr Cys Ser Ser
            180                 185                 190

Asp Val Trp Ser Gly Ala Ser Pro Lys Ser Asp Lys Asn Glu Tyr Ala
        195                 200                 205

Phe Met Gly Ser Leu Ile Ile Gln Glu Val Val Arg Glu Leu Leu Gly
    210                 215                 220

Lys Gly Leu Ser Gly Ala Lys Val Leu Leu Ala Gly Ser Ser Ala
225                 230                 235                 240

Gly Gly Thr Gly Val Leu Leu Asn Val Asp Arg Val Ala Glu Leu Leu
                245                 250                 255

Glu Glu Leu Gly Tyr Pro Ser Ile Gln Val Arg Gly Leu Ala Asp Ser
            260                 265                 270

Gly Trp Phe Leu Asp Asn Lys Gln Tyr Arg Arg Ser Asp Cys Ile Asp
        275                 280                 285

Thr Ile Asn Cys Ala Pro Thr Asp Ala Ile Arg Arg Gly Ile Arg Tyr
    290                 295                 300

Trp Ser Gly Met Val Pro Glu Arg Cys Gln Arg Gln Phe Lys Glu Gly
305                 310                 315                 320

Glu Glu Trp Asn Cys Phe Phe Gly Tyr Lys Val Tyr Pro Thr Leu Arg
                325                 330                 335

Cys Pro Val Phe Val Val Gln Trp Leu Phe Asp Glu Ala Gln Leu Thr
            340                 345                 350

Val Asp Asn Val His Leu Thr Gly Gln Pro Val Gln Glu Gly Gln Trp
        355                 360                 365

Leu Tyr Ile Gln Asn Leu Gly Arg Glu Leu Arg Gly Thr Leu Lys Asp
    370                 375                 380

Val Gln Ala Ser Phe Ala Pro Ala Cys Leu Ser His Glu Ile Ile Ile
385                 390                 395                 400

Arg Ser Tyr Trp Thr Asp Val Gln Val Lys Gly Thr Ser Leu Pro Arg
                405                 410                 415

Ala Leu His Cys Trp Asp Arg Ser Phe His Asp Ser His Lys Ala Ser
            420                 425                 430

Lys Thr Pro Met Lys Gly Cys Pro Phe His Leu Val Asp Ser Cys Pro
        435                 440                 445

Trp Pro His Cys Asn Pro Ser Cys Pro Thr Ile Arg Asp Gln Phe Thr
    450                 455                 460

Gly Gln Glu Met Asn Val Ala Gln Phe Leu Met His Met Gly Phe Asp
465                 470                 475                 480
```

```
Val Gln Thr Val Ala Gln Gln Gly Met Glu Pro Ser Lys Leu Leu
            485                 490                 495
Gly Met Leu Ser Asn Gly Asn
            500

<210> SEQ ID NO 96
<211> LENGTH: 496
<212> TYPE: PRT
<213> ORGANISM: Homo sapiens
<220> FEATURE:
<221> NAME/KEY: misc_feature
<222> LOCATION: (1)..(496)
<223> OTHER INFORMATION: Human NOTUM N132A/R133A

<400> SEQUENCE: 96

Met Gly Arg Gly Val Arg Val Leu Leu Leu Ser Leu Leu His Cys
1               5                   10                  15

Ala Gly Gly Ser Glu Gly Arg Lys Thr Trp Arg Arg Gly Gln Gln
                20                  25                  30

Pro Pro Pro Pro Arg Thr Glu Ala Ala Pro Ala Ala Gly Gln Pro
            35                  40                  45

Val Glu Ser Phe Pro Leu Asp Phe Thr Ala Val Glu Gly Asn Met Asp
    50                  55                  60

Ser Phe Met Ala Gln Val Lys Ser Leu Ala Gln Ser Leu Tyr Pro Cys
65                  70                  75                  80

Ser Ala Gln Gln Leu Asn Glu Asp Leu Arg Leu His Leu Leu Leu Asn
                85                  90                  95

Thr Ser Val Thr Cys Asn Asp Gly Ser Pro Ala Gly Tyr Tyr Leu Lys
                100                 105                 110

Glu Ser Arg Gly Ser Arg Arg Trp Leu Leu Phe Leu Glu Gly Gly Trp
                115                 120                 125

Tyr Cys Phe Ala Ala Glu Asn Cys Asp Ser Arg Tyr Asp Thr Met Arg
    130                 135                 140

Arg Leu Met Ser Ser Arg Asp Trp Pro Arg Thr Arg Thr Gly Thr Gly
145                 150                 155                 160

Ile Leu Ser Ser Gln Pro Glu Glu Asn Pro Tyr Trp Trp Asn Ala Asn
                165                 170                 175

Met Val Phe Ile Pro Tyr Cys Ser Ser Asp Val Trp Ser Gly Ala Ser
                180                 185                 190

Ser Lys Ser Glu Lys Asn Glu Tyr Ala Phe Met Gly Ala Leu Ile Ile
                195                 200                 205

Gln Glu Val Val Arg Glu Leu Leu Gly Arg Gly Leu Ser Gly Ala Lys
    210                 215                 220

Val Leu Leu Leu Ala Gly Ser Ser Ala Gly Gly Thr Gly Val Leu Leu
225                 230                 235                 240

Asn Val Asp Arg Val Ala Glu Gln Leu Glu Lys Leu Gly Tyr Pro Ala
                245                 250                 255

Ile Gln Val Arg Gly Leu Ala Asp Ser Gly Trp Phe Leu Asp Asn Lys
                260                 265                 270

Gln Tyr Arg His Thr Asp Cys Val Asp Thr Ile Thr Cys Ala Pro Thr
                275                 280                 285

Glu Ala Ile Arg Arg Gly Ile Arg Tyr Trp Asn Gly Val Val Pro Glu
    290                 295                 300

Arg Cys Arg Arg Gln Phe Gln Glu Gly Glu Glu Trp Asn Cys Phe Phe
305                 310                 315                 320
```

```
Gly Tyr Lys Val Tyr Pro Thr Leu Arg Cys Pro Val Phe Val Gln
            325                 330                 335

Trp Leu Phe Asp Glu Ala Gln Leu Thr Val Asp Asn Val His Leu Thr
        340                 345                 350

Gly Gln Pro Val Gln Glu Gly Leu Arg Leu Tyr Ile Gln Asn Leu Gly
            355                 360                 365

Arg Glu Leu Arg His Thr Leu Lys Asp Val Pro Ala Ser Phe Ala Pro
370                 375                 380

Ala Cys Leu Ser His Glu Ile Ile Ile Arg Ser His Trp Thr Asp Val
385                 390                 395                 400

Gln Val Lys Gly Thr Ser Leu Pro Arg Ala Leu His Cys Trp Asp Arg
            405                 410                 415

Ser Leu His Asp Ser His Lys Ala Ser Lys Thr Pro Leu Lys Gly Cys
        420                 425                 430

Pro Val His Leu Val Asp Ser Cys Pro Trp Pro His Cys Asn Pro Ser
            435                 440                 445

Cys Pro Thr Val Arg Asp Gln Phe Thr Gly Gln Glu Met Asn Val Ala
450                 455                 460

Gln Phe Leu Met His Met Gly Phe Asp Met Gln Thr Val Ala Gln Pro
465                 470                 475                 480

Gln Gly Leu Glu Pro Ser Glu Leu Leu Gly Met Leu Ser Asn Gly Ser
            485                 490                 495

<210> SEQ ID NO 97
<211> LENGTH: 496
<212> TYPE: PRT
<213> ORGANISM: Homo sapiens
<220> FEATURE:
<221> NAME/KEY: misc_feature
<222> LOCATION: (1)..(496)
<223> OTHER INFORMATION: Human NOTUM E134A/N135A

<400> SEQUENCE: 97

Met Gly Arg Gly Val Arg Val Leu Leu Leu Ser Leu Leu His Cys
1               5                   10                  15

Ala Gly Gly Ser Glu Gly Arg Lys Thr Trp Arg Arg Gly Gln Gln
            20                  25                  30

Pro Pro Pro Pro Arg Thr Glu Ala Ala Pro Ala Ala Gly Gln Pro
        35                  40                  45

Val Glu Ser Phe Pro Leu Asp Phe Thr Ala Val Glu Gly Asn Met Asp
            50                  55                  60

Ser Phe Met Ala Gln Val Lys Ser Leu Ala Gln Ser Leu Tyr Pro Cys
65                  70                  75                  80

Ser Ala Gln Gln Leu Asn Glu Asp Leu Arg Leu His Leu Leu Asn
                85                  90                  95

Thr Ser Val Thr Cys Asn Asp Gly Ser Pro Ala Gly Tyr Tyr Leu Lys
            100                 105                 110

Glu Ser Arg Gly Ser Arg Arg Trp Leu Leu Phe Leu Glu Gly Gly Trp
        115                 120                 125

Tyr Cys Phe Asn Arg Ala Ala Cys Asp Ser Arg Tyr Asp Thr Met Arg
130                 135                 140

Arg Leu Met Ser Ser Arg Asp Trp Pro Arg Thr Arg Thr Gly Thr Gly
145                 150                 155                 160

Ile Leu Ser Ser Gln Pro Glu Glu Asn Pro Tyr Trp Trp Asn Ala Asn
            165                 170                 175

Met Val Phe Ile Pro Tyr Cys Ser Ser Asp Val Trp Ser Gly Ala Ser
```

```
            180                 185                 190
Ser Lys Ser Glu Lys Asn Glu Tyr Ala Phe Met Gly Ala Leu Ile Ile
        195                 200                 205
Gln Glu Val Val Arg Glu Leu Leu Gly Arg Gly Leu Ser Gly Ala Lys
    210                 215                 220
Val Leu Leu Leu Ala Gly Ser Ser Ala Gly Gly Thr Gly Val Leu Leu
225                 230                 235                 240
Asn Val Asp Arg Val Ala Glu Gln Leu Glu Lys Leu Gly Tyr Pro Ala
                245                 250                 255
Ile Gln Val Arg Gly Leu Ala Asp Ser Gly Trp Phe Leu Asp Asn Lys
            260                 265                 270
Gln Tyr Arg His Thr Asp Cys Val Asp Thr Ile Thr Cys Ala Pro Thr
        275                 280                 285
Glu Ala Ile Arg Arg Gly Ile Arg Tyr Trp Asn Gly Val Val Pro Glu
    290                 295                 300
Arg Cys Arg Arg Gln Phe Gln Glu Gly Glu Glu Trp Asn Cys Phe Phe
305                 310                 315                 320
Gly Tyr Lys Val Tyr Pro Thr Leu Arg Cys Pro Val Phe Val Val Gln
                325                 330                 335
Trp Leu Phe Asp Glu Ala Gln Leu Thr Val Asp Asn Val His Leu Thr
            340                 345                 350
Gly Gln Pro Val Gln Glu Gly Leu Arg Leu Tyr Ile Gln Asn Leu Gly
        355                 360                 365
Arg Glu Leu Arg His Thr Leu Lys Asp Val Pro Ala Ser Phe Ala Pro
    370                 375                 380
Ala Cys Leu Ser His Glu Ile Ile Ile Arg Ser His Trp Thr Asp Val
385                 390                 395                 400
Gln Val Lys Gly Thr Ser Leu Pro Arg Ala Leu His Cys Trp Asp Arg
                405                 410                 415
Ser Leu His Asp Ser His Lys Ala Ser Lys Thr Pro Leu Lys Gly Cys
            420                 425                 430
Pro Val His Leu Val Asp Ser Cys Pro Trp Pro His Cys Asn Pro Ser
        435                 440                 445
Cys Pro Thr Val Arg Asp Gln Phe Thr Gly Gln Glu Met Asn Val Ala
    450                 455                 460
Gln Phe Leu Met His Met Gly Phe Asp Met Gln Thr Val Ala Gln Pro
465                 470                 475                 480
Gln Gly Leu Glu Pro Ser Glu Leu Leu Gly Met Leu Ser Asn Gly Ser
                485                 490                 495

<210> SEQ ID NO 98
<211> LENGTH: 496
<212> TYPE: PRT
<213> ORGANISM: Homo sapiens
<220> FEATURE:
<221> NAME/KEY: misc_feature
<222> LOCATION: (1)..(496)
<223> OTHER INFORMATION: Human NOTUM D137A/R139A

<400> SEQUENCE: 98

Met Gly Arg Gly Val Arg Val Leu Leu Leu Ser Leu Leu His Cys
1               5                   10                  15

Ala Gly Gly Ser Glu Gly Arg Lys Thr Trp Arg Arg Gly Gln Gln
            20                  25                  30

Pro Pro Pro Pro Arg Thr Glu Ala Ala Pro Ala Ala Gly Gln Pro
        35                  40                  45
```

-continued

```
Val Glu Ser Phe Pro Leu Asp Phe Thr Ala Val Gly Asn Met Asp
     50                  55                  60

Ser Phe Met Ala Gln Val Lys Ser Leu Ala Gln Ser Leu Tyr Pro Cys
 65                  70                  75                  80

Ser Ala Gln Gln Leu Asn Glu Asp Leu Arg Leu His Leu Leu Leu Asn
                 85                  90                  95

Thr Ser Val Thr Cys Asn Asp Gly Ser Pro Ala Gly Tyr Tyr Leu Lys
                100                 105                 110

Glu Ser Arg Gly Ser Arg Arg Trp Leu Leu Phe Leu Glu Gly Gly Trp
                115                 120                 125

Tyr Cys Phe Asn Arg Glu Asn Cys Ala Ser Ala Tyr Asp Thr Met Arg
    130                 135                 140

Arg Leu Met Ser Ser Arg Asp Trp Pro Arg Thr Arg Thr Gly Thr Gly
145                 150                 155                 160

Ile Leu Ser Ser Gln Pro Glu Glu Asn Pro Tyr Trp Trp Asn Ala Asn
                165                 170                 175

Met Val Phe Ile Pro Tyr Cys Ser Ser Asp Val Trp Ser Gly Ala Ser
                180                 185                 190

Ser Lys Ser Glu Lys Asn Glu Tyr Ala Phe Met Gly Ala Leu Ile Ile
            195                 200                 205

Gln Glu Val Val Arg Glu Leu Leu Gly Arg Gly Leu Ser Gly Ala Lys
    210                 215                 220

Val Leu Leu Leu Ala Gly Ser Ser Ala Gly Gly Thr Gly Val Leu Leu
225                 230                 235                 240

Asn Val Asp Arg Val Ala Glu Gln Leu Glu Lys Leu Gly Tyr Pro Ala
                245                 250                 255

Ile Gln Val Arg Gly Leu Ala Asp Ser Gly Trp Phe Leu Asp Asn Lys
            260                 265                 270

Gln Tyr Arg His Thr Asp Cys Val Asp Thr Ile Thr Cys Ala Pro Thr
    275                 280                 285

Glu Ala Ile Arg Arg Gly Ile Arg Tyr Trp Asn Gly Val Val Pro Glu
    290                 295                 300

Arg Cys Arg Arg Gln Phe Gln Glu Gly Glu Glu Trp Asn Cys Phe Phe
305                 310                 315                 320

Gly Tyr Lys Val Tyr Pro Thr Leu Arg Cys Pro Val Phe Val Val Gln
                325                 330                 335

Trp Leu Phe Asp Glu Ala Gln Leu Thr Val Asp Asn Val His Leu Thr
                340                 345                 350

Gly Gln Pro Val Gln Glu Gly Leu Arg Leu Tyr Ile Gln Asn Leu Gly
            355                 360                 365

Arg Glu Leu Arg His Thr Leu Lys Asp Val Pro Ala Ser Phe Ala Pro
    370                 375                 380

Ala Cys Leu Ser His Glu Ile Ile Arg Ser His Trp Thr Asp Val
385                 390                 395                 400

Gln Val Lys Gly Thr Ser Leu Pro Arg Ala Leu His Cys Trp Asp Arg
                405                 410                 415

Ser Leu His Asp Ser His Lys Ala Ser Lys Thr Pro Leu Lys Gly Cys
                420                 425                 430

Pro Val His Leu Val Asp Ser Cys Pro Trp Pro His Cys Asn Pro Ser
            435                 440                 445

Cys Pro Thr Val Arg Asp Gln Phe Thr Gly Gln Glu Met Asn Val Ala
    450                 455                 460
```

```
Gln Phe Leu Met His Met Gly Phe Asp Met Gln Thr Val Ala Gln Pro
465                 470                 475                 480

Gln Gly Leu Glu Pro Ser Glu Leu Leu Gly Met Leu Ser Asn Gly Ser
            485                 490                 495

<210> SEQ ID NO 99
<211> LENGTH: 496
<212> TYPE: PRT
<213> ORGANISM: Homo sapiens
<220> FEATURE:
<221> NAME/KEY: misc_feature
<222> LOCATION: (1)..(496)
<223> OTHER INFORMATION: Human NOTUM R144A/R145A

<400> SEQUENCE: 99

Met Gly Arg Gly Val Arg Val Leu Leu Leu Ser Leu Leu His Cys
1               5                   10                  15

Ala Gly Gly Ser Glu Gly Arg Lys Thr Trp Arg Arg Gly Gln Gln
                20                  25                  30

Pro Pro Pro Pro Pro Arg Thr Glu Ala Ala Pro Ala Ala Gly Gln Pro
                35                  40                  45

Val Glu Ser Phe Pro Leu Asp Phe Thr Ala Val Glu Gly Asn Met Asp
50                  55                  60

Ser Phe Met Ala Gln Val Lys Ser Leu Ala Gln Ser Leu Tyr Pro Cys
65                  70                  75                  80

Ser Ala Gln Gln Leu Asn Glu Asp Leu Arg Leu His Leu Leu Leu Asn
                85                  90                  95

Thr Ser Val Thr Cys Asn Asp Gly Ser Pro Ala Gly Tyr Tyr Leu Lys
                100                 105                 110

Glu Ser Arg Gly Ser Arg Arg Trp Leu Leu Phe Leu Glu Gly Gly Trp
                115                 120                 125

Tyr Cys Phe Asn Arg Glu Asn Cys Asp Ser Arg Tyr Asp Thr Met Ala
                130                 135                 140

Ala Leu Met Ser Ser Arg Asp Trp Pro Arg Thr Arg Thr Gly Thr Gly
145                 150                 155                 160

Ile Leu Ser Ser Gln Pro Glu Glu Asn Pro Tyr Trp Trp Asn Ala Asn
                165                 170                 175

Met Val Phe Ile Pro Tyr Cys Ser Ser Asp Val Trp Ser Gly Ala Ser
                180                 185                 190

Ser Lys Ser Glu Lys Asn Glu Tyr Ala Phe Met Gly Ala Leu Ile Ile
                195                 200                 205

Gln Glu Val Val Arg Glu Leu Leu Gly Arg Gly Leu Ser Gly Ala Lys
                210                 215                 220

Val Leu Leu Leu Ala Gly Ser Ser Ala Gly Gly Thr Gly Val Leu Leu
225                 230                 235                 240

Asn Val Asp Arg Val Ala Glu Gln Leu Glu Lys Leu Gly Tyr Pro Ala
                245                 250                 255

Ile Gln Val Arg Gly Leu Ala Asp Ser Gly Trp Phe Leu Asp Asn Lys
                260                 265                 270

Gln Tyr Arg His Thr Asp Cys Val Asp Thr Ile Thr Cys Ala Pro Thr
                275                 280                 285

Glu Ala Ile Arg Arg Gly Ile Arg Tyr Trp Asn Gly Val Val Pro Glu
                290                 295                 300

Arg Cys Arg Arg Gln Phe Gln Glu Gly Glu Glu Trp Asn Cys Phe Phe
305                 310                 315                 320

Gly Tyr Lys Val Tyr Pro Thr Leu Arg Cys Pro Val Phe Val Val Gln
```

```
                        325                 330                 335
Trp Leu Phe Asp Glu Ala Gln Leu Thr Val Asp Asn Val His Leu Thr
                340                 345                 350
Gly Gln Pro Val Gln Glu Gly Leu Arg Leu Tyr Ile Gln Asn Leu Gly
            355                 360                 365
Arg Glu Leu Arg His Thr Leu Lys Asp Val Pro Ala Ser Phe Ala Pro
        370                 375                 380
Ala Cys Leu Ser His Glu Ile Ile Ile Arg Ser His Trp Thr Asp Val
385                 390                 395                 400
Gln Val Lys Gly Thr Ser Leu Pro Arg Ala Leu His Cys Trp Asp Arg
                405                 410                 415
Ser Leu His Asp Ser His Lys Ala Ser Lys Thr Pro Leu Lys Gly Cys
                420                 425                 430
Pro Val His Leu Val Asp Ser Cys Pro Trp Pro His Cys Asn Pro Ser
            435                 440                 445
Cys Pro Thr Val Arg Asp Gln Phe Thr Gly Gln Glu Met Asn Val Ala
        450                 455                 460
Gln Phe Leu Met His Met Gly Phe Asp Met Gln Thr Val Ala Gln Pro
465                 470                 475                 480
Gln Gly Leu Glu Pro Ser Glu Leu Leu Gly Met Leu Ser Asn Gly Ser
                485                 490                 495

<210> SEQ ID NO 100
<211> LENGTH: 496
<212> TYPE: PRT
<213> ORGANISM: Homo sapiens
<220> FEATURE:
<221> NAME/KEY: misc_feature
<222> LOCATION: (1)..(496)
<223> OTHER INFORMATION: Human NOTUM R150A/D151A

<400> SEQUENCE: 100

Met Gly Arg Gly Val Arg Val Leu Leu Leu Ser Leu Leu His Cys
1               5                   10                  15
Ala Gly Gly Ser Glu Gly Arg Lys Thr Trp Arg Arg Gly Gln Gln
                20                  25                  30
Pro Pro Pro Pro Arg Thr Glu Ala Ala Pro Ala Ala Gly Gln Pro
            35                  40                  45
Val Glu Ser Phe Pro Leu Asp Phe Thr Ala Val Glu Gly Asn Met Asp
        50                  55                  60
Ser Phe Met Ala Gln Val Lys Ser Leu Ala Gln Ser Leu Tyr Pro Cys
65                  70                  75                  80
Ser Ala Gln Gln Leu Asn Glu Asp Leu Arg Leu His Leu Leu Leu Asn
                85                  90                  95
Thr Ser Val Thr Cys Asn Asp Gly Ser Pro Ala Gly Tyr Tyr Leu Lys
                100                 105                 110
Glu Ser Arg Gly Ser Arg Arg Trp Leu Leu Phe Leu Glu Gly Gly Trp
            115                 120                 125
Tyr Cys Phe Asn Arg Glu Asn Cys Asp Ser Arg Tyr Asp Thr Met Arg
        130                 135                 140
Arg Leu Met Ser Ser Ala Ala Trp Pro Arg Thr Arg Thr Gly Thr Gly
145                 150                 155                 160
Ile Leu Ser Ser Gln Pro Glu Glu Asn Pro Tyr Trp Trp Asn Ala Asn
                165                 170                 175
Met Val Phe Ile Pro Tyr Cys Ser Ser Asp Val Trp Ser Gly Ala Ser
                180                 185                 190
```

Ser Lys Ser Glu Lys Asn Glu Tyr Ala Phe Met Gly Ala Leu Ile Ile
        195                 200                 205

Gln Glu Val Val Arg Glu Leu Leu Gly Arg Gly Leu Ser Gly Ala Lys
    210                 215                 220

Val Leu Leu Leu Ala Gly Ser Ala Gly Thr Gly Val Leu Leu
225                 230                 235                 240

Asn Val Asp Arg Val Ala Glu Gln Leu Glu Lys Leu Gly Tyr Pro Ala
                245                 250                 255

Ile Gln Val Arg Gly Leu Ala Asp Ser Gly Trp Phe Leu Asp Asn Lys
                260                 265                 270

Gln Tyr Arg His Thr Asp Cys Val Asp Thr Ile Thr Cys Ala Pro Thr
            275                 280                 285

Glu Ala Ile Arg Arg Gly Ile Arg Tyr Trp Asn Gly Val Val Pro Glu
        290                 295                 300

Arg Cys Arg Arg Gln Phe Gln Glu Gly Glu Glu Trp Asn Cys Phe Phe
305                 310                 315                 320

Gly Tyr Lys Val Tyr Pro Thr Leu Arg Cys Pro Val Phe Val Gln
                325                 330                 335

Trp Leu Phe Asp Glu Ala Gln Leu Thr Val Asp Asn Val His Leu Thr
                340                 345                 350

Gly Gln Pro Val Gln Glu Gly Leu Arg Leu Tyr Ile Gln Asn Leu Gly
            355                 360                 365

Arg Glu Leu Arg His Thr Leu Lys Asp Val Pro Ala Ser Phe Ala Pro
        370                 375                 380

Ala Cys Leu Ser His Glu Ile Ile Ile Arg Ser His Trp Thr Asp Val
385                 390                 395                 400

Gln Val Lys Gly Thr Ser Leu Pro Arg Ala Leu His Cys Trp Asp Arg
                405                 410                 415

Ser Leu His Asp Ser His Lys Ala Ser Lys Thr Pro Leu Lys Gly Cys
                420                 425                 430

Pro Val His Leu Val Asp Ser Cys Pro Trp Pro His Cys Asn Pro Ser
            435                 440                 445

Cys Pro Thr Val Arg Asp Gln Phe Thr Gly Gln Glu Met Asn Val Ala
        450                 455                 460

Gln Phe Leu Met His Met Gly Phe Asp Met Gln Thr Val Ala Gln Pro
465                 470                 475                 480

Gln Gly Leu Glu Pro Ser Glu Leu Leu Gly Met Leu Ser Asn Gly Ser
                485                 490                 495

<210> SEQ ID NO 101
<211> LENGTH: 495
<212> TYPE: DNA
<213> ORGANISM: Artificial Sequence
<220> FEATURE:
<223> OTHER INFORMATION: Synthetic: 1.802 heavy chain variable region
      polynucleotide sequence

<400> SEQUENCE: 101
atggactcca ggctcaattt agttttcctt gtccttattt taaaaggtgt ccagtgtgag    60
gtgcagctgg tggagtctgg gggaggctta gtgaagcctg agggtccct gaaactctcc    120 tgtgcagcct ctggattcac tttcagtgac tatggaatgc actggtttcg tcaggctcca    180
gagaaggggc tggagtgggt tgcatatatt agtagtggca gtagaaccgt ctactatgca    240
gacacagtga agggccgatt caccatctcc agagacaatg ccaagaacac cctgtccctg    300

```
caaatgacca gtctgaggtc tgaggacacg gccatgtatt actgtgcgag gaaacattac    360
aacggtggat acttcgatgt ctggggcaca gggaccacgg tcaccgtctc ctcagccaaa    420
acgacacccc catctgtcta ccactggcc cctggatctg ctgcccaaac taactccatg     480
gtgaccctgg gatgc                                                     495
```

<210> SEQ ID NO 102
<211> LENGTH: 482
<212> TYPE: DNA
<213> ORGANISM: Artificial Sequence
<220> FEATURE:
<223> OTHER INFORMATION: Synthetic: 1.802 light chain variable region
       polynucleotide sequence

<400> SEQUENCE: 102

```
atcctctctt ccagctctca gagatggaga cagacacact cctgttatgg gtactgctgc     60
tctgggttcc aggttccact ggtgacattg tgctgacaca gtctcctgct tccttagctg    120
tatctctggg gcagagggcc accatctcat gcagggccag caaaattgtc agtacatctg    180
gctatagtta tatgcactgg taccaacaga accaggaca gccgcccaaa ctcctcatct     240
atcttgcatc caacctagaa tctggggtcc ctgccaggtt cagtggcagt gggtctggga    300
cagacttcac cctcaacatc catcctgtgg aggaggagga tgctgcaacc tattactgtc    360
agcacagtag ggagcttcct cccacgttcg gctcggggac aaagttggaa ataaaacggg    420
ctgatgctgc accaactgta tccatcttcc caccatccag tgagcagtta acatctggag    480
gt                                                                   482
```

<210> SEQ ID NO 103
<211> LENGTH: 570
<212> TYPE: DNA
<213> ORGANISM: Artificial Sequence
<220> FEATURE:
<223> OTHER INFORMATION: Synthetic: 1.815 heavy chain variable region
       polynucleotide sequence

<400> SEQUENCE: 103

```
tctgacagag gagccaagcc ctggattccc aggtcctcac attcagtgat cagcactgaa     60
cacagaccac tcaccatgga ctccaggctc aatttagttt tccttgtcct tattttaaaa    120
ggtgtccagt gtgatgtgca actgctggaa tctgggggag gcttagtgca gcctggaggg    180
tcccggaaac tctcctgtgc agcctctgga ttcacttca gtgactttgg aatgcactgg     240
gttcgtcagg ctccagagaa ggggctggag tgggtcgcat acagtagtag tggcggtact    300
accgtctact atgcagacac ggtgaagggc cgactcaccc tctccagaga caattccaag    360
aacaccctgt tcctggaaat gaccagtcta aggtctgagg acacggccat gtattactgt    420
gcaagagcgt cctatgatgg agggtacttt gactgctggg gccaaggcac ctctctcaca    480
gtctcctcag ccaaaacgac accccatct gtctatccac tggcccctgg atctgctgcc    540
caaactaact ccatggtgac cctgggatgc                                     570
```

<210> SEQ ID NO 104
<211> LENGTH: 497
<212> TYPE: DNA
<213> ORGANISM: Artificial Sequence
<220> FEATURE:
<223> OTHER INFORMATION: Synthetic: 1.815 light chain variable region
       polynucleotide sequence

<400> SEQUENCE: 104

```
atcctctctt ccagctctca gagatggaga cagacacact cctgttatgg gtactgctgc    60
tctgggttcc aggttccact ggtgacattg tgctgacaca gtctcctgct tccttagctg   120
tatctctggg gcagagggcc accatctcat gcagggccag caaaagtgtc agtacatctg   180
gctatagtta tatacactgg taccaacaga accaggaca gccacccaaa ctcctcatct    240
atcttgcatc cgacctagaa tctggggtcc ctgccaggtt cagtggcagt ggatctgggg   300
cagccttcac cctcaacatc catcctgtgg aggaggagga tgctgcaacc tattactgtc   360
accacagtag ggagcttcca ttcacgttcg gctcgggac aaagttggaa ataaaacggg     420
ctgatgctgc accaactgta tccatcttcc caccatccag tgagcagtta acatctggag   480
gtgcctcagt cgtgtgc                                                   497
```

<210> SEQ ID NO 105
<211> LENGTH: 575
<212> TYPE: DNA
<213> ORGANISM: Artificial Sequence
<220> FEATURE:
<223> OTHER INFORMATION: Synthetic: 1.846 heavy chain variable region
      polynucleotide sequence

<400> SEQUENCE: 105

```
agaggagcca aaccctggat tcccaggtcc tcacattcag tgatcagcac tgaacacaga    60
ccactcacca tggactccag gctcaattta gttttccttg tccttatttt aaaaggtgtc   120
cagtgtgagg tgcagctggt ggagtctggg ggagacttag tgaagcctgg agggtccctg   180
aaactctcct gtgcagcctc tggattcact ttcagtgact atggaatgca ctggcttcgt   240
caggctccag agaaggggct ggagtggtt gcatatatta gtagtggcag tactaccctc    300
tcctatgcaa acacaatgaa gggccgattc accatctcca gagacaatgc caagaaaacc   360
ctgtccctgc aaatgaccag tctgaggtct gaggacacgg ccatttatta ctgtgcgcgg   420
aaaaattaca cggtggtta cttcgatgtc tggggcacag gaccacggt caccgtctcc     480 tcagccaaaa caacaccccc atcagtctat ccactggccc ctgggtgtgg agatacaact   540
ggttcctctg tgactctggg atgcctggtc aaggg                               575
```

<210> SEQ ID NO 106
<211> LENGTH: 484
<212> TYPE: DNA
<213> ORGANISM: Artificial Sequence
<220> FEATURE:
<223> OTHER INFORMATION: Synthetic: 1.846 light chain variable region
      polynucleotide sequence

<400> SEQUENCE: 106

```
atcctctctt ccagctctca gagatggaga cagacacact cctgttatgg gtactgctgc    60
tctgggttcc aggttccact ggtgacattg tgctgacaca gtctcctgct tccttagttg   120
tatctctggg gcagagggcc accatctcat gcagggccag caaaagtgtc agtgaatctg   180
gctatagtta tatgcactgg taccaacaga accaggaca gccacccaaa ctcctcatct    240
atcttgcatc caacctagag tctggggtcc ctgccaggtt cagtggcagt gggtctggga   300
cagacttcac cctcaacatc catcctgtgg aggaggggga tgctacaacc tattactgtc   360
agcacagtag ggtccttcct cccacgttcg gctcgggac aaagttggaa ataaaacggg     420
ctgatgctgc accaactgta tccatcttcc caccatccag tgagcagtta acatctggag   480
gtgc                                                                 484
```

<210> SEQ ID NO 107
<211> LENGTH: 535
<212> TYPE: DNA
<213> ORGANISM: Artificial Sequence
<220> FEATURE:
<223> OTHER INFORMATION: Synthetic: 2.78 heavy chain variable region
      polynucleotide sequence

<400> SEQUENCE: 107

```
gacagaggag ccaagccctg gattcccagg tcctcacatt cagtgatcag cactgaacac    60
agaccactca ccatggactc caggctcaat ttagttttcc ttgtccttat tttaaaggt    120 gtccagtgtg atgtgcagct ggtggagtct gggggaggct tagtgcagcc tggagggtcc   180
cggaaactct cctgtgcagc ctctggattc actttcagta gctttggcat gcactgggtt   240
cgtcaggctc cagagaaggg actggagtgg gtcgcataca ttactagtgg cagtggtgcc   300
atctactatg cagacacagt gaggggccga ttcaccatct ccagagacac tcccaagaac   360
accctgttcc tgcagatgac cagtctaagg tctgaggaca cggccatgta ttactgtgca   420
agatcggctg atggtttgga ctactggggt caaggaacct cagtcaccgt ctcctcagcc   480
aaaacaacac ccccatcagt ctatccactg gcccctgggt gtggagatac aactg        535
```

<210> SEQ ID NO 108
<211> LENGTH: 488
<212> TYPE: DNA
<213> ORGANISM: Artificial Sequence
<220> FEATURE:
<223> OTHER INFORMATION: Synthetic: 2.78 light chain variable region
      polynucleotide sequence

<400> SEQUENCE: 108

```
cagcctcaca ctgatcacac acagacatga gtgtggccac tcaggtcctg gggttgctgc    60
tgctgtggct tacagatgcc agatgtgaca tccagatgac tcagtctcca gcctccctat   120
atgtatctgt gggagaaact gtcaccatca catgtcgagc aagtgagaat atttacagta   180
atttagcatg gtatcagcag aaacagggaa atctcctcag ctcctggtc tatggtgcaa    240 caaacttagc agatggtgtg ccatcaaggt tcagtggcag tggatcaggc acacagtatt   300
ccctcaagat caacagcctg aagtctgaag attttgggag ttattactgt caacattttt   360
ggggtactcc attcacgttc ggctcgggga caaagttgga ataaaacgg gctgatgctg    420 caccaactgt atccatcttc ccaccatcca gtgagcagtt aacatctgga ggtgcctcag   480
tcgtgtgc                                                            488
```

<210> SEQ ID NO 109
<211> LENGTH: 536
<212> TYPE: DNA
<213> ORGANISM: Artificial Sequence
<220> FEATURE:
<223> OTHER INFORMATION: Synthetic: 2.1029 heavy chain variable region
      polynucleotide sequence

<400> SEQUENCE: 109

```
atctcctcac tagagccccc atcagagcat ggctgtcctg gtgctgttcc tctgcctggt    60
tgcatttcca agctgtgtcc tgtcccaggt gcagctgaag gagtcaggac ctggcctggt   120
ggcgccctca cagagcctgt ccatcacttg cactgtctct gggttttcat taaccagcta   180
tggtgtacac tgggttcgcc agcctccagg aaagggtctg gagtggctgg agtaatatg    240 ggctggtgga agcacaaatt ataattcggc tctcatgtcc agactgagca tcagcaaaga   300
caactccaag agccaagttt tcttaaaaat gaacagtctg caaactgatg acacagccat   360
```

```
ctacttctgt gccagagatg gcgactacgg tactatctac gctatggact actggggtca    420
aggaacctca gtcaccgtct cctcagccaa acaacagcc ccatcggtct atccactggc     480
ccctgtgtgt ggagatacaa ctggctcctc ggtgactcta ggatgcctgg tcaagg        536
```

<210> SEQ ID NO 110
<211> LENGTH: 487
<212> TYPE: DNA
<213> ORGANISM: Artificial Sequence
<220> FEATURE:
<223> OTHER INFORMATION: Synthetic: 2.1029 light chain variable region
      polynucleotide sequence

<400> SEQUENCE: 110

```
attgaagtca agactcagcc tggacatgat gtcctctgct cagttccttg gtctcctgtt    60
gctctgtttt caaggtacca gatgtgatat ccagatgaca cagactacat cctccctgtc   120
tgcctctctg ggagacagag tcaccatcag ttgcagggca agtcaggaca ttagcaatta   180
tttaaactgg tatcagcaga aaccagatgg aactgttaaa ctcctgatct actacacatc   240
aagattacac tcaggagtcc catcaaggtt cactggcagt gggtctggaa cagattattc   300
tctcaccatt agcaacctgg agcaagaaga tattgccact tactttttgcc aacagggtaa   360 aacgcttcct cggacgttcg gtggaggcac catgctggaa atcaaacggg ctgatgctgc   420
accaactgta tccatcttcc caccatccag tgagcagtta acatctggag gtgcctcagt   480
cgtgtgc                                                              487
```

<210> SEQ ID NO 111
<211> LENGTH: 348
<212> TYPE: DNA
<213> ORGANISM: Artificial Sequence
<220> FEATURE:
<223> OTHER INFORMATION: Synthetic: Humanized Ab (HumAb) 2.78 heavy
      chain variable region polynucleotide sequence

<400> SEQUENCE: 111

```
gaggtgcagc tggtggagag cggcggcggc ctggtgcagc ccggcggcag cctgagactg    60
agctgcgccg ccagcggctt caccttcagc agcttcggca tgcactgggt gagacaggcc   120
cccggcaagg gcctggagtg ggtgagctac atcaccagcg gcagcggcgc catctactac   180
gccgacagcg tgaagggcag attcaccatc agcagagaca cgccaagaa cagcctgtac   240 ctgcagatga acagcctgag agccgaggac accgccgtgt actactgcgc cagaagcgcc   300
gacggcctgg actactgggg ccagggcacc accgtgaccg tgagcagc                348
```

<210> SEQ ID NO 112
<211> LENGTH: 1425
<212> TYPE: DNA
<213> ORGANISM: Artificial Sequence
<220> FEATURE:
<223> OTHER INFORMATION: Synthetic: HumAb 2.78 heavy chain
      polynucleotide sequence

<400> SEQUENCE: 112

```
atgcgtactc tggctatcct tgcagctatt ctgcttgttg cactgcaggc tcaagcggag    60
gtgcagctgg tggagagcgg cggcggcctg gtgcagcccg gcggcagcct gagactgagc   120
tgcgccgcca gcggcttcac cttcagcagc ttcggcatgc actgggtgag acaggcccc    180 ggcaagggcc tggagtgggt gagctacatc accagcggca gcggcgccat ctactacgcc   240
gacagcgtga agggcagatt caccatcagc agagacaacg ccaagaacag cctgtacctg   300
```

```
cagatgaaca gcctgagagc cgaggacacc gccgtgtact actgcgccag aagcgccgac    360
ggcctggact actggggcca gggcaccacc gtgaccgtga gcagcgatgt gtggggccag    420
ggcaccaccg tgaccgtgag cagcgcgtcg accaagggcc atcggtctct ccccctggcg    480
ccctgctcca ggagcacctc cgagagcaca gcggccctgg gctgcctggt caaggactac    540
ttccccgaac cggtgacggt gtcgtggaac tcaggcgctc tgaccagcgg cgtgcacacc    600
ttcccggctg tcctacagtc ctcaggactc tactccctca gcagcgtggt gaccgtgacc    660
tccagcaact cggcaccca gacctacacc tgcaacgtag atcacaagcc agcaacacc     720 aaggtggaca agacagttga gcgcaaatgt tgtgtcgagt gcccaccgtg cccagcacca    780
cctgtggcag accgtcagt cttcctcttc cccccaaaac ccaaggacac cctcatgatc     840
tcccggaccc ctgaggtcac gtgcgtggtg gtggacgtga gccacgaaga ccccgaggtc    900
cagttcaact ggtacgtgga cggcatggag gtgcataatg ccaagacaaa gccgcgggag    960
gagcagttca acagcacgtt ccgtgtggtc agcgtcctca ccgtcgtgca ccaggactgg   1020
ctgaacggca aggagtacaa gtgcaaggtc tccaacaaag gcctcccagc ccccatcgag   1080
aaaaccatct ccaaaaccaa agggcagccc gagaaccac aggtgtacac cctgccccca   1140
tcccgggagg agatgaccaa gaaccaggtc agcctgacct gcctggtcaa aggcttctac   1200
cccagcgaca tcgccgtgga gtgggagagc aatgggcagc cggagaacaa ctacaagacc   1260
acacctccca tgctggactc cgacggctcc ttcttcctct acagcaagct caccgtggac   1320
aagagcaggt ggcagcaggg gaacgtcttc tcatgctccg tgatgcatga ggctctgcac   1380
aaccactaca cacagaagag cctctccctg tctccgggta aatga                  1425

<210> SEQ ID NO 113
<211> LENGTH: 318
<212> TYPE: DNA
<213> ORGANISM: Artificial Sequence
<220> FEATURE:
<223> OTHER INFORMATION: Synthetic: HumAb 2.78 light chain variable
      region polynucleotide sequence

<400> SEQUENCE: 113
gacatccaga tgacccagag ccccagcagc ctgagcgcca gcgtgggcga cagagtgacc    60
atcacctgca gagccagcga gaacatctac agcaacctgg cctggtacca gcagaagccc   120
ggcaaggccc ccaagctgct gatctacggc gccaccaacc tggccgacgg cgtgcccagc   180
agattcagcg gcagcggcag cggcaccgac ttcaccctga ccatcagcag cctgcagccc   240
gaggacttcg ccacctacta ctgccagcac ttctggggca cccccttcac cttcggccag   300
ggcaccaagg tggagatc                                                 318

<210> SEQ ID NO 114
<211> LENGTH: 702
<212> TYPE: DNA
<213> ORGANISM: Artificial Sequence
<220> FEATURE:
<223> OTHER INFORMATION: Synthetic: HumAb 2.78 light chain
      polynucleotide sequence

<400> SEQUENCE: 114
atgaaaatcc tgattctcgg tatcttcctg tttctctgtt ctactccagc ttgggcagac    60
atccagatga cccagagccc cagcagcctg agcgccagcg tgggcgacag agtgaccatc   120
acctgcagag ccagcgagaa catctacagc aacctggcct ggtaccagca gaagcccggc   180
```

| | |
|---|---|
| aaggccccca agctgctgat ctacggcgcc accaacctgg ccgacggcgt gcccagcaga | 240 |
| ttcagcggca gcggcagcgg caccgacttc accctgacca tcagcagcct gcagcccgag | 300 |
| gacttcgcca cctactactg ccagcacttc tggggcaccc ccttcacctt cggccagggc | 360 |
| accaaggtgg agatcaaacg tacggtggct gcaccatctg tcttcatctt cccgccatct | 420 |
| gatgagcagt tgaaatctgg aactgcctct gttgtgtgcc tgctgaataa cttctatccc | 480 |
| agagaggcca agtacagtg gaaggtggat aacgccctcc aatcgggtaa ctcccaggag | 540 |
| agtgtcacag agcaggacag caaggacagc acctacagcc tcagcagcac cctgacgctg | 600 |
| agcaaagcag actacgagaa acacaaagtc tacgcctgcg aagtcaccca tcagggcctg | 660 |
| agctcgcccg tcacaaagag cttcaacagg ggagagtgtt ga | 702 |

<210> SEQ ID NO 115
<211> LENGTH: 360
<212> TYPE: DNA
<213> ORGANISM: Artificial Sequence
<220> FEATURE:
<223> OTHER INFORMATION: Synthetic: HumAb 2.1029 heavy chain variable
      region polynucleotide sequence

<400> SEQUENCE: 115

| | |
|---|---|
| caggtgcagc tgcaggagag cggccccggc ctggtgaagc ccagcgagac cctgagcctg | 60 |
| acctgcaccg tgagcggctt cagcctgacc agctacggcg tgcactggat cagacagccc | 120 |
| cccggcaagg gcctggagtg gatcggcgtg atctgggccg gcggcagcac caactacaac | 180 |
| cccagcctga gagcagagt gaccatcagc gtggacacca gcaagaacca gttcagcctg | 240 |
| aagctgagca gcgtgaccgc cgccgacacc gccgtgtact actgcgccag agacggcgac | 300 |
| tacggcacca tctacgccat ggactactgg ggccagggca ccctggtgac cgtgagcagc | 360 |

<210> SEQ ID NO 116
<211> LENGTH: 1437
<212> TYPE: DNA
<213> ORGANISM: Artificial Sequence
<220> FEATURE:
<223> OTHER INFORMATION: Synthetic: HumAb 2.1029 heavy chain
      polynucleotide sequence

<400> SEQUENCE: 116

| | |
|---|---|
| atgcgtactc tggctatcct tgcagctatt ctgcttgttg cactgcaggc tcaagcgcag | 60 |
| gtgcagctgc aggagagcgg ccccggcctg gtgaagccca gcgagaccct gagcctgacc | 120 |
| tgcaccgtga gcggcttcag cctgaccagc tacggcgtgc actggatcag acagcccccc | 180 |
| ggcaagggcc tggagtggat cggcgtgatc tgggccggcg gcagcaccaa ctacaacccc | 240 |
| agcctgaaga gcagagtgac catcagcgtg gacaccagca agaaccagtt cagcctgaag | 300 |
| ctgagcagcg tgaccgccgc cgacaccgcc gtgtactact gcgccagaga cggcgactac | 360 |
| ggcaccatct acgccatgga ctactggggc cagggcaccc tggtgaccgt gagcagcgat | 420 |
| gtgtggggcc agggcaccac cgtgaccgtg agcagcgcgt cgaccaaggg cccatcggtc | 480 |
| ttccccctgg cgccctgctc caggagcacc tccgagcagca gcggccct gggctgcctg | 540 |
| gtcaaggact acttccccga accggtgacg gtgtcgtgga actcaggcgc tctgaccagc | 600 |
| ggcgtgcaca ccttcccggc tgtcctacag tcctcaggac tctactccct cagcagcgtg | 660 |
| gtgaccgtga cctccagcaa cttcggcacc cagacctaca cctgcaacgt agatcacaag | 720 |
| cccagcaaca ccaaggtgga caagacagtt gagcgcaaat gttgtgtcga gtgcccaccg | 780 |
| tgcccagcac cacctgtggc aggaccgtca gtcttcctct tccccccaaa acccaaggac | 840 |

```
acccctcatga tctcccggac ccctgaggtc acgtgcgtgg tggtggacgt gagccacgaa      900
gaccccgagg tccagttcaa ctggtacgtg gacggcatgg aggtgcataa tgccaagaca      960
aagccgcggg aggagcagtt caacagcacg ttccgtgtgg tcagcgtcct caccgtcgtg     1020
caccaggact ggctgaacgg caaggagtac aagtgcaagg tctccaacaa aggcctccca     1080
gcccccatcg agaaaaccat ctccaaaacc aaagggcagc ccgagaacc acaggtgtac      1140 accctgcccc catcccggga ggagatgacc aagaaccagg tcagcctgac ctgcctggtc     1200
aaaggcttct accccagcga catcgccgtg gagtgggaga gcaatgggca gccggagaac     1260
aactacaaga ccacacctcc catgctggac tccgacggct ccttcttcct ctacagcaag     1320
ctcaccgtgg acaagagcag gtggcagcag gggaacgtct tctcatgctc cgtgatgcat     1380
gaggctctgc acaaccacta cacacagaag agcctctccc tgtctccggg taaatga       1437
```

<210> SEQ ID NO 117
<211> LENGTH: 318
<212> TYPE: DNA
<213> ORGANISM: Artificial Sequence
<220> FEATURE:
<223> OTHER INFORMATION: Synthetic: HumAb 2.1029 light chain variable
      region polynucleotide sequence

<400> SEQUENCE: 117

```
gacatccaga tgacccagag ccccagcagc ctgagcgcca gcgtgggcga cagagtgacc       60
atcacctgca gagccagcca ggacatcagc aactacctga actggtacca gcagaagccc      120
ggcaaggccc ccaagctgct gatctactac accagcagac tgcacagcgg cgtgcccagc      180
agattcagcg gcagcggcag cggcaccgac ttcaccttca ccatcagcag cctgcagccc      240
gaggacatcg ccacctacta ctgccagcag ggcaagaccc tgcccagaac cttcggcggc      300
ggcaccaagg tggagatc                                                    318
```

<210> SEQ ID NO 118
<211> LENGTH: 702
<212> TYPE: DNA
<213> ORGANISM: Artificial Sequence
<220> FEATURE:
<223> OTHER INFORMATION: Synthetic: HumAb 2.1029 light chain
      polynucleotide sequence

<400> SEQUENCE: 118

```
atgaaaatcc tgattctcgg tatcttcctg tttctctgtt ctactccagc ttgggcagac       60
atccagatga cccagagccc cagcagcctg agcgccagcg tgggcgacag agtgaccatc      120
acctgcagag ccagccagga catcagcaac tacctgaact ggtaccagca gaagcccggc      180
aaggccccca agctgctgat ctactacacc agcagactgc acagcggcgt gcccagcaga      240
ttcagcggca gcggcagcgg caccgacttc accttcacca tcagcagcct gcagcccgag      300
gacatcgcca cctactactg ccagcagggc aagaccctgc ccagaacctt cggcggcggc      360
accaaggtgg agatcaaacg tacggtggct gcaccatctg tcttcatctt cccgccatct      420
gatgagcagt tgaaatctgg aactgcctct gttgtgtgcc tgctgaataa cttctatccc      480
agagaggcca agtacagtg gaaggtggat aacgccctcc aatcgggtaa ctcccaggag      540
agtgtcacag agcaggacag caaggacagc acctacagcc tcagcagcac cctgacgctg      600
agcaaagcag actacgagaa acacaaagtc tacgcctgcg aagtcaccca tcagggcctg      660
agctcgcccg tcacaaagag cttcaacagg ggagagtgtt ga                        702
```

<210> SEQ ID NO 119
<211> LENGTH: 357
<212> TYPE: DNA
<213> ORGANISM: Artificial Sequence
<220> FEATURE:
<223> OTHER INFORMATION: Synthetic: HumAb 1.802 heavy chain variable
      region polynucleotide sequence

<400> SEQUENCE: 119
gaggtgcagc tggtggagag cggcggcggc ctggtgcagc ccggcggcag cctgagactg      60
agctgcgccg ccagcggctt caccttcagc gactacggca tgcactgggt gagacaggcc     120
cccggcaagg gcctggagtg ggtgagctac atcagcagcg gcagcagaac cgtgtactac     180
gccgacagcg tgaagggcag attcaccatc agcagagaca cgccaagaa cagcctgtac     240 ctgcagatga acagcctgag agacgaggac accgccgtgt actactgcgc cagaaagcac     300
tacaacggcg gctacttcga cgtgtggggc cagggcaccc tggtgaccgt gagcagc       357

<210> SEQ ID NO 120
<211> LENGTH: 1434
<212> TYPE: DNA
<213> ORGANISM: Artificial Sequence
<220> FEATURE:
<223> OTHER INFORMATION: Synthetic: HumAb 1.802 heavy chain
      polynucleotide sequence

<400> SEQUENCE: 120
atgcgtactc tggctatcct tgcagctatt ctgcttgttg cactgcaggc tcaagcggag      60
gtgcagctgg tggagagcgg cggcggcctg gtgcagcccg gcggcagcct gagactgagc     120
tgcgccgcca gcggcttcac cttcagcgac tacggcatgc actgggtgag acaggccccc     180
ggcaagggcc tggagtgggt gagctacatc agcagcggca gcagaaccgt gtactacgcc     240
gacagcgtga agggcagatt caccatcagc agagacaacg ccaagaacag cctgtacctg     300
cagatgaaca gcctgagaga cgaggacacc gccgtgtact actgcgccag aaagcactac     360
aacggcggct acttcgacgt gtggggccag ggcaccctgg tgaccgtgag cagcgatgtg     420
tggggccagg gcaccaccgt gaccgtgagc agcgcgtcga ccaagggccc atcggtcttc     480
cccctggcgc cctgctccag gagcacctcc gagagcacag cggccctggg ctgcctggtc     540
aaggactact ccccgaacc ggtgacggtg tcgtggaact caggcgctct gaccagcggc     600
gtgcacacct tcccggctgt cctacagtcc tcaggactct actccctcag cagcgtggtg     660
accgtgacct ccagcaactt cggcacccag acctacacct gcaacgtaga tcacaagccc     720
agcaacacca aggtggacaa gacagttgag cgcaaatgtt gtgtcgagtg cccaccgtgc     780
ccagcaccac ctgtggcagg accgtcagtc ttcctcttcc cccaaaaacc caaggacacc     840
ctcatgatct cccggacccc tgaggtcacg tgcgtggtgg tggacgtgag ccacgaagac     900
cccgaggtcc agttcaactg gtacgtggac ggcatggagg tgcataatgc caagacaaag     960
ccgcgggagg agcagttcaa cagcacgttc cgtgtggtca gcgtcctcac cgtcgtgcac    1020
caggactggc tgaacggcaa ggagtacaag tgcaaggtct ccaacaaagg cctcccagcc    1080
cccatcgaga aaaccatctc caaaaccaaa gggcagcccc gagaaccaca ggtgtacacc    1140
ctgcccccat cccgggagga gatgaccaag aaccaggtca gcctgacctg cctggtcaaa    1200
ggcttctacc ccagcgacat cgccgtggag tgggagagca tgggcagccg gagaacaac    1260 tacaagacca cacctcccat gctggactcc gacggctcct tcttcctcta cagcaagctc    1320
accgtggaca agagcaggtg gcagcagggg aacgtcttct catgctccgt gatgcatgag    1380

```
gctctgcaca accactacac acagaagagc ctctccctgt ctccgggtaa atga         1434
```

```
<210> SEQ ID NO 121
<211> LENGTH: 330
<212> TYPE: DNA
<213> ORGANISM: Artificial Sequence
<220> FEATURE:
<223> OTHER INFORMATION: Synthetic: HumAb 1.802 light chain variable
      region polynucleotide sequence

<400> SEQUENCE: 121
gacatcgtga tgacccagag ccccgacagc ctggccgtga gcctgggcga gagagccacc    60
atcaactgca gagccagcaa gatcgtgagc accagcggct acagctacat gcactggtac   120
cagcagaagc ccggccagcc ccccaagctg ctgatctacc tggccagcaa cctggagagc   180
ggcgtgcccg acagattcag cggcagcggc agcggcaccg acttcaccct gaccatcagc   240
agcctgcagg ccgaggacgt ggccgtgtac tactgccagc acagcagaga gctgccccccc  300 accttcggcc agggcaccaa gctggagatc                                    330
```

```
<210> SEQ ID NO 122
<211> LENGTH: 714
<212> TYPE: DNA
<213> ORGANISM: Artificial Sequence
<220> FEATURE:
<223> OTHER INFORMATION: Synthetic: HumAb 1.802 light chain
      polynucleotide sequence

<400> SEQUENCE: 122
atgaaaatcc tgattctcgg tatcttcctg tttctctgtt ctactccagc ttgggcagac    60
atcgtgatga cccagagccc cgacagcctg gccgtgagcc tgggcgagag agccaccatc   120
aactgcagag ccagcaagat cgtgagcacc agcggctaca gctacatgca ctggtaccag   180
cagaagcccg gccagccccc caagctgctg atctacctgg ccagcaacct ggagagcggc   240
gtgcccgaca gattcagcgg cagcggcagc ggcaccgact tcaccctgac catcagcagc   300
ctgcaggccg aggacgtggc cgtgtactac tgccagcaca gcagagagct gccccccacc   360
ttcggccagg gcaccaagct ggagatcaaa cgtacggtgg ctgcaccatc tgtcttcatc   420
ttcccgccat ctgatgagca gttgaaatct ggaactgcct ctgttgtgtg cctgctgaat   480
aacttctatc ccagagaggc caaagtacag tggaaggtgg ataacgccct ccaatcgggt   540
aactcccagg agagtgtcac agagcaggac agcaaggaca gcacctacag cctcagcagc   600
accctgacgc tgagcaaagc agactacgag aaacacaaag tctacgcctg cgaagtcacc   660
catcagggcc tgagctcgcc cgtcacaaag agcttcaaca ggggagagtg ttga         714
```

```
<210> SEQ ID NO 123
<211> LENGTH: 357
<212> TYPE: DNA
<213> ORGANISM: Artificial Sequence
<220> FEATURE:
<223> OTHER INFORMATION: Synthetic: HumAb 1.815 heavy chain variable
      region polynucleotide sequence

<400> SEQUENCE: 123
caggtgcagc tggtggagag cggcggcggc ctggtgaagc ccggcggcag cctgagactg    60
agctgcgccg ccagcggctt caccttcagc gacttcggca tgcactggat cagacaggcc   120
cccggcaagg gcctggagtg ggtgagctac agcagcagcg gcggcaccac cgtgtactac   180
gccgacagcg tgaagggcag attcaccatc agcagagaca cgccaagaa cagcctgtac   240
```
ctgcagatga acagcctgag agccgaggac accgccgtgt actactgcgc cagagccagc    300
tacgacggcg gctacttcga ctgctggggc cagggcacca ccgtgaccgt gagcagc       357

<210> SEQ ID NO 124
<211> LENGTH: 1434
<212> TYPE: DNA
<213> ORGANISM: Artificial Sequence
<220> FEATURE:
<223> OTHER INFORMATION: Synthetic: HumAb 1.815 heavy chain
      polynucleotide sequence

<400> SEQUENCE: 124
atgcgtactc tggctatcct tgcagctatt ctgcttgttg cactgcaggc tcaagcgcag     60
gtgcagctgg tggagagcgg cggcggcctg gtgaagcccg gcggcagcct gagactgagc    120
tgcgccgcca gcggcttcac cttcagcgac ttcggcatgc actggatcag acaggccccc    180
ggcaagggcc tggagtgggt gagctacagc agcagcggcg gcaccaccgt gtactacgcc    240
gacagcgtga agggcagatt caccatcagc agagacaacg ccaagaacag cctgtacctg    300
cagatgaaca gcctgagagc cgaggacacc gccgtgtact actgcgccag agccagctac    360
gacggcggct acttcgactg ctggggccag ggcaccaccg tgaccgtgag cagcgatgtg    420
tggggccagg gcaccaccgt gaccgtgagc agcgcgtcga ccaagggccc atcggtcttc    480
cccctggcgc cctgctccag gagcacctcc gagagcacag cggccctggg ctgcctggtc    540
aaggactact cccccgaacc ggtgacggtg tcgtggaact caggcgctct gaccagcggc    600
gtgcacacct tcccggctgt cctacagtcc tcaggactct actccctcag cagcgtggtg    660
accgtgacct ccagcaactt cggcacccag acctacacct gcaacgtaga tcacaagccc    720
agcaacacca aggtggacaa gacagttgag cgcaaatgtt gtgtcgagtg cccaccgtgc    780
ccagcaccac ctgtggcagg accgtcagtc ttcctcttcc ccccaaaacc caaggacacc    840
ctcatgatct cccggacccc tgaggtcacg tgcgtggtgg tggacgtgag ccacgaagac    900
cccgaggtcc agttcaactg gtacgtggac ggcatggagg tgcataatgc caagacaaag    960
ccgcgggagg agcagttcaa cagcacgttc cgtgtggtca gcgtcctcac cgtcgtgcac   1020
caggactggc tgaacggcaa ggagtacaag tgcaaggtct ccaacaaagg cctcccagcc   1080
cccatcgaga aaaccatctc caaaaccaaa gggcagcccc gagaaccaca ggtgtacacc   1140
ctgcccccat cccgggagga gatgaccaag aaccaggtca gcctgacctg cctggtcaaa   1200
ggcttctacc ccagcgacat cgccgtggag tgggagagca atgggcagcc ggagaacaac   1260
tacaagacca cacctcccat gctggactcc gacggctcct tcttcctcta cagcaagctc   1320
accgtggaca agagcaggtg gcagcagggg aacgtcttct catgctccgt gatgcatgag   1380
gctctgcaca accactacac acagaagagc ctctccctgt ctccgggtaa atga          1434

<210> SEQ ID NO 125
<211> LENGTH: 330
<212> TYPE: DNA
<213> ORGANISM: Artificial Sequence
<220> FEATURE:
<223> OTHER INFORMATION: Synthetic: HumAb 1.815 light chain variable
      region polynucleotide sequence

<400> SEQUENCE: 125
gacatcgtga tgacccagag ccccgacagc ctggccgtga gcctgggcga gagagccacc     60
atcaactgca gagccagcaa gagcgtgagc accagcggct acagctacat ccactggtac    120

```
cagcagaagc ccggccagcc ccccaagctg ctgatctacc tggccagcga cctggagagc    180
ggcgtgcccg acagattcag cggcagcggc agcggcaccg acttcaccct gaccatcagc    240
agcctgcagg ccgaggacgt ggccgtgtac tactgccacc agcagagaga gctgcccttc    300
accttcggcc agggcaccaa gctggagatc                                     330
```

<210> SEQ ID NO 126
<211> LENGTH: 714
<212> TYPE: DNA
<213> ORGANISM: Artificial Sequence
<220> FEATURE:
<223> OTHER INFORMATION: Synthetic: HumAb 1.815 light chain
      polynucleotide sequence

<400> SEQUENCE: 126

```
atgaaaatcc tgattctcgg tatcttcctg tttctctgtt ctactccagc ttgggcagac     60
atcgtgatga cccagagccc cgacagcctg gccgtgagcc tgggcgagag agccaccatc    120
aactgcagag ccagcaagag cgtgagcacc agcggctaca gctacatcca ctggtaccag    180
cagaagcccg ccagcccccc caagctgctg atctacctgg ccagcgacct ggagagcggc    240
gtgcccgaca gattcagcgg cagcggcagc ggcaccgact tcaccctgac catcagcagc    300
ctgcaggccg aggacgtggc cgtgtactac tgccaccaca gcagagagct gcccttcacc    360
ttcggccagg gcaccaagct ggagatcaaa cgtacggtgg ctgcaccatc tgtcttcatc    420
ttcccgccat ctgatgagca gttgaaatct ggaactgcct ctgttgtgtg cctgctgaat    480
aacttctatc ccagagaggc caaagtacag tggaaggtgg ataacgccct ccaatcgggt    540
aactcccagg agagtgtcac agagcaggac agcaaggaca gcacctacag cctcagcagc    600
accctgacgc tgagcaaagc agactacgag aaacacaaag tctacgcctg cgaagtcacc    660
catcagggcc tgagctcgcc cgtcacaaag agcttcaaca ggggagagtg ttga          714
```

<210> SEQ ID NO 127
<211> LENGTH: 357
<212> TYPE: DNA
<213> ORGANISM: Artificial Sequence
<220> FEATURE:
<223> OTHER INFORMATION: Synthetic: HumAb 1.846 heavy chain variable
      region polynucleotide sequence

<400> SEQUENCE: 127

```
gaggtgcagc tggtggagag cggcggcggc ctggtgcagc ccggcggcag cctgagactg     60
agctgcgccg ccagcggctt caccttcagc gactacggca tgcactgggt gagacaggcc    120
cccggcaagg gcctggagtg ggtgagctac atcagcagcg gcagcaccac cctgagctac    180
gccgacagcg tgaagggcag attcaccatc agcagagaca cgccaagaa cagcctgtac    240 ctgcagatga acagcctgag agacgaggac accgccgtgt actactgcgc cagaaagaac    300
tacaacggcg gctacttcga cgtgtggggc cagggcaccc tggtgaccgt gagcagc       357
```

<210> SEQ ID NO 128
<211> LENGTH: 1434
<212> TYPE: DNA
<213> ORGANISM: Artificial Sequence
<220> FEATURE:
<223> OTHER INFORMATION: Synthetic: HumAb 1.846 heavy chain
      polynucleotide sequence

<400> SEQUENCE: 128

```
atgcgtactc tggctatcct tgcagctatt ctgcttgttg cactgcaggc tcaagcggag     60
```

| | |
|---|---|
| gtgcagctgg tggagagcgg cggcggcctg gtgcagcccg cggcagcct gagactgagc | 120 |
| tgcgccgcca gcggcttcac cttcagcgac tacggcatgc actgggtgag acaggccccc | 180 |
| ggcaagggcc tggagtgggt gagctacatc agcagcggca gcaccaccct gagctacgcc | 240 |
| gacagcgtga agggcagatt caccatcagc agagacaacg ccaagaacag cctgtacctg | 300 |
| cagatgaaca gcctgagaga cgaggacacc gccgtgtact actgcgccag aaagaactac | 360 |
| aacggcggct acttcgacgt gtggggccag ggcaccctgg tgaccgtgag cagcgatgtg | 420 |
| tggggccagg gcaccaccgt gaccgtgagc agcgcgtcga ccaagggccc atcggtcttc | 480 |
| cccctggcgc cctgctccag gagcacctcc gagagcacag cggccctggg ctgcctggtc | 540 |
| aaggactact tccccgaacc ggtgacggtg tcgtggaact caggcgctct gaccagcggc | 600 |
| gtgcacacct tcccggctgt cctacagtcc tcaggactct actccctcag cagcgtggtg | 660 |
| accgtgacct ccagcaactt cggcacccag acctacacct gcaacgtaga tcacaagccc | 720 |
| agcaacacca aggtggacaa gacagttgag cgcaaatgtt gtgtcgagtg cccaccgtgc | 780 |
| ccagcaccac ctgtggcagg accgtcagtc ttcctcttcc ccccaaaacc caaggacacc | 840 |
| ctcatgatct cccggacccc tgaggtcacg tgcgtggtgg tggacgtgag ccacgaagac | 900 |
| cccgaggtcc agttcaactg gtacgtggac ggcatggagg tgcataatgc caagacaaag | 960 |
| ccgcgggagg agcagttcaa cagcacgttc cgtgtggtca gcgtcctcac cgtcgtgcac | 1020 |
| caggactggc tgaacggcaa ggagtacaag tgcaaggtct ccaacaaagg cctcccagcc | 1080 |
| cccatcgaga aaaccatctc caaaaccaaa gggcagcccc gagaaccaca ggtgtacacc | 1140 |
| ctgcccccat cccgggagga gatgaccaag aaccaggtca gcctgacctg cctggtcaaa | 1200 |
| ggcttctacc ccagcgacat cgccgtggag tgggagagca atgggcagcc ggagaacaac | 1260 |
| tacaagacca cacctcccat gctggactcc gacggctcct tcttcctcta cagcaagctc | 1320 |
| accgtggaca gagcaggtg gcagcagggg aacgtcttct catgctccgt gatgcatgag | 1380 |
| gctctgcaca accactacac acagaagagc ctctccctgt ctccgggtaa atga | 1434 |

<210> SEQ ID NO 129
<211> LENGTH: 330
<212> TYPE: DNA
<213> ORGANISM: Artificial Sequence
<220> FEATURE:
<223> OTHER INFORMATION: Synthetic: HumAb 1.846 light chain variable
    region polynucleotide sequence

<400> SEQUENCE: 129

| | |
|---|---|
| gacatcgtga tgacccagag ccccgacagc ctggccgtga gcctgggcga gagagccacc | 60 |
| atcaactgca gagccagcaa gagcgtgagc gagagcggct acagctacat gcactggtac | 120 |
| cagcagaagc ccggccagcc ccccaagctg ctgatctacc tggccagcaa cctggagagc | 180 |
| ggcgtgcccg acagattcag cggcagcggc agcggcaccg acttcaccct gaccatcagc | 240 |
| agcctgcagg ccgaggacgt ggccgtgtac tactgccagc acagcagagt gctgcccccc | 300 |
| accttcggcc agggcaccaa gctggagatc | 330 |

<210> SEQ ID NO 130
<211> LENGTH: 714
<212> TYPE: DNA
<213> ORGANISM: Artificial Sequence
<220> FEATURE:
<223> OTHER INFORMATION: Synthetic: HumAb 1.846 light chain
    polynucleotide sequence

<400> SEQUENCE: 130

-continued

```
atgaaaatcc tgattctcgg tatcttcctg tttctctgtt ctactccagc ttgggcagac      60
atcgtgatga cccagagccc cgacagcctg gccgtgagcc tgggcgagag agccaccatc     120
aactgcagag ccagcaagag cgtgagcgag agcggctaca gctacatgca ctggtaccag     180
cagaagcccg ccagccccc caagctgctg atctacctgg ccagcaacct ggagagcggc      240
gtgcccgaca gattcagcgg cagcggcagc ggcaccgact tcaccctgac catcagcagc     300
ctgcaggccg aggacgtggc cgtgtactac tgccagcaca gcagtgctgc cccccccacc     360
tccggccagg gcaccaagct ggagatcaaa cgtacggtgg ctgcaccatc tgtcttcatc     420
ttcccgccat ctgatgagca gttgaaatct ggaactgcct ctgttgtgtg cctgctgaat     480
aacttctatc ccagagaggc caaagtacag tggaaggtgg ataacgccct ccaatcgggt     540
aactcccagg agagtgtcac agagcaggac agcaaggaca gcacctacag cctcagcagc     600
accctgacgc tgagcaaagc agactacgag aaacacaaag tctacgcctg cgaagtcacc     660
catcagggcc tgagctcgcc cgtcacaaag agcttcaaca ggggagagtg ttga           714
```

<210> SEQ ID NO 131
<211> LENGTH: 496
<212> TYPE: PRT
<213> ORGANISM: Cynomolgus monkey
<220> FEATURE:
<221> NAME/KEY: misc_feature
<222> LOCATION: (1)..(496)
<223> OTHER INFORMATION: Cynomolgus monkey NOTUM

<400> SEQUENCE: 131

```
Met Gly Arg Gly Val Arg Val Leu Leu Leu Gly Leu Leu His Cys
1               5                   10                  15

Ala Gly Gly Ser Glu Gly Arg Lys Thr Trp Arg Arg Gly Gln Gln
                20                  25                  30

Pro Pro Pro Pro Arg Thr Glu Ala Ala Pro Ala Ala Gly Gln Pro
                35                  40                  45

Val Glu Ser Phe Pro Leu Asp Phe Thr Ala Val Glu Gly Asn Met Asp
    50                  55                  60

Ser Phe Met Ala Gln Val Lys Ser Leu Ala Gln Ser Leu Tyr Pro Cys
65                  70                  75                  80

Ser Ala Gln Gln Leu Asn Glu Asp Leu Arg Leu His Leu Leu Asn
                85                  90                  95

Thr Ser Val Thr Cys Asn Asp Gly Ser Pro Ala Gly Tyr Tyr Leu Lys
                    100                 105                 110

Glu Ser Arg Gly Ser Arg Arg Trp Leu Leu Phe Leu Glu Gly Gly Trp
            115                 120                 125

Tyr Cys Phe Asn Arg Glu Asn Cys Asp Ser Arg Tyr Asn Thr Met Arg
130                 135                 140

Arg Leu Met Ser Ser Arg Asp Trp Pro Arg Thr Arg Thr Gly Thr Gly
145                 150                 155                 160

Ile Leu Ser Ser Gln Pro Glu Glu Asn Pro Tyr Trp Trp Asn Ala Asn
                165                 170                 175

Met Val Phe Ile Pro Tyr Cys Ser Ser Asp Val Trp Ser Gly Ala Ser
                180                 185                 190

Ser Lys Ser Glu Lys Asn Glu Tyr Ala Phe Met Gly Ala Leu Ile Ile
            195                 200                 205

Gln Glu Val Val Arg Glu Leu Leu Gly Arg Gly Leu Ser Gly Ala Lys
        210                 215                 220
```

-continued

```
Val Leu Leu Leu Ala Gly Ser Ser Ala Gly Gly Thr Gly Val Leu Leu
225                 230                 235                 240

Asn Val Asp Arg Val Ala Glu Gln Leu Glu Glu Leu Gly Tyr Pro Ala
                245                 250                 255

Ile Gln Val Arg Gly Leu Ala Asp Ser Gly Trp Phe Leu Asp Asn Lys
                260                 265                 270

Gln Tyr Arg His Thr Asp Cys Val Asp Thr Ile Thr Cys Ala Pro Thr
            275                 280                 285

Glu Ala Ile Arg Arg Gly Ile Arg Tyr Trp Asn Gly Val Val Pro Glu
        290                 295                 300

Arg Cys Arg Arg Gln Phe Gln Glu Gly Glu Trp Asn Cys Phe Phe
305                 310                 315                 320

Gly Tyr Lys Ile Tyr Pro Thr Leu Arg Cys Pro Val Phe Val Val Gln
                325                 330                 335

Trp Leu Phe Asp Glu Ala Gln Leu Thr Val Asp Asn Val His Leu Thr
                340                 345                 350

Gly Gln Pro Val Gln Glu Ser Gln Arg Leu Tyr Ile Gln Asn Leu Gly
            355                 360                 365

Arg Glu Leu Arg His Thr Leu Lys Asp Val Pro Ala Ser Phe Ala Pro
        370                 375                 380

Ala Cys Leu Ser His Glu Ile Ile Ile Arg Ser His Trp Thr Asp Val
385                 390                 395                 400

Gln Val Lys Gly Thr Ser Leu Pro Arg Ala Leu His Cys Trp Asp Arg
                405                 410                 415

Ser Leu His Asp Ser His Lys Thr Ser Lys Thr Pro Leu Lys Gly Cys
                420                 425                 430

Pro Val His Leu Val Asp Ser Cys Pro Trp Pro His Cys Asn Pro Ser
            435                 440                 445

Cys Pro Thr Val Arg Asp Gln Phe Thr Gly Gln Glu Met Asn Val Ala
        450                 455                 460

Gln Phe Leu Met His Met Gly Phe Asp Val Gln Thr Val Ala Gln Gln
465                 470                 475                 480

Gln Gly Pro Glu Pro Ser Lys Leu Leu Gly Leu Pro Ser Asp Gly Ser
                485                 490                 495
```

ANTIBODIES THAT BIND NOTUM PECTINACETYLESTERASE

This application is a divisional application of Ser. No. 14/952,264, filed Nov. 25, 2015, now abandoned, which is a continuation of U.S. application Ser. No. 13/885,815, filed Jul. 31, 2013, now abandoned, which is a § 371 national stage of International Application No. PCT/US2011/061785, filed Nov. 22, 2011, which claims the benefit of U.S. Provisional Application No. 61/416,927, filed Nov. 24, 2010, each of which is incorporated by reference herein in its entirety for any purpose.

1. SEQUENCE LISTING

The present application is filed with a Sequence Listing in electronic format. The Sequence Listing is provided as a file entitled "2019-02-11_01136-0003-02US_Seq_List.txt" created on Feb. 11, 2019, which is 188,016 bytes in size. The information in the electronic format of the sequence listing is incorporated herein by reference in its entirety.

2. FIELD OF THE INVENTION

This invention relates to antibody inhibitors of Notum Pectinacetylesterase, compositions comprising them, and methods of their use.

3. BACKGROUND OF THE INVENTION

Bone health depends on the coordinated activities of bone forming osteoblasts and bone resorbing osteoclasts. "Bone turnover reflects a balance between these anabolic and catabolic cellular functions and ensures that the mature skeleton can repair itself when damaged and sustain its endocrine function by release of minerals such as calcium and phosphorous into the circulation." Allen, J. G. et al., *J. Med. Chem.*, 53 (Jun. 10, 2010), pp. 4332-4353, 4332. Many disease states alter this balance, resulting in increased or decreased bone mass or changes in bone quality. Gradual loss of bone mineral density is known as osteopenia; severe loss of bone is known as osteoporosis. Id.

The current standard of care for the treatment and prevention of osteoporosis utilizes the bisphosphonate class of oral, small molecule antiresportives. Id. at 4333. Zoledronic acid, raloxifene, calcium, and vitamin D supplements are also typically used in the osteoporosis treatment. Id. While antiresorptive agents can help prevent bone loss, anabolic agents "are capable of increasing bone mass to a greater degree . . . and also have the capacity to improve bone quality and increase bone strength." Guo, H., et al., *J. Med. Chem.*, 53 (Feb. 25, 2010), pp. 1819-1829, 1819. In the United States, human PTH is the only FDA-approved anabolic agent. Id.; Allen at 4333. "Because of the paucity of available anabolic agents for osteoporosis treatment, there is an urgent need to develop small molecular compounds to treat this disease that are nontoxic, cost-effective, and easy to administer." Guo, at 1819.

"Although the development of pharmacological agents that stimulate bone formation is less advanced compared to antiresorptive therapies, several pathways are known to facilitate osteoblast function." Allen at 4338. These pathways include bone morphogenic proteins, transforming growth factor β, parathyroid hormone, insulin-like growth factor, fibroblast growth factor, and wingless-type MMTV integration site (WNT) signaling. Id. Guo and coworkers recently reported results concerning the first of these pathways. Guo, supra. In particular, they reported that certain substituted benzothiophene and benzofuran compounds enhance bone morphogenic protein 2 expression in mice and rats. Two of the compounds reportedly stimulate bone formation and trabecular connectivity restoration in vivo. Id. at 1819.

Another of these pathways is the WNT pathway, which is implicated in a variety of developmental and regenerative processes. Allen at 4340. The pathway is complex, however, and much about it and about how its components affect bone remains unclear. For example, it has been suggested that LRP-5, mutations of which are associated with increased bone mass in humans, and β-catenin, through which canonical WNT signaling occurs, "may not be linked directly via WNT signaling to the control of bone mass." Id.

Recent analysis of gene expression data has led to the identification of new targets of WNT signaling. See, e.g., Torisu, Y., et al., *Cancer Sci.*, 99(6):1139-1146, 1143 (2008). One such target is Notum Pectinacetylesterase, also known as NOTUM and LOC174111.

4. SUMMARY OF THE INVENTION

In some embodiments, a monoclonal antibody that binds human notum pectinacetylesterase (NOTUM) and neutralizes at least one activity of NOTUM is provided. In some embodiments, the antibody binds to a NOTUM selected from mouse NOTUM, guinea pig NOTUM, cynomolgus monkey NOTUM, and rhesus monkey NOTUM. In some embodiments, the antibody has at least one activity selected from reducing NOTUM activity in a trisodium 8-octanoyloxypyrene-1,3,6-trisulfonate (OPTS) assay in vitro, and reducing NOTUM activity in a Wnt signaling assay in vitro. In some embodiments, the antibody has at least one activity selected from increasing serum PINP levels in vivo, increasing bone mineral density in vivo, increasing midshaft femur cortical thickness in vivo, increasing midshaft femur bone area in vivo, increasing midshaft humerus cortical thickness in vivo, increasing endocortical bone formation in vivo, increasing the proportion of cortical bone volume in the LV5 vertebral body in vivo, and increasing the proportion of femoral neck bone volume to femoral neck total volume in vivo. In some embodiments, an antibody that binds NOTUM binds to a polypeptide having the amino acid sequence of SEQ ID NO: 1 with $K_D$ of less than 50 nM, less than 20 nM, or less than 10 nM.

In some embodiments, the antibody has at least one binding characteristic selected from: a) binds to a polypeptide having the amino acid sequence of SEQ ID NO: 83 with a binding affinity that is at least 5-fold stronger than the binding affinity of the antibody for a polypeptide having the amino acid sequence of SEQ ID NO: 84; b) binds to a polypeptide having the amino acid sequence of SEQ ID NO: 85 with a binding affinity that is at least 5-fold stronger than the binding affinity of the antibody for a polypeptide having the amino acid sequence of SEQ ID NO: 86; c) binds to a polypeptide having the amino acid sequence of SEQ ID NO: 1 with a binding affinity that is at least 5-fold stronger than the binding affinity of the antibody for a polypeptide having the amino acid sequence of SEQ ID NO: 94; d) binds to a polypeptide having the amino acid sequence of SEQ ID NO: 1 with a binding affinity that is at least 5-fold stronger than the binding affinity of the antibody for a polypeptide having the amino acid sequence of SEQ ID NO: 99; e) binds to a polypeptide having the amino acid sequence of SEQ ID NO: 95 with a binding affinity that is at least 5-fold stronger than the binding affinity of the antibody for a polypeptide having the amino acid sequence of SEQ ID NO: 2; f) competes for binding to NOTUM with an antibody comprising a heavy chain variable region having an amino acid sequence of SEQ ID NO: 7 and a light chain variable region having the amino acid sequence of SEQ ID NO: 8; g) competes for binding to NOTUM with an antibody comprising a heavy chain variable region having an amino acid sequence of SEQ ID NO: 15 and a light chain variable region having the amino acid sequence of SEQ ID NO: 16; h) competes for binding to NOTUM with an antibody comprising a heavy chain variable region having an amino acid sequence of SEQ ID NO: 23 and a light chain variable region having the amino acid sequence of SEQ ID NO: 24; i) competes for binding to NOTUM with an antibody comprising a heavy chain variable region having an amino acid sequence of SEQ ID NO: 31 and a light chain variable region having the amino acid sequence of SEQ ID NO: 32; j) competes for binding to NOTUM with an antibody comprising a heavy chain variable region having an amino acid sequence of SEQ ID NO: 39 and a light chain variable region having the amino acid sequence of SEQ ID NO: 40; k) competes for binding to NOTUM with an antibody comprising a heavy chain variable region having an amino acid sequence of SEQ ID NO: 47 and a light chain variable region having the amino acid sequence of SEQ ID NO: 48; and l) competes for binding to NOTUM with an antibody comprising a heavy chain variable region having an amino acid sequence of SEQ ID NO: 55 and a light chain variable region having the amino acid sequence of SEQ ID NO: 56.

In some embodiments, the antibody is selected from a mouse antibody, a chimeric antibody, a humanized antibody, and a human antibody.

In some embodiments, an antibody that binds NOTUM comprises a heavy chain and a light chain, wherein the heavy chain comprises at least one CDR selected from: a) a CDR1 comprising an amino acid sequence selected from SEQ ID NOs: 9, 17, 25, 33, 41, 49, and 90; b) a CDR2 comprising an amino acid sequence selected from SEQ ID NOs: 10, 18, 26, 34, 42, and 50; and c) a CDR3 comprising an amino acid sequence selected from SEQ ID NOs: 11, 19, 27, 35, 43, 51, and 91. In some embodiments, the heavy chain comprises a set comprising a CDR1, a CDR2, and a CDR3, wherein the set is selected from: a) a set comprising a CDR1 having the amino acid sequence of SEQ ID NO: 9, a CDR2 having the amino acid sequence of SEQ ID NO: 10, and a CDR3 having the amino acid sequence of SEQ ID NO: 11; b) a set comprising a CDR1 having the amino acid sequence of SEQ ID NO: 90, a CDR2 having the amino acid sequence of SEQ ID NO: 18, and a CDR3 having the amino acid sequence of SEQ ID NO: 91; c) a set comprising a CDR1 having the amino acid sequence of SEQ ID NO: 17, a CDR2 having the amino acid sequence of SEQ ID NO: 18, and a CDR3 having the amino acid sequence of SEQ ID NO: 19; d) a set comprising a CDR1 having the amino acid sequence of SEQ ID NO: 90, a CDR2 having the amino acid sequence of SEQ ID NO: 26, and a CDR3 having the amino acid sequence of SEQ ID NO: 27; e) a set comprising a CDR1 having the amino acid sequence of SEQ ID NO: 25, a CDR2 having the amino acid sequence of SEQ ID NO: 26, and a CDR3 having the amino acid sequence of SEQ ID NO: 27; f) a set comprising a CDR1 having the amino acid sequence of SEQ ID NO: 90, a CDR2 having the amino acid sequence of SEQ ID NO: 34, and a CDR3 having the amino acid sequence of SEQ ID NO: 91; g) a set comprising a CDR1 having the amino acid sequence of SEQ ID NO: 33, a CDR2 having the amino acid sequence of SEQ ID NO: 34, and a CDR3 having the amino acid sequence of SEQ ID NO: 35; h) a set comprising a CDR1 having the amino acid sequence of SEQ ID NO: 41, a CDR2 having the amino acid sequence of SEQ ID NO: 42, and a CDR3 having the amino acid sequence of SEQ ID NO: 43; i) a set comprising a CDR1 having the amino acid sequence of SEQ ID NO: 49, a CDR2 having the amino acid sequence of SEQ ID NO: 50, and a CDR3 having the amino acid sequence of SEQ ID NO: 51; and j) a set comprising a CDR1 having the amino acid sequence of SEQ ID NO: 57, a CDR2 having the amino acid sequence of SEQ ID NO: 58, and a CDR3 having the amino acid sequence of SEQ ID NO: 59. In some embodiments, the heavy chain comprises a heavy chain variable regions comprising an amino acid sequence selected from SEQ ID NOs: 7, 15, 23, 31, 39, 47, 63, 67, 71, 75, and 79.

In some embodiments, an antibody that binds NOTUM comprises a heavy chain and a light chain, wherein the light chain comprises at least one CDR selected from: a) a CDR1 comprising an amino acid sequence selected from SEQ ID NOs: 12, 20, 28, 36, 44, 52, and 92; b) a CDR2 comprising an amino acid sequence selected from SEQ ID NOs: 13, 21, 29, 37, 45, 53, 61, and 93; and c) a CDR3 comprising an amino acid sequence selected from SEQ ID NOs: 14, 22, 30, 38, 46, 54, and 62. In some embodiments, the light chain comprises a set comprising a CDR1, a CDR2, and a CDR3, wherein the set is selected from: a) a set comprising a CDR1 having the amino acid sequence of SEQ ID NO: 12, a CDR2 having the amino acid sequence of SEQ ID NO: 13, and a CDR3 having the amino acid sequence of SEQ ID NO: 14; b) a set comprising a CDR1 having the amino acid sequence of SEQ ID NO: 92, a CDR2 having the amino acid sequence of SEQ ID NO: 93, and a CDR3 having the amino acid sequence of SEQ ID NO: 22; c) a set comprising a CDR1 having the amino acid sequence of SEQ ID NO: 20, a CDR2 having the amino acid sequence of SEQ ID NO: 21, and a CDR3 having the amino acid sequence of SEQ ID NO: 22; d) a set comprising a CDR1 having the amino acid sequence of SEQ ID NO: 92, a CDR2 having the amino acid sequence of SEQ ID NO: 93, and a CDR3 having the amino acid sequence of SEQ ID NO: 30; e) a set comprising a CDR1 having the amino acid sequence of SEQ ID NO: 28, a CDR2 having the amino acid sequence of SEQ ID NO: 29, and a CDR3 having the amino acid sequence of SEQ ID NO: 30; f) a set comprising a CDR1 having the amino acid sequence of SEQ ID NO: 92, a CDR2 having the amino acid sequence of SEQ ID NO: 93, and a CDR3 having the amino acid sequence of SEQ ID NO: 38; g) a set comprising a CDR1 having the amino acid sequence of SEQ ID NO: 36, a CDR2 having the amino acid sequence of SEQ ID NO: 37, and a CDR3 having the amino acid sequence of SEQ ID NO: 38; h) a set comprising a CDR1 having the amino acid sequence of SEQ ID NO: 44, a CDR2 having the amino acid sequence of SEQ ID NO: 45, and a CDR3 having the amino acid sequence of SEQ ID NO: 46; i) a set comprising a CDR1 having the amino acid sequence of SEQ ID NO: 52, a CDR2 having the amino acid sequence of SEQ ID NO: 53, and a CDR3 having the amino acid sequence of SEQ ID NO: 54; and j) a set comprising a CDR1 having the amino acid sequence of SEQ ID NO: 60, a CDR2 having the amino acid sequence of SEQ ID NO: 61, and a CDR3 having the amino acid sequence of SEQ ID NO: 62. In some embodiments, the light chain comprises a light chain variable regions comprising an amino acid sequence selected from SEQ ID NOs: 8, 16, 24, 32, 40, 48, 56, 65, 69, 73, 77, and 81.

In some embodiments, an antibody that binds NOTUM comprises a heavy chain variable region and a light chain variable region, wherein: a) the heavy chain variable region comprises a CDR1 having the amino acid sequence of SEQ ID NO: 9, a CDR2 having the amino acid sequence of SEQ ID NO: 10, and a CDR3 having the amino acid sequence of SEQ ID NO: 11, and wherein the light chain variable region comprises a CDR1 having the amino acid sequence of SEQ ID NO: 12, a CDR2 having the amino acid sequence of SEQ ID NO: 13, and a CDR3 having the amino acid sequence of SEQ ID NO: 14; or b) the heavy chain variable region comprises a CDR1 having the amino acid sequence of SEQ ID NO: 90, a CDR2 having the amino acid sequence of SEQ ID NO: 18, and a CDR3 having the amino acid sequence of SEQ ID NO: 91, and wherein the light chain variable region comprises a CDR1 having the amino acid sequence of SEQ ID NO: 92, a CDR2 having the amino acid sequence of SEQ ID NO: 93, and a CDR3 having the amino acid sequence of SEQ ID NO: 22; or c) the heavy chain variable region comprises a CDR1 having the amino acid sequence of SEQ ID NO: 17, a CDR2 having the amino acid sequence of SEQ ID NO: 18, and a CDR3 having the amino acid sequence of SEQ ID NO: 19, and the light chain variable region comprises a CDR1 having the amino acid sequence of SEQ ID NO: 20, a CDR2 having the amino acid sequence of SEQ ID NO: 21, and a CDR3 having the amino acid sequence of SEQ ID NO: 22; or d) the heavy chain variable region comprises a CDR1 having the amino acid sequence of SEQ ID NO: 90, a CDR2 having the amino acid sequence of SEQ ID NO: 26, and a CDR3 having the amino acid sequence of SEQ ID NO: 27, and wherein the light chain variable region comprises a CDR1 having the amino acid sequence of SEQ ID NO: 92, a CDR2 having the amino acid sequence of SEQ ID NO: 93, and a CDR3 having the amino acid sequence of SEQ ID NO: 30; or e) the heavy chain variable region comprises a CDR1 having the amino acid sequence of SEQ ID NO: 25, a CDR2 having the amino acid sequence of SEQ ID NO: 26, and a CDR3 having the amino acid sequence of SEQ ID NO: 27, and wherein the light chain variable region comprises a CDR1 having the amino acid sequence of SEQ ID NO: 28, a CDR2 having the amino acid sequence of SEQ ID NO: 29, and a CDR3 having the amino acid sequence of SEQ ID NO: 30; or f) the heavy chain variable region comprises a CDR1 having the amino acid sequence of SEQ ID NO: 90, a CDR2 having the amino acid sequence of SEQ ID NO: 34, and a CDR3 having the amino acid sequence of SEQ ID NO: 91, and wherein the light chain variable region comprises a CDR1 having the amino acid sequence of SEQ ID NO: 92, a CDR2 having the amino acid sequence of SEQ ID NO: 93, and a CDR3 having the amino acid sequence of SEQ ID NO: 38; or g) the heavy chain variable region comprises a CDR1 having the amino acid sequence of SEQ ID NO: 33, a CDR2 having the amino acid sequence of SEQ ID NO: 34, and a CDR3 having the amino acid sequence of SEQ ID NO: 35, and the light chain variable region comprises a CDR1 having the amino acid sequence of SEQ ID NO: 36, a CDR2 having the amino acid sequence of SEQ ID NO: 37, and a CDR3 having the amino acid sequence of SEQ ID NO: 38; or h) the heavy chain variable region comprises a CDR1 having the amino acid sequence of SEQ ID NO: 41, a CDR2 having the amino acid sequence of SEQ ID NO: 42, and a CDR3 having the amino acid sequence of SEQ ID NO: 43, and wherein the light chain variable region comprises a CDR1 having the amino acid sequence of SEQ ID NO: 44, a CDR2 having the amino acid sequence of SEQ ID NO: 45, and a CDR3 having the amino acid sequence of SEQ ID NO: 46; or i) the heavy chain variable region comprises a CDR1 having the amino acid sequence of SEQ ID NO: 49, a CDR2 having the amino acid sequence of SEQ ID NO: 50, and a CDR3 having the amino acid sequence of SEQ ID NO: 51, and wherein the light chain variable region comprises a CDR1 having the amino acid sequence of SEQ ID NO: 52, a CDR2 having the amino acid sequence of SEQ ID NO: 53, and a CDR3 having the amino acid sequence of SEQ ID NO: 54; or j) the heavy chain variable region comprises a CDR1 having the amino acid sequence of SEQ ID NO: 57, a CDR2 having the amino acid sequence of SEQ ID NO: 58, and a CDR3 having the amino acid sequence of SEQ ID NO: 59, and wherein the light chain variable region comprises a CDR1 having the amino acid sequence of SEQ ID NO: 60, a CDR2 having the amino acid sequence of SEQ ID NO: 61, and a CDR3 having the amino acid sequence of SEQ ID NO: 62.

In some embodiments, an antibody that binds NOTUM comprises a heavy chain variable region and a light chain variable region, wherein a) the heavy chain variable region comprises the amino acid sequence of SEQ ID NO: 7 and the light chain variable region comprises the amino acid sequence of SEQ ID NO: 8; or b) the heavy chain variable region comprises the amino acid sequence of SEQ ID NO: 15 and the light chain variable region comprises the amino acid sequence of SEQ ID NO: 16; or c) the heavy chain variable region comprises the amino acid sequence of SEQ ID NO: 71 and the light chain variable region comprises the amino acid sequence of SEQ ID NO: 73; or d) the heavy chain comprises the amino acid sequence of SEQ ID NO: 72 and the light chain comprises the amino acid sequence of SEQ ID NO: 74; or e) the heavy chain variable region comprises the amino acid sequence of SEQ ID NO: 23 and the light chain variable region comprises the amino acid sequence of SEQ ID NO: 24; or f) the heavy chain variable region comprises the amino acid sequence of SEQ ID NO: 75 and the light chain variable region comprises the amino acid sequence of SEQ ID NO: 77; or g) the heavy chain comprises the amino acid sequence of SEQ ID NO: 76 and the light chain comprises the amino acid sequence of SEQ ID NO: 78; or h) the heavy chain variable region comprises the amino acid sequence of SEQ ID NO: 31 and the light chain variable region comprises the amino acid sequence of SEQ ID NO: 32; or i) the heavy chain variable region comprises the amino acid sequence of SEQ ID NO: 79 and the light chain variable region comprises the amino acid sequence of SEQ ID NO: 81; or j) the heavy chain comprises the amino acid sequence of SEQ ID NO: 80 and the light chain comprises the amino acid sequence of SEQ ID NO: 82; or k) the heavy chain variable region comprises the amino acid sequence of SEQ ID NO: 39 and the light chain variable region comprises the amino acid sequence of SEQ ID NO: 40; or l) the heavy chain variable region comprises the amino acid sequence of SEQ ID NO: 67 and the light chain variable region comprises the amino acid sequence of SEQ ID NO: 69; or m) the heavy chain comprises the amino acid sequence of SEQ ID NO: 68 and the light chain comprises the amino acid sequence of SEQ ID NO: 70; or n) the heavy chain variable region comprises the amino acid sequence of SEQ ID NO: 47 and the light chain variable region comprises the amino acid sequence of SEQ ID NO: 48; or o) the heavy chain variable region comprises the amino acid sequence of SEQ ID NO: 55 and the light chain variable region comprises the amino acid sequence of SEQ ID NO: 56; or p) the heavy chain variable region comprises the amino acid sequence of SEQ ID NO: 63 and the light chain variable region comprises the amino acid sequence of SEQ ID NO: 65; or q) the heavy chain comprises the amino acid sequence of SEQ ID NO: 64 and the light chain comprises the amino acid sequence of SEQ ID NO: 66.

In some embodiments, a nucleic acid molecule is provided that comprises a polynucleotide sequence that encodes a heavy chain or a light chain of an antibody that binds NOTUM and neutralizes at least one activity of NOTUM. In some embodiments, the nucleic acid molecule comprises a first polynucleotide sequence that encodes the heavy chain, and a second polynucleotide sequence that encodes the light chain. In some embodiments, the nucleic acid molecule is a vector. In some embodiments, a host cell comprising a nucleic acid molecule that comprises a polynucleotide sequence that encodes a heavy chain or a light chain of an antibody that binds NOTUM and neutralizes at least one activity of NOTUM is provided. In some embodiments, a host cell comprising a nucleic acid molecule that comprises a first polynucleotide sequence that encodes a heavy chain, and a second polynucleotide sequence that encodes a light chain, is provided. In some embodiments, a host cell comprises a first nucleic acid molecule comprising a polynucleotide sequence that encodes a heavy chain, and a second nucleic acid molecule comprising a polynucleotide sequence that encodes a light chain. In some embodiments, a method of producing an antibody that binds to NOTUM and neutralizes at least one activity of NOTUM is provided, comprising incubating a host cell under conditions sufficient to express the antibody.

In some embodiments, a pharmaceutical composition comprising an antibody that binds NOTUM and neutralizes at least one activity of NOTUM is provided. In some embodiments, a method of stimulating endocortical bone formation in a patient, comprising administering an effective amount of the pharmaceutical composition is provided. In some embodiments, a method of treating, managing, or preventing a disease or disorder characterized by bone loss in a patient, comprising administering an effective amount of the pharmaceutical composition is provided. In some embodiments, the disease or disorder is osteoporosis. In some embodiments, a single unit dosage form comprising the pharmaceutical composition is provided.

5. BRIEF DESCRIPTION OF THE FIGURES

FIG. 1 provides a graphical representation of differences between the cortical thicknesses of various bone sites in NOTUM homozygous knockout mice ("HOM") and those in their wildtype littermates ("WT").

Figure 2:
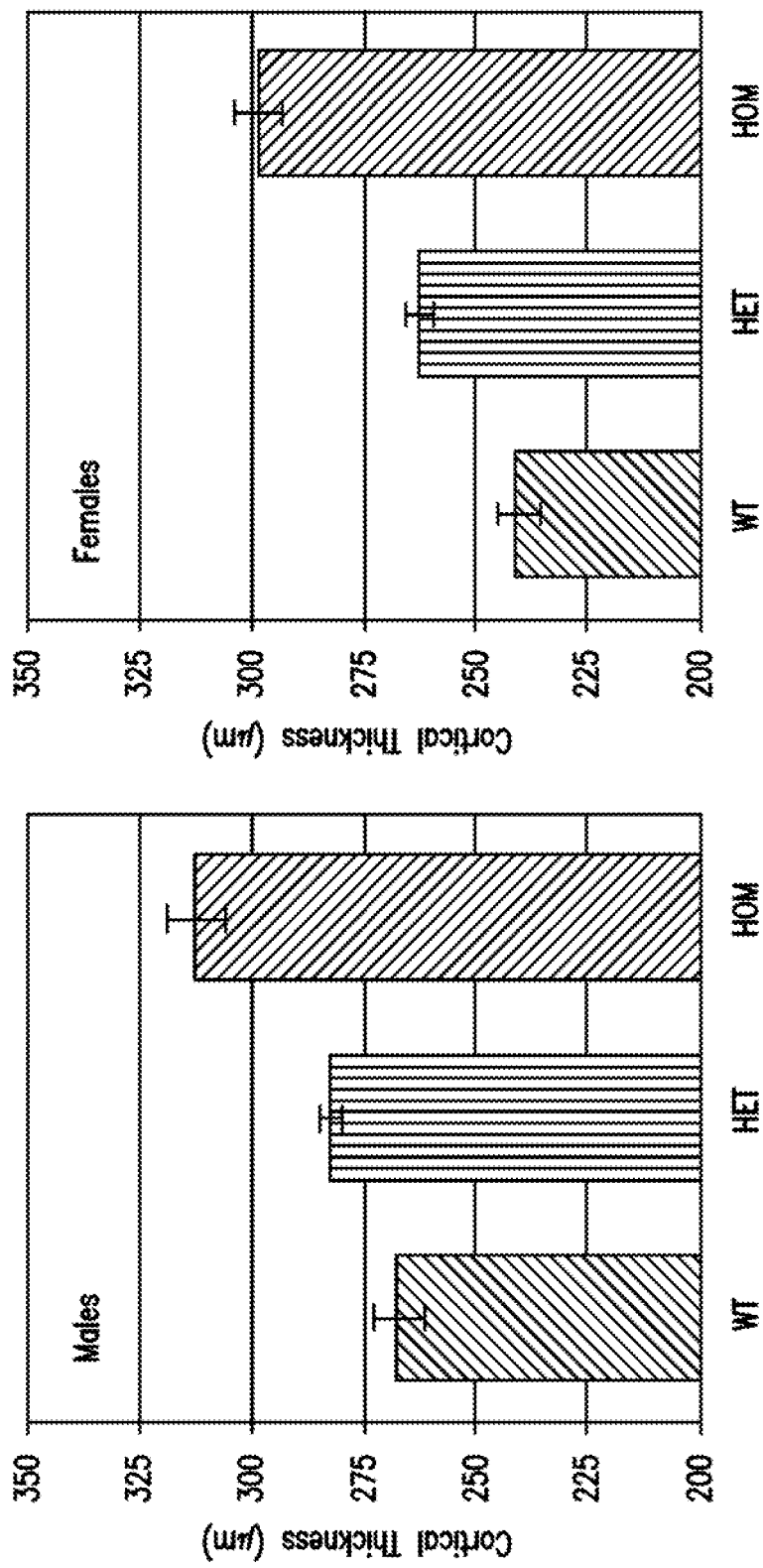

FIG. 2 provides a graphical representation of an increase in cortical bone thicknesses observed in both NOTUM homozygous and heterozygous ("HET") knockout mice as compared to their wildtype littermates.

Figure 3:
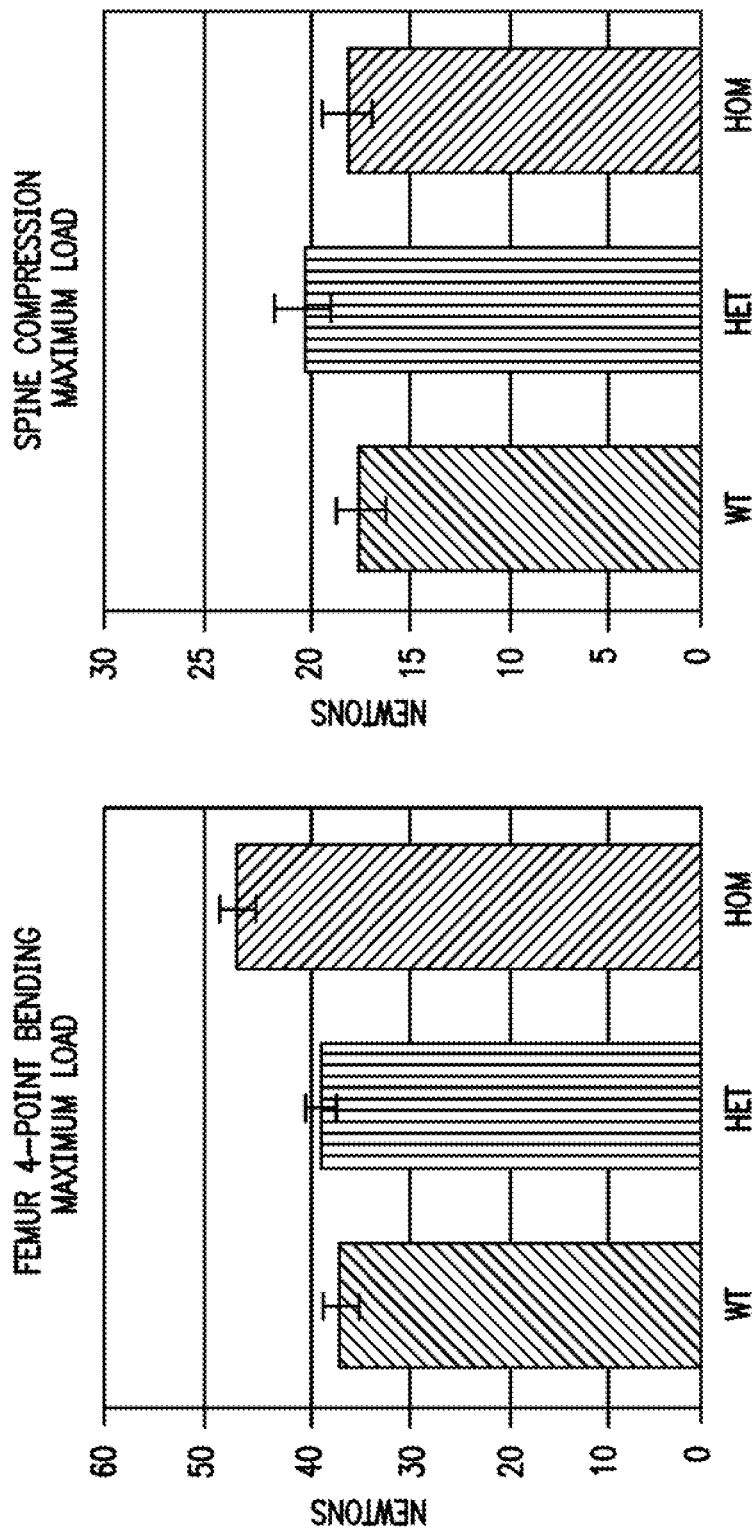

FIG. 3 provides a graphical representation of results obtained from femur breaking strength and spine compression tests performed on the bones of male NOTUM homozygous and heterozygous knockout mice and their wildtype littermates.

Figure 4:
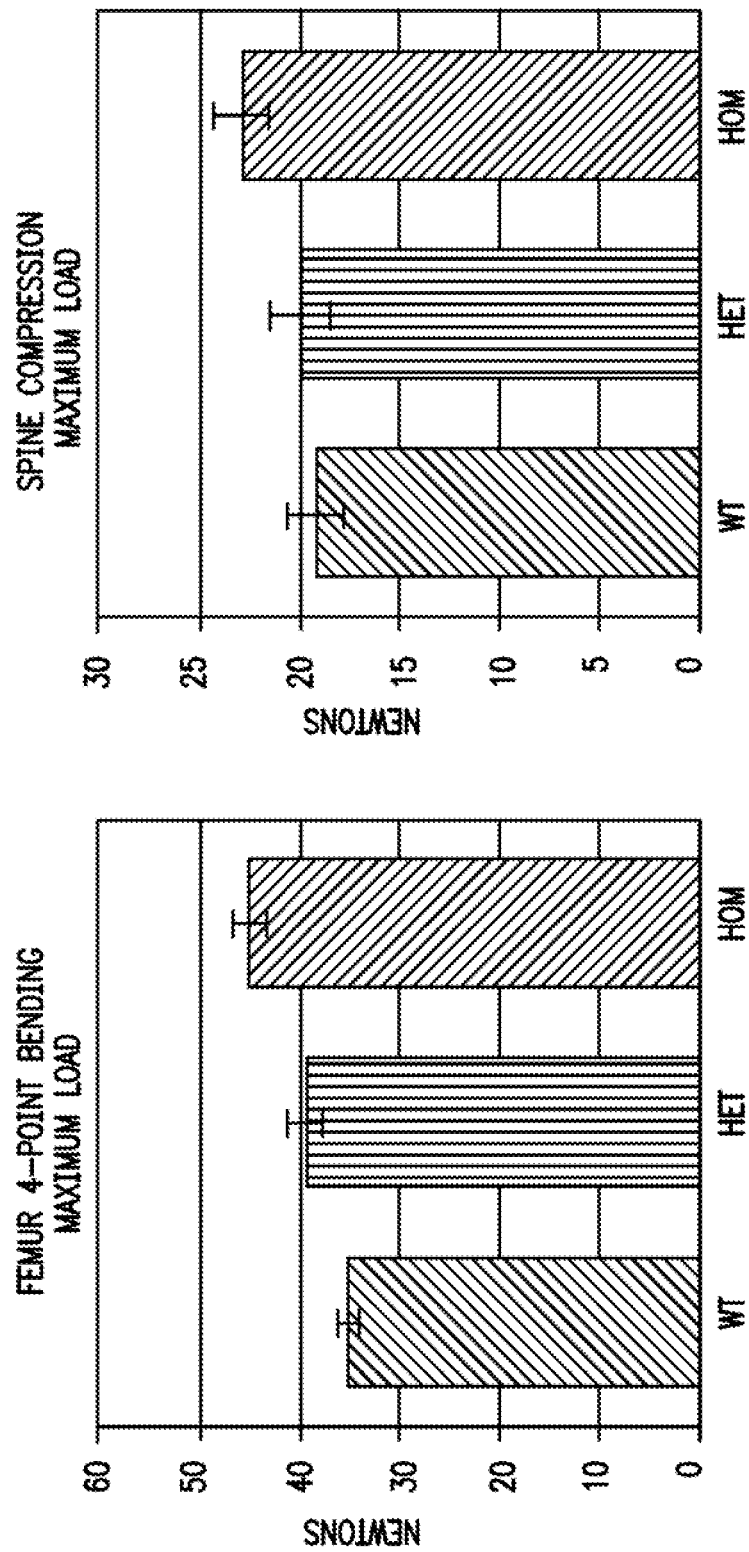
Figure 5:
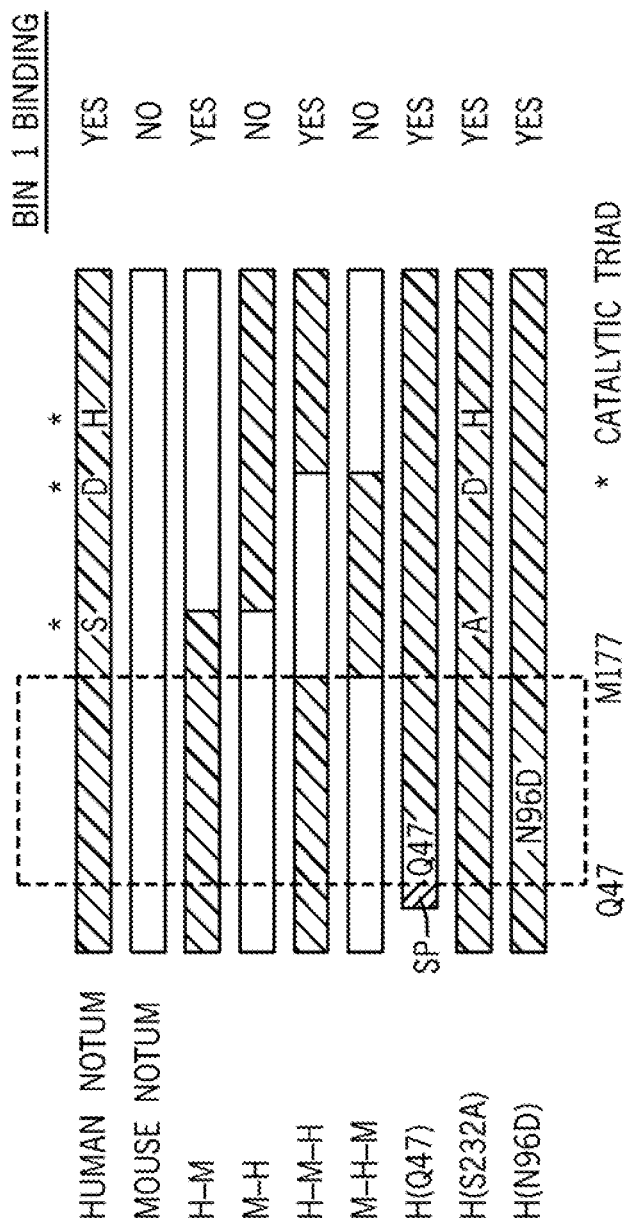

FIG. 4 provides a graphical representation of results obtained from femur breaking strength and spine compression tests performed on the bones of female NOTUM homozygous and heterozygous knockout mice and their wildtype littermates FIG. 5 provides a graphical representation of certain human/mouse chimeric proteins, and indicates a region that appears to be involved in binding of NOTUM neutralizing antibodies in Bin 1, as described in Example 6.7.

Figure 6:
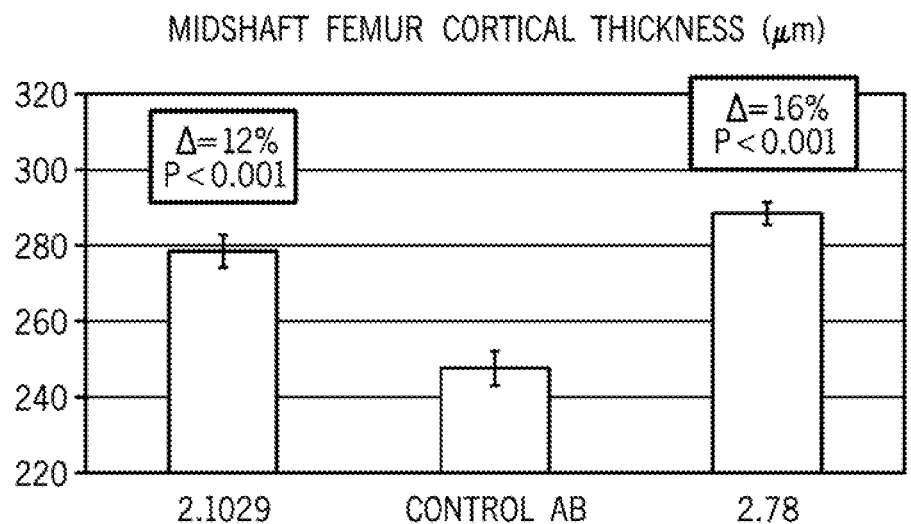

FIG. 6 provides a graphical representation of midshaft femur cortical thickness measurements obtained in mice after eight weeks of administering MAb 2.1029 or MAb 2.78, as described in Example 6.9.1.

Figure 7:
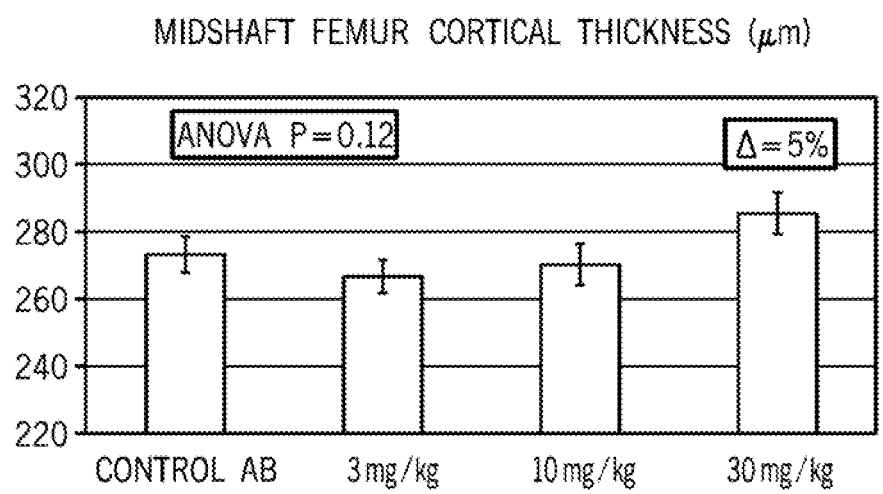

FIG. 7 provides a graphical representation of midshaft femur cortical thickness measurements obtained in mice after four weeks of administering various dosages of MAb 2.1029, as described in Example 6.9.2.

Figure 8A:
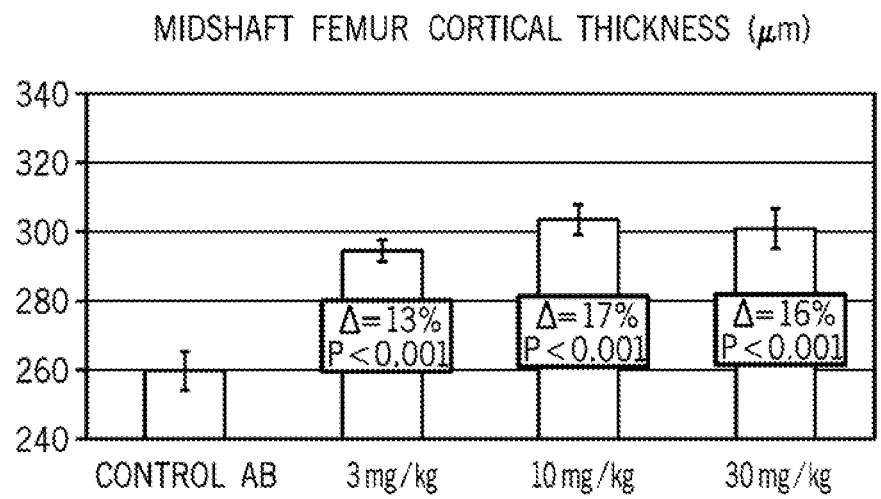
Figure 8B:
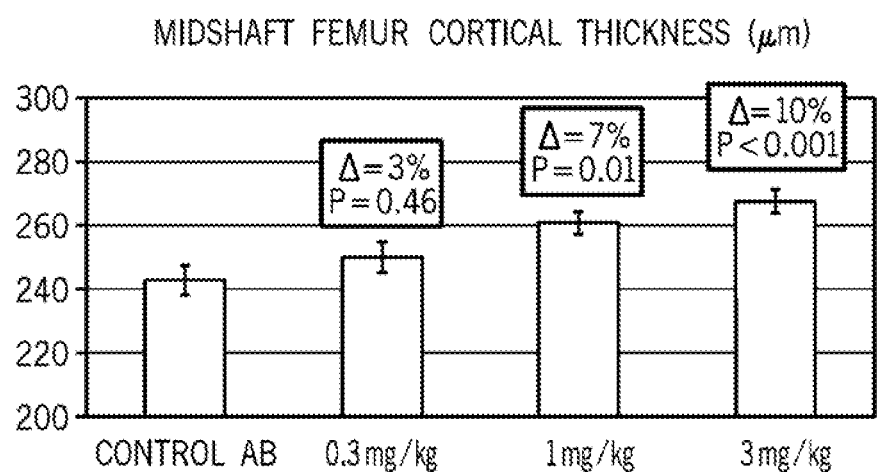

FIGS. 8A-B provide a graphical representation of midshaft femur cortical thickness measurements obtained in mice after four weeks of administering various dosages of MAb 2.78b, as described in Example 6.9.3. FIG. 8A shows 3 mg/kg, 10 mg/kg, and 30 mg/kg dosages of MAb 2.78b. FIG. 8B shows 0.3 mg/kg, 1 mg/kg, and 3 mg/kg dosages of MAb 2.78b.

Figure 9A:
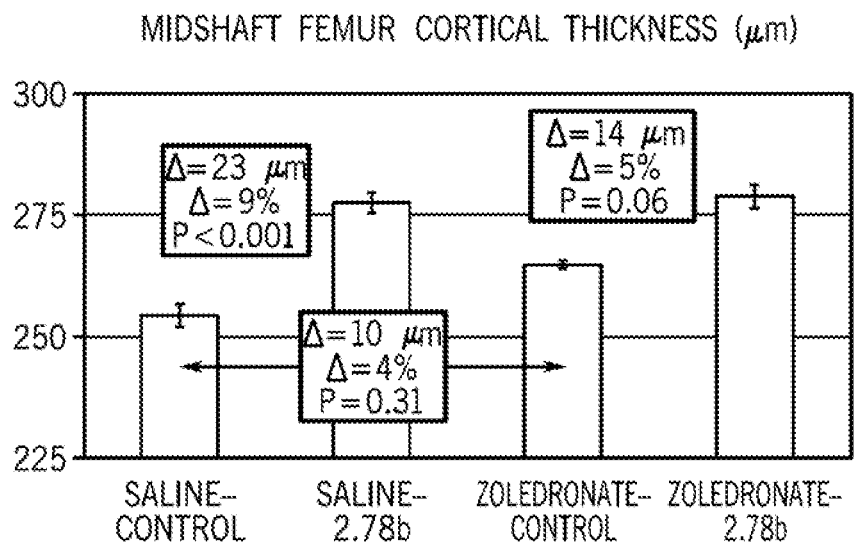
Figure 9B:
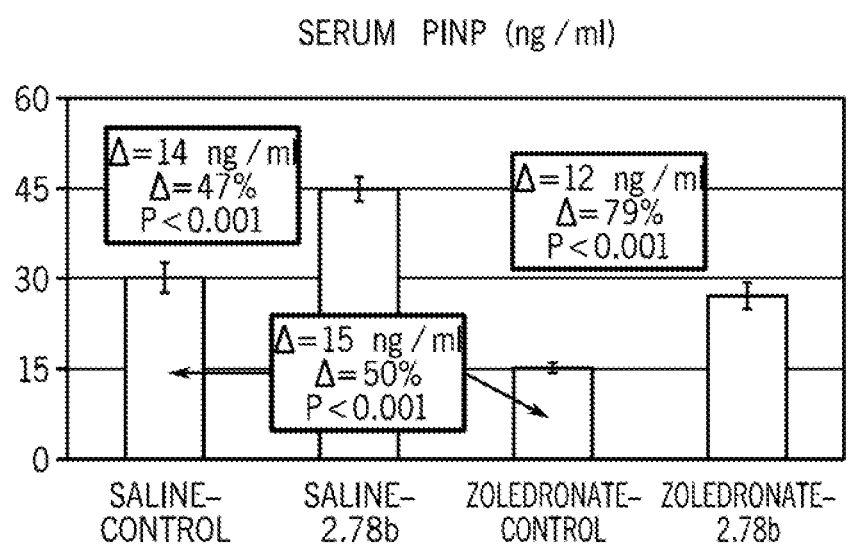

FIGS. 9A-B provide a graphical representation of midshaft femur cortical thickness measurements (A) and serum PINP levels (B) obtained in mice after 4 weeks of administering MAb 2.78b, with and without pretreatment with zoledronate, as described in Example 6.9.4.

Figure 10:
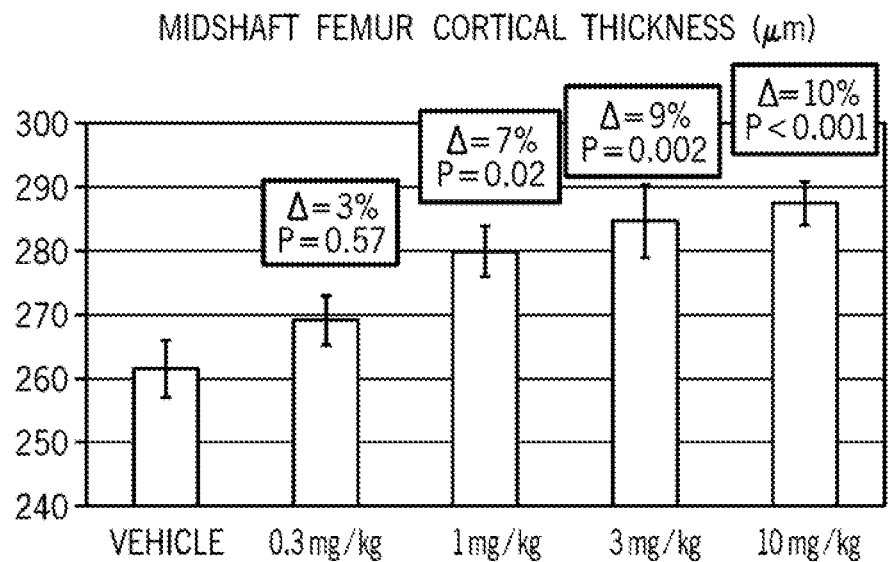

FIG. 10 provides a graphical representation of midshaft femur cortical thickness measurements obtained in mice after 4 weeks of administering MAb 2.78a, as described in Example 6.9.5.

Figure 11A:
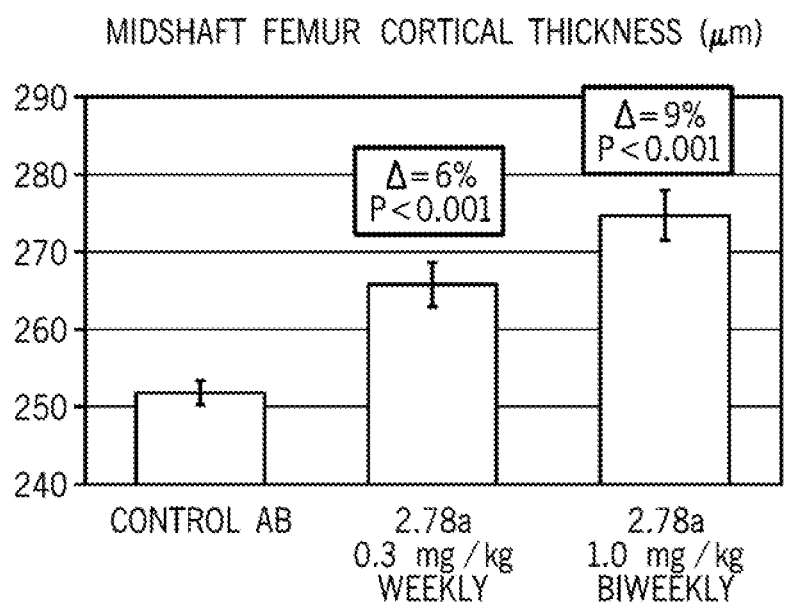
Figure 11B:
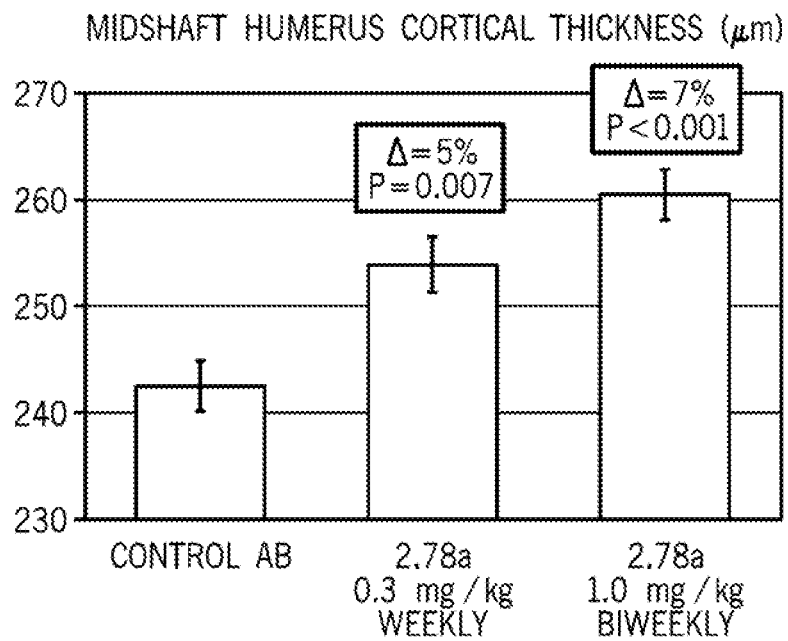

FIGS. 11A-B provide a graphical representation of midshaft femur cortical thickness measurements (A) and midshaft humerus cortical thickness measurements (B) obtained in mice after 12 weeks of administering MAb 2.78a, as described in Example 6.9.6.

Figure 12A:
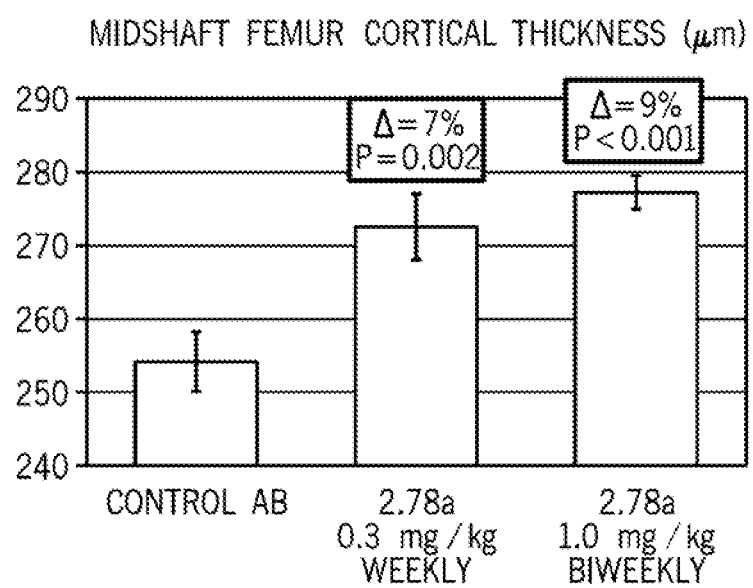
Figure 12B:
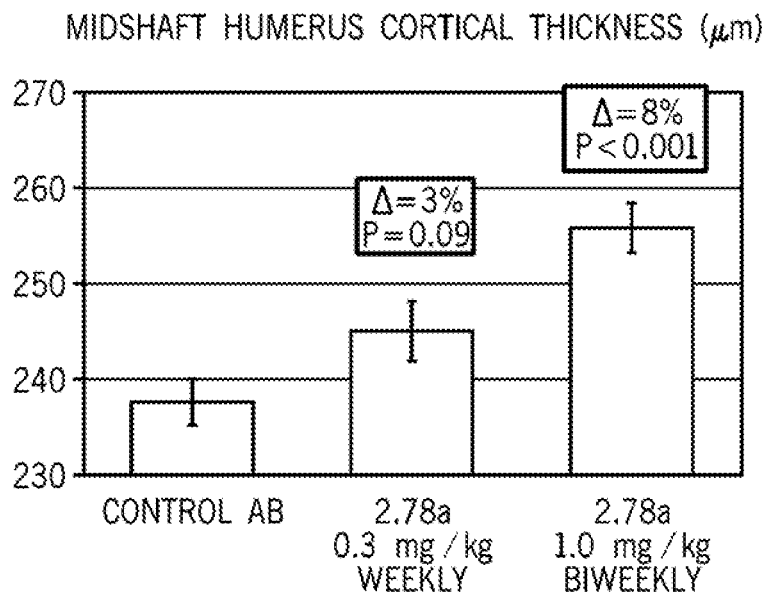
Figure 12C:
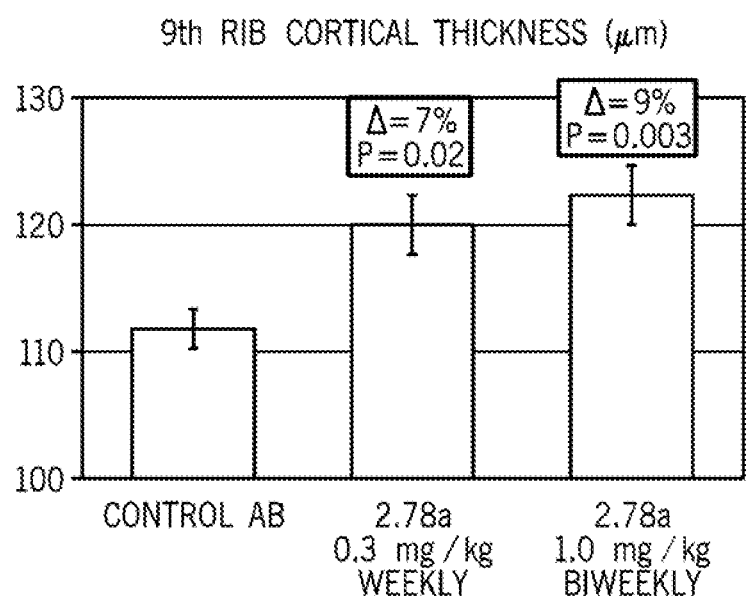

FIGS. 12A-C provide a graphical representation of midshaft femur cortical thickness measurements (A), midshaft humerus cortical thickness measurements (B), and ninth rib cortical thickness (C) obtained in mice after 24 weeks of administering MAb 2.78a, as described in Example 6.9.6.

Figure 13A:
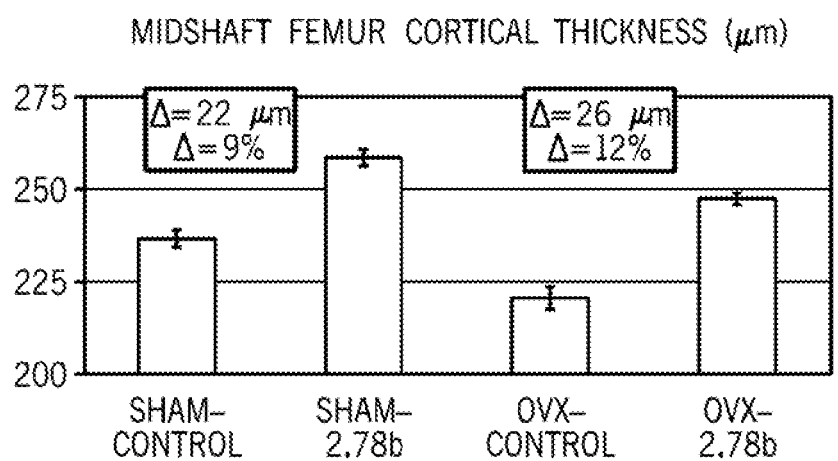
Figure 13B:
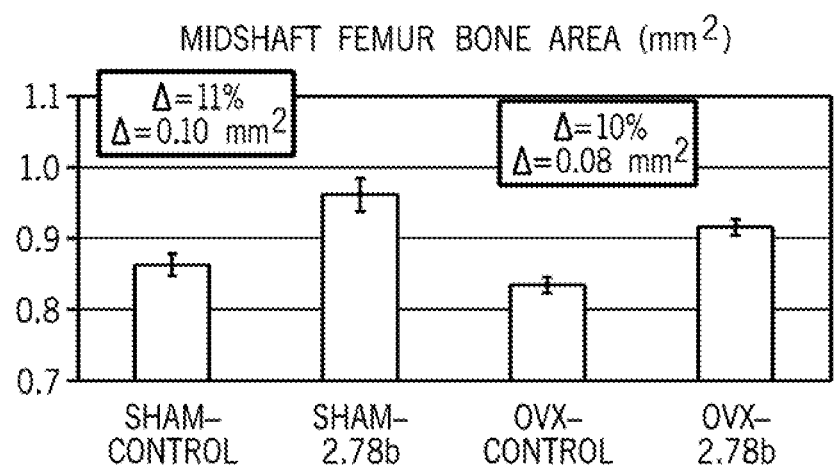

FIGS. 13A-B provide a graphical representation of midshaft femur cortical thickness (A) and midshaft femur mineralized bone area (B) in sham surgery and ovariectomized mice administered NOTUM neutralizing antibody 2.78b or control antibody, as described in Example 6.10.3.

Figure 14A:
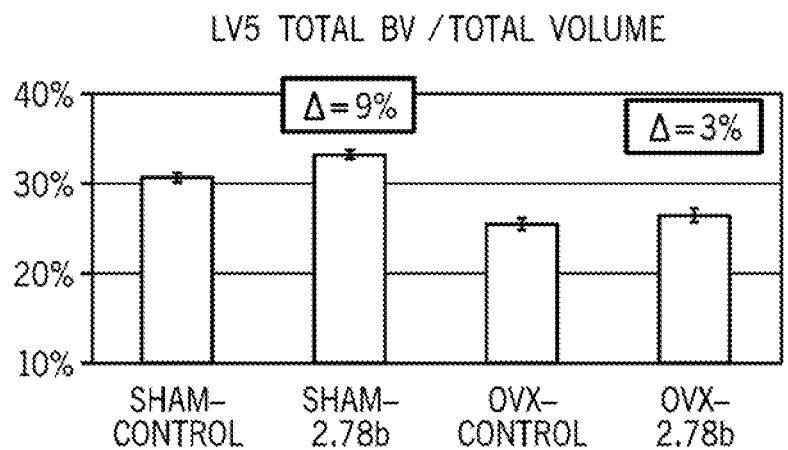
Figure 14B:
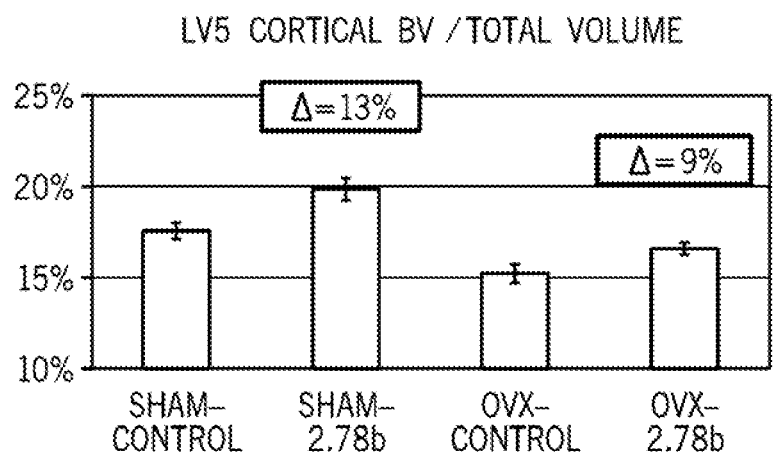
Figure 14C:
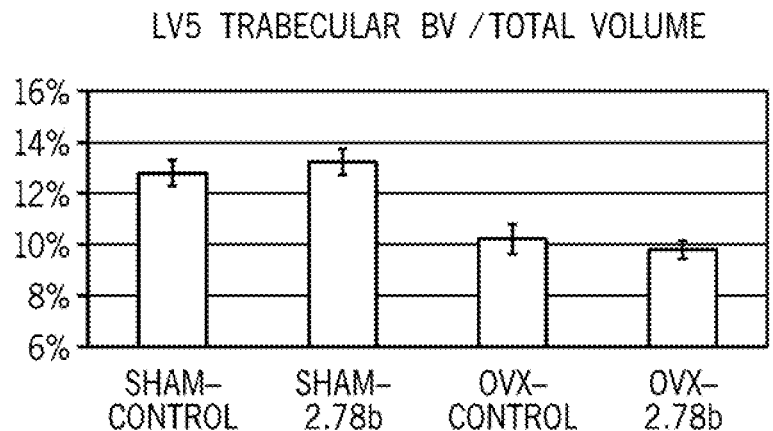

FIGS. 14A-C provide a graphical representation of the proportion in the LV5 vertebral body of bone volume to total volume (A), the proportion in the LV5 vertebral body of cortical bone volume to total volume (B), and the proportion in the LV5 vertebral body of trabecular bone volume to total volume (C) in sham surgery and ovariectomized mice administered NOTUM neutralizing antibody 2.78b or control antibody, as described in Example 6.10.3.

Figure 15:
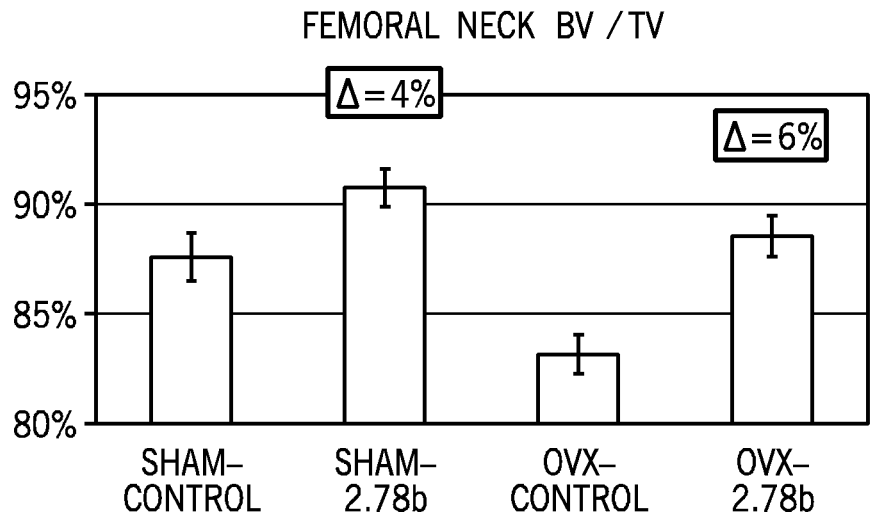

FIG. 15 provides a graphical representation of the proportion of femoral neck bone volume to total volume in sham surgery and ovariectomized mice administered NOTUM neutralizing antibody 2.78b or control antibody, as described in Example 6.10.3.

Figure 16:
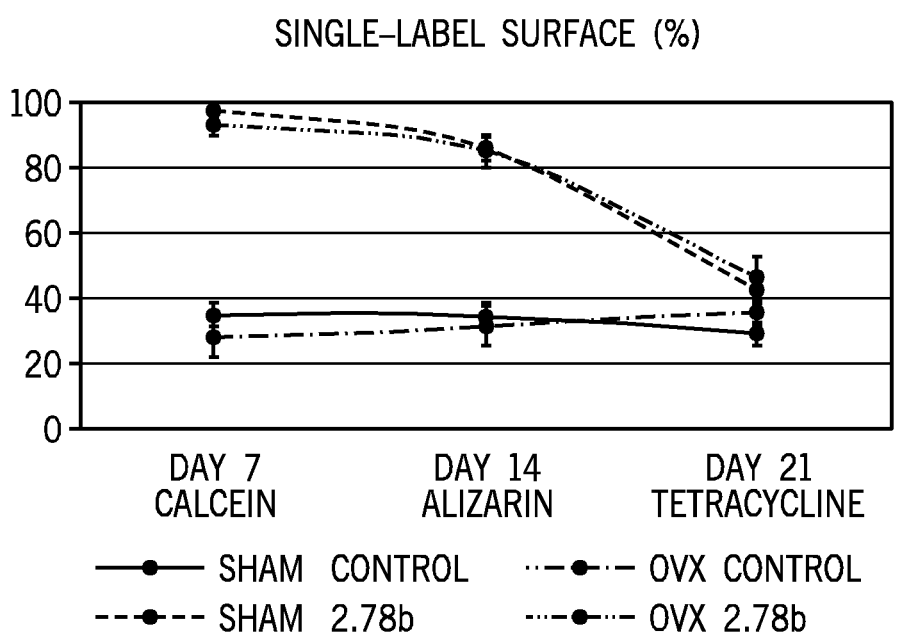

FIG. 16 provides a graphical representation of the percentage of the endocortical surface of the midshaft femur cross-sections that were labeled with calcein, alizarin, and tetracycline in sham surgery and ovariectomized mice administered NOTUM neutralizing antibody 2.78b or control antibody, as described in Example 6.10.4.

Figure 17A:
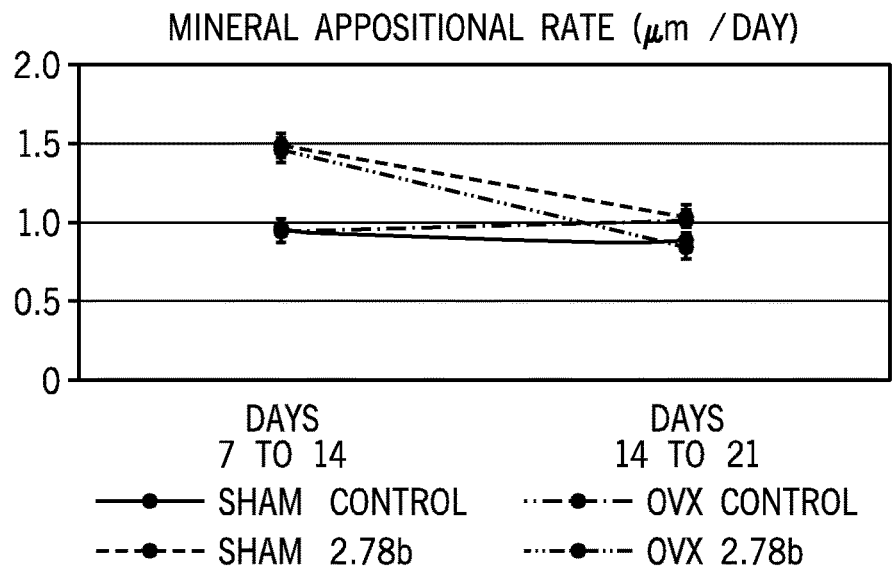
Figure 17B:
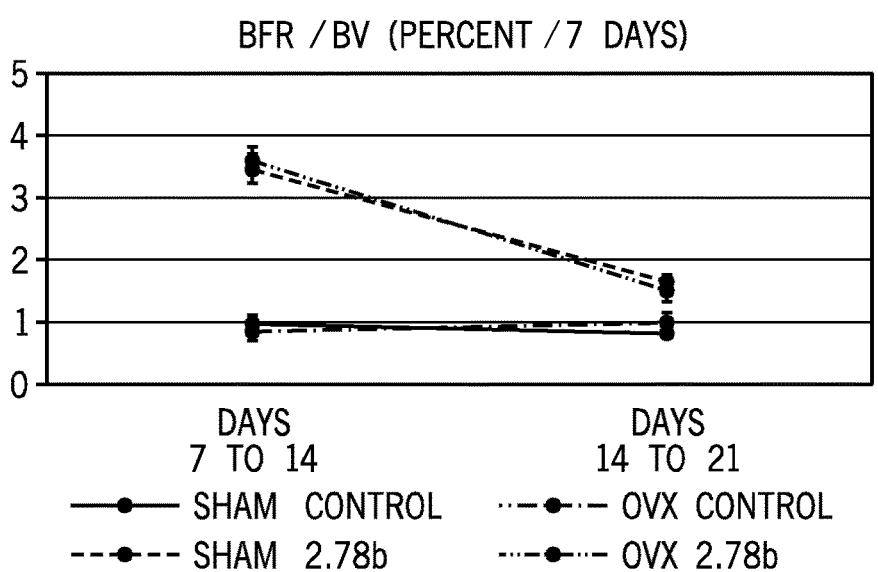

FIGS. 17A-B provide a graphical representation of the mineral apositional rate (A) and the volume-referent bone formation rate (B) in sham surgery and ovariectomized mice administered NOTUM neutralizing antibody 2.78b or control antibody, as described in Example 6.10.4.

6. DETAILED DESCRIPTION OF THE INVENTION

This invention is based, in part, on the discovery that inhibition of NOTUM can affect endocortical bone formation. Particular aspects of the invention are based on studies of mice lacking a functional NOTUM gene ("knockout mice"), on the development of antibodies that inhibit NOTUM, and on the discovery that such antibodies can be used to stimulate cortical bone formation in mice and rats.

The section headings used herein are for organizational purposes only and are not to be construed as limiting the subject matter described. All documents, or portions of documents, cited in this application, including patents, patent applications, articles, books, and treatises are hereby expressly incorporated by reference in their entirety for any purpose. In the event that one or more of the incorporated literature and similar materials defines a term that contradicts that term's definition in this application, this application controls.

6.1. Definitions

The term "antibody," as used herein, refers to an intact antibody or a fragment of an antibody that competes with the intact antibody for antigen binding. Antibody fragments include, but are not limited to, Fab, Fab', F(ab')$_2$, Fv, scFv, Fd, diabodies, and other antibody fragments that retain at least a portion of the variable region of an intact antibody. See, e.g., Hudson et al. (2003) *Nat. Med.* 9:129-134. In some embodiments, antibody fragments are produced by enzymatic or chemical cleavage of intact antibodies. In some embodiments, antibody fragments are produced by recombinant DNA techniques.

The term "antigen-binding site" refers to a portion of an antibody capable of specifically binding an antigen. In some embodiments, an antigen-binding site is provided by one or more antibody variable regions.

The term "binding affinity" refers to a qualitative or quantitative determination of the strength with which an antibody binds to an antigen. In some embodiments, the binding affinity is the dissociation constant ($K_D$) of the antibody for the antigen. In some embodiments, the binding affinity of an antibody for an antigen is determined qualitatively, such as relative to the binding affinity of a different antibody for an antigen, or relative to the binding affinity of the same antibody for a different antigen (such as the antigen with one or more changes in its amino acid sequence). The binding affinity of an antibody for a first antigen is considered "stronger" than its affinity for a second antigen, for example, when the $K_D$ of the antibody for the first antigen is lower than the $K_D$ of the antibody for the second antigen. In some embodiments, the binding affinity of an antibody for a first antigen is considered "stronger" when the $K_D$ of the antibody for the first antigen is at least 1.5-fold, at least 2-fold, at least 3-fold, at least 5-fold, or at least 10-fold lower than the $K_D$ of the antibody for the second antigen. Conversely, the binding affinity of an antibody for a first antigen is considered "weaker" than its affinity for a second antigen, for example, when the $K_D$ of the antibody for the first antigen is higher than the $K_D$ of the antibody for the second antigen. In some embodiments, the binding affinity of an antibody for a first antigen is considered "weaker" when the $K_D$ of the antibody for the first antigen is at least 1.5-fold, at least 2-fold, at least 3-fold, at least 5-fold, or at least 10-fold higher than the $K_D$ of the antibody for the second antigen.

A "chimeric" antibody refers to an antibody made up of components from at least two different sources. In some embodiments, a chimeric antibody comprises a portion of an antibody derived from a first species fused to another molecule, e.g., a portion of an antibody derived from a second species. In some such embodiments, a chimeric antibody comprises a portion of an antibody derived from a non-human animal fused to a portion of an antibody derived from a human. In some such embodiments, a chimeric antibody comprises all or a portion of a variable region of an antibody derived from a non-human animal fused to a constant region of an antibody derived from a human.

The term "epitope" refers to any polypeptide determinant capable of specifically binding to an immunoglobulin or a T-cell receptor. In some embodiments, an epitope is a region of an antigen that is specifically bound by an antibody. In some embodiments, an epitope may include chemically active surface groupings of molecules such as amino acids, sugar side chains, phosphoryl, or sulfonyl groups. In some embodiments, an epitope may have specific three dimensional structural characteristics (e.g., a "conformational" epitope) and/or specific charge characteristics.

An epitope is defined as "the same" as another epitope if a particular antibody specifically binds to both epitopes. In some embodiments, polypeptides having different primary amino acid sequences may comprise epitopes that are the same. Different antibodies are said to bind to the same epitope if they compete for specific binding to that epitope.

A "fragment" of a reference polypeptide refers to a contiguous stretch of amino acids from any portion of the reference polypeptide. A fragment may be of any length that is less than the length of the reference polypeptide. In some embodiments, a fragment is a contiguous stretch of amino acids from any portion of the reference polypeptide that has a particular activity or contains a particular epitope.

The term "human antibody" refers to a monoclonal antibody that contains human antibody sequences and does not contain antibody sequences from a non-human animal. In some embodiments, a human antibody may contain synthetic sequences not found in native antibodies. The term is not limited by the manner in which the antibodies are made. For example, in various embodiments, a human antibody may be made in a transgenic mouse, by phage display, by human B-lymphocytes, or by recombinant methods.

A "humanized" antibody refers to a non-human antibody that has been modified so that it more closely matches (in amino acid sequence) a human antibody. A humanized antibody is thus a type of chimeric antibody. In some embodiments, amino acid residues outside of the antigen binding residues of the variable region of the non-human antibody are modified. In some embodiments, a humanized antibody is constructed by replacing all or a portion of one or more complementarity determining region (CDRs) of a human antibody with all or a portion of one or more CDRs from another antibody, such as a non-human antibody, having the desired antigen binding specificity. In some embodiments, a humanized antibody comprises variable regions in which all or substantially all of the CDRs correspond to CDRs of a non-human antibody and all or substantially all of the framework regions (FRs) correspond to FRs of a human antibody. In some embodiments, one or more amino acids within one or more CDRs of the non-human antibody are changed in the humanized antibody, e.g., through a process of affinity maturation. Exemplary methods of affinity maturation are known in the art. In some such embodiments, a humanized antibody further comprises a constant region (Fc) of a human antibody.

Unless otherwise indicated, the term "include" has the same meaning as "include, but are not limited to," the term "includes" has the same meaning as "includes, but is not limited to," and the term "including" has the same meaning as "including, but not limited to." Similarly, the term "such as" has the same meaning as the term "such as, but not limited to."

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

The term "monoclonal antibody" refers to an antibody from a substantially homogeneous population of antibodies that specifically bind to the same epitope. In some embodiments, a monoclonal antibody is secreted by a hybridoma. In some such embodiments, a hybridoma is produced according to some methods known to those skilled in the art. See, e.g., Kohler and Milstein (1975) Nature 256: 495-499. In some embodiments, a monoclonal antibody is produced using recombinant DNA methods (see, e.g., U.S. Pat. No. 4,816,567). In some embodiments, a monoclonal antibody refers to an antibody fragment isolated from a phage display library. See, e.g., Clackson et al. (1991) Nature 352: 624-628, and Marks et al. (1991) J. Mol. Biol. 222: 581-597. For various other monoclonal antibody production techniques, see, e.g., Harlow and Lane (1988) Antibodies: A Laboratory Manual (Cold Spring Harbor Laboratory, Cold Spring Harbor, N.Y.).

The term "neutralizing antibody" or "antibody that neutralizes" refers to an antibody that reduces at least one activity of a polypeptide comprising the epitope to which the antibody specifically binds. In some embodiments, a neutralizing antibody reduces an activity of the polypeptide in vitro and/or in vivo.

The term "NOTUM" refers to notum pectinaceylesterase having an amino acid sequence from any vertebrate or mammalian source, including human, bovine, chicken, rodent, mouse, rat, porcine, ovine, primate, monkey, and guinea pig, unless specified otherwise. The term also refers to fragments and variants of native NOTUM that maintain at least one in vivo or in vitro activity of a native NOTUM. The term encompasses full-length unprocessed precursor forms of NOTUM as well as mature forms resulting from post-translational cleavage of a signal peptide and other forms of proteolytic processing. In some embodiments, a full-length, unprocessed human NOTUM has the amino acid sequence set forth in SEQ ID NO: 1. In some embodiments, a full-length, unprocessed mouse NOTUM has the amino acid sequence set forth in SEQ ID NO: 2.

The terms "polypeptide," "peptide," and "protein" are used interchangeably herein to refer to a polymer of amino acid residues. The terms apply to amino acid polymers containing naturally occurring amino acids as well as amino acid polymers in which one or more amino acid residues is an artificial chemical analogue of a corresponding naturally occurring amino acid. The amino acid polymers can be of any length. The term "native polypeptide" refers to a naturally occurring polypeptide.

Unless otherwise indicated, the terms "prevent," "preventing" and "prevention" contemplate an action that occurs before a patient begins to suffer from the specified disease or disorder, which inhibits or reduces the severity of the disease or disorder. In other words, the terms encompass prophylaxis.

Unless otherwise indicated, a "prophylactically effective amount" of a compound is an amount sufficient to prevent a disease or condition, or one or more symptoms associated with the disease or condition, or prevent its recurrence. A "prophylactically effective amount" of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

An antibody "specifically binds" an antigen when it preferentially recognizes the antigen in a complex mixture of proteins and/or macromolecules. In some embodiments, an antibody comprises an antigen-binding site that specifically binds to a particular epitope. In some such embodiments, the antibody is capable of binding different antigens so long as the different antigens comprise that particular epitope. In some instances, for example, homologous proteins from different species may comprise the same epitope. In some embodiments, an antibody is said to specifically bind an antigen when the dissociation constant ($K_D$) is ≤1 µM, in some embodiments, when the dissociation constant is ≤100 nM, and in some embodiments, when the dissociation constant is ≤10 nM.

The terms "subject" and "patient" include both humans and animals. In some embodiments, a subject or patient is a mammal. In some such embodiments, a subject or patient is a human.

Unless otherwise indicated, a "therapeutically effective amount" of a compound is an amount sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder, or retards or slows the progression of the disease or disorder.

6.2. Antibodies

6.2.1. Exemplary Antibody Structure

A native antibody typically has a tetrameric structure. A tetramer typically comprises two identical pairs of polypeptide chains, each pair having one light chain (In some embodiments, about 25 kDa) and one heavy chain (In some embodiments, about 50-70 kDa). In a native antibody, a heavy chain comprises a variable region, VH, and three constant regions, CH1, CH2, and CH3. The VH domain is at the amino-terminus of the heavy chain, and the CH3 domain is at the carboxy-terminus. In a native antibody, a light chain comprises a variable region, VL, and a constant region, CL. The variable region of the light chain is at the amino-terminus of the light chain. In a native antibody, the variable regions of each light/heavy chain pair typically form the antigen binding site. The constant regions are typically responsible for effector function.

Native human light chains are typically classified as kappa and lambda light chains. Native human heavy chains are typically classified as mu, delta, gamma, alpha, or epsilon, and define the antibody's isotype as IgM, IgD, IgG, IgA, and IgE, respectively. IgG has subclasses, including IgG1, IgG2, IgG3, and IgG4. IgM has subclasses including IgM1 and IgM2. IgA has subclasses including IgA1 and IgA2. Within native human light and heavy chains, the variable and constant regions are typically joined by a "J" region of about 12 or more amino acids, with the heavy chain also including a "D" region of about 10 more amino acids. See, e.g., Fundamental Immunology (1989) Ch. 7 (Paul, W., ed., 2nd ed. Raven Press, N.Y.).

In a native antibody, the variable regions typically exhibit the same general structure in which relatively conserved framework regions (FRs) are joined by three hypervariable regions, also called complementarity determining regions (CDRs). The CDRs from the two chains of each pair typically are aligned by the framework regions, which may enable binding to a specific epitope. From N-terminus to C-terminus, both light and heavy chain variable regions typically comprise the domains FR1, CDR1, FR2, CDR2, FR3, CDR3 and FR4. The CDRs on the heavy chain are referred to as H1, H2, and H3, while the CDRs on the light chain are referred to as L1, L2, and L3. Typically, CDR3 is the greatest source of molecular diversity within the antigen binding site. H3, for example, in certain instances, can be as short as two amino acid residues or greater than 26. The assignment of amino acids to each domain is typically in accordance with the definitions of Kabat et al. (1991) Sequences of Proteins of Immunological Interest (National Institutes of Health, Publication No. 91-3242, vols. 1-3, Bethesda, Md.); Chothia, C., and Lesk, A. M. (1987) J. Mol. Biol. 196:901-917; or Chothia, C. et al. Nature 342:878-883 (1989). In the present application, the term "CDR" refers to a CDR from either the light or heavy chain, unless otherwise specified.

A "Fab" fragment comprises one light chain and the CH1 and variable region of one heavy chain. The heavy chain of a Fab molecule cannot form a disulfide bond with another heavy chain molecule. A "Fab'" fragment comprises one light chain and one heavy chain that comprises additional constant region, extending between the CH1 and CH2 domains. An interchain disulfide bond can be formed between two heavy chains of a Fab' fragment to form a "F(ab')2" molecule.

An "Fv" fragment comprises the variable regions from both the heavy and light chains, but lacks the constant regions. A single-chain Fv (scFv) fragment comprises heavy and light chain variable regions connected by a flexible linker to form a single polypeptide chain with an antigen-binding region. Exemplary single chain antibodies are discussed in detail in WO 88/01649 and U.S. Pat. Nos. 4,946,778 and 5,260,203. In certain instances, a single variable region (i.e., a heavy chain variable region or a light chain variable region) may have the ability to recognize and bind antigen.

As used herein, the term "heavy chain" refers to a polypeptide comprising sufficient heavy chain variable region sequence to confer antigen specificity either alone or in combination with a light chain.

As used herein, the term "light chain" refers to a polypeptide comprising sufficient light chain variable region sequence to confer antigen specificity either alone or in combination with a heavy chain.

6.2.2. Exemplary Antibodies

In some embodiments, monoclonal antibodies that specifically bind to NOTUM are provided. In some such embodiments, the monoclonal antibodies are neutralizing antibodies that reduce at least one activity of NOTUM in vivo and/or in vitro.

In some embodiments, a neutralizing antibody against NOTUM reduces NOTUM activity in a trisodium 8-octanoyloxypyrene-1,3,6-trisulfonate (OPTS) assay in vitro. In some embodiments, a neutralizing antibody against NOTUM reduces NOTUM activity in a Wnt signaling assay in vitro.

In some embodiments, a neutralizing antibody against NOTUM increases serum PINP levels in vivo when administered to a subject in a sufficient amount and for a sufficient duration. Exemplary dosages and dosing schedules for administering a sufficient amount for a sufficient duration are discussed herein. In some embodiments, a neutralizing antibody against NOTUM increases bone mineral density. In some embodiments, a neutralizing antibody against NOTUM increases midshaft femur cortical thickness in vivo. In some embodiments, a neutralizing antibody against NOTUM increases midshaft femur bone area in vivo. In some embodiments, a neutralizing antibody against NOTUM increases midshaft humerus cortical thickness in vivo. In some embodiments, a neutralizing antibody against NOTUM increases endocortical bone formation in vivo. In some embodiments, a neutralizing antibody against NOTUM increases the proportion of cortical bone volume in the LV5 vertebral body in vivo. By "proportion of cortical bone volume in the LV5 vertebral body" is meant the proportion of cortical bone volume to total volume of the LV5 vertebral body. In some embodiments, a neutralizing antibody against NOTUM increases the proportion of femoral neck bone volume to total volume of the femoral neck in vivo.

In some embodiments, neutralizing antibodies that specifically bind to mouse NOTUM are provided. In some embodiments, neutralizing antibodies that specifically bind to human NOTUM are provided. In some embodiments, neutralizing antibodies that bind to a region from Q47 to M177 of human NOTUM are provided. In some embodiments, neutralizing antibodies that depend upon a region from Q47 to M177 of human NOTUM for binding are provided. In some embodiments, neutralizing antibodies that specifically bind to the same region of NOTUM from different species (i.e., antibodies that demonstrate cross-reactivity) are provided. In some embodiments, neutralizing antibodies that bind to human NOTUM and NOTUM from at least one species selected from mouse, rat, guinea pig, cynomolgus monkey, marmoset, and rhesus macaque, are provided. In some such embodiments, the antibodies specifically bind to both non-human primate NOTUM and human NOTUM. In some embodiments, the antibodies specifically bind to both mouse NOTUM and human NOTUM.

In some embodiments, neutralizing antibodies that bind to a region of human NOTUM from Q47 to M177 are provided. In some embodiments, neutralizing antibodies that depend upon a region of human NOTUM from Q47 to M177 for binding are provided. In some embodiments, NOTUM neutralizing antibodies are provided that bind to human-mouse chimeric NOTUM (SEQ ID NO: 83) with an affinity that is at least 5-fold, at least 10-fold, or at least 20-fold stronger than the affinity for mouse-human chimeric NOTUM (SEQ ID NO: 84). In some embodiments, NOTUM neutralizing antibodies are provided that bind to human-mouse-human chimeric NOTUM (SEQ ID NO: 85) with an affinity that is at least 5-fold, at least 10-fold, or at least 20-fold stronger than the affinity for mouse-human-mouse chimeric NOTUM (SEQ ID NO: 86). In some embodiments, NOTUM neutralizing antibodies are provided that bind to human NOTUM (SEQ ID NO: 1) with an affinity that is at least 5-fold, at least 10-fold, or at least 20-fold stronger than the affinity for NOTUM D141S (SEQ ID NO: 94). In some embodiments, NOTUM neutralizing antibodies are provided that bind to mouse NOTUM S148D (SEQ ID NO: 95) with an affinity that is at least 5-fold, at least 10-fold, or at least 20-fold stronger than the affinity for mouse NOTUM (SEQ ID NO: 2). In some embodiments, NOTUM neutralizing antibodies are provided that bind to human NOTUM (SEQ ID NO: 1) with an affinity that is at least 5-fold, at least 10-fold, or at least 20-fold stronger than the affinity for human NOTUM R144A/R145A (SEQ ID NO: 99).

In some embodiments, a neutralizing antibody against NOTUM binds to human NOTUM (SEQ ID NO: 1) with an affinity ($K_D$) of less than 100 nM, less than 50 nM, less than 40 nM, less than 30 nM, less than 25 nM, less than 20 nM, less than 15 nM, less than 10 nM, less than 5 nM, less than 3 nM, or less than 2 nM, determined as described in Example 6.8. In some embodiments, a neutralizing antibody against NOTUM has an $IC_{50}$ in an OPTS assay of less than 100 nM, less than 75 nM, less than 50 nM, less than 40 nM, less than 30 nM, less than 25 nM, less than 20 nM, less than 15 nM, or less than 10 nM, determined as described in Example 6.4.1. In some embodiments, a neutralizing antibody against NOTUM has an $IC_{50}$ in a Wnt signaling assay of less than 100 nM, less than 75 nM, less than 50 nM, less than 40 nM, less than 30 nM, less than 25 nM, less than 20 nM, less than 15 nM, or less than 10 nM, determined as described in Example 6.4.2. In some embodiments, the $IC_{50}$ is for human NOTUM. In some embodiments, the $IC_{50}$ is for mouse NOTUM.

In some embodiments, neutralizing antibodies are non-human monoclonal antibodies. In some such embodiments, neutralizing antibodies are rodent monoclonal antibodies. In some such embodiments, neutralizing antibodies are mouse monoclonal antibodies. In some embodiments, neutralizing antibodies are chimeric monoclonal antibodies. In some embodiments, neutralizing antibodies are humanized monoclonal antibodies. In some embodiments, neutralizing antibodies are human monoclonal antibodies. In some embodiments, chimeric, humanized, and/or human monoclonal antibodies are useful as therapeutic antibodies in humans.

In some embodiments, neutralizing antibodies are antibody fragments. Exemplary antibody fragments include, but are not limited to, Fab, Fab', F(ab')$_2$, Fv, scFv, Fd, diabodies, and the like.

Nonlimiting exemplary NOTUM neutralizing antibodies include MAbs 1.731, 1.802, 1.815, 1.846, 2.1029, 2.55, and 2.78. Each of MAbs 1.731, 1.802, 1.815, 1.846, 2.1029, 2.55, and 2.78 neutralizes at least one activity of NOTUM. Further, at least MAbs 1.802, 1.815, 1.846, and 2.78 are dependent for binding to NOTUM on at least a portion of the region of human NOTUM bounded by amino acids Q47 to M177. In some embodiments, a NOTUM neutralizing antibody competes for binding to NOTUM with at least one antibody selected from MAbs 1.731, 1.802, 1.815, 1.846, 2.1029, 2.55, and 2.78. In some embodiments, a NOTUM neutralizing antibody binds to an epitope of NOTUM that at least partially overlaps with the epitope bound by at least one antibody selected from MAbs 1.731, 1.802, 1.815, 1.846, 2.1029, 2.55, and 2.78. In addition, in some embodiments, an antibody that competes for binding to NOTUM with at least one antibody selected from MAbs 1.731, 1.802, 1.815, 1.846, 2.1029, 2.55, and 2.78 is predicted to be a NOTUM neutralizing antibody. The sequences of the CDRs and variable regions of MAbs 1.731, 1.802, 1.815, 1.846, 2.1029, 2.55, and 2.78 are shown in Section 7, below.

In some embodiments, NOTUM neutralizing antibodies are provided that bind to the same epitope to which MAb 1.731 binds. In some embodiments, NOTUM neutralizing antibodies are provided that bind to the same epitope to which MAb 1.802 binds. In some embodiments, NOTUM neutralizing antibodies are provided that bind to the same epitope to which MAb 1.815 binds. In some embodiments, NOTUM neutralizing antibodies are provided that bind to the same epitope to which MAb 1.846 binds. In some embodiments, NOTUM neutralizing antibodies are provided that bind to the same epitope to which MAb 2.1029 binds. In some embodiments, NOTUM neutralizing antibodies are provided that bind to the same epitope to which MAb 2.55 binds. In some embodiments, NOTUM neutralizing antibodies are provided that bind to the same epitope to which MAb 2.78 binds.

In some embodiments, a NOTUM neutralizing antibody comprises a heavy chain variable region selected from SEQ ID NOs: 7, 15, 23, 31, 39, and 47. In some embodiments, a NOTUM neutralizing antibody comprises a light chain variable region selected from SEQ ID NOs: 8, 16, 24, 32, 40, and 48. In some embodiments, a NOTUM neutralizing antibody comprises a heavy chain variable region having the amino acid sequence of SEQ ID NO: 7, and a light chain variable region having the amino acid sequence of SEQ ID NO: 8. In some embodiments, a NOTUM neutralizing antibody comprises a heavy chain variable region having the amino acid sequence of SEQ ID NO: 15, and a light chain variable region having the amino acid sequence of SEQ ID NO: 16. In some embodiments, a NOTUM neutralizing antibody comprises a heavy chain variable region having the amino acid sequence of SEQ ID NO: 23, and a light chain variable region having the amino acid sequence of SEQ ID NO: 24. In some embodiments, a NOTUM neutralizing antibody comprises a heavy chain variable region having the amino acid sequence of SEQ ID NO: 31, and a light chain variable region having the amino acid sequence of SEQ ID NO: 32. In some embodiments, a NOTUM neutralizing antibody comprises a heavy chain variable region having the amino acid sequence of SEQ ID NO: 39, and a light chain variable region having the amino acid sequence of SEQ ID NO: 40. In some embodiments, a NOTUM neutralizing antibody comprises a heavy chain variable region having the amino acid sequence of SEQ ID NO: 47, and a light chain variable region having the amino acid sequence of SEQ ID NO: 48.

In some embodiments, a NOTUM neutralizing antibody comprises a heavy chain CDR1 selected from SEQ ID NOs: 9, 17, 25, 33, 41, 49, and 90. In some embodiments, a NOTUM neutralizing antibody comprises a heavy chain CDR2 selected from SEQ ID NOs: 10, 18, 26, 34, 42, and 50. In some embodiments, a NOTUM neutralizing antibody comprises a heavy chain CDR3 selected from SEQ ID NOs: 11, 19, 27, 35, 43, 51, and 91. In some embodiments, a NOTUM neutralizing antibody comprises a heavy chain comprising a CDR1 having the amino acid sequence of SEQ ID NO: 9, a CDR2 having the amino acid sequence of SEQ ID NO: 10, and a CDR3 having the amino acid sequence of SEQ ID NO: 11. In some embodiments, a NOTUM neutralizing antibody comprises a heavy chain comprising a CDR1 having an amino acid sequence selected from SEQ ID NOs: 17 and 90, a CDR2 having the amino acid sequence of SEQ ID NO: 18, and a CDR3 having an amino acid sequence selected from SEQ ID NOs: 19 and 91. In some embodiments, a NOTUM neutralizing antibody comprises a heavy chain comprising a CDR1 having the amino acid sequence of SEQ ID NO: 17, a CDR2 having the amino acid sequence of SEQ ID NO: 18, and a CDR3 having the amino acid sequence of SEQ ID NO: 19. In some embodiments, a NOTUM neutralizing antibody comprises a heavy chain comprising a CDR1 having an amino acid sequence selected from SEQ ID NOs: 25 and 90, a CDR2 having the amino acid sequence of SEQ ID NO: 26, and a CDR3 having the amino acid sequence of SEQ ID NO: 27. In some embodiments, a NOTUM neutralizing antibody comprises a heavy chain comprising a CDR1 having the amino acid sequence of SEQ ID NO: 25, a CDR2 having the amino acid sequence of SEQ ID NO: 26, and a CDR3 having the amino acid sequence of SEQ ID NO: 27. In some embodiments, a NOTUM neutralizing antibody comprises a heavy chain comprising a CDR1 having an amino acid sequence selected from SEQ ID NOs: 33 and 90, a CDR2 having the amino acid sequence of SEQ ID NO: 34, and a CDR3 having an amino acid sequence selected from SEQ ID NOs: 35 and 91. In some embodiments, a NOTUM neutralizing antibody comprises a heavy chain comprising a CDR1 having the amino acid sequence of SEQ ID NO: 33, a CDR2 having the amino acid sequence of SEQ ID NO: 34, and a CDR3 having the amino acid sequence of SEQ ID NO: 35. In some embodiments, a NOTUM neutralizing antibody comprises a heavy chain comprising a CDR1 having the amino acid sequence of SEQ ID NO: 41, a CDR2 having the amino acid sequence of SEQ ID NO: 42, and a CDR3 having the amino acid sequence of SEQ ID NO: 43. In some embodiments, a NOTUM neutralizing antibody comprises a heavy chain comprising a CDR1 having the amino acid sequence of SEQ ID NO: 49, a CDR2 having the amino acid sequence of SEQ ID NO: 50, and a CDR3 having the amino acid sequence of SEQ ID NO: 51. In some embodiments, a NOTUM neutralizing antibody comprises a heavy chain comprising a CDR1 having the amino acid sequence of SEQ ID NO: 57, a CDR2 having the amino acid sequence of SEQ ID NO: 58, and a CDR3 having the amino acid sequence of SEQ ID NO: 59. In some embodiments, $X_1$ in SEQ ID NO: 90 is selected from Y and F. In some embodiments, $X_2$ in SEQ ID NO: 91 is selected from H and N.

In some embodiments, a NOTUM neutralizing antibody comprises a light chain CDR1 selected from SEQ ID NOs: 12, 20, 28, 36, 44, 52, 60, and 92. In some embodiments, a NOTUM neutralizing antibody comprises a light chain CDR2 selected from SEQ ID NOs: 13, 21, 29, 37, 45, 53, 61, and 93. In some embodiments, a NOTUM neutralizing antibody comprises a light chain CDR3 selected from SEQ ID NOs: 14, 22, 30, 38, 46, 54, and 62. In some embodiments, a NOTUM neutralizing antibody comprises a light chain comprising a CDR1 having the amino acid sequence of SEQ ID NO: 12, a CDR2 having the amino acid sequence of SEQ ID NO: 13, and a CDR3 having the amino acid sequence of SEQ ID NO: 14. In some embodiments, a NOTUM neutralizing antibody comprises a light chain comprising a CDR1 having an amino acid sequence selected from SEQ ID NOs: 20 and 92, a CDR2 having an amino acid sequence selected from SEQ ID NOs: 21 and 93, and a CDR3 having the amino acid sequence of SEQ ID NO: 22. In some embodiments, a NOTUM neutralizing antibody comprises a light chain comprising a CDR1 having the amino acid sequence of SEQ ID NO: 20, a CDR2 having the amino acid sequence of SEQ ID NO: 21, and a CDR3 having the amino acid sequence of SEQ ID NO: 22. In some embodiments, a NOTUM neutralizing antibody comprises a light chain comprising a CDR1 having an amino acid sequence selected from SEQ ID NOs: 28 and 92, a CDR2 having an amino acid sequence selected from SEQ ID NOs: 29 and 93, and a CDR3 having the amino acid sequence of SEQ ID NO: 30. In some embodiments, a NOTUM neutralizing antibody comprises a light chain comprising a CDR1 having the amino acid sequence of SEQ ID NO: 28, a CDR2 having the amino acid sequence of SEQ ID NO: 29, and a CDR3 having the amino acid sequence of SEQ ID NO: 30. In some embodiments, a NOTUM neutralizing antibody comprises a light chain comprising a CDR1 having an amino acid sequence selected from SEQ ID NOs: 36 and 92, a CDR2 having an amino acid sequence selected from SEQ ID NOs: 37 and 93, and a CDR3 having the amino acid sequence of SEQ ID NO: 38. In some embodiments, a NOTUM neutralizing antibody comprises a light chain comprising a CDR1 having the amino acid sequence of SEQ ID NO: 36, a CDR2 having the amino acid sequence of SEQ ID NO: 37, and a CDR3 having the amino acid sequence of SEQ ID NO: 38. In some embodiments, a NOTUM neutralizing antibody comprises a light chain comprising a CDR1 having the amino acid sequence of SEQ ID NO: 44, a CDR2 having the amino acid sequence of SEQ ID NO: 45, and a CDR3 having the amino acid sequence of SEQ ID NO: 46. In some embodiments, a NOTUM neutralizing antibody comprises a light chain comprising a CDR1 having the amino acid sequence of SEQ ID NO: 52, a CDR2 having the amino acid sequence of SEQ ID NO: 53, and a CDR3 having the amino acid sequence of SEQ ID NO: 54. In some embodiments, a NOTUM neutralizing antibody comprises a light chain comprising a CDR1 having the amino acid sequence of SEQ ID NO: 60, a CDR2 having the amino acid sequence of SEQ ID NO: 61, and a CDR3 having the amino acid sequence of SEQ ID NO: 62. In some embodiments, $X_3$ in SEQ ID NO: 92 is selected from I and S; $X_4$ in SEQ ID NO: 92 is selected from T and E; and $X_5$ in SEQ ID NO: 92 is selected from M and I. In some embodiments, $X_6$ in SEQ ID NO: 93 is selected from D and N.

In some embodiments, a NOTUM neutralizing antibody comprises a heavy chain comprising a CDR1 having the amino acid sequence of SEQ ID NO: 9, a CDR2 having the amino acid sequence of SEQ ID NO: 10, and a CDR3 having the amino acid sequence of SEQ ID NO: 11; and a light chain comprising a CDR1 having the amino acid sequence of SEQ ID NO: 12, a CDR2 having the amino acid sequence of SEQ ID NO: 13, and a CDR3 having the amino acid sequence of SEQ ID NO: 14. In some embodiments, a NOTUM neutralizing antibody comprises a heavy chain comprising a CDR1 having an amino acid sequence selected from SEQ ID NOs: 17 and 90, a CDR2 having the amino acid sequence of SEQ ID NO: 18, and a CDR3 having an amino acid sequence selected from SEQ ID NOs: 19 and 91; and a light chain comprising a CDR1 having an amino acid sequence selected from SEQ ID NOs: 20 and 92, a CDR2 having an amino acid sequence selected from SEQ ID NOs: 21 and 93, and a CDR3 having the amino acid sequence of SEQ ID NO: 22. In some embodiments, a NOTUM neutralizing antibody comprises a heavy chain comprising a CDR1 having the amino acid sequence of SEQ ID NO: 17, a CDR2 having the amino acid sequence of SEQ ID NO: 18, and a CDR3 having the amino acid sequence of SEQ ID NO: 19; and a light chain comprising a CDR1 having the amino acid sequence of SEQ ID NO: 20, a CDR2 having the amino acid sequence of SEQ ID NO: 21, and a CDR3 having the amino acid sequence of SEQ ID NO: 22. In some embodiments, a NOTUM neutralizing antibody comprises a heavy chain comprising a CDR1 having an amino acid sequence selected from SEQ ID NOs: 25 and 90, a CDR2 having the amino acid sequence of SEQ ID NO: 26, and a CDR3 having the amino acid sequence of SEQ ID NO: 27; and a light chain comprising a CDR1 having an amino acid sequence selected from SEQ ID NOs: 28 and 92, a CDR2 having an amino acid sequence selected from SEQ ID NOs: 29 and 93, and a CDR3 having the amino acid sequence of SEQ ID NO:

30. In some embodiments, a NOTUM neutralizing antibody comprises a heavy chain comprising a CDR1 having the amino acid sequence of SEQ ID NO: 25, a CDR2 having the amino acid sequence of SEQ ID NO: 26, and a CDR3 having the amino acid sequence of SEQ ID NO: 27; and a light chain comprising a CDR1 having the amino acid sequence of SEQ ID NO: 28, a CDR2 having the amino acid sequence of SEQ ID NO: 29, and a CDR3 having the amino acid sequence of SEQ ID NO: 30. In some embodiments, a NOTUM neutralizing antibody comprises a heavy chain comprising a CDR1 having an amino acid sequence selected from SEQ ID NOs: 33 and 90, a CDR2 having the amino acid sequence of SEQ ID NO: 34, and a CDR3 having an amino acid sequence selected from SEQ ID NOs: 35 and 91; and a light chain comprising a CDR1 having an amino acid sequence selected from SEQ ID NOs: 36 and 92, a CDR2 having an amino acid sequence selected from SEQ ID NOs: 37 and 93, and a CDR3 having the amino acid sequence of SEQ ID NO: 38. In some embodiments, a NOTUM neutralizing antibody comprises a heavy chain comprising a CDR1 having the amino acid sequence of SEQ ID NO: 33, a CDR2 having the amino acid sequence of SEQ ID NO: 34, and a CDR3 having the amino acid sequence of SEQ ID NO: 35; and a light chain comprising a CDR1 having the amino acid sequence of SEQ ID NO: 36, a CDR2 having the amino acid sequence of SEQ ID NO: 37, and a CDR3 having the amino acid sequence of SEQ ID NO: 38. In some embodiments, a NOTUM neutralizing antibody comprises a heavy chain comprising a CDR1 having the amino acid sequence of SEQ ID NO: 41, a CDR2 having the amino acid sequence of SEQ ID NO: 42, and a CDR3 having the amino acid sequence of SEQ ID NO: 43; and a light chain comprising a CDR1 having the amino acid sequence of SEQ ID NO: 44, a CDR2 having the amino acid sequence of SEQ ID NO: 45, and a CDR3 having the amino acid sequence of SEQ ID NO: 46. In some embodiments, a NOTUM neutralizing antibody comprises a heavy chain comprising a CDR1 having the amino acid sequence of SEQ ID NO: 49, a CDR2 having the amino acid sequence of SEQ ID NO: 50, and a CDR3 having the amino acid sequence of SEQ ID NO: 51; and a light chain comprising a CDR1 having the amino acid sequence of SEQ ID NO: 52, a CDR2 having the amino acid sequence of SEQ ID NO: 53, and a CDR3 having the amino acid sequence of SEQ ID NO: 54. In some embodiments, a NOTUM neutralizing antibody comprises a heavy chain comprising a CDR1 having the amino acid sequence of SEQ ID NO: 57, a CDR2 having the amino acid sequence of SEQ ID NO: 58, and a CDR3 having the amino acid sequence of SEQ ID NO: 59; and a light chain comprising a CDR1 having the amino acid sequence of SEQ ID NO: 60, a CDR2 having the amino acid sequence of SEQ ID NO: 61, and a CDR3 having the amino acid sequence of SEQ ID NO: 62. In some embodiments, $X_1$ in SEQ ID NO: 90 is selected from Y and F. In some embodiments, $X_2$ in SEQ ID NO: 91 is selected from H and N. In some embodiments, $X_3$ in SEQ ID NO: 92 is selected from I and S; $X_4$ in SEQ ID NO: 92 is selected from T and E; and $X_5$ in SEQ ID NO: 92 is selected from M and I. In some embodiments, $X_6$ in SEQ ID NO: 93 is selected from D and N.

In some embodiments, NOTUM neutralizing antibodies that specifically bind human NOTUM are provided. In some embodiments, NOTUM neutralizing antibodies that specifically bind to the same epitope in NOTUM from different species (i.e., antibodies that demonstrate cross-reactivity) are provided. In some embodiments, NOTUM neutralizing antibodies that specifically bind human NOTUM and also specifically bind at least one species of NOTUM selected from mouse, rat, guinea pig, cynomolgus monkey, marmoset, and rhesus macaque are provided. In some embodiments, NOTUM neutralizing antibodies that specifically bind human NOTUM and NOTUM from at least one species of non-human primate are provided. In some embodiments, NOTUM neutralizing antibodies that specifically bind human NOTUM and mouse NOTUM are provided.

6.2.2.1. Chimerized and Humanized Monoclonal Antibodies

In some embodiments, non-human antibodies are chimerized. In some embodiments, mouse monoclonal antibodies that specifically bind human NOTUM are chimerized. Certain exemplary methods for making chimeric antibodies are provided, for example, in Morrison et al. (1984) *Proc. Nat'l Acad. Sci. USA* 81:6851-6855; Neuberger et al. (1984) *Nature* 312:604-608; Takeda et al. (1985) *Nature* 314:452-454; and U.S. Pat. Nos. 6,075,181 and 5,877,397.

In some embodiments, non-human antibodies are "humanized." In some embodiments, mouse monoclonal antibodies that specifically bind human NOTUM are humanized. In some embodiments, mouse monoclonal antibodies raised against mouse NOTUM, but which specifically bind (i.e., cross react) with human NOTUM, are humanized. In some embodiments, humanized antibodies retain their binding specificity and have reduced immunogenicity (e.g., reduced human anti-mouse antibody (HAMA) response) when administered to a human. In some embodiments, humanization is achieved by methods including CDR grafting and human engineering, as described in detail below.

In some embodiments of humanized antibodies, one or more complementarity determining regions (CDRs) from the light and heavy chain variable regions of an antibody with the desired binding specificity (the "donor" antibody) are grafted onto human framework regions (FRs) in an "acceptor" antibody. Exemplary CDR grafting is described, e.g., in U.S. Pat. Nos. 6,180,370, 5,693,762, 5,693,761, 5,585,089, and 5,530,101; Queen et al. (1989) *Proc. Nat'l Acad. Sci. USA* 86:10029-10033. In some embodiments, one or more CDRs from the light and heavy chain variable regions are grafted onto consensus human FRs in an acceptor antibody. To create consensus human FRs, in some embodiments, FRs from several human heavy chain or light chain amino acid sequences are aligned to identify a consensus amino acid sequence.

In some embodiments, certain FR amino acids in the acceptor antibody are replaced with FR amino acids from the donor antibody. In certain such embodiments, FR amino acids from the donor antibody are amino acids that contribute to the affinity of the donor antibody for the target antigen. See, e.g., in U.S. Pat. Nos. 6,180,370, 5,693,762, 5,693,761, 5,585,089, and 5,530,101; Queen et al. (1989) *Proc. Nat'l Acad. Sci. USA* 86:10029-10033. In some embodiments, computer programs are used for modeling donor and/or acceptor antibodies to identify residues that are likely to be involved in binding antigen and/or to contribute to the structure of the antigen binding site, thus assisting in the selection of residues, such as FR residues, to be replaced in the donor antibody.

In some embodiments, CDRs from a donor antibody are grafted onto an acceptor antibody comprising a human constant region. In some such embodiments, FRs are also grafted onto the acceptor. In some embodiments, CDRs from a donor antibody are derived from a single chain Fv antibody. In some embodiments, FRs from a donor antibody are derived from a single chain Fv antibody. In some embodiments, grafted CDRs in a humanized antibody are further modified (e.g., by amino acid substitutions, deletions, or insertions) to increase the affinity of the humanized antibody for the target antigen. In some embodiments, grafted FRs in a humanized antibody are further modified (e.g., by amino acid substitutions, deletions, or insertions) to increase the affinity of the humanized antibody for the target antigen.

In some embodiments, non-human antibodies may be humanized using a "human engineering" method. See, e.g., U.S. Pat. Nos. 5,766,886 and 5,869,619. In some embodiments of human engineering, information on the structure of antibody variable domains (e.g., information obtained from crystal structures and/or molecular modeling) is used to assess the likelihood that a given amino acid residue in a variable region is (a) involved in antigen binding, (b) exposed on the antibody surface (i.e., accessible to solvent), or (c) buried within the antibody variable region (i.e., involved in maintaining the structure of the variable region). Furthermore, in some embodiments, human variable region consensus sequences are generated to identify residues that are conserved among human variable regions. In some embodiments, that information provides guidance as to whether an amino acid residue in the variable region of a non-human antibody should be substituted.

In some embodiments, a humanized NOTUM neutralizing antibody comprises a heavy chain comprising at least one of CDR1, CDR2, and CDR3 of an antibody selected from MAbs 1.731, 1.802, 1.815, 1.846, 2.1029, 2.55, and 2.78. In some embodiments, a NOTUM neutralizing antibody comprises a heavy chain comprising CDR1, CDR2, and CDR3 of an antibody selected from MAbs 1.731, 1.802, 1.815, 1.846, 2.1029, 2.55, and 2.78. In some embodiments, a NOTUM neutralizing antibody comprises a light chain comprising at least one of CDR1, CDR2, and CDR3 of an antibody selected from MAbs 1.731, 1.802, 1.815, 1.846, 2.1029, 2.55, and 2.78. In some embodiments, a NOTUM neutralizing antibody comprises a light chain comprising CDR1, CDR2, and CDR3 of an antibody selected from MAbs 1.731, 1.802, 1.815, 1.846, 2.1029, 2.55, and 2.78. In some embodiments, a NOTUM neutralizing antibody comprises heavy chain CDR1, CDR2, and CDR3, and light chain CDR1, CDR2, and CDR3 from an antibody selected from MAbs 1.731, 1.802, 1.815, 1.846, 2.1029, 2.55, and 2.78.

In some embodiments, a NOTUM neutralizing antibody comprises a heavy chain comprising an amino acid sequence selected from SEQ ID NOs: 63, 67, 71, 75, and 79. In some embodiments, a NOTUM neutralizing antibody comprises a heavy chain comprising an amino acid sequence selected from SEQ ID NOs: 64, 68, 72, 76, and 80. In some embodiments, a NOTUM neutralizing antibody comprises a light chain comprising an amino acid sequence selected from SEQ ID NOs: 65, 69, 73, 77, and 81. In some embodiments, a NOTUM neutralizing antibody comprises a light chain comprising an amino acid sequence selected from SEQ ID NOs: 66, 70, 74, 78, and 82. In some embodiments, a NOTUM neutralizing antibody comprises a heavy chain comprising the amino acid sequence of SEQ ID NO: 63 and a light chain comprising the amino acid sequence of SEQ ID NO: 65. In some embodiments, a NOTUM neutralizing antibody comprises a heavy chain comprising the amino acid sequence of SEQ ID NO: 67 and a light chain comprising the amino acid sequence of SEQ ID NO: 69. In some embodiments, a NOTUM neutralizing antibody comprises a heavy chain comprising the amino acid sequence of SEQ ID NO: 71 and a light chain comprising the amino acid sequence of SEQ ID NO: 73. In some embodiments, a NOTUM neutralizing antibody comprises a heavy chain comprising the amino acid sequence of SEQ ID NO: 75 and a light chain comprising the amino acid sequence of SEQ ID NO: 77. In some embodiments, a NOTUM neutralizing antibody comprises a heavy chain comprising the amino acid sequence of SEQ ID NO: 79 and a light chain comprising the amino acid sequence of SEQ ID NO: 81. In some embodiments, a NOTUM neutralizing antibody comprises a heavy chain comprising the amino acid sequence of SEQ ID NO: 64 and a light chain comprising the amino acid sequence of SEQ ID NO: 66. In some embodiments, a NOTUM neutralizing antibody comprises a heavy chain comprising the amino acid sequence of SEQ ID NO: 68 and a light chain comprising the amino acid sequence of SEQ ID NO: 70. In some embodiments, a NOTUM neutralizing antibody comprises a heavy chain comprising the amino acid sequence of SEQ ID NO: 72 and a light chain comprising the amino acid sequence of SEQ ID NO: 74. In some embodiments, a NOTUM neutralizing antibody comprises a heavy chain comprising the amino acid sequence of SEQ ID NO: 76 and a light chain comprising the amino acid sequence of SEQ ID NO: 78. In some embodiments, a NOTUM neutralizing antibody comprises a heavy chain comprising the amino acid sequence of SEQ ID NO: 80 and a light chain comprising the amino acid sequence of SEQ ID NO: 82.

6.2.2.2. Antibody Isotypes

In some embodiments, an antibody against NOTUM is of any isotype selected from IgM, IgD, IgG, IgA, and IgE. In some embodiments, an antibody against NOTUM is of the IgG isotype. In certain such embodiments, an antibody is of the subclass IgG1, IgG2, IgG3, or IgG4. In some embodiments, an antibody against NOTUM is of the IgM isotype. In certain such embodiments, an antibody is of the subclass IgM1 or IgM2. In some embodiments, an antibody against NOTUM is of the IgA isotype. In certain such embodiments, an antibody is of the subclass IgA1 or IgA2. An antibody against NOTUM may comprise a lambda or kappa light chain constant region of, e.g., either human or mouse origin. In some embodiments, an antibody against NOTUM comprises a human kappa light chain constant region and a human IgG1, IgG2, or IgG4 heavy chain constant region. In some embodiments, an antibody against NOTUM comprises a mouse kappa light chain and a mouse IgG1 or IgG2 heavy chain.

6.2.2.3. Modified Antibodies

In some embodiments, an antibody is modified to alter one or more of its properties. In some embodiments, a modified antibody may possess advantages over an unmodified antibody, such as increased stability, increased time in circulation, or decreased immunogenicity (see, e.g., U.S. Pat. No. 4,179,337). In some embodiments, an antibody is modified by linking it to a nonproteinaceous moiety. In some embodiments, an antibody is modified by altering the glycosylation state of the antibody, e.g., by altering the number, type, linkage, and/or position of carbohydrate chains on the antibody. In some embodiments, an antibody is altered so that it is not glycosylated.

In some embodiments, one or more chemical moieties are linked to the amino acid backbone and/or carbohydrate residues of the antibody. Certain exemplary methods for linking a chemical moiety to an antibody are known to those skilled in the art. Such methods include, but are not limited to, acylation reactions or alkylation reactions. See, e.g, EP 0 401 384; Malik et al. (1992), *Exp. Hematol.*, 20:1028-1035; Francis (1992) *Focus on Growth Factors* 3(2):4-10, published by Mediscript, Mountain Court, Friern Barnet Lane, London N20 OLD, UK; EP 0 154 316; EP 0 401 384; WO 92/16221; WO 95/34326; WO 95/13312; WO 96/11953; WO 96/19459 and WO 96/19459. In some embodiments, any of these reactions are used to generate an antibody that is chemically modified at its amino-terminus.

In some embodiments, an antibody is linked to a detectable label, such as an enzymatic, fluorescent, isotopic or affinity label. In certain such embodiments, a detectable label allows for the detection or isolation of the antibody. In some embodiments, a detectable label allows for the detection of an antigen bound by the antibody.

In some embodiments, an antibody is modified by linking it to one or more polymers. In some embodiments, an antibody is linked to one or more water-soluble polymers. In certain such embodiments, linkage to a water-soluble polymer reduces the likelihood that the antibody will precipitate in an aqueous environment, such as a physiological environment. In some embodiments, a therapeutic antibody is linked to a water-soluble polymer. In some embodiments, one skilled in the art can select a suitable water-soluble polymer based on considerations including whether the polymer/antibody conjugate will be used in the treatment of a patient and, if so, the pharmacological profile of the antibody (e.g., half-life, dosage, activity, antigenicity, and/or other factors).

Certain exemplary clinically acceptable, water-soluble polymers include, but are not limited to, polyethylene glycol (PEG); polyethylene glycol propionaldehyde; copolymers of ethylene glycol/propylene glycol; monomethoxy-polyethylene glycol; carboxymethylcellulose; dextran; polyvinyl alcohol (PVA); polyvinyl pyrrolidone, poly-1, 3-dioxolane; poly-1,3,6-trioxane; ethylene/maleic anhydride copolymer; poly-β-amino acids (either homopolymers or random copolymers); poly(n-vinyl pyrrolidone)polyethylene glycol; polypropylene glycol homopolymers (PPG) and other polyalkylene oxides; polypropylene oxide/ethylene oxide copolymers; polyoxyethylated polyols (POG) (e.g., glycerol) and other polyoxyethylated polyols; polyoxyethylated sorbitol, polyoxyethylated glucose, colonic acids or other carbohydrate polymers; and Ficoll, dextran, or mixtures thereof. Certain exemplary PEGs include, but are not limited to, certain forms known in the art to be useful in antibody modification, such as mono-$(C_1-C_{10})$ alkoxy- or aryloxy-PEG. In some embodiments, PEG propionaldehyde may have advantages in manufacturing due to its stability in water.

In some embodiments, a water-soluble polymer is of any molecular weight. In some embodiments, a water-soluble polymer is branched or unbranched. In some embodiments, a water-soluble polymer has an average molecular weight of about 2 kDa to about 100 kDa, including all points between the end points of the range. In some embodiments, a water-soluble polymer has an average molecular weight of about 5 kDa to about 40 kDa. In some embodiments, a water-soluble polymer has an average molecular weight of about 10 kDa to about 35 kDa. In some embodiments, a water-soluble polymer has an average molecular weight of about 15 kDa to about 30 kDa.

In some embodiments, an antibody is linked to polyethylene glycol (PEG; i.e., an antibody is "pegylated"). In various embodiments, PEG has low toxicity in mammals. See Carpenter et al. (1971) *Toxicol. Appl. Pharmacol.,* 18:35-40. Notably, a PEG adduct of adenosine deaminase was approved in the United States for use in humans for the treatment of severe combined immunodeficiency syndrome. In various embodiments, PEG may reduce the immunogenicity of antibodies. For example, in some embodiments, linkage of PEG to an antibody having non-human sequences may reduce the antigenicity of that antibody when administered to a human.

In some embodiments, a polymer is linked to one or more reactive amino acid residues in an antibody. Certain exemplary reactive amino acid residues include, but are not limited to, the alpha-amino group of the amino-terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, and activated glycosyl chains linked to certain asparagine, serine or threonine residues. Certain exemplary activated forms of PEG ("PEG reagents") suitable for direct reaction with proteins are known to those skilled in the art. For example, in some embodiments, PEG reagents suitable for linkage to amino groups include, but are not limited to, active esters of carboxylic acid or carbonate derivatives of PEG, for example, those in which the leaving groups are N-hydroxysuccinimide, p-nitrophenol, imidazole or 1-hydroxy-2-nitrobenzene-4-sulfonate. In some embodiments, PEG reagents containing maleimido or haloacetyl groups are used to modify sulfhydryl groups. In some embodiments, PEG reagents containing amino, hydrazine and/or hydrazide groups may be used in reactions with aldehydes generated by periodate oxidation of carbohydrate groups in proteins.

In some embodiments, a water-soluble polymer has at least one reactive group. In some embodiments, an activated derivative of a water-soluble polymer, such as PEG, is created by reacting the water-soluble polymer with an activating group. In some embodiments, an activating group may be monofunctional, bifunctional, or multifunctional. Certain exemplary activating groups that can be used to link a water-soluble polymer to two or more antibodies include, but are not limited to, the following groups: sulfone (e.g., chlorosulfone, vinylsulfone and divinylsulfone), maleimide, sulfhydryl, thiol, triflate, tresylate, azidirine, oxirane and 5-pyridyl. In some embodiments, a PEG derivative is typically stable against hydrolysis for extended periods in aqueous environments at pHs of about 11 or less. In some embodiments, a PEG derivative linked to another molecule, such as an antibody, confers stability from hydrolysis on that molecule. Certain exemplary homobifunctional PEG derivatives include, but are not limited to, PEG-bis-chlorosulfone and PEG-bis-vinylsulfone (see WO 95/13312).

6.2.3. Certain Methods of Making Monoclonal Antibodies 6.2.3.1. Certain Hybridoma Methods In some embodiments, monoclonal antibodies are produced by standard techniques. In some embodiments, monoclonal antibodies are produced by hybridoma-based methods. Certain such methods are known to those skilled in the art. See, e.g., Kohler et al. (1975) *Nature* 256:495-497; Harlow and Lane (1988) *Antibodies: A Laboratory Manual* Ch. 6 (Cold Spring Harbor Laboratory, Cold Spring Harbor, N.Y.). In certain such embodiments, a suitable animal, such as a mouse, rat, hamster, monkey, or other mammal, is immunized with an immunogen to produce antibody-secreting cells. In some embodiments, the antibody-secreting cells are B-cells, such as lymphocytes or splenocytes. In some embodiments, lymphocytes (e.g., human lymphocytes) are immunized in vitro to generate antibody-secreting cells. See, e.g., Borreback et al. (1988) *Proc. Nat'l Acad. Sci. USA* 85:3995-3999.

In some embodiments, antibody secreting cells are fused with an "immortalized" cell line, such as a myeloid-type cell line, to produce hybridoma cells. In some embodiments, hybridoma cells that produce the desired antibodies are identified, for example, by ELISA. In some embodiments, such cells can then be subcloned and cultured using standard methods. In some embodiments, such cells can also be grown in vivo as ascites tumors in a suitable animal host. In some embodiments, monoclonal antibodies are isolated from hybridoma culture medium, serum, or ascites fluid using standard separation procedures, such as affinity chromatography. Guidance for the production of hybridomas and the purification of monoclonal antibodies according to certain embodiments is provided, for example, in Harlow and Lane (1988) *Antibodies: A Laboratory Manual* Ch. 8 (Cold Spring Harbor Laboratory, Cold Spring Harbor, N.Y.).

In some embodiments, mouse monoclonal antibodies are produced by immunizing genetically altered mice with an immunogen. In certain such embodiments, the mice are NOTUM-deficient mice, which partially or completely lack NOTUM function. In certain such embodiments, the mice are "knockout" mice that lack all or part of a gene encoding NOTUM. In some embodiments, such knockout mice are immunized with mouse NOTUM. In some embodiments, such knockout mice are immunized with human NOTUM.

In some embodiments, human monoclonal antibodies are raised in transgenic animals (e.g., mice) that are capable of producing human antibodies. See, e.g., U.S. Pat. Nos. 6,075,181 A and 6,114,598 A; and WO 98/24893 A2. For example, in some embodiments, human immunoglobulin genes are introduced (e.g., using yeast artificial chromosomes, human chromosome fragments, or germline integration) into mice in which the endogenous Ig genes have been inactivated. See, e.g., Jakobovits et al. (1993) *Nature* 362:255-258; Tomizuka et al. (2000) *Proc. Nat'l Acad. Sci. USA* 97:722-727; and Mendez et al. (1997) *Nat. Genet.* 15:146-156 (describing the XenoMouse II® line of transgenic mice).

In some embodiments, such transgenic mice are immunized with an immunogen. In certain such embodiments, lymphatic cells (such as B-cells) from mice that express antibodies are obtained. In certain such embodiments, such recovered cells are fused with an "immortalized" cell line, such as a myeloid-type cell line, to produce hybridoma cells. In certain such embodiments, hybridoma cells are screened and selected to identify those that produce antibodies specific to the antigen of interest. Certain exemplary methods and transgenic mice suitable for the production of human monoclonal antibodies are described, e.g., in Jakobovits et al. (1993) *Nature* 362:255-258; Jakobovits (1995) *Curr. Opin. Biotechnol.* 6:561-566; Lonberg et al. (1995) *Int'l Rev. Immunol.* 13:65-93; Fishwild et al. (1996) *Nat. Biotechnol.* 14:845-851; Mendez et al. (1997) *Nat. Genet.* 15:146-156; Green (1999) *J. Immunol. Methods* 231:11-23; Tomizuka et al. (2000) *Proc. Nat'l Acad. Sci. USA* 97:722-727; and reviewed in Little et al. (2000) *Immunol. Today* 21:364-370; and WO 98/24893. In some embodiments, human monoclonal antibodies against NOTUM are suitable for use as therapeutic antibodies. See Part V.G., below.

6.2.3.2. Certain Display-Based Methods

In some embodiments, human monoclonal antibodies are produced using a display-based method, such as, for example, any of those described below.

In some embodiments, a monoclonal antibody is produced using phage display techniques. Various antibody phage display methods are known to those skilled in the art and are described, for example, in Hoogenboom, *Overview of Antibody Phage-Display Technology and Its Applications*, from *Methods in Molecular Biology: Antibody Phage Display: Methods and Protocols* (2002) 178:1-37 (O'Brien and Aitken, eds., Human Press, Totowa, N.J.). For example, in some embodiments, a library of antibodies are displayed on the surface of a filamentous phage, such as the nonlytic filamentous phage fd or M13. In some embodiments, the antibodies are antibody fragments, such as scFvs, Fabs, Fvs with an engineered intermolecular disulfide bond to stabilize the $V_H$-$V_L$ pair, and diabodies. In some embodiments, antibodies with the desired binding specificity can then be selected. Nonlimiting exemplary embodiments of antibody phage display methods are described in further detail below.

In some embodiments, an antibody phage-display library can be prepared using certain methods known to those skilled in the art. See, e.g., Hoogenboom, *Overview of Antibody Phage-Display Technology and Its Applications*, from *Methods in Molecular Biology: Antibody Phage Display: Methods and Protocols* (2002) 178:1-37 (O'Brien and Aitken, eds., Human Press, Totowa, N.J.). In some embodiments, variable gene repertoires are prepared by PCR amplification of genomic DNA or cDNA derived from the mRNA of antibody-secreting cells. For example, in some embodiments, cDNA is prepared from mRNA of B-cells. In some embodiments, cDNA encoding the variable regions of heavy and light chains is amplified, for example, by PCR.

In some embodiments, heavy chain cDNA and light chain cDNA are cloned into a suitable vector. In some embodiments, heavy chain cDNA and light chain cDNA are randomly combined during the cloning process, thereby resulting in the assembly of a cDNA library encoding diverse scFvs or Fabs. In some embodiments, heavy chain cDNA and light chain cDNA are ligated before being cloned into a suitable vector. In some embodiments, heavy chain cDNA and light chain cDNA are ligated by stepwise cloning into a suitable vector.

In some embodiments, cDNA is cloned into a phage display vector, such as a phagemid vector. Certain exemplary phagemid vectors, such as pCES1, are known to those skilled in the art. In some embodiments, cDNA encoding both heavy and light chains is present on the same vector. For example, in some embodiments, cDNA encoding scFvs are cloned in frame with all or a portion of gene III, which encodes the minor phage coat protein pIII. In certain such embodiments, the phagemid directs the expression of the scFv-pIII fusion on the phage surface. Alternatively, in some embodiments, cDNA encoding heavy chain (or light chain) is cloned in frame with all or a portion of gene III, and cDNA encoding light chain (or heavy chain) is cloned downstream of a signal sequence in the same vector. The signal sequence directs expression of the light chain (or heavy chain) into the periplasm of the host cell, where the heavy and light chains assemble into Fab fragments. Alternatively, in some embodiments, cDNA encoding heavy chain and cDNA encoding light chain are present on separate vectors. In certain such embodiments, heavy chain and light chain cDNA is cloned separately, one into a phagemid and the other into a phage vector, which both contain signals for in vivo recombination in the host cell.

In some embodiments, recombinant phagemid or phage vectors are introduced into a suitable bacterial host, such as *E. coli*. In some embodiments using phagemid, the host is infected with helper phage to supply phage structural proteins, thereby allowing expression of phage particles carrying the antibody-pIII fusion protein on the phage surface.

In some embodiments, "synthetic" antibody libraries are constructed using repertoires of variable genes that are rearranged in vitro. For example, in some embodiments, individual gene segments encoding heavy or light chains (V-D-J or V-J, respectively) are randomly combined using PCR. In some embodiments, additional sequence diversity can be introduced into the CDRs, and possibly FRs, e.g., by error prone PCR. In some such embodiments, additional sequence diversity is introduced into CDR3, e.g., H3 of the heavy chain.

In some embodiments, "naïve" or "universal" phage display libraries are constructed as described above using nucleic acid from an unimmunized animal. In some embodiments, the unimmunized animal is a human. In some embodiments, "immunized" phage display libraries are constructed as described above using nucleic acid from an immunized animal. In some embodiments, the immunized animal is a human, rat, mouse, hamster, or monkey. In certain such embodiments, the animals are immunized with any of the immunogens described below.

Certain exemplary universal human antibody phage display libraries are available from commercial sources. Certain exemplary libraries include, but are not limited to, the HuCAL® series of libraries from MorphoSys AG (Martinstreid/Munich, Germany); libraries from Crucell (Leiden, the Netherlands) using MAbstract® technology; the n-CoDeR™ Fab library from BioInvent (Lund, Sweden); and libraries available from Cambridge Antibody Technology (Cambridge, UK).

In some embodiments, the selection of antibodies having the desired binding specificity from a phage display library is achieved by successive panning steps. In some embodiments of panning, library phage preparations are exposed to antigen. In certain such embodiments, the phage-antigen complexes are washed, and unbound phage are discarded. In certain such embodiments, bound phage are recovered and subsequently amplified by infecting *E. coli*. In certain such embodiments, monoclonal antibody-producing phage may be cloned by picking single plaques. In some embodiments, the above process is repeated.

In some embodiments, the antigen used in panning is any of the immunogens described below. In some embodiments, the antigen is immobilized on a solid support to allow purification of antigen-binding phage by affinity chromatography. In some embodiments, the antigen is biotinylated, thereby allowing the separation of bound phage from unbound phage using streptavidin-coated magnetic beads. In some embodiments, the antigen may be immobilized on cells (for direct panning), in tissue cryosections, or on membranes (e.g., nylon or nitrocellulose membranes). Other variations of certain panning procedures may be routinely determined by one skilled in the art.

In some embodiments, a yeast display system is used to produce monoclonal antibodies. In certain such systems, an antibody is expressed as a fusion protein with all or a portion of the yeast AGA2 protein, which becomes displayed on the surface of the yeast cell wall. In certain such embodiments, yeast cells expressing antibodies with the desired binding specificity can then be identified by exposing the cells to fluorescently labeled antigen. In certain such embodiments, yeast cells that bind the antigen can then be isolated by flow cytometry. See, e.g., Boder et al. (1997) *Nat. Biotechnol.* 15:553-557.

6.2.3.3. Certain Affinity Maturation Methods

In some embodiments, the affinity of an antibody for a particular antigen is increased by subjecting the antibody to affinity maturation (or "directed evolution") in vitro. In vivo, native antibodies undergo affinity maturation through somatic hypermutation followed by selection. Some in vitro methods mimic that in vivo process, thereby allowing the production of antibodies having affinities that equal or surpass that of native antibodies.

In some embodiments of affinity maturation, mutations are introduced into a nucleic acid sequence encoding the variable region of an antibody having the desired binding specificity. See, e.g., Hudson et al. (2003) *Nat. Med.* 9:129-134; Brekke et al. (2002) *Nat. Reviews* 2:52-62. In some embodiments, mutations are introduced into the variable region of the heavy chain, light chain, or both. In some embodiments, mutations are introduced into one or more CDRs. In certain such embodiments, mutations are introduced into H3, L3, or both. In some embodiments, mutations are introduced into one or more FRs. In some embodiments, a library of mutations is created, for example, in a phage, ribosome, or yeast display library, so that antibodies with increased affinity may be identified by standard screening methods. See, e.g., Boder et al. (2000) *Proc. Nat'l Acad. Sci. USA* 97:10701-10705; Foote et al. (2000) *Proc. Nat'l Acad. Sci. USA* 97:10679-10681; Hoogenboom, *Overview of Antibody Phage-Display Technology and Its Applications*, from *Methods in Molecular Biology: Antibody Phage Display: Methods and Protocols* (2002) 178:1-37 (O'Brien and Aitken, eds., Human Press, Totowa, N.J.); and Hanes et al. (1998) *Proc. Nat'l Acad. Sci. USA* 95:14130-14135.

In some embodiments, mutations are introduced by site-specific mutagenesis based on information on the antibody's structure, e.g., the antigen binding site. In some embodiments, mutations are introduced using combinatorial mutagenesis of CDRs. In some embodiments, all or a portion of the variable region coding sequence is randomly mutagenized, e.g., using *E. coli* mutator cells, homologous gene rearrangement, or error prone PCR. In some embodiments, mutations are introduced using "DNA shuffling." See, e.g., Crameri et al. (1996) *Nat. Med.* 2:100-102; Fermer et al. (2004) *Tumor Biol.* 25:7-13.

In some embodiments, "chain shuffling" is used to generate antibodies with increased affinity. In some embodiments of chain shuffling, one of the chains, e.g., the light chain, is replaced with a repertoire of light chains, while the other chain, e.g., the heavy chain, is unchanged, thus providing specificity. In certain such embodiments, a library of chain shuffled antibodies is created, wherein the unchanged heavy chain is expressed in combination with each light chain from the repertoire of light chains. In some embodiments, such libraries may then be screened for antibodies with increased affinity. In some embodiments, both the heavy and light chains are sequentially replaced. In some embodiments, only the variable regions of the heavy and/or light chains are replaced. In some embodiments, only a portion of the variable regions, e.g., CDRs, of the heavy and/or light chains are replaced. See, e.g., Hudson et al. (2003) *Nat. Med.* 9:129-134; Brekke et al. (2002) *Nat. Reviews* 2:52-62; Kang et al. (1991) *Proc. Nat'l Acad. Sci. USA* 88:11120-11123; Marks et al. (1992) *Biotechnol.* 10:779-83.

In some embodiments, mouse monoclonal antibodies that specifically bind human NOTUM (including mouse monoclonal antibodies raised against mouse NOTUM but which specifically bind (i.e., cross react) with human NOTUM) are subject to sequential chain shuffling. In some embodiments, for example, the heavy chain of a given mouse monoclonal antibody is combined with a new repertoire of human light chains, and antibodies with the desired affinity are selected. In certain such embodiments, the light chains of the selected antibodies are then combined with a new repertoire of human heavy chains, and antibodies with the desired affinity are selected. Thus, in some embodiments, human antibodies having the desired antigen binding specificity and affinity are selected.

Alternatively, in some embodiments, the heavy chain of a given mouse monoclonal antibody is combined with a new repertoire of human light chains, and antibodies with the desired affinity are selected from this first round of shuffling. In some embodiments, the light chain of the original mouse monoclonal antibody is combined with a new repertoire of human heavy chains, and antibodies with the desired affinity are selected from this second round of shuffling. In some embodiments, human light chains from the antibodies selected in the first round of shuffling are then combined with human heavy chains from the antibodies selected in the second round of shuffling. Thus, in some embodiments, human antibodies having the desired antigen binding specificity and affinity are selected.

In some embodiments, a "ribosome display" method is used that alternates antibody selection with affinity maturation. In some embodiments of a ribosome display method, antibody-encoding nucleic acid is amplified by RT-PCR between the selection steps. Thus, in some embodiments, error prone polymerases may be used to introduce mutations into the nucleic acid. A nonlimiting example of such a method is described in detail in Hanes et al. (1998) *Proc. Nat'l Acad. Sci. USA* 95:14130-14135.

6.2.3.4. Certain Recombinant Methods

In some embodiments, a monoclonal antibody is produced by recombinant techniques. See, e.g., U.S. Pat. No. 4,816,567. In certain such embodiments, nucleic acid encoding monoclonal antibody chains are cloned and expressed in a suitable host cell. For example, in some embodiments, RNA can be prepared from cells expressing the desired antibody, such as mature B-cells or hybridoma cells, using standard methods. In some embodiments, the RNA can then be used to make cDNA using standard methods. In some embodiments, cDNA encoding a heavy or light chain polypeptide is amplified, for example, by PCR, using specific oligonucleotide primers. In some embodiments, the cDNA is cloned into a suitable expression vector. In some embodiments, the expression vector is then transformed or transfected into a suitable host cell, such as a host cell that does not endogenously produce antibody. Certain exemplary host cells include, but are not limited to, *E. coli*, COS cells, Chinese hamster ovary (CHO) cells, and myeloma cells. In some embodiments, wherein heavy and light chains are coexpressed in the same host, reconstituted antibody may be isolated.

In some embodiments, cDNA encoding a heavy or light chain can be modified. For example, in some embodiments, the constant region of a mouse heavy or light chain can be replaced with the constant region of a human heavy or light chain. In this manner, in some embodiments, a chimeric antibody can be produced which possesses human antibody constant regions but retains the binding specificity of a mouse antibody.

In some embodiments, a nucleic acid molecule comprises a polynucleotide sequence that encodes the heavy chain or the light chain of a NOTUM neutralizing antibody. In some embodiments, a single nucleic acid molecule comprises a first polynucleotide sequence that encodes the heavy chain of a NOTUM neutralizing antibody and a second polynucleotide sequence that encodes the light chain of a NOTUM neutralizing antibody. In some embodiments, for example, when the antibody is a single-chain Fv (scFv), the coding sequence for the heavy chain and the coding sequence for the light chain are part of a continuous coding sequence such that a single polypeptide is expressed, which comprises both the heavy chain and the light chain of the antibody. In some embodiments, a single nucleic acid molecule that encodes both a heavy chain and a light chain is capable of expressing the two chains as separate polypeptides. In some such embodiments, each chain is under the control of a separate promoter. In some embodiments, the two chains are under the control of the same promoter. One skilled in the art can select a suitable configuration and suitable control elements for the heavy and light chain of the NOTUM neutralizing antibody according to the intended application.

In some embodiments, the nucleic acid is a vector, such as an expression vector suitable for expressing the heavy chain and/or light chain in a particular host cell. One skilled in the art can select a suitable expression vector, or expression vectors, according to the host cell to be used for expression. Many exemplary such vectors are known in the art.

In some embodiments, a nucleic acid molecule comprises a polynucleotide sequence that encodes a heavy chain of a NOTUM neutralizing antibody selected from MAbs 1.731, 1.802, 1.815, 1.846, 2.1029, 2.55, 2.78, and humanized versions of such MAbs. In some such embodiments, a nucleic acid molecule comprises a polynucleotide sequence selected from SEQ ID NOs: 101, 103, 105, 107, 109, 111, 112, 115, 116, 119, 120, 123, 124, 127, and 128. In some embodiments, a nucleic acid molecule comprises a polynucleotide sequence that encodes a light chain of a NOTUM neutralizing antibody selected from MAbs 1.731, 1.802, 1.815, 1.846, 2.1029, 2.55, 2.78, and humanized versions of such MAbs. In some such embodiments, a nucleic acid molecule comprises a polynucleotide sequence selected from SEQ ID NOs: 102, 104, 106, 108, 110, 113, 114, 117, 118, 121, 122, 125, 126, 129, and 130. In some embodiments, a nucleic acid molecule comprises a first polynucleotide sequence that encodes the heavy chain and a second polynucleotide sequence that encodes the light chain, of a NOTUM neutralizing antibody selected from MAbs 1.731, 1.802, 1.815, 1.846, 2.1029, 2.55, 2.78, and humanized versions of such MAbs.

In some embodiments, recombinant antibodies can be expressed in certain cell lines. In some embodiments, sequences encoding particular antibodies can be used for transformation of a suitable mammalian host cell. According to certain embodiments, transformation can be by any known method for introducing polynucleotides into a host cell. Certain exemplary methods include, but are not limited to, packaging the polynucleotide in a virus (or into a viral vector) and transducing a host cell with the virus (or vector) and using certain transfection procedures known in the art, as exemplified by U.S. Pat. Nos. 4,399,216, 4,912,040, 4,740,461, and 4,959,455. In some embodiments, the transformation procedure used may depend upon the host to be transformed. Certain exemplary methods for introduction of heterologous polynucleotides into mammalian cells are known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

Certain exemplary mammalian cell lines available as hosts for expression are known in the art and include, but are not limited to, many immortalized cell lines available from the American Type Culture Collection (ATCC), including Chinese hamster ovary (CHO) cells, HeLa cells, baby hamster kidney (BHK) cells, monkey kidney cells (COS), human hepatocellular carcinoma cells (e.g., Hep G2), and a number of other cell lines. In some embodiments, cell lines may be selected by determining which cell lines produce high levels of antibodies that specifically bind NOTUM.

6.3. Methods of Treatment

This invention encompasses a method of stimulating endocortical bone formation in a patient, which comprises administering to a patient in need thereof an effective amount of an antibody of the invention. It also encompasses a method of increasing cortical bone thickness, comprising administering to a patient in need thereof an effective amount of an antibody of the invention.

This invention encompasses a method of treating, managing, or preventing a disease or disorder associated with bone loss, which comprises administering to a patient in need thereof a therapeutically or prophylactically effective amount of an antibody of the invention. Examples of diseases and disorders include osteoporosis (e.g., postmenopausal osteoporosis, steroid- or glucocorticoid-induced osteoporosis, male osteoporosis, and idiopathic osteoporosis), osteopenia, and Paget's disease.

Also encompassed by the invention is a method of treating, managing, or preventing bone fractures, which comprises administering to a patient in need thereof a therapeutically or prophylactically effective amount of an antibody of the invention. Particular bone fractures are associated with metastatic bone disease, i.e., cancer that has metastasized to bone. Examples of cancers that can metastasize to bone include prostate, breast, lung, thyroid, and kidney cancer.

This invention also encompasses a method of treating, managing, or preventing bone loss associated with, or caused by, a disease or disorder, which comprises administering to a patient in need thereof a therapeutically or prophylactically effective amount of an antibody of the invention. Examples of diseases and disorders include celiac disease, Crohn's Disease, Cushing's syndrome, hyperparathyroidism, inflammatory bowel disease, and ulcerative colitis.

Nonlimiting exemplary patients that may benefit from methods of this invention include men and women aged 55 years or older, post-menopausal women, and patients suffering from renal insufficiency.

Antibodies of the invention can be administered in combination (e.g., at the same or at different times) with other drugs known to be useful in the treatment, management, or prevention of diseases or conditions affecting the bone. Examples include: androgen receptor modulators; bisphosphonates; calcitonin; calcium sensing receptor antagonists; RANKL antibodies, cathepsin K inhibitors; estrogen and estrogen receptor modulators; integrin binders, antibodies, and receptor antagonists; parathyroid hormone (PTH) and analogues and mimics thereof; and vitamin D and synthetic vitamin D analogues.

Examples of androgen receptor modulators include finasteride and other 5α-reductase inhibitors, nilutamide, flutamide, bicalutamide, liarozole, and abiraterone acetate.

Examples of bisphosphonates include alendronate, cimadronate, clodronate, etidronate, ibandronate, incadronate, minodronate, neridronate, olpadronate, pamidronate, piridronate, risedronate, tiludronate, and zolendronate, and pharmaceutically acceptable salts and esters thereof.

Examples of cathepsin K inhibitors include VEL-0230, AAE581 (balicatib), MV061194, SB-462795 (relacatib), MK-0822 (odanacatib), and MK-1256.

Examples of estrogen and estrogen receptor modulators include naturally occurring estrogens (e.g., 7-estradiol, estrone, and estriol), conjugated estrogens (e.g., conjugated equine estrogens), oral contraceptives, sulfated estrogens, progestogen, estradiol, droloxifene, raloxifene, lasofoxifene, TSE-424, tamoxifen, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

Examples of integrin binders, antibodies, and receptor antagonists include vitaxin (MEDI-522), cilengitide and L-000845704.

6.4. Pharmaceutical Formulations

This invention encompasses pharmaceutical compositions comprising one or more antibodies of the invention, and optionally one or more other drugs, such as those described above.

In some embodiments, a NOTUM neutralizing antibody may be used as a therapeutic antibody. Exemplary NOTUM neutralizing antibodies to be used as therapeutic antibodies include, but are not limited to, chimeric antibodies, humanized antibodies, and human antibodies. Those skilled in the art are familiar with the use of antibodies as therapeutic agents.

In some embodiments, a pharmaceutical composition is provided that comprises an effective amount of an antibody to NOTUM and a pharmaceutically acceptable diluent, carrier, solubilizer, emulsifier, preservative and/or adjuvant. In some embodiments, a pharmaceutical composition is provided that comprises an effective amount of an antibody to NOTUM and an effective amount of at least one additional therapeutic agent, together with a pharmaceutically acceptable diluent, carrier, solubilizer, emulsifier, preservative and/or adjuvant. In some embodiments, at least one additional therapeutic agent is selected from those described above.

In some embodiments, formulation materials for pharmaceutical compositions are nontoxic to recipients at the dosages and concentrations employed.

In some embodiments, the pharmaceutical composition comprises formulation materials for modifying, maintaining or preserving, for example, the pH, osmolarity, viscosity, clarity, color, isotonicity, odor, sterility, stability, rate of dissolution or release, adsorption or penetration of the composition. In some embodiments, suitable formulation materials include, but are not limited to, amino acids (for example, glycine, glutamine, asparagine, arginine and lysine); antimicrobials; antioxidants (for example, ascorbic acid, sodium sulfite and sodium hydrogen-sulfite); buffers (for example, borate, bicarbonate, Tris-HCl, citrates, phosphates and other organic acids); bulking agents (for example, mannitol and glycine); chelating agents (for example, ethylenediamine tetraacetic acid (EDTA)); complexing agents (for example, caffeine, polyvinylpyrrolidone, beta-cyclodextrin, and hydroxypropyl-beta-cyclodextrin); fillers; monosaccharides, disaccharides, and other carbohydrates (for example, glucose, mannose and dextrins); proteins (for example, serum albumin, gelatin and immunoglobulins); coloring, flavoring, and diluting agents; emulsifying agents; hydrophilic polymers (for example, polyvinylpyrrolidone); low molecular weight polypeptides; salt-forming counterions (for example, sodium); preservatives (for example, benzalkonium chloride, benzoic acid, salicylic acid, thimerosal, phenethyl alcohol, methylparaben, propylparaben, chlorhexidine, sorbic acid and hydrogen peroxide); solvents (for example, glycerin, propylene glycol and polyethylene glycol); sugar alcohols (for example, mannitol and sorbitol); suspending agents; surfactants or wetting agents (for example, pluronics, PEG, sorbitan esters, polysorbates (for example, polysorbate 20 and polysorbate 80), triton, tromethamine, lecithin, cholesterol, and tyloxapal);

stability enhancing agents (for example, sucrose and sorbitol); tonicity enhancing agents (for example, alkali metal halides (for example, sodium or potassium chloride), mannitol, and sorbitol); delivery vehicles; diluents; excipients; and pharmaceutical adjuvants. (*Remington's Pharmaceutical Sciences*, 18$^{th}$ Edition, A. R. Gennaro, ed., Mack Publishing Company (1990).

In some embodiments, an antibody to NOTUM or other therapeutic molecule is linked to a half-life extending vehicle. Nonlimiting exemplary half-life extending vehicles include those known in the art. Such vehicles include, but are not limited to, the Fc domain, polyethylene glycol, and dextran. Exemplary such vehicles are described, e.g., in published PCT Application No. WO 99/25044.

In some embodiments, an optimal pharmaceutical composition will be determined by one skilled in the art depending upon, for example, the intended route of administration, delivery format, and desired dosage. See, e.g., Remington's Pharmaceutical Sciences, supra. In some embodiments, such compositions may influence the physical state, stability, rate of in vivo release, or rate of in vivo clearance of a neutralizing antibody.

In some embodiments, a primary vehicle or carrier in a pharmaceutical composition may be either aqueous or non-aqueous in nature. For example, in some embodiments, a suitable vehicle or carrier may be water for injection, physiological saline solution, or artificial cerebrospinal fluid, possibly supplemented with other materials common in compositions for parenteral administration. Exemplary vehicles include, but are not limited to, neutral buffered saline and saline mixed with serum albumin. In some embodiments, pharmaceutical compositions comprise Tris buffer of about pH 7.0-8.5, or acetate buffer of about pH 4.0-5.5, which may further include sorbitol or a suitable substitute therefor. In some embodiments, a composition comprising an antibody to NOTUM, with or without at least one additional therapeutic agents, may be prepared for storage by mixing the selected composition having the desired degree of purity with optional formulation agents (*Remington's Pharmaceutical Sciences*, supra) in the form of a lyophilized cake or an aqueous solution. In some embodiments, a composition comprising an antibody to NOTUM, with or without at least one additional therapeutic agent, may be formulated as a lyophilizate using appropriate excipients such as sucrose.

In some embodiments, a pharmaceutical composition is selected for parenteral delivery. In some embodiments, a pharmaceutical composition is selected for inhalation or for delivery through the digestive tract, such as orally. Various techniques for preparing pharmaceutically acceptable compositions are within the skill of one skilled in the art.

In some embodiments, formulation components are present in concentrations that are acceptable to the site of administration. In some embodiments, buffers are used to maintain the composition at physiological pH or at a slightly lower pH, typically within a pH range of from about 5 to about 8.

In some embodiments, when parenteral administration is contemplated, a pharmaceutical composition may be in the form of a pyrogen-free, parenterally acceptable aqueous solution comprising the desired antibody to NOTUM, with or without additional therapeutic agents, in a pharmaceutically acceptable vehicle. In some embodiments, a vehicle for parenteral injection is sterile distilled water in which the antibody to NOTUM, with or without at least one additional therapeutic agent, is formulated as a sterile, isotonic solution, properly preserved. In some embodiments, the preparation can involve the formulation of the desired molecule with an agent, such as injectable microspheres, bio-erodible particles, polymeric compounds (such as polylactic acid or polyglycolic acid), beads or liposomes, that may provide for the controlled or sustained release of the product which may then be delivered via a depot injection. In some embodiments, hyaluronic acid may also be used, and may have the effect of promoting sustained duration in the circulation. In some embodiments, implantable drug delivery devices may be used to introduce the desired molecule.

In some embodiments, a pharmaceutical composition may be formulated for inhalation. In some embodiments, an antibody to NOTUM, with or without at least one additional therapeutic agent, may be formulated as a dry powder for inhalation. In some embodiments, an inhalation solution comprising an antibody to NOTUM, with or without at least one additional therapeutic agent, may be formulated with a propellant for aerosol delivery. In some embodiments, solutions may be nebulized.

In some embodiments, a formulation may be administered orally. In some embodiments, an antibody to NOTUM, with or without at least one additional therapeutic agent, that is administered in this fashion may be formulated with or without carriers customarily used in the compounding of solid dosage forms such as tablets and capsules. In some embodiments, a capsule may be designed to release the active portion of the formulation at the point in the gastrointestinal tract when bioavailability is maximized and pre-systemic degradation is minimized. In some embodiments, at least one additional agent can be included to facilitate absorption of the antibody to NOTUM with or without any additional therapeutic agents. In some embodiments, diluents, flavorings, low melting point waxes, vegetable oils, lubricants, suspending agents, tablet disintegrating agents, and/or binders may also be employed.

In some embodiments, a pharmaceutical composition comprises an effective amount of an antibody to NOTUM, with or without at least one additional therapeutic agent, in a mixture with non-toxic excipients which are suitable for the manufacture of tablets. In some embodiments, by dissolving the tablets in sterile water, or another appropriate vehicle, solutions may be prepared in unit-dose form. Exemplary excipients include, but are not limited to, inert diluents (for example, calcium carbonate, sodium carbonate, sodium bicarbonate, lactose, and calcium phosphate); binding agents (for example, starch, gelatin, and acacia); and lubricating agents (for example, magnesium stearate, stearic acid, and talc).

Additional pharmaceutical compositions will be evident to those skilled in the art, including formulations comprising an antibody to NOTUM, with or without at least one additional therapeutic agent, in sustained- or controlled-delivery formulations. Exemplary sustained- or controlled-delivery formulations include, but are not limited to, liposome carriers, bio-erodible microparticles, porous beads, and depot injections. Various techniques for preparing formulations are known to those skilled in the art. In some embodiments, sustained-release preparations may include semipermeable polymer matrices in the form of shaped articles, e.g. films or microcapsules. Exemplary sustained release matrices include, but are not limited to, polyesters, hydrogels, polylactides (see, e.g., U.S. Pat. No. 3,773,919 and EP 058,481), copolymers of L-glutamic acid and gamma ethyl-L-glutamate (see, e.g., Sidman et al. (1983) *Biopolymers* 22:547-556), poly (2-hydroxyethyl-methacrylate) (see, e.g., Langer et al. (1981) *J. Biomed. Mater. Res.* 15:167-277 and Langer (1982) *Chem. Tech.* 12:98-105), ethylene vinyl acetate (Langer et al., supra), and poly-D(−)-3-hydroxybutyric acid (EP 133,988). In some embodiments, sustained release compositions may include liposomes, which can be prepared, in some embodiments, by any of several methods known in the art. See e.g., Eppstein et al. (1985) *Proc. Natl. Acad. Sci. USA,* 82:3688-3692; EP 036,676; EP 088,046; and EP 143,949.

In some embodiments, a pharmaceutical composition to be used for in vivo administration typically is sterile. In some embodiments, this may be accomplished by filtration through sterile filtration membranes. In some embodiments, where the composition is lyophilized, sterilization using this method may be conducted either prior to or following lyophilization and reconstitution. In some embodiments, the composition for parenteral administration may be stored in lyophilized form or in a solution. In some embodiments, parenteral compositions generally are placed into a container having a sterile access port, for example, an intravenous solution bag or vial having a stopper pierceable by a hypodermic injection needle.

In some embodiments, once the pharmaceutical composition has been formulated, it may be stored in sterile vials as a solution, suspension, gel, emulsion, solid, or as a dehydrated or lyophilized powder. In some embodiments, such formulations may be stored either in a ready-to-use form or in a form (e.g., lyophilized) that is reconstituted prior to administration.

In some embodiments, kits for producing a single-dose administration unit are provided. In some embodiments, the kits may each contain both a first container having a dried protein and a second container having an aqueous formulation. In some embodiments, kits containing single or multichambered pre-filled syringes (e.g., liquid syringes and lyosyringes) are included.

In some embodiments, the effective amount of a pharmaceutical composition comprising an antibody to NOTUM, with or without at least one additional therapeutic agent, to be employed therapeutically will depend, for example, upon the context and objectives of treatment. One skilled in the art will appreciate that the appropriate dosage levels for treatment, according to some embodiments, will thus vary depending, in part, upon the molecule delivered, the indication for which the antibody to NOTUM, with or without at least one additional therapeutic agent, is being used, the route of administration, and the size (body weight, body surface or organ size) and/or condition (the age and general health) of the patient. In some embodiments, the clinician may titer the dosage and modify the route of administration to obtain the optimal therapeutic effect. In some embodiments, a typical dosage may range from about 0.1 µg/kg of patient body weight, up to about 100 mg/kg or more, depending on the factors mentioned above. In some embodiments, the dosage may range from 0.1 µg/kg up to about 100 mg/kg; 1 µg/kg up to about 100 mg/kg; or 5 µg/kg up to about 100 mg/kg, including all points (including fractions) between any of the foregoing endpoints. In some embodiments, the dosage is between about 1 mg/kg body weight and about 60 mg/kg body weight. In some embodiments, the dosage is about 1 mg/kg body weight, about 3 mg/kg body weight, about 5 mg/kg body weight, about 10 mg/kg body weight, about 20 mg/kg body weight, about 30 mg/kg body weight, about 40 mg/kg body weight, about 50 mg/kg body weight, or about 60 mg/kg body weight.

In some embodiments, a human dose of a neutralizing antibody against NOTUM is determined based on the efficacious dose of the same antibody in another species, such as mice, dogs, monkeys, etc. In some embodiments, a human dose of a neutralizing antibody against NOTUM is determined using "Guidance for Industry: Estimating the Maximum Safe Starting Dose in Initial Clinical Trials for Therapeutics in Adult Healthy Volunteers," U.S. Department of Health and Human Services, Food and Drug Administration, and Center for Drug Evaluation and Research (CDER), July 2005 (Pharmacology and Toxicology).

In some embodiments, a suitable dosage may be determined by one skilled in the art, for example, based on animal studies.

In various embodiments, a neutralizing antibody against NOTUM is administered to a patient twice per week, once per week, once every two weeks, once per month, once every other month, or even less frequently.

In some embodiments, the frequency of dosing will take into account the pharmacokinetic parameters of an antibody to NOTUM and, if applicable, any additional therapeutic agents in the formulation used. In some embodiments, a clinician will administer the composition until a dosage is reached that achieves the desired effect. In some embodiments, the composition may therefore be administered as a single dose, or as two or more doses (which may or may not contain the same amount of the desired molecule) over time, or as a continuous infusion via an implantation device or catheter. In some embodiments, further refinement of the appropriate dosage is routinely made by those skilled in the art and is within the ambit of tasks routinely performed by them. In some embodiments, appropriate dosages may be ascertained through use of appropriate dose-response data. In some embodiments, a patient receives one dose of a pharmaceutical composition comprising an antibody to NOTUM. In some embodiments, a patient receives one, two, three, or four doses per day of a pharmaceutical composition comprising an antibody to NOTUM. In some embodiments, a patient receives one, two, three, four, five, or six doses per week of a pharmaceutical composition comprising an antibody to NOTUM. In some embodiments, a patient receives one, two, three, or four doses per month of a pharmaceutical composition comprising an antibody to NOTUM.

In some embodiments, the route of administration of the pharmaceutical composition is in accord with known methods, e.g. orally, through injection by subcutaneous, intravenous, intraperitoneal, intracerebral (intra-parenchymal), intracerebroventricular, intramuscular, intra-ocular, intraarterial, intraportal, or intralesional routes; by sustained release systems or by implantation devices. In some embodiments, the compositions may be administered by bolus injection or continuously by infusion, or by implantation device.

In some embodiments, the composition may be administered locally via implantation of a membrane, sponge or another appropriate material onto which the desired molecule has been absorbed or encapsulated. In some embodiments, where an implantation device is used, the device may be implanted into any suitable tissue or organ, and delivery of the desired molecule may be via diffusion, timed-release bolus, or continuous administration.

In some embodiments, an antibody to NOTUM, with or without at least one additional therapeutic agent, is delivered by implanting certain cells that have been genetically engineered, using methods such as those described herein, to express and secrete the polypeptides. In some embodiments, such cells may be animal or human cells, and may be autologous, heterologous, or xenogeneic. In some embodiments, the cells may be immortalized. In some embodiments, in order to decrease the chance of an immunological response, the cells may be encapsulated to avoid infiltration of surrounding tissues. In some embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

7. EXAMPLES

7.1. Knock-Out Mouse

Mice homozygous for a genetically engineered mutation in the murine ortholog of the human NOTUM gene were generated using corresponding mutated embryonic stem (ES) cell clones from the OMNIBANK collection of mutated murine ES cell clones (see generally, U.S. Pat. No. 6,080,576). In brief, ES cell clones containing a mutagenic viral insertion into the murine NOTUM locus were microinjected into blastocysts which were in turn implanted into pseudopregnant female hosts and carried to term. The resulting chimeric offspring were subsequently bred to C57 black 6 female mice and the offspring checked for the germline transmission of the knocked-out NOTUM allele. Animals heterozygous for the mutated NOTUM allele were subsequently bred to produce offspring that were homozygous for the mutated NOTUM allele, heterozygous for the mutated NOTUM allele, or wild type offspring at an approximate ratio of 1:2:1.

Mice homozygous (−/−) for the disruption of the NOTUM gene were studied in conjunction with mice heterozygous (+/−) for the disruption of the NOTUM gene and wild-type (+1+) litter mates. During this analysis, the mice were subject to a medical work-up using an integrated suite of medical diagnostic procedures designed to assess the function of the major organ systems in a mammalian subject. By studying the homozygous (−/−) "knockout" mice in the described numbers and in conjunction with heterozygous (+/−) and wild-type (+1+) litter mates, more reliable and repeatable data were obtained.

As shown in FIG. 1, male mice having homozygous disruption of the NOTUM gene ("homs") exhibited greater cortical thicknesses at various bone sites, compared to their wildtype littermates at 16 weeks of age (number of mice N=10 for both groups). These differences, which were measured by microCT (Scanco µCT40), were: 28% (p<0.001) at midshaft femur; 19% (p<0.001) at midshaft humerus; 17% (p<0.001) at midshaft tibia; and 11% (p<0.001) at tibia-fibula junction. As shown in FIG. 2, at 16 weeks of age, the midshaft femur cortical bone thickness of mice heterozygous for the NOTUM mutation ("hets") was also greater than that of their wildtype littermates: male hets (N=50) exhibited a 6% (p=0.007) increase compared to their wildtype littermates (N=23); and female hets (N=57) exhibited a 9% (p<0.001) increase compared to their wildtype littermates (N=22).

Practical manifestations of the observed redistribution of bone formation in NOTUM animals are reflected in FIGS. 3 and 4, which show results of femur breaking strength tests (performed by SkeleTech, now Ricerca Biosciences) using a standard 4-point bending test. As shown in FIG. 3, which provides results obtained for male mice at 16 weeks of age, hets (N=20) exhibited a 5% (p=0.54) increase in femur breaking strength compared to their wildtype littermates (N=23), whereas homs (N=17) exhibited a 28% (p<0.001) increase. On the other hand, spine compression tests of both NOTUM homs and hets did not show a significant reduction in maximum spine compression loads as compared to wildtype controls. Similar results were obtained for female mice at 16 weeks of age. As shown in FIG. 4, hets (N=20) exhibited a 12% (p=0.04) increase in femur breaking strength compared to their wildtype littermates (N=21), whereas homs (N=18) exhibited a 28% (p<0.001) increase. Analysis of these and other data revealed a strong correlation between cortical thickness and femur breaking strength.

7.2. Production and Purification of Recombinant NOTUM Proteins

The full-length coding sequences for human, catalytically inactive human (S232A), mouse, catalytically inactive mouse (S239A), rat, guinea pig, cynomolgus monkey, and rhesus monkey NOTUM, each with a C-terminal 6×His epitope tag, were subcloned into the expression vector pIRESpuro2 (Clontech). The expression constructs can be used to generate conditioned medium containing secreted NOTUM protein by transient transfection, or to establish stable transfectants for the generation of larger quantities of conditioned medium, e.g., for subsequent purification of NOTUM protein.

HEK293F cells were transfected using Lipofectamine2000 (Invitrogen) and grown in suspension culture in Freestyle 293 Expression Medium (Invitrogen) in shaker flasks. For transient transfections, conditioned medium was harvested four days after transfection, sterile filtered and stored at 4° C. For the generation of cell lines stably expressing NOTUM protein, genomic integration of the expression plasmid was selected for in the presence of puromycin.

Expression and secretion of NOTUM protein was confirmed by Western blot of cell lysates and/or conditioned medium, using an anti-His antibody. Subcloning of NOTUM-producing bulk stable transfectants by limiting dilution enabled the identification by anti-His Western blot of individual clones expressing NOTUM at relatively high levels.

To produce purified mouse and human NOTUM proteins at 10-20 mg scale, clonal HEK293F cell lines expressing either mouse or human NOTUM were expanded in suspension culture to a volume of 3 L. When the cell density at this volume reached 1×10^6 viable cells per ml, the cells were pelleted by centrifugation and resuspended in fresh Freestyle 293 Expression Medium and maintained in culture for a further 96 hours without additional medium changes. After 96 hours, cultures were harvested, cells were pelleted by centrifugation, and the conditioned medium was sterile filtered and stored at 4° C. for subsequent processing.

Immediately prior to purification, NOTUM-containing conditioned medium was concentrated from 3 L to 1 L and then buffer exchanged into nickel immobilized metal affinity chromatography (IMAC) buffer (20 mM Tris-HCl, 10 mM imidazole, 0.5 M NaCl, pH 7.4) by tangential flow filtration using a membrane with a 10 kDa nominal molecular weight cut off. Concentrated, buffer exchanged conditioned medium was then applied to an equilibrated, nickel charged, metal chelating column. Bound protein was washed and eluted using an imidazole concentration gradient. Elution fractions containing pure NOTUM protein were pooled and dialyzed against phosphate buffered saline to remove the elution buffer. Purified, dialyzed protein was aliquotted and frozen at −80° C.

For each batch of protein, one aliquot was used to determine protein concentration by bicinchoninic acid (BCA) assay (Thermo Scientific, Rockford, Ill.), purity by SDS PAGE followed by Coomassie or silver staining, activity in both the cell-free OPTS enzymatic assay (described in Example 6.4.1, below) and the cell-based Wnt signaling assay (described in Example 6.4.2, below), and endotoxin concentration by Limulus Amoebocyte Lysate (LAL) assay (Lonza, Basel, Switzerland).

7.3. Generation of Mouse Monoclonal Antibodies to NOTUM

Antibodies were raised against purified recombinant human and mouse NOTUM proteins in two separate immunization campaigns.

In Campaign 1, mice homozygous for a gene trap insertion in the NOTUM gene and therefore lacking endogenous NOTUM protein were immunized with human NOTUM protein as follows. Mice were primed with 20 µg human NOTUM protein in complete Freund's adjuvant injected intraperitoneally. Mice were boosted with 20 µg human NOTUM protein in incomplete Freund's adjuvant injected intraperitoneally every two to three weeks. Mice exhibiting a robust serum titer against human NOTUM as determined by ELISA received a final boost of 10 µg human NOTUM protein in PBS injected intravenously (i.v.).

In Campaign 2, mice homozygous for a gene trap insertion in the NOTUM gene were immunized via the hind footpads with a priming immunization of 10 µg mouse NOTUM protein in TiterMax adjuvant with CpG DNA followed by ten boosts of 10 µg mouse NOTUM protein in Alum adjuvant with CpG DNA at three or four day intervals. Inguinal and popliteal lymph nodes were harvested from high titer mice after a final footpad boost with 10 µg mouse NOTUM protein in PBS.

Spleens from i.v. boosted mice or lymph nodes from footpad immunized mice were collected four days after the final boost and were minced and strained to yield a cell suspension. Red blood cells were lysed and the cell suspension was enriched for B-cells by negative selection using magnetic beads coated with antibodies specific for non-B-cell populations. Hybridomas were generated by electro-cell fusion of enriched B-cells with mouse NS1 myeloma cells and were seeded onto 96-well plates in hybridoma medium containing hypoxanthine and aminopterin to select for viable B-cell/myeloma cell hybridomas.

Hybridomas were screened for the production of NOTUM-specific antibodies by assaying hybridoma conditioned medium for immunoreactivity with passively adsorbed NOTUM protein in an ELISA format. Hundreds of hybridomas secreting antibody specific for mouse and/or human NOTUM were found from both immunization campaigns.

7.4. NOTUM Neutralization Assays 7.4.1. OPTS Assay

In the OPTS assay, trisodium 8-octanoyloxypyrene-1,3,6-trisulfonate (OPTS), a water soluble enzyme substrate for fluorimetric assays of esterases and lipases, is used to measure NOTUM activity. Enzymatic cleavage of the ester bond in OPTS yields a fluorescent product.

It was found that hybridoma conditioned medium in general interfered in the OPTS assay perhaps due to the release from dying cells of hydrolases that could also cleave the OPTS. For this reason, additional hybridoma conditioned medium was generated for those lines originally showing the highest level of binding activity by ELISA and antibody was purified in a 96-well format by affinity chromatography using protein A beads. These purified antibodies were then tested in the OPTS assay at a four-fold dilution without prior quantitation.

Antibodies were tested in quadruplicate in 384-well plates. 12.5 µl containing 125 ng of purified NOTUM in 4× reaction buffer (20 mM CaCl2), 2 mM MgCl2, 50 mM Tris-HCl, pH7.4) was added to 12.5 µl of purified antibody. After mixing, antibody and NOTUM were incubated at room temperature for 20 minutes followed by addition of 25 µl of 1.25 µM OPTS (Sigma, catalog #74875) in 50 mM Tric-HCl, pH7.4. After mixing, the enzyme reaction was allowed to proceed at room temperature for 10 minutes before being stopped by addition of 25 µl of 3% SDS. Plates were read on an Envision plate reader with an excitation wavelength of 485 nm and emission wavelength of 535 nm to quantify the amount of cleavage product.

Screening of 1,135 human NOTUM immunoreactive hybridomas from Campaign 1 yielded three antibodies that showed greater than 70% inhibition of human NOTUM. These three together with an additional five hybridomas exhibiting some degree of neutralization in the OPTS assay were selected for subcloning by limiting dilution and small scale purified antibody production by protein A affinity chromatography using 50 ml conditioned medium from clonal hybridomas.

OPTS assay screening of 1,056 mouse NOTUM immunoreactive hybridomas identified from Campaign 2 yielded six antibodies that showed greater than 50% inhibition of mouse NOTUM. These six together with an additional six hybridomas exhibiting some degree of neutralization in the OPTS assay were selected for subcloning by limiting dilution and small scale purified antibody production by protein A affinity chromatography using 50 ml conditioned medium from clonal hybridomas.

7.4.2. Wnt Signaling Assay

NOTUM can act as a negative regulator of Wnt signaling. Antibody neutralizing activity, determined through the effect on Wnt signaling, was determined in a Wnt signaling assay, which uses CellSensor® technology and conditioned media prepared as follows. Plasmid containing human NOTUM in pcDNA3.1(+) vector was transfected into HEK293 cells and clones were selecting by growing in presence of 400 µg/mL of G418. Condition media from these cells was used for the assay. L cells overexpressing and secreting Wnt3a into the conditioned media were purchased from ATCC.

The assay protocol was as follows. CellSensor® LEF/TCF-bla FreeStyle™ 293F cells (Invitrogen) were grown to near confluency in 15-cm plates in DMEM with 10% Dialyzed FBS, 5 µg/ml Blasticidin (Invitrogen, R210-01), 0.1 mM NEAA, 25 mM HEPES and 1×GPS. Cells were trypsinized by first rinsing with PBS, followed by addition of 5 mL trypsin and incubation of plates at room temperature for two minutes. A total of 10 mL of assay media (Opti-MEM, plus 0.5% dialyzed FBS, 0.1 mM NEAA, 1 mM sodium pyruvate, 10 mM HEPES, 1×GPS) was then added per 15 cm plate. Cells were counted and suspended at 50,000 cells per mL. Cells were seeded into Biocoat 384-well plates (Fisher, Catalogue #356663) at a density of 10000 cells per 20 µL per well. After incubation of cells at 37° C. for 3 hours, 10 µL of 30 mM LiCl in assay medium was added per well, followed by incubation at 37° C. overnight. The next day, 15 µL of antibody and 15 µL of purified NOTUM, both in assay medium, were coincubated in a total volume of 45 µL assay medium at room temperature for 30 minutes in a 96-well plate. NOTUM was used in a concentration previously determined to give 50% inhibition in the assay, typically 25 nM. Following the 30 minute incubation, 15 µL of undiluted L-Wnt3a conditioned medium was added to the 45 µL antibody/NOTUM mixture, and 10 µl of the resulting mixture was added to the wells of the 384-well plate containing the CellSensor® cells, in quadruplicate. Controls included wells lacking any cells, wells lacking NOTUM, and wells lacking L-Wnt3a conditioned medium. The assay plate was incubated for 5 hours at 37° C. to enable Wnt-mediated beta-lactamase upregulation, and then 8 µl Live-BLAzer™-FRET B/G Substrate (CCF4-AM, Invitrogen) was added to each well and the plate incubated in the dark at room temperature for 3 hours. Plates were then read on an Envision plate reader using an excitation wavelength of 400 nm and emission wavelengths of 460 nm and 535 nm.

7.5. Characterization of NOTUM Neutralizing Antibodies

Antibodies purified from clonal hybridomas were characterized with respect to their species cross-reactivity by ELISA, their ability to recognize reduced, denatured NOTUM protein by Western blot, and their neutralizing potency in the cell-free OPTS assay and the cell-based Wnt signaling assay, both of which are described above in Example 6.4.

Functional testing of monoclonal antibodies from Campaign 1 revealed three antibodies, 1.802, 1.815, 1.846, that neutralize human NOTUM in both the OPTS and Wnt signaling assays with an $IC_{50}$ in the range of 1 to 10 nM. These antibodies do not have any effect on the activity of mouse NOTUM and were shown by ELISA to bind human NOTUM but not mouse NOTUM. Furthermore, these antibodies recognized human NOTUM only weakly when NOTUM protein was passively adsorbed to the assay plate and were much more sensitive to anti-His displayed human NOTUM protein.

Table 1 shows the results of various characterization experiments for certain antibodies from Campaign 1. The data in the "Bin" column was generated using the method described in Example 6.6, below.

TABLE 1

Characterization of certain antibodies raised against human NOTUM

| Antibody | Isotype | Bin | OPTS $IC_{50}$ (nM; human NOTUM) | Wnt signaling $IC_{50}$ (nM; human NOTUM) | OPTS $IC_{50}$ (nM; mouse NOTUM) | Wnt signaling $IC_{50}$ (nM; mouse NOTUM) | Mouse NOTUM binding | Western blot binding |
|---|---|---|---|---|---|---|---|---|
| 1.802 | IgG1 | 1 | 6.44 | 5.71 | No inhibition | No inhibition | No | No |
| 1.815 | IgG1 | 1 | 7.62 | 6.88 | No inhibition | nd | No | No |
| 1.846 | IgG2b | 1 | 10.07 | 1.70 | No inhibition | nd | No | No |
| 1.731 | IgG1 | 3 | >166.67 | 15.52 | 196.74 | No inhibition | Yes | Yes |
| 1.655 | IgG1 | 3 | >166.67 | nd | >166.67 | nd | nd | Yes |
| 1.168 | IgG2a | 4 | 56.61 | No inhibition | No inhibition | nd | Yes | Yes |
| 1.712 | IgG2a | 2 | 125.36 | 58.49 | No inhibition | nd | Yes | Yes |
| 1.807 | IgG2a | 2 | nd | No inhibition | No inhibition | nd | Yes | Yes |

Functional testing of monoclonal antibodies from Campaign 2 revealed interesting activity profiles. In particular, MAb 2.78 neutralized both mouse and human NOTUM in both the OPTS and Wnt signaling assays with an $IC_{50}$ in the range of 3 to 50 nM while MAb 2.1029 neutralized both mouse and human NOTUM in the OPTS assay with an $IC_{50}$ in the range of 5 to 30 nM but only human NOTUM in the Wnt signaling assay with an $IC_{50}$ of 14 nM. This latter observation was ascribed to there being some difference in the quality of the recombinant mouse and human NOTUM proteins. One known difference between the proteins is that recombinant mouse NOTUM exists as multimers/aggregates to a much greater extent than does recombinant human NOTUM. Neither 2.78 nor 2.1029 recognized reduced, denatured NOTUM protein by Western blotting and both were substantially more immunoreactive with anti-His displayed NOTUM than with passively adsorbed NOTUM.

Table 2 shows the results of various characterization experiments for certain antibodies from Campaign 2. The data in the "Bin" column was generated using the method described in Example 6.6, below.

TABLE 2

Characterization of certain antibodies raised against mouse NOTUM

| Antibody | Isotype | Bin | OPTS $IC_{50}$ (nM; mouse NOTUM) | Wnt signaling $IC_{50}$ (nM; mouse NOTUM) | OPTS $IC_{50}$ (nM; human NOTUM) | Wnt signaling $IC_{50}$ (nM; human NOTUM) | Human NOTUM binding | Western blot binding |
|---|---|---|---|---|---|---|---|---|
| 2.78 | IgG2b | 2 | 35.65 | 3.75 | 15.49 | 45.94 | Yes | No |
| 2.1029 | IgG2a | 3 | 29.19 | No inhibition | 5.77 | 14.02 | Yes | No |

TABLE 2-continued

Characterization of certain antibodies raised against mouse NOTUM

| Antibody | Isotype | Bin | OPTS IC$_{50}$ (nM; mouse NOTUM) | Wnt signaling IC$_{50}$ (nM; mouse NOTUM) | OPTS IC$_{50}$ (nM; human NOTUM) | Wnt signaling IC$_{50}$ (nM; human NOTUM) | Human NOTUM binding | Western blot binding |
|---|---|---|---|---|---|---|---|---|
| 2.816 | IgG2a | 3 | 31.70 | No inhibition | No inhibition | 39.11 | Yes | No |
| 2.856 | IgG2b | 3 | 37.70 | No inhibition | No inhibition | No inhibition | Yes | No |
| 2.1001 | IgG2b | 3 | >166.67 | No inhibition | No inhibition | No inhibition | No | Yes |
| 2.55 | IgG2a | 1 | 26.13 | No inhibition | No inhibition | No inhibition | Yes | Yes |
| 2.1002 | IgG2a | 1 | 42.39 | No inhibition | No inhibition | No inhibition | Yes | Yes |
| 2.497 | IgG2a | 1 | 54.95 | No inhibition | No inhibition | No inhibition | Yes | Yes |
| 2.341 | IgG2a | 1 | 56.95 | No inhibition | No inhibition | No inhibition | Yes | Yes |
| 2.236 | IgG2a | 1 | 64.54 | No inhibition | No inhibition | No inhibition | Yes | Yes |
| 2.688 | IgG2a | 4 | No inhibition | No inhibition | 12.84‡ | No inhibition | Yes | No |
| 2.1006 | IgG2a | 5 | >166.67 | No inhibition | >166.67‡ | No inhibition | Yes | Yes |

‡Maximum inhibition ≈ 50%.

7.6. Binding Competition Studies Using NOTUM Neutralizing Antibodies

Antibodies from both immunization campaigns were assessed for their ability to interfere with each other's binding to NOTUM protein in an epitope binning assay. This assay was performed in an ELISA format using anti-His captured NOTUM protein. The captured NOTUM protein was incubated with an excess of an unlabelled NOTUM-specific antibody (the 'blocking' antibody) followed by addition of a biotinylated NOTUM-specific antibody (the 'probe' antibody). Binding of the probe antibody was measured using HRP conjugated to streptavidin. If the two antibodies compete for binding in the same epitope space or if the blocking antibody otherwise affects the ability of the probe antibody to bind, e.g., by allosteric interference, no signal is generated. If the two antibodies do not interfere with one another, a signal similar to that of the biotinylated antibody tested in the absence of blocking antibody is generated. Antibodies are tested in a reciprocal matrix format. Typically, a pair of antibodies will show the same level of interference regardless of which of the two is the blocking antibody and which is the probe antibody. Antibodies exhibiting similar profiles are assigned to the same epitope 'bin'.

Using this methodology it was shown that MAbs 1.802, 1.815, 1.846, 2.78, and 2.1029 all interfere with each other's binding to human NOTUM while they do not interfere with the binding of several other less potent neutralizers or non-neutralizers.

7.7. Epitope Mapping of NOTUM Neutralizing Antibodies

In an effort to map the amino acids involved in binding of human NOTUM-specific MAbs 1.802, 1.815, and 1.846, human/mouse chimeric NOTUM proteins were produced by transient transfection in HEK293F of expression constructs encoding NOTUM open reading frames with a mixture of human and mouse sequences. By Western blotting with anti-His antibody and by OPTS assay it was shown that conditioned media from these transfections contained functional NOTUM chimeras.

FIG. 5 shows schematic representations of the human/mouse chimeric NOTUM proteins used in this experiment. The sequences of those proteins are shown in Section 7 (Table of Sequences). The conditioned media were used in ELISA format to determine antibody specificity. Based on loss of human-specific MAb binding to particular chimeras it was determined that MAbs 1.802, 1.815, and 1.846 (all of which are "Bin 1" antibodies) depend on human NOTUM amino acids between Q47 and M177 for binding. See FIG. 5. Within this region, mouse and human NOTUM differ at five positions (R115K, D141S. R150K, R154H, and Y171H, based on the human sequence numbering). Human NOTUM point mutants were generated by transient transfection of constructs expressing human NOTUM with the mouse amino acid at each of these five positions and the point mutants were all shown to be functional in the OPTS assay. By ELISA, MAbs 1.802, 1.815, and 1.846 bound all point mutants except human NOTUM D141S, indicating that this amino acid is important for their binding to human NOTUM. Mouse NOTUM with the reciprocal point mutation, mouse NOTUM S148D was generated by transient transfection, shown to be active in the OPTS assay, and was shown to support binding of the human NOTUM-specific MAbs. Therefore, the species specificity of MAbs 1.802, 1.815, and 1.846 appears to be dependent upon the amino acid at position 141 in human NOTUM, which is aspartic acid in the native human NOTUM protein.

The chimera approach could not be used to map amino acids involved in binding of MAbs 2.78 or 2.1029 because those cross-react with both human and mouse NOTUM. Based on the finding that MAbs 1.802, 1.815, 1.846, 2.78, and 2.1029 interfere with one another's binding, alanine scanning mutagenesis of charged amino acid residues in the vicinity of D141 was performed. Five human NOTUM mutants were constructed, each with a pair of charged residues mutated to alanines: human NOTUM N132A/R133A (SEQ ID NO: 96); human NOTUM E134A/N135A (SEQ ID NO: 97); human NOTUM D137A/R139A (SEQ ID NO: 98); human NOTUM R144A/R145A (SEQ ID NO: 99); and human NOTUM R150A/D151A (SEQ ID NO: 100). All five human mutants were effectively expressed and secreted after transient transfection. Four of the five mutants exhibited significant activity in the OPTS assay while the fifth (human NOTUM D137A/R139A) showed little to no activity. All five mutants were detected in ELISA format by at least some of the Campaign 1 and Campaign 2 MAbs. MAb 2.78 failed to bind human NOTUM D137A/R139A and human NOTUM R144A/R145A, while MAbs 1.802, 1.815, and 1.846 failed to bind only NOTUM R144A/R145A. MAb 2.1029 was immunoreactive with all five of the alanine mutants.

7.8. Binding Affinities of NOTUM Neutralizing Antibodies

Binding affinities of certain anti-NOTUM MAbs was determined using a Biacore 3000. In order to obtain meaningful affinity values for binding to multimeric mouse NOTUM protein, antibody FAb fragments were generated by digestion of whole IgG with the protease Ficin, followed by removal of undigested IgG and Fc fragments by protein A affinity chromatography. Affinity values for binding of FAbs and whole IgG to human NOTUM corresponded, and their affinity values were in the single to low double digit nM range, as shown in Table 3.

TABLE 3

Binding affinity of certain antibodies raised against human and mouse NOTUM

| Antibody or fragment | $K_D$ (nM) | $k_{on}$ (M$^{-1}$sec$^{-1}$) | $k_{off}$ (M$^{-1}$sec$^{-1}$) |
|---|---|---|---|
| Affinity for human NOTUM | | | |
| 1.802 IgG | 1.42 | $2.57 \times 10^5$ | $3.65 \times 10^{-4}$ |
| 1.802 Fab | 0.91 | $8.99 \times 10^5$ | $8.20 \times 10^{-4}$ |
| 2.78 IgG | 17.6 | $4.79 \times 10^4$ | $8.41 \times 10^{-4}$ |
| 2.78 Fab | 15.4 | $8.77 \times 10^4$ | $1.36 \times 10^{-3}$ |
| 2.1029 IgG | 5.99 | $1.51 \times 10^5$ | $9.08 \times 10^{-4}$ |
| Affinity for mouse NOTUM | | | |
| 1.802 Fab | No binding observed | | |
| 2.78 Fab | 4.99 | $3.91 \times 10^4$ | $1.95 \times 10^{-4}$ |

7.9. Administration of NOTUM Neutralizing Antibodies to Mice 7.9.1. Administration of NOTUM Neutralizing Antibodies Weekly for 8 Weeks Eight week old male F1 hybrid (129×C57) mice were administered NOTUM neutralizing antibody 2.1029 or 2.78b, or a control antibody, by intraperitoneal injection at 30 mg/kg once per week for eight weeks. There were 12 mice per group. At the end of the study, the mice were sacrificed. Bone mass and architecture were determined by microCT following necropsy, using a Scanco μCT40 with a threshold value of 240, an integration time of 200 milliseconds, and an X-ray tube voltage of 55 keV.

As shown in FIG. 6, midshaft femur cortical thickness increased by 12% (P<0.001) with administration of NOTUM neutralizing antibody 2.1029, and 16% (P<0.001) with administration of NOTUM neutralizing antibody 2.78b, as compared to the control antibody.

7.9.2. Administration of NOTUM Neutralizing Antibody 2.1029 Weekly for 4 Weeks

Eight week old male F1 hybrid (129×C57) mice were administered NOTUM neutralizing antibody 2.1029 by intraperitoneal injection at 3 mg/kg, 10 mg/kg, or 30 mg/kg once per week for four weeks. There were 10 mice per group. At the end of the study, the mice were sacrificed. Bone mass and architecture were determined by microCT following necropsy, using a Scanco μCT40 with a threshold value of 240, an integration time of 200 milliseconds, and an X-ray tube voltage of 55 keV.

As shown in FIG. 7, midshaft femur cortical thickness increased by 5% (P=0.12) with administration of 30 mg/kg NOTUM neutralizing antibody 2.1029, relative to administration of control antibody.

7.9.3. Administration of NOTUM Neutralizing Antibody 2.78b Weekly for 4 Weeks

Eight week old male F1 hybrid (129×C57) mice were administered NOTUM neutralizing antibody 2.78b by intraperitoneal injection at 3 mg/kg, 10 mg/kg, or 30 mg/kg once per week for four weeks. There were 10 mice per group in the first experiment. In a second experiment, NOTUM neutralizing antibody 2.78b was administered by intraperitoneal injection at 0.3 mg/kg, 1 mg/kg, or 3 mg/kg once per week for four weeks. There were 12 mice per group in the second experiment. At the end of each study, the mice were sacrificed. Bone mass and architecture were determined by microCT following necropsy, using a Scanco μCT40 with a threshold value of 240, an integration time of 200 milliseconds, and an X-ray tube voltage of 55 keV.

As shown in FIG. 8A, midshaft femur cortical thickness increased by 13% (P<0.001), 17% (P<0.001), and 16% (P<0.001) with administration of 3 mg/kg, 10 mg/kg, and 30 mg/kg, respectively, of NOTUM neutralizing antibody 2.78b, relative to administration of control antibody, in the first experiment. As shown in FIG. 8B, midshaft femur cortical thickness increased by 3% (P=0.46), 7% (P=0.01), and 10% (P<0.001) with administration of 0.3 mg/kg, 1 mg/kg, and 3 mg/kg, respectively, of NOTUM neutralizing antibody 2.78b, relative to administration of control antibody, in the second experiment.

7.9.4. Administration of NOTUM Neutralizing Antibody 2.78b Weekly for 4 Weeks with Zoledronate Pretreatment 28-week old male F1 hybrid mice (129×C57) were administered a single dose 50 μg/kg zoledronate by intraperitoneal injection. Four weeks after the dose of zolendronate, the mice were administered 10 mg/kg NOTUM neutralizing antibody 2.78b by i.p. injection weekly for 4 weeks. At the end of each study, the mice were sacrificed. There were 11 or 12 mice per group. Bone mass and architecture were determined by microCT following necropsy, using a Scanco μCT40 with a threshold value of 240, an integration time of 200 milliseconds, and an X-ray tube voltage of 55 keV. In addition, serum levels of PINP, which is a marker of bone formation, were measured using a commercially available ELISA assay (Immunodiagnostic Systems, Scottsdale, Ariz.) at day 7 after the first dose of Mab 2.78b.

As shown in FIG. 9A, the midshaft femur cortical thickness increased by 10 μm, or 4% (P=0.31), in mice administered zoledronate and control antibody, relative to mice administered saline and control antibody. Midshaft femur cortical thickness increased by 23 μm, or 9% (P<0.001), in mice administered NOTUM neutralizing antibody 2.78b without zoledronate pretreatment, relative to mice administered saline and control antibody, and increased by 14 μm, or 5% (P=0.06), in mice administered NOTUM neutralizing antibody 2.78b with zoledronate pretreatment, relative to mice administered zoledronate and control antibody. FIG. 9B shows that serum PINP levels decreased by 15 ng/mL, or 50% (P<0.001) in mice administered zolendronate treatment and control antibody, relative to mice administered saline and control antibody. PINP levels increased by 14 ng/mL, or 47% (P<0.001) in mice administered NOTUM neutralizing antibody 2.78b without zoledronate pretreatment, relative to mice administered saline and control antibody, and increased by 12 ng/mL, or 79% (P<0.001) in mice administered NOTUM neutralizing antibody 2.78b with zoledronate pretreatment, relative to mice administered zoledronate and control antibody.

7.9.5. Administration of NOTUM Neutralizing Antibody 2.78a for 4 Weeks

For this experiment, Mab 2.78 (also referred to as "2.78b"), which is an IgG2b antibody, was reformatted as an IgG2a antibody (IgG2a antibodies often have longer half-lives than IgG2b antibodies). Reformatted Mab 2.78 is referred to as "2.78a."

13-week old male F1 hybrid mice (129×C57) were administered NOTUM neutralizing antibody 2.78a by intraperitoneal injection at 0.3 mg/kg, 1 mg/kg, 3 mg/kg, or 10 mg/kg once per week for four weeks. There were 10 or 12 mice per group. At the end of each study, the mice were sacrificed. Bone mass and architecture were determined by microCT following necropsy, using a Scanco µCT40 with a threshold value of 240, an integration time of 200 milliseconds, and an X-ray tube voltage of 55 keV.

As shown in FIG. 10, midshaft femur cortical thickness increased by 3% (P=0.57), 7% (P=0.02), 9% (P=0.002), and 10% (P<0.001) with administration of 0.3 mg/gk, 1 mg/kg, 3 mg/kg, and 10 mg/kg, respectively, of NOTUM neutralizing antibody 2.78a in that experiment.

7.9.6. Administration of NOTUM Neutralizing Antibody 2.78a Weekly or Biweekly for 12 Weeks Ten week old male F1 hybrid mice (129×C57) were administered a control antibody, 0.3 mg/kg NOTUM neutralizing antibody 2.78a by i.p. injection weekly for 12 weeks, or 1 mg/kg NOTUM neutralizing antibody 2.78a by i.p. injection every other week (biweekly) for 12 weeks or 24 weeks. There were twelve mice per administration group. At the end of each study, the mice were sacrificed. Bone mass and architecture were determined by microCT following necropsy, using a Scanco µCT40 with a threshold value of 240, an integration time of 200 milliseconds, and an X-ray tube voltage of 55 keV.

As shown in FIG. 11A, the midshaft femur cortical thickness increased by 6% (P<0.001) and 9% (P<0.001) in mice administered 0.3 mg/kg weekly and 1 mg/kg biweekly, respectively, of NOTUM neutralizing antibody 2.78a for 12 weeks. Similarly, as shown in FIG. 11B, the midshaft humerus cortical thickness increased by 5% (P=0.007) and 7% (P<0.001) in mice administered 0.3 mg/kg weekly and 1 mg/kg biweekly, respectively, of NOTUM neutralizing antibody 2.78a for 12 weeks.

As shown in FIG. 12A, the midshaft femur cortical thickness increased by 7% (P=0.002) and 9% (P<0.001) in mice administered 0.3 mg/kg weekly and 1 mg/kg biweekly, respectively, of NOTUM neutralizing antibody 2.78a for 24 weeks. As shown in FIG. 12B, the midshaft humerus cortical thickness increased by 3% (P=0.09) and 8% (P<0.001) in mice administered 0.3 mg/kg weekly and 1 mg/kg biweekly, respectively, of NOTUM neutralizing antibody 2.78a for 24 weeks. Finally, as shown in FIG. 12C, the ninth rib cortical thickness increased by 7% (P=0.02) and 9% (P=0.003) in mice administered 0.3 mg/kg weekly and 1 mg/kg biweekly, respectively, of NOTUM neutralizing antibody 2.78a for 24 weeks.

7.10. Administration of NOTUM Neutralizing Antibodies to Ovariectomized Mice 7.10.1. Ovariectomy Sixteen-week-old albino C57BL/6J female mice were ovariectomized or given sham surgery. Serum levels of PINP, which is a marker of bone formation, and CTX, which is a marker of bone resorption, were measured using a commercially available ELISA assay (Immunodiagnostic Systems, Scottsdale, Ariz.) in the interval after ovariectomy and before administration of NOTUM neutralizing antibody, to confirm that increased bone remodelling was occurring after ovariectomy.

Following surgery and prior to the start of treatment, ovariectomized mice showed increased bone remodeling relative to sham surgery mice, as shown in Table 4. Since trabecular bone contains many more bone cells than cortical bone, these data likely reflect primarily increased trabecular bone remodeling.

TABLE 4

Bone marker levels following surgery

| Marker | Weeks after surgery | Sham surgery (N = 10) | OVX surgery (N = 10) | Statistics |
|---|---|---|---|---|
| PINP (ng/ml) | 1 | 36.4 ± 0.9 | 50.6 ± 5.3 | Δ = 39% P = 0.02 |
| CTX (ng/ml) | 2 | 10.5 ± 0.9 | 14.1 ± 0.9 | Δ = 33% P = 0.01 |
| PINP (ng/ml) | 4 | 41.2 ± 2.3 | 54.8 ± 2.5 | Δ = 33% P = 0.001 |

7.10.2. Administration of NOTUM Neutralizing Antibody 2.78b to Ovariectomized Mice NOTUM neutralizing antibody 2.78b or a control antibody was administered at 10 mg/kg by intraperitoneal injection once per week for 4 weeks, starting 8 weeks after surgery. The study included the treatment groups shown in Table 5.

TABLE 5

Treatment groups in ovariectomy (OVX) study

| Number of mice | Surgery | Antibody |
|---|---|---|
| 13 | Sham | Control |
| 13* | Sham | NOTUM |
| 10 | OVX | Control |
| 11 | OVX | NOTUM |

*There were originally 14 mice in this group, but one mouse died during the study.

To assess the location and extent of new bone formation, fluorochrome bone labels were administered on treatment days 7, 14, and 21 (i.e., with the $2^{nd}$, $3^{rd}$, and $4^{th}$ treatments). Calcein, which fluoresces green, was administered on day 7; alizarin, which fluoresces red, was administered on day 14; and tetracycline, which fluoresces yellow, was administered on day 21. The mice were sacrificed at the end of the 4 week treatment. Uterine weight at necropsy confirmed that the ovariectomy surgery was successful. (Data not shown.)

7.10.3. Bone Mass and Architecture in NOTUM Neutralizing Antibody-Treated Ovariectomized Mice Bone mass and architecture were determined by microCT following necropsy, using a Scanco µCT40 with a threshold value of 240, an integration time of 200 milliseconds, and an X-ray tube voltage of 55 keV. The midshaft femur, LV5 vertebral body, and the femoral neck were scanned.

As shown in FIG. 13A, the midshaft femur cortical thickness increased by 22 µm, or 9%, in sham surgery mice administered NOTUM neutralizing antibody 2.78b, relative to sham surgery mice administered control antibody, and increased by 26 µm, or 12%, in ovariectomized mice administered NOTUM neutralizing antibody 2.78b, relative to ovariectomized mice administered control antibody. As shown in FIG. 13B, the midshaft femur mineralized bone area increased by 0.1 mm$^2$, or 11%, in sham surgery mice administered NOTUM neutralizing antibody 2.78b, relative to sham surgery mice administered control antibody, and increased by 0.08 mm$^2$, or 10%, in ovariectomized mice administered NOTUM neutralizing antibody 2.78b, relative to ovariectomized mice administered control antibody.

As shown in FIG. 14A, the proportion in the LV5 vertebral body of total (cortical plus trabecular) bone volume to total volume increased by 9% in sham surgery mice administered NOTUM neutralizing antibody 2.78b, relative to sham surgery mice administered control antibody, and increased by 3% in ovariectomized mice administered NOTUM neutralizing antibody 2.78b, relative to ovariectomized mice administered control antibody. As shown in FIG. 14B, the proportion in the LV5 vertebral body of cortical bone volume to total volume increased by 13% in sham surgery mice administered NOTUM neutralizing antibody 2.78b, relative to sham surgery mice administered control antibody, and increased by 9% in ovariectomized mice administered NOTUM neutralizing antibody 2.78b, relative to ovariectomized mice administered control antibody. As shown in FIG. 14C, the proportion in the LV5 vertebral body of trabecular bone volume to total volume was not significantly affected by administration of NOTUM neutralizing antibody 2.78b in either the sham surgery mice or the ovariectomized mice.

Finally, as shown in FIG. 15, the proportion of femoral neck bone volume to total volume increased by 4% in sham surgery mice administered NOTUM neutralizing antibody 2.78b, relative to sham surgery mice administered control antibody, and increased by 6% in ovariectomized mice administered NOTUM neutralizing antibody 2.78b, relative to ovariectomized mice administered control antibody.

7.10.4. Bone Histomorphometry in NOTUM Neutralizing Antibody-Treated Ovariectomized Mice Femur shafts were embedded in methylmethacrylate using a rapid embedding protocol. See Brommage and Vafai, *Calcified Tissue Int'l* 67: 479 (2000). Midshaft cross-sections with a thickness of about 80 μm were prepared using a Leica SP1600 bone saw. Sections were then examined with an Olympus BX60 fluorescent microscope. Various bone histomorphometric parameters were determined using OsteoMeasure™ software (OsteoMetrics, Decatur, Ga.). Both static parameters (such as bone area and thickness) and dynamic parameters (such as single label surface (SLS), mineral aposition rater (MAR), and bone formation rate (BFR)) were measured at 100× magnification.

FIG. 16 shows the percentage of the endocortical surface of the midshaft femur cross-sections that were labeled with calcein, which was administered on day 7, with alizarin, which was administered on day 14, and with tetracycline, which was administered on day 21. Table 6 shows the statistical analysis of the data in FIG. 16. Mice administered NOTUM neutralizing antibody 2.78b showed a significantly higher percentage of endocortical labeling at days 7 and 14 compared to mice administered control antibody.

TABLE 6

Two-factor ANOVA of Single-Label Surface %

| Two-Factor ANOVA | Day 7 | Day 14 | Day 21 |
|---|---|---|---|
| Effect of Ovariectomy | P = 0.16 | P = 0.65 | P = 0.28 |
| Effect of Treatment | P < 0.001 | P < 0.001 | P = 0.02 |
| Effect of Interaction | P = 0.66 | P = 0.74 | P = 0.77 |

FIG. 17 shows the mineral appositional rate (A) and the volume-referent bone formation rate (B) of sham surgery and ovariectomized mice that were administered control antibody or NOTUM neutralizing antibody 2.78b. The mineral appositional rate (FIG. 17A) was determined by measuring the distance between the calcein label (day 7) and the alizarin label (day 14) and dividing by 7 to obtain the "days 7 to 14 rate," and measuring the distance between the alizarin label (day 14) and the tetracycline label (day 21) and dividing by 7 to obtain the "days 14 to 21 rate." Table 7 shows the statistical analysis of the data in FIG. 17A. Mice administered NOTUM neutralizing antibody 2.78b showed a greater rate of mineral apposition than mice administered control antibody during the time period from days 7 to 14.

TABLE 7

Two-factor ANOVA of Mineral Appositional Rate

| Two-Factor ANOVA | Days 7 to 14 | Days 14 to 21 |
|---|---|---|
| Effect of Ovariectomy | P = 0.80 | P = 0.70 |
| Effect of Treatment | P < 0.001 | P = 0.82 |
| Effect of Interaction | P = 0.86 | P = 0.02 |

The volume-referent bone formation rate (FIG. 17B) was determined by standard calculations involving multiplying the endocortical mineralization surface (percentage of double-labeled surface plus one-half of the single labeled surface, derived from FIG. 16) by the mineral apposition rate (see FIG. 17A). The result is the bone formation rate divided by the bone volume, expressed as a percentage per 7 days. Table 8 shows the statistical analysis of the data in FIG. 17B. As evident in FIG. 17B, the bone formation rate per bone volume is significantly higher in mice administered NOTUM neutralizing antibody 2.78b than in mice administered control antibody.

TABLE 8

Two-factor ANOVA of Volume-Referent Bone Formation Rate

| Two-Factor ANOVA | Days 7 to 14 | Days 14 to 21 |
|---|---|---|
| Effect of Ovariectomy | P = 0.95 | P = 0.80 |
| Effect of Treatment | P < 0.001 | P < 0.001 |
| Effect of Interaction | P = 0.39 | P = 0.30 |

7.11. Identification of Species Suitable for Testing NOTUM Neutralizing Antibodies Based upon multi-species protein sequence alignments taken from the public domain, it was predicted that MAbs 1.802, 1.815, and 1.846 would bind to guinea pig NOTUM and that this species might therefore be suitable for preclinical studies. To test this hypothesis, guinea pig NOTUM was cloned and expressed by transient transfection, and shown to be active in the OPTS assay. MAbs 1.802, 1.815, and 1.846 were found to bind to guinea pig NOTUM by ELISA and MAb 1.802 was shown to neutralize guinea pig NOTUM activity in the OPTS assay. MAb 2.78 bound guinea pig NOTUM with lower affinity than MAb 1.802, and had correspondingly lower inhibiting activity in the OPTS assay. MAb 2.1029 bound guinea pig NOTUM only weakly, and did not significantly inhibit it in the OPTS assay.

Cynomolgus and rhesus monkey NOTUM were cloned from cDNA preparations from those species. Analysis of the sequences revealed that the amino acid at the position equivalent to human NOTUM D141 is an asparagine, which is different from the amino acid at that position in both mouse and human NOTUM. Active (as determined by OPTS assay) cynomolgus and rhesus NOTUM proteins were generated by transient transfection, and it was found that MAb 1.802 neither binds nor inhibits either protein. An active human NOTUM point mutant, human NOTUM D141N, was generated by transient transfection, and it was found that MAb 1.802 does not bind to that human NOTUM point mutant.

MAb 2.78 bound both cynomolgus and rhesus NOTUM weakly by ELISA, but did not inhibit either protein significantly in the OPTS assay. In contrast, MAb 2.1029 bound both cynomolgus and rhesus monkey NOTUM by ELISA as

7.12. Antibody Sequencing and Humanization

Heavy and light chain variable regions were sequenced by specific RT-PCR using total RNA from the relevant hybridoma cell line followed by sequencing of the PCR product. The heavy and light chain variable regions from four Campaign 1 antibodies: 1.731, 1.802, 1.815, and 1.846, and three Campaign 2 antibodies: 2.1029, 2.55, and 2.78, were sequenced. The variable region sequences, without signal sequences, for each of those antibodies are shown in Section 7 (Table of Sequences), below. Section 7 also shows the sequences for the heavy and light chain CDR1, CDR2, and CDR3 for each of those antibodies. The following table shows the SEQ ID NOs corresponding to the heavy and light chain variable regions, and to CDR1, CDR2, and CDR3, for each of those antibodies.

TABLE 9

SEQ ID NOs for heavy and light chain variable regions and CDRs

| Mouse antibody | Heavy chain variable region SEQ ID NO (CDR1, CDR2, CDR3 SEQ ID NOs) | Light chain variable region SEQ ID NO (CDR1, CDR2, CDR3 SEQ ID NOs) |
|---|---|---|
| 1.731 | 7 (9, 10, 11) | 8 (12, 13, 14) |
| 1.802 | 15 (17, 18, 19) | 16 (20, 21, 22) |
| 1.815 | 23 (25, 26, 27) | 24 (28, 29, 30) |
| 1.846 | 31 (33, 34, 35) | 32 (36, 37, 38) |
| 2.1029 | 39 (41, 42, 43) | 40 (44, 45, 46) |
| 2.55 | 47 (49, 50, 51) | 48 (52, 53, 54) |
| 2.78 | 55 (57, 58, 59) | 56 (60, 61, 62) |

Certain heavy and light chain CDRs were found to have high homology among two or more of the sequenced antibodies. MAbs 1.802 and 1.846 share an identical heavy chain CDR1 (GFTFSDYGMH; SEQ ID NOs: 17 and 33), while heavy chain CDR1 of MAb 1.815 (GFTFSDFGMH; SEQ ID NO: 25) differs from MAbs 1.802 and 1.846 by only one conservative amino acid substitution (Phenylalanine (F) in place of Tyrosine (Y)). The consensus sequence for the heavy chain CDR1 for those antibodies is therefore GFTFSDX$_1$GMH (SEQ ID NO: 90), wherein X$_1$ is F or Y. Heavy chain CDR3 of MAbs 1.802 and 1.846 differ by only one conservative amino acid substitution (histidine (H) versus asparagine (N)). The consensus sequence for the heavy chain CDR3 for those antibodies is therefore KX$_2$YNGGYFDV (SEQ ID NO: 91), wherein X$_2$ is H or N. MAbs 1.802 and 1.846 share an identical light chain CDR2 (LASNLES; SEQ ID NOs: 21 and 37), while light chain CDR2 of MAb 1.815 (LASDLES; SEQ ID NO: 29) differs from MAbs 1.802 and 1.846 by only one conservative amino acid substitution (aspartic acid (D) in place of asparagine (N)). The consensus sequence for the light chain CDR2 for those antibodies is therefore LASX$_6$LES (SEQ ID NO: 93), wherein X$_6$ is D or N. Finally, a consensus sequence for the light chain CDR1 for the three antibodies from Campaign 1, 1.802, 1.846, and 1.815, is RASKX$_3$VSX$_4$SGYSYX$_5$H (SEQ ID NO: 92), wherein X$_3$ is I or S, X$_4$ is T or E, and X$_5$ is M or I.

BLAST searching was performed against public databases to identify the human germline variable region sequences with greatest similarity to each of the mouse heavy and light chain variable regions. Using the AbM definition, CDRs from the mouse variable regions were then grafted in silico into these human germline variable sequences in place of the human germline CDRs. The resulting humanized variable regions for five of the mouse antibodies (2.78, 2.1029, 1.802, 1.815, and 1.846) were synthesized with a 5' leader sequence encoding an in-frame signal peptide and cloned upstream of sequence encoding human IgG2 constant regions in the case of the heavy chain variable sequences or human kappa constant region in the case of the light chain variable sequences. The sequences for each of the humanized variable regions are shown in Section 7 (Table of Sequences), below, along with the sequences for the full-length humanized heavy and light chains (without the signal peptide).

Coding sequences for full length humanized heavy and light chains were subcloned into mammalian expression vectors and corresponding heavy and light chain constructs were cotransfected into CHO—S cells. The resulting conditioned media were checked by Western blotting with an anti-human secondary antibody to confirm expression and secretion of intact humanized antibody. The conditioned media were then tested in ELISA format to determine whether the humanized antibodies retained the capacity to bind human NOTUM protein. Humanized MAbs 1.802, 1.815, 1.846, and 2.1029 bound human NOTUM while humanized MAb 2.78 exhibited little to no binding to either human or mouse NOTUM.

All references cited above are incorporated herein by reference in their entireties for any purpose.

8

Table of Sequences

| SEQ ID NO | Description | Sequence |
|---|---|---|
| 1 | Human NOTUM | MGRGVRVLLL LSLLHCAGGS EGRKTWRRRG QQPPPPPRTE AAPAAGQPVE SFPLDFTAVE GNMDSFMAQV KSLAQSLYPC SAQQLNEDLR LHLLLNTSVT CNDGSPAGYY LKESRGSRRW LLFLEGGWYC FNRENCDSRY DTMRRLMSSR DWPRTRTGTG ILSSQPEENP YWWNANMVFI PYCSSDVWSG ASSKSEKNEY AFMGALIIQE VVRELLGRGL SGAKVLLLAG SSAGGTGVLL NVDRVAEQLE KLGYPAIQVR GLADSGWFLD NKQYRHTDCV DTITCAPTEA IRRGIRYWNG VVPERCRRQF QEGEEWNCFF GYKVYPTLRC PVFVVQWLFD EAQLTVDNVH LTGQPVQEGL RLYIQNLGRE LRHTLKDVPA SFAPACLSHE IIIRSHWTDV QVKGTSLPRA LHCWDRSLHD SHKASKTPLK GCPVHLVDSC PWPHCNPSCP TVRDQFTGQE MNVAQFLMHM GFDMQTVAQP QGLEPSELLG MLSNGS |
| 2 | Mouse NOTUM | MGGEVRVLLL LGLLHWVGGS EGRKTWRRRG QQPPQPPPPP PLPQRAEVEP GAGQPVESFP LDFTAVEGNM DSFMAQVKSL AQSLYPCSAQ QLNEDLRLHL LLNTSVTCND GSPAGYYLKE SKGSRRWLLF LEGGWYCFNR ENCDSRYSTM RRLMSSKDWP HTRTGTGILS SQPEENPHWW NANMVFIPYC SSDVWSGASP KSDKNEYAFM GSLIIQEVVR ELLGKGLSGA KVLLLAGSSA GGTGVLLNVD |

| | | |
|---|---|---|
| SEQ ID NO | Description | Sequence |
| | | RVAELLEELG YPSIQVRGLA DSGWFLDNKQ YRRSDCIDTI NCAPTDAIRR GIRYWSGMVP ERCQRQFKEG EEWNCFFGYK VYPTLRCPVF VVQWLFDEAQ LTVDNVHLTG QPVQEGQWLY IQNLGRELRG TLKDVQASFA PACLSHEIII RSYWTDVQVK GTSLPRALHC WDRSFHDSHK ASKTPMKGCP FHLVDSCPWP HCNPSCPTIR DQFTGQEMNV AQFLMHMGFD VQTVAQQQGM EPSKLLGMLS NGN |
| 3 | Human NOTUM S232A | MGRGVRVLLL LSLLHCAGGS EGRKTWRRRG QQPPPPPRTE AAPAAGQPVE SFPLDFTAVE GNMDSFMAQV KSLAQSLYPC SAQQLNEDLR LHLLLNTSVT CNDGSPAGYY LKESRGSRRW LLFLEGGWYC FNRENCDSRY DTMRRLMSSR DWPRTRTGTG ILSSQPEENP YWWNANMVFI PYCSSDVWSG ASSKSEKNEY AFMGALIIQE VVRELLGRGL SGAKVLLLAG SAAGGTGVLL NVDRVAEQLE KLGYPAIQVR GLADSGWFLD NKQYRHTDCV DTITCAPTEA IRRGIRYWNG VVPERCRRQF QEGEEWNCFF GYKVYPTLRC PVFVVQWLFD EAQLTVDNVH LTGQPVQEGL RLYIQNLGRE LRHTLKDVPA SFAPACLSHE IIIRSHWTDV QVKGTSLPRA LHCWDRSLHD SHKASKTPLK GCPVHLVDSC PWPHCNPSCP TVRDQFTGQE MNVAQFLMHM GFDMQTVAQP QGLEPSELLG MLSNGS |
| 4 | Mouse NOTUM S239A mutant | MGGEVRVLLL LGLLHWVGGS EGRKTWRRRG QQPPQPPPPP PLPQRAEVEP GAGQPVESFP LDFTAVEGNM DSFMAQVKSL AQSLYPCSAQ QLNEDLRLHL LLNTSVTCND GSPAGYYLKE SKGSRRWLLF LEGGWYCFNR ENCDSRYSTM RRLMSSKDWP HTRTGTGILS SQPEENPHWW NANMVFIPYC SSDVWSGASP KSDKNEYAFM GSLIIQEVVR ELLGKGLSGA KVLLLAGSAA GGTGVLLNVD RVAELLEELG YPSIQVRGLA DSGWFLDNKQ YRRSDCIDTI NCAPTDAIRR GIRYWSGMVP ERCQRQFKEG EEWNCFFGYK VYPTLRCPVF VVQWLFDEAQ LTVDNVHLTG QPVQEGQWLY IQNLGRELRG TLKDVQASFA PACLSHEIII RSYWTDVQVK GTSLPRALHC WDRSFHDSHK ASKTPMKGCP FHLVDSCPWP HCNPSCPTIR DQFTGQEMNV AQFLMHMGFD VQTVAQQQGM EPSKLLGMLS NGN |
| 5 | Guinea pig NOTUM | MGRGVRVLFL LGLLHWAGGG EGRKTWRRRG QQPAPAPLPP QRTEAAPGTG QPVESFPLDF TAVEGNMDSF MAQVKSLAQS LYPCSAQQLN EDLRLHLLLN TSVTCNDGSP AGYYLKESKG SRRWLLFLEG GWYCFSRENC DSRYDTMRRL MSSKDWPQTR TGTGILSSQP EENPYWWNAN MVFIPYCSSD VWSGASSKSE KNEYVFMGAL IIREVVQELL GRGLSGAKVL LLAGSSAGGT GVLLNVDRVA EQLEQLGYPA IQVRGLADSG WFLDNKQYRR TDCVDTVTCA PTEAIRRGIR YWNGMVPERC RSQFKEGEEW NCFLGYKVYP TLRCPVFVVQ WLFDEAQLTA DNAHLTGQPV QEGQWLYIQN LGHELRNTLK DVPASFAPAC LSHEIIIRSH WTDVQVKGTS LPRALHCWDR SLHDSHKASK TPLKGCPIHL VDSCPWPHCN PSCPTIRDQF TGQEMNVAQF LMHMGFDVQT VAQQQGLEPS KLLGMLSSGS |
| | Cynomolgus monkey NOTUM | MGRGVRVLLL LGLLHCAGGS EGRKTWRRRG QQPPPPPRTE AAPAAGQPVE SFPLDFTAVE GNMDSFMAQV KSLAQSLYPC SAQQLNEDLR LHLLLNTSVT CNDGSPAGYY LKESRGSRRW LLFLEGGWYC FNRENCDSRY NTMRRLMSSR DWPRTRTGTG ILSSQPEENP YWWNANMVFI PYCSSDVWSG ASSKSEKNEY AFMGALIIQE VVRELLGRGL SGAKVLLLAG SSAGGTGVLL NVDRVAEQLE ELGYPAIQVR GLADSGWFLD NKQYRHTDCV DTITCAPTEA IRRGIRYWNG VVPERCRRQF QEGEEWNCFF GYKIYPTLRC PVFVVQWLFD EAQLTVDNVH LTGQPVQESQ RLYIQNLGRE LRHTLKDVPA SFAPACLSHE IIIRSHWTDV QVKGTSLPRA LHCWDRSLHD SHKTSKTPLK GCPVHLVDSC PWPHCNPSCP TVRDQFTGQE MNVAQFLMHM GFDVQTVAQQ QGPEPSKLLG LPSDGS |
| 6 | Rhesus macaque NOTUM | MGRGVRVLLL LGLLHCAGGS EGRKTWRRRG QQPPPPPRTE AAPAAGQPVE SFPLDFTAVE GNMDSFMAQV KSLAQSLYPC SAQQLNEDLR LHLLLNTSVT CNDGSPAGYY LKESRGSRRW LLFLEGGWYC FNRENCDSRY NTMRRLMSSR DWPRTRTGTG ILSSQPEENP YWWNANMVFI PYCSSDVWSG ASSKSEKNEY AFMGALIIQE VVRELLGRGL SGAKVLLLAG SSAGGTGVLL NVDRVAEQLE ELGYPAIQVR GLADSGWFLD NKQYRHTDCV DTITCAPTEA IRRGIRYWNG VVPERCRRQF QEGEEWNCFF GYKIYPTLRC PVFVVQWLFD EAQLTVDNVH LTGQPVQESQ RLYIQNLGRE LRHTLKDVPA SFAPACLSHE IIIRSHWTDV QVKGTSLPRA LHCWDRSLHD SHKNSKTPLK GCPVHLVDSC PWPHCNPSCP TVRDQFTGQE MNVAQFLMHM GFDVQTVAQQ QGPEPSKLLG LPSDGS |
| 7 | MAb 1.731 heavy chain variable region | EVQLQQSGPE LVKPGASVKV SCKASGYPFT DYFIHWVKQT HGKSLEWIGY FFPKNGANGY NQKFEGKVTL TVDKSSSTAY MELRSLTSED SAVYYCARRY GNYYSMDYWG QGTSVTVSSA KTTPP |
| 8 | MAb 1.731 light chain variable region | SFVMTQTPKF LLVSAGDRVT ITCKASQSVG DDVAWYQQKP GQSPTLLIYR VSNRYTGVPD RFTGSGYGTD FTFTINTVQA EDLAVYFCQQ DYSSPYTFGG GTQLEVKRAD AAP |
| 9 | MAb 1.731 heavy chain CDR1 | GYPFTDYFIH |

Table of Sequences

| SEQ ID NO | Description | Sequence |
|---|---|---|
| 10 | MAb 1.731 heavy chain CDR2 | YFFPKNGANG |
| 11 | MAb 1.731 heavy chain CDR3 | RYGNYYSMDY |
| 12 | MAb 1.731 light chain CDR1 | KASQSVGDDVA |
| 13 | MAb 1.731 light chain CDR2 | RVSNRYT |
| 14 | MAb 1.731 light chain CDR3 | QQDYSSPYT |
| 15 | MAb 1.802 heavy chain variable region | EVQLVESGGG LVKPGGSLKL SCAASGFTFS DYGMHWFRQA PEKGLEWVAY ISSGSRTVYY ADTVKGRFTI SRDNAKNTLS LQMTSLRSED TAMYYCARKH YNGGYFDVWG TGTTVTVSSA KTTP |
| 16 | MAb 1.802 light chain variable region | DIVLTQSPAS LAVSLGQRAT ISCRASKIVS TSGYSYMHWY QQKPGQPPKL LIYLASNLES GVPARFSGSG SGTDFTLNIH PVEEEDAATY YCQHSRELPP TFGSGTKLEI KRADAAP |
| 17 | MAb 1.802 heavy chain CDR1 | GFTFSDYGMH |
| 18 | MAb 1.802 heavy chain CDR2 | YISSGSRTVY |
| 19 | MAb 1.802 heavy chain CDR3 | KHYNGGYFDV |
| 20 | MAb 1.802 light chain CDR1 | RASKIVSTSGYSYMH |
| 21 | MAb 1.802 light chain CDR2 | LASNLES |
| 22 | MAb 1.802 light chain CDR3 | QHSRELPPT |
| 23 | MAb 1.815 heavy chain variable region | DVQLLESGGG LVQPGGSRKL SCAASGFTFS DFGMHWVRQA PEKGLEWVAY SSSSGGTTVYY ADTVKGRLTL SRDNSKNTLF LEMTSLRSED TAMYYCARAS YDGGYFDCWG QGTSLTVSSA KTTPP |
| 24 | MAb 1.815 light chain variable region | DIVLTQSPAS LAVSLGQRAT ISCRASKSVS TSGYSYIHWY QQKPGQPPKL LIYLASDLES GVPARFSGSG SGAAFTLNIH PVEEEDAATY YCHHSRELPF TFGSGTKLEI KRADAAP |
| 25 | MAb 1.815 heavy chain CDR1 | GFTFSDFGMH |
| 26 | MAb 1.815 heavy chain CDR2 | YSSSGGTTVY |
| 27 | MAb 1.815 heavy chain CDR3 | ASYDGGYFDC |
| 28 | MAb 1.815 light chain CDR1 | RASKSVSTSGYSYIH |
| 29 | MAb 1.815 light chain CDR2 | LASDLES |
| 30 | MAb 1.815 light chain CDR3 | HHSRELPFT |
| 31 | MAb 1.846 heavy chain variable region | EVQLVESGGD LVKPGGSLKL SCAASGFTFS DYGMHWLRQA PEKGLEWVAY ISSGSTTLSY ANTMKGRFTI SRDNAKKTLS LQMTSLRSED TAIYYCARKN YNGGYFDVWG TGTTVTVSSA KTTPP |
| 32 | MAb 1.846 light chain variable region | DIVLTQSPAS LVVSLGQRAT ISCRASKSVS ESGYSYMHWY QQKPGQPPKL LIYLASNLES GVPARFSGSG SGTDFTLNIH PVEEGDATTY YCQHSRVLPP TFGSGTKLEI KRADAAP |

| | | |
|---|---|---|
| SEQ ID NO | Description | Sequence |
| 33 | MAb 1.846 heavy chain CDR1 | GFTFSDYGMH |
| 34 | MAb 1.846 heavy chain CDR2 | YISSGSTTLS |
| 35 | MAb 1.846 heavy chain CDR3 | KNYNGGYFDV |
| 36 | MAb 1.846 light chain CDR1 | RASKSVSESGYSYMH |
| 37 | MAb 1.846 light chain CDR2 | LASNLES |
| 38 | MAb 1.846 light chain CDR3 | QHSRVLPPT |
| 39 | MAb 2.1029 heavy chain variable region | QVQLKESGPG LVAPSQSLSI TCTVSGFSLT SYGVHWVRQP PGKGLEWLGV IWAGGSTNYN SALMSRLSIS KDNSKSQVFL KMNSLQTDDT AIYFCARDGD YGTIYAMDYW GQGTSVTVSS AKTTAPS |
| 40 | MAb 2.1029 light chain variable region | DIQMTQTTSS LSASLGDRVT ISCRASQDIS NYLNWYQQKP DGTVKLLIYY TSRLHSGVPS RFTGSGSGTD YSLTISNLEQ EDIATYFCQQ GKTLPRTFGG GTMLEIKRAD AAP |
| 41 | MAb 2.1029 heavy chain CDR1 | GFSLTSYGVH |
| 42 | MAb 2.1029 heavy chain CDR2 | VIWAGGSTN |
| 43 | MAb 2.1029 heavy chain CDR3 | DGDYGTIYAMDY |
| 44 | MAb 2.1029 light chain CDR1 | RASQDISNYLN |
| 45 | MAb 2.1029 light chain CDR2 | YTSRLHS |
| 46 | MAb 2.1029 light chain CDR3 | QQGKTLPRT |
| 47 | MAb 2.55 heavy chain variable region | EVQLQQSGTV LARPGALVKM SCKASGYTFT SYWMHWVKQR PGQGLEWIGA IYPGKSDTRY NQKFKDKAKL TAVTSTSTAY MDLSSLTDED SAVYYCSRRY GNFYAMDYWG QGTSVTVSSA KTTAPS |
| 48 | MAb 2.55 light chain variable region | SIVMTQTPKF LLVSAGDRVT MTCKASQSVS NDVAWYQQKP GQSPELLIYY ASDRYTGVPD RFTGSGYGTD FTLTISTVQA EDLAVYFCQQ DYSSPYTFGG GTKLETKRAD AAP |
| 49 | MAb 2.55 heavy chain CDR1 | GYTFTSYWMH |
| 50 | MAb 2.55 heavy chain CDR2 | AIYPGKSDTR |
| 51 | MAb 2.55 heavy chain CDR3 | RYGNFYAMDY |
| 52 | MAb 2.55 light chain CDR1 | KASQSVSNDVA |
| 53 | MAb 2.55 light chain CDR2 | YASDRYT |
| 54 | MAb 2.55 light chain CDR3 | QQDYSSPYT |
| 55 | MAb 2.78 heavy chain variable region | DVQLVESGGG LVQPGGSRKL SCAASGFTFS SFGMHWVRQA PEKGLEWVAY ITSGSGAIYY ADTVRGRFTI SRDTPKNTLF LQMTSLRSED TAMYYCARSA DGLDYWGQGT SVTVSSAKTT PPS |

| SEQ ID NO | Description | Sequence |
|---|---|---|
| 56 | MAb 2.78 light chain variable region | DIQMTQSPAS LYVSVGETVT ITCRASENIY SNLAWYQQKQ GKSPQLLVYG ATNLADGVPS RFSGSGSGTQ YSLKINSLKS EDFGSYYCQH FWGTPFTFGS GTKLEIKRAD AAP |
| 57 | MAb 2.78 heavy chain CDR1 | GFTFSSFGMH |
| 58 | MAb 2.78 heavy chain CDR2 | YITSGSGAIY |
| 59 | MAb 2.78 heavy chain CDR3 | SADGLDY |
| 60 | MAb 2.78 light chain CDR1 | RASENIYSNLA |
| 61 | MAb 2.78 light chain CDR2 | GATNLAD |
| 62 | MAb 2.78 light chain CDR3 | QHFWGTPFT |
| 63 | Humanized Ab (HumAb) 2.78 heavy chain variable region | EVQLVESGGG LVQPGGSLRL SCAASGFTFS SFGMHWVRQA PGKGLEWVSY ITSGSGAIYY ADSVKGRFTI SRDNAKNSLY LQMNSLRAED TAVYYCARSA DGLDYWGQGT TVTVSS |
| 64 | HumAb 2.78 heavy chain | EVQLVESGGG LVQPGGSLRL SCAASGFTFS SFGMHWVRQA PGKGLEWVSY ITSGSGAIYY ADSVKGRFTI SRDNAKNSLY LQMNSLRAED TAVYYCARSA DGLDYWGQGT TVTVSSDVWG QGTTVTVSSA STKGPSVFPL APCSRSTSES TAALGCLVKD YFPEPVTVSW NSGALTSGVH TFPAVLQSSG LYSLSSVVTV TSSNFGTQTY TCNVDHKPSN TKVDKTVERK CCVECPPCPA PPVAGPSVFL FPPKPKDTLM ISRTPEVTCV VVDVSHEDPE VQFNWYVDGM EVHNAKTKPR EEQFNSTFRV VSVLTVVHQD WLNGKEYKCK VSNKGLPAPI EKTISKTKGQ PREPQVYTLP PSREEMTKNQ VSLTCLVKGF YPSDIAVEWE SNGQPENNYK TTPPMLDSDG SFFLYSKLTV DKSRWQQGNV FSCSVMHEAL HNHYTQKSLS LSPGK |
| 65 | HumAb 2.78 light chain variable region | DIQMTQSPSS LSASVGDRVT ITCRASENIY SNLAWYQQKP GKAPKLLIYG ATNLADGVPS RFSGSGSGTD FTLTISSLQP EDFATYYCQH FWGTPFTFGQ GTKVEI |
| 66 | HumAb 2.78 light chain | DIQMTQSPSS LSASVGDRVT ITCRASENIY SNLAWYQQKP GKAPKLLIYG ATNLADGVPS RFSGSGSGTD FTLTISSLQP EDFATYYCQH FWGTPFTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 67 | HumAb 2.1029 heavy chain variable region | QVQLQESGPG LVKPSETLSL TCTVSGFSLT SYGVHWIRQP PGKGLEWIGV IWAGGSTNYN PSLKSRVTIS VDTSKNQFSL KLSSVTAADT AVYYCARDGD YGTIYAMDYW GQGTLVTVSS |
| 68 | HumAb 2.1029 heavy chain | QVQLQESGPG LVKPSETLSL TCTVSGFSLT SYGVHWIRQP PGKGLEWIGV IWAGGSTNYN PSLKSRVTIS VDTSKNQFSL KLSSVTAADT AVYYCARDGD YGTIYAMDYW GQGTLVTVSS DVWGQGTTVT VSSASTKGPS VFPLAPCSRS TSESTAALGC LVKDYFPEPV TVSWNSGALT SGVHTFPAVL QSSGLYSLSS VVTVTSSNFG TQTYTCNVDH KPSNTKVDKT VERKCCVECP CPAPPVAGP SVFLFPPKPK DTLMISRTPE VTCVVVDVSH EDPEVQFNWY VDGMEVHNAK TKPREEQFNS TFRVVSVLTV VHQDWLNGKE YKCKVSNKGL PAPIEKTISK TKGQPREPQV YTLPPSREEM TKNQVSLTCL VKGFYPSDIA VEWESNGQPE NNYKTTPPML DSDGSFFLYS KLTVDKSRWQ QGNVFSCSVM HEALHNHYTQ KSLSLSPGK |
| 69 | HumAb 2.1029 light chain variable region | DIQMTQSPSS LSASVGDRVT ITCRASQDIS NYLNWYQQKP GKAPKLLIYY TSRLHSGVPS RFSGSGSGTD FTFTISSLQP EDIATYYCQQ GKTLPRTFGG GTKVEI |
| 70 | HumAb 2.1029 light chain | DIQMTQSPSS LSASVGDRVT ITCRASQDIS NYLNWYQQKP GKAPKLLIYY TSRLHSGVPS RFSGSGSGTD FTFTISSLQP EDIATYYCQQ GKTLPRTFGG GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |

-continued

| SEQ ID NO | Description | Sequence |
|---|---|---|
| 71 | HumAb 1.802 heavy chain variable region | EVQLVESGGG LVQPGGSLRL SCAASGFTFS DYGMHWVRQA PGKGLEWVSY ISSGSRTVYY ADSVKGRFTI SRDNAKNSLY LQMNSLRDED TAVYYCARKH YNGGYFDVWG QGTLVTVSS |
| 72 | HumAb 1.802 heavy chain | EVQLVESGGG LVQPGGSLRL SCAASGFTFS DYGMHWVRQA PGKGLEWVSY ISSGSRTVYY ADSVKGRFTI SRDNAKNSLY LQMNSLRDED TAVYYCARKH YNGGYFDVWG QGTLVTVSSD VWGQGTTVTV SSASTKGPSV FPLAPCSRST SESTAALGCL VKDYFPEPVT VSWNSGALTS GVHTFPAVLQ SSGLYSLSSV VTVTSSNFGT QTYTCNVDHK PSNTKVDKTV ERKCCVECPP CPAPPVAGPS VFLFPPKPKD TLMISRTPEV TCVVVDVSHE DPEVQFNWYV DGMEVHNAKT KPREEQFNST FRVVSVLTVV HQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| 73 | HumAb 1.802 light chain variable region | DIVMTQSPDS LAVSLGERAT INCRASKIVS TSGYSYMHWY QQKPGQPPKL LIYLASNLES GVPDRFSGSG SGTDFTLTIS SLQAEDVAVY YCQHSRELPP TFGQGTKLEI |
| 74 | HumAb 1.802 light chain | DIVMTQSPDS LAVSLGERAT INCRASKIVS TSGYSYMHWY QQKPGQPPKL LIYLASNLES GVPDRFSGSG SGTDFTLTIS SLQAEDVAVY YCQHSRELPP TFGQGTKLEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 75 | HumAb 1.815 heavy chain variable region | QVQLVESGGG LVKPGGSLRL SCAASGFTFS DFGMHWIRQA PGKGLEWVSY SSSGGTTVYY ADSVKGRFTI SRDNAKNSLY LQMNSLRAED TAVYYCARAS YDGGYFDCWG QGTTVTVSS |
| 76 | HumAb 1.815 heavy chain | QVQLVESGGG LVKPGGSLRL SCAASGFTFS DFGMHWIRQA PGKGLEWVSY SSSGGTTVYY ADSVKGRFTI SRDNAKNSLY LQMNSLRAED TAVYYCARAS YDGGYFDCWG QGTTVTVSSD VWGQGTTVTV SSASTKGPSV FPLAPCSRST SESTAALGCL VKDYFPEPVT VSWNSGALTS GVHTFPAVLQ SSGLYSLSSV VTVTSSNFGT QTYTCNVDHK PSNTKVDKTV ERKCCVECPP CPAPPVAGPS VFLFPPKPKD TLMISRTPEV TCVVVDVSHE DPEVQFNWYV DGMEVHNAKT KPREEQFNST FRVVSVLTVV HQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| 77 | HumAb 1.815 light chain variable region | DIVMTQSPDS LAVSLGERAT INCRASKSVS TSGYSYIHWY QQKPGQPPKL LIYLASDLES GVPDRFSGSG SGTDFTLTIS SLQAEDVAVY YCHHSRELPF TFGQGTKLEI |
| 78 | HumAb 1.815 light chain | DIVMTQSPDS LAVSLGERAT INCRASKSVS TSGYSYIHWY QQKPGQPPKL LIYLASDLES GVPDRFSGSG SGTDFTLTIS SLQAEDVAVY YCHHSRELPF TFGQGTKLEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 79 | HumAb 1.846 heavy chain variable region | EVQLVESGGG LVQPGGSLRL SCAASGFTFS DYGMHWVRQA PGKGLEWVSY ISSGSTTLSY ADSVKGRFTI SRDNAKNSLY LQMNSLRDED TAVYYCARKN YNGGYFDVWG QGTLVTVSS |
| 80 | HumAb 1.846 heavy chain | EVQLVESGGG LVQPGGSLRL SCAASGFTFS DYGMHWVRQA PGKGLEWVSY ISSGSTTLSY ADSVKGRFTI SRDNAKNSLY LQMNSLRDED TAVYYCARKN YNGGYFDVWG QGTLVTVSSD VWGQGTTVTV SSASTKGPSV FPLAPCSRST SESTAALGCL VKDYFPEPVT VSWNSGALTS GVHTFPAVLQ SSGLYSLSSV VTVTSSNFGT QTYTCNVDHK PSNTKVDKTV ERKCCVECPP CPAPPVAGPS VFLFPPKPKD TLMISRTPEV TCVVVDVSHE DPEVQFNWYV DGMEVHNAKT KPREEQFNST FRVVSVLTVV HQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| 81 | HumAb 1.846 light chain variable region | DIVMTQSPDS LAVSLGERAT INCRASKSVS ESGYSYMHWY QQKPGQPPKL LIYLASNLES GVPDRFSGSG SGTDFTLTIS SLQAEDVAVY YCQHSRVLPP TFGQGTKLEI |
| 82 | HumAb 1.846 light chain | DIVMTQSPDS LAVSLGERAT INCRASKSVS ESGYSYMHWY QQKPGQPPKL LIYLASNLES GVPDRFSGSG SGTDFTLTIS SLQAEDVAVY YCQHSRVLPP TFGQGTKLEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |

Table of Sequences

| SEQ ID NO | Description | Sequence |
|---|---|---|
| 90 | Campaign 1 heavy chain CDR1 consensus | GFTFSDX2GMH |
| 91 | Campaign 1 heavy chain CDR3 consensus | KX2YNGGYFDV |
| 92 | Campaign 1 light chain CDR1 consensus | RASKX3VSX4SGYSYX5H |
| 93 | Campaign 1 light chain CDR2 consensus | LASX6LES |
| 83 | Human-mouse chimeric NOTUM | MGRGVRVLLL LSLLHCAGGS EGRKTWRRRG QQPPPPPRTE AAPAAGQPVE SFPLDFTAVE GNMDSFMAQV KSLAQSLYPC SAQQLNEDLR LHLLLNTSVT CNDGSPAGYY LKESRGSRRW LLFLEGGWYC FNRENCDSRY DTMRRLMSSR DWPRTRTGTG ILSSQPEENP YWWNANMVFI PYCSSDVWSG ASSKSEKNEY AFMGALIIQE VVRELLGRGL SGAKVLLLAG SSAGGTGVLL NVDRVAEQLE KLGYPAIQVR GLADSGWFLD NKQYRRSDCI DTINCAPTDA IRRGIRYWSG MVPERCRQF KEGEEWNCFF GYKVYPTLRC PVFVVQWLFD EAQLTVDNVH LTGQPVQEGQ WLYIQNLGRE LRGTLKDVQA SFAPACLSHE IIIRSYWTDV QVKGTSLPRA LHCWDRSFHD SHKASKTPMK GCPFHLVDSC PWPHCNPSCP TIRDQFTGQE MNVAQFLMHM GFDVQTVAQQ QGMEPSKLLG MLSNGN |
| 84 | Mouse-human chimeric NOTUM | MGGEVRVLLL LGLLHWVGGS EGRKTWRRRG QQPPQPPPPP PLPQRAEVEP GAGQPVESFP LDFTAVEGNM DSFMAQVKSL AQSLYPCSAQ QLNEDLRLHL LLNTSVTCND GSPAGYYLKE SKGSRRWLLF LEGGWYCFNR ENCDSRYSTM RRLMSSKDWP HTRTGTGILS SQPEENPHWW NANMVFIPYC SSDVWSGASP KSDKNEYAFM GSLIIQEVVR ELLGKGLSGA KVLLLAGSSA GGTGVLLNVD RVAELLEELG YPSIQVRGLA DSGWFLDNKQ YRHTDCVDTI TCAPTEAIRR GIRYWNGVVP ERCRRQFQEG EEWNCFFGYK VYPTLRCPVF VVQWLFDEAQ LTVDNVHLTG QPVQEGLRLY IQNLGRELRH TLKDVPASFA PACLSHEIII RSHWTDVQVK GTSLPRALHC WDRSLHDSHK ASKTPLKGCP VHLVDSCPWP HCNPSCPTVR DQFTGQEMNV AQFLMHMGFD MQTVAQPQGL EPSELLGMLS NGS |
| 85 | Human-mouse-human chimeric NOTUM | MGRGVRVLLL LSLLHCAGGS EGRKTWRRRG QQPPPPPRTE AAPAAGQPVE SFPLDFTAVE GNMDSFMAQV KSLAQSLYPC SAQQLNEDLR LHLLLNTSVT CNDGSPAGYY LKESRGSRRW LLFLEGGWYC FNRENCDSRY DTMRRLMSSR DWPRTRTGTG ILSSQPEENP YWWNANMVFI PYCSSDVWSG ASPKSDKNEY AFMGSLIIQE VVRELLGKGL SGAKVLLLAG SSAGGTGVLL NVDRVAELLE ELGYPSIQVR GLADSGWFLD NKQYRRSDCI DTINCAPTDA IRRGIRYWSG MVPERCRQF KEGEEWNCFF GYKVYPTLRC PVFVVQWLFD EAQLTVDNVH LTGQPVQEGL RLYIQNLGRE LRHTLKDVPA SFAPACLSHE IIIRSHWTDV QVKGTSLPRA LHCWDRSLHD SHKASKTPLK GCPVHLVDSC PWPHCNPSCP TVRDQFTGQE MNVAQFLMHM GFDMQTVAQP QGLEPSELLG MLSNGS |
| 86 | Mouse-human-mouse chimeric NOTUM | MGGEVRVLLL LGLLHWVGGS EGRKTWRRRG QQPPQPPPPP PLPQRAEVEP GAGQPVESFP LDFTAVEGNM DSFMAQVKSL AQSLYPCSAQ QLNEDLRLHL LLNTSVTCND GSPAGYYLKE SKGSRRWLLF LEGGWYCFNR ENCDSRYSTM RRLMSSKDWP HTRTGTGILS SQPEENPHWW NANMVFIPYC SSDVWSGASS KSEKNEYAFM GALIIQEVVR ELLGRGLSGA KVLLLAGSSA GGTGVLLNVD RVAEQLEKLG YPAIQVRGLA DSGWFLDNKQ YRHTDCVDTI TCAPTEAIRR GIRYWNGVVP ERCRRQFQEG EEWNCFFGYK VYPTLRCPVF VVQWLFDEAQ LTVDNVHLTG QPVQEGQWLY IQNLGRELRG TLKDVQASFA PACLSHEIII RSYWTDVQVK GTSLPRALHC WDRSFHDSHK ASKTPMKGCP FHLVDSCPWP HCNPSCPTIR DQFTGQEMNV AQFLMHMGFD VQTVAQQQGM EPSKLLGMLS NGN |
| 87 | Human NOTUM (Δ1-46); CD33 signal peptide in italics | MPLLLLLPLL WAGALAQPVE SFPLDFTAVE GNMDSFMAQV KSLAQSLYPC SAQQLNEDLR LHLLLNTSVT CNDGSPAGYY LKESRGSRRW LLFLEGGWYC FNRENCDSRY DTMRRLMSSR DWPRTRTGTG ILSSQPEENP YWWNANMVFI PYCSSDVWSG ASSKSEKNEY AFMGALIIQE VVRELLGRGL SGAKVLLLAG SSAGGTGVLL NVDRVAEQLE KLGYPAIQVR GLADSGWFLD NKQYRHTDCV DTITCAPTEA IRRGIRYWNG VVPERCRRQF QEGEEWNCFF GYKVYPTLRC PVFVVQWLFD EAQLTVDNVH LTGQPVQEGL RLYIQNLGRE LRHTLKDVPA SFAPACLSHE IIIRSHWTDV QVKGTSLPRA LHCWDRSLHD SHKASKTPLK GCPVHLVDSC PWPHCNPSCP TVRDQFTGQE MNVAQFLMHM GFDMQTVAQP QGLEPSELLG MLSNGS |

Table of Sequences

| SEQ ID NO | Description | Sequence |
|---|---|---|
| 88 | Human NOTUM N96D | MGRGVRVLLL LSLLHCAGGS EGRKTWRRRG QQPPPPPRTE AAPAAGQPVE SFPLDFTAVE GNMDSFMAQV KSLAQSLYPC SAQQLNEDLR LHLLLDTSVT CNDGSPAGYY LKESRGSRRW LLFLEGGWYC FNRENCDSRY DTMRRLMSSR DWPRTRTGTG ILSSQPEENP YWWNANMVFI PYCSSDVWSG ASSKSEKNEY AFMGALIIQE VVRELLGRGL SGAKVLLLAG SSAGGTGVLL NVDRVAEQLE KLGYPAIQVR GLADSGWFLD NKQYRHTDCV DTITCAPTEA IRRGIRYWNG VVPERCRRQF QEGEEWNCFF GYKVYPTLRC PVFVVQWLFD EAQLTVDNVH LTGQPVQEGL RLYIQNLGRE LRHTLKDVPA SFAPACLSHE IIIRSHWTDV QVKGTSLPRA LHCWDRSLHD SHKASKTPLK GCPVHLVDSC PWPHCNPSCP TVRDQFTGQE MNVAQFLMHM GFDMQTVAQP QGLEPSELLG MLSNGS |
| 89 | Human NOTUM Q47-M177 | QPVE SFPLDFTAVE GNMDSFMAQV KSLAQSLYPC SAQQLNEDLR LHLLLNTSVT CNDGSPAGYY LKESRGSRRW LLFLEGGWYC FNRENCDSRY DTMRRLMSSR DWPRTRTGTG ILSSQPEENP YWWNANM |
| 94 | Human NOTUM D141S | MGRGVRVLLL LSLLHCAGGS EGRKTWRRRG QQPPPPPRTE AAPAAGQPVE SFPLDFTAVE GNMDSFMAQV KSLAQSLYPC SAQQLNEDLR LHLLLNTSVT CNDGSPAGYY LKESRGSRRW LLFLEGGWYC FNRENCDSRY STMRRLMSSR DWPRTRTGTG ILSSQPEENP YWWNANMVFI PYCSSDVWSG ASSKSEKNEY AFMGALIIQE VVRELLGRGL SGAKVLLLAG SSAGGTGVLL NVDRVAEQLE KLGYPAIQVR GLADSGWFLD NKQYRHTDCV DTITCAPTEA IRRGIRYWNG VVPERCRRQF QEGEEWNCFF GYKVYPTLRC PVFVVQWLFD EAQLTVDNVH LTGQPVQEGL RLYIQNLGRE LRHTLKDVPA SFAPACLSHE IIIRSHWTDV QVKGTSLPRA LHCWDRSLHD SHKASKTPLK GCPVHLVDSC PWPHCNPSCP TVRDQFTGQE MNVAQFLMHM GFDMQTVAQP QGLEPSELLG MLSNGS |
| 95 | Mouse NOTUM S148D | MGGEVRVLLL LGLLHWVGGS EGRKTWRRRG QQPPQPPPPP PLPQRAEVEP GAGQPVESFP LDFTAVEGNM DSFMAQVKSL AQSLYPCSAQ QLNEDLRLHL LLNTSVTCND GSPAGYYLKE SKGSRRWLLF LEGGWYCFNR ENCDSRYDTM RRLMSSKDWP HTRTGTGILS SQPEENPHWW NANMVFIPYC SSDVWSGASP KSDKNEYAFM GSLIIQEVVR ELLGKGLSGA KVLLLAGSSA GGTGVLLNVD RVAELLEELG YPSIQVRGLA DSGWFLDNKQ YRRSDCIDTI NCAPTDAIRR GIRYWSGMVP ERCQRQFKEG EEWNCFFGYK VYPTLRCPVF VVQWLFDEAQ LTVDNVHLTG QPVQEGQWLY IQNLGRELRG TLKDVQASFA PACLSHEIII RSYWTDVQVK GTSLPRALHC WDRSFHDSHK ASKTPMKGCP FHLVDSCPWP HCNPSCPTIR DQFTGQEMNV AQFLMHMGFD VQTVAQQQGM EPSKLLGMLS NGN |
| 96 | Human NOTUM N132A/R133A | MGRGVRVLLL LSLLHCAGGS EGRKTWRRRG QQPPPPPRTE AAPAAGQPVE SFPLDFTAVE GNMDSFMAQV KSLAQSLYPC SAQQLNEDLR LHLLLNTSVT CNDGSPAGYY LKESRGSRRW LLFLEGGWYC FAAENCDSRY DTMRRLMSSR DWPRTRTGTG ILSSQPEENP YWWNANMVFI PYCSSDVWSG ASSKSEKNEY AFMGALIIQE VVRELLGRGL SGAKVLLLAG SSAGGTGVLL NVDRVAEQLE KLGYPAIQVR GLADSGWFLD NKQYRHTDCV DTITCAPTEA IRRGIRYWNG VVPERCRRQF QEGEEWNCFF GYKVYPTLRC PVFVVQWLFD EAQLTVDNVH LTGQPVQEGL RLYIQNLGRE LRHTLKDVPA SFAPACLSHE IIIRSHWTDV QVKGTSLPRA LHCWDRSLHD SHKASKTPLK GCPVHLVDSC PWPHCNPSCP TVRDQFTGQE MNVAQFLMHM GFDMQTVAQP QGLEPSELLG MLSNGS |
| 97 | Human NOTUM E134A/N135A | MGRGVRVLLL LSLLHCAGGS EGRKTWRRRG QQPPPPPRTE AAPAAGQPVE SFPLDFTAVE GNMDSFMAQV KSLAQSLYPC SAQQLNEDLR LHLLLNTSVT CNDGSPAGYY LKESRGSRRW LLFLEGGWYC FNRAACDSRY DTMRRLMSSR DWPRTRTGTG ILSSQPEENP YWWNANMVFI PYCSSDVWSG ASSKSEKNEY AFMGALIIQE VVRELLGRGL SGAKVLLLAG SSAGGTGVLL NVDRVAEQLE KLGYPAIQVR GLADSGWFLD NKQYRHTDCV DTITCAPTEA IRRGIRYWNG VVPERCRRQF QEGEEWNCFF GYKVYPTLRC PVFVVQWLFD EAQLTVDNVH LTGQPVQEGL RLYIQNLGRE LRHTLKDVPA SFAPACLSHE IIIRSHWTDV QVKGTSLPRA LHCWDRSLHD SHKASKTPLK GCPVHLVDSC PWPHCNPSCP TVRDQFTGQE MNVAQFLMHM GFDMQTVAQP QGLEPSELLG MLSNGS |
| 98 | Human NOTUM D137A/R139A | MGRGVRVLLL LSLLHCAGGS EGRKTWRRRG QQPPPPPRTE AAPAAGQPVE SFPLDFTAVE GNMDSFMAQV KSLAQSLYPC SAQQLNEDLR LHLLLNTSVT CNDGSPAGYY LKESRGSRRW LLFLEGGWYC FNRENCASAY DTMRRLMSSR DWPRTRTGTG ILSSQPEENP YWWNANMVFI PYCSSDVWSG ASSKSEKNEY AFMGALIIQE VVRELLGRGL SGAKVLLLAG SSAGGTGVLL NVDRVAEQLE KLGYPAIQVR GLADSGWFLD NKQYRHTDCV DTITCAPTEA IRRGIRYWNG VVPERCRRQF QEGEEWNCFF GYKVYPTLRC PVFVVQWLFD EAQLTVDNVH LTGQPVQEGL RLYIQNLGRE LRHTLKDVPA SFAPACLSHE IIIRSHWTDV QVKGTSLPRA LHCWDRSLHD SHKASKTPLK GCPVHLVDSC PWPHCNPSCP TVRDQFTGQE MNVAQFLMHM GFDMQTVAQP QGLEPSELLG MLSNGS |
| 99 | Human NOTUM R144A/R145A | MGRGVRVLLL LSLLHCAGGS EGRKTWRRRG QQPPPPPRTE AAPAAGQPVE SFPLDFTAVE GNMDSFMAQV KSLAQSLYPC SAQQLNEDLR LHLLLNTSVT CNDGSPAGYY LKESRGSRRW LLFLEGGWYC FNRENCDSRY DTMAALMSSR |

Table of Sequences

| SEQ ID NO | Description | Sequence |
|---|---|---|
| | | DWPRTRTGTG ILSSQPEENP YWWNANMVFI PYCSSDVWSG ASSKSEKNEY |
| | | AFMGALIIQE VVRELLGRGL SGAKVLLLAG SSAGGTGVLL NVDRVAEQLE |
| | | KLGYPAIQVR GLADSGWFLD NKQYRHTDCV DTITCAPTEA IRRGIRYWNG |
| | | VVPERCRRQF QEGEEWNCFF GYKVYPTLRC PVFVVQWLFD EAQLTVDNVH |
| | | LTGQPVQEGL RLYIQNLGRE LRHTLKDVPA SFAPACLSHE IIIRSHWTDV |
| | | QVKGTSLPRA LHCWDRSLHD SHKASKTPLK GCPVHLVDSC PWPHCNPSCP |
| | | TVRDQFTGQE MNVAQFLMHM GFDMQTVAQP QGLEPSELLG MLSNGS |
| 100 | Human NOTUM R150A/D151A | MGRGVRVLLL LSLLHCAGGS EGRKTWRRRG QQPPPPPRTE AAPAAGQPVE |
| | | SFPLDFTAVE GNMDSFMAQV KSLAQSLYPC SAQQLNEDLR LHLLLNTSVT |
| | | CNDGSPAGYY LKESRGSRRW LLFLEGGWYC FNRENCDSRY DTMRRLMSSA |
| | | AWPRTRTGTG ILSSQPEENP YWWNANMVFI PYCSSDVWSG ASSKSEKNEY |
| | | AFMGALIIQE VVRELLGRGL SGAKVLLLAG SSAGGTGVLL NVDRVAEQLE |
| | | KLGYPAIQVR GLADSGWFLD NKQYRHTDCV DTITCAPTEA IRRGIRYWNG |
| | | VVPERCRRQF QEGEEWNCFF GYKVYPTLRC PVFVVQWLFD EAQLTVDNVH |
| | | LTGQPVQEGL RLYIQNLGRE LRHTLKDVPA SFAPACLSHE IIIRSHWTDV |
| | | QVKGTSLPRA LHCWDRSLHD SHKASKTPLK GCPVHLVDSC PWPHCNPSCP |
| | | TVRDQFTGQE MNVAQFLMHM GFDMQTVAQP QGLEPSELLG MLSNGS |
| 101 | 1.802 heavy chain variable region polynucleotide sequence | ATGGACTCCA GGCTCAATTT AGTTTTCCTT GTCCTTATTT TAAAAGGTGT CCAGTGTGAG GTGCAGCTGG TGGAGTCTGG GGGAGGCTTA GTGAAGCCTG GAGGGTCCCT GAAACTCTCC TGTGCAGCCT CTGGATTCAC TTTCAGTGAC TATGGAATGC ACTGGTTTCG TCAGGCTCCA GAGAAGGGGC TGGAGTGGGT TGCATATATT AGTAGTGGCA GTAGAACCGT CTACTATGCA GACACAGTGA AGGGCCGATT CACCATCTCC AGAGACAATG CCAAGAACAC CCTGTCCCTG CAAATGACCA GTCTGAGGTC TGAGGACACG GCCATGTATT ACTGTGCGAG GAAACATTAC AACGGTGGAT ACTTCGATGT CTGGGGCACA GGGACCACGG TCACCGTCTC CTCAGCCAAA ACGACACCCC CATCTGTCTA TCCACTGGCC CCTGGATCTG CTGCCCAAAC TAACTCCATG GTGACCCTGG ATGC |
| 102 | 1.802 light chain variable region polynucleotide sequence | ATCCTCTCTT CCAGCTCTCA GAGATGGAGA CAGACACACT CCTGTTATGG GTACTGCTGC TCTGGGTTCC AGGTTCCACT GGTGACATTG TGCTGACACA GTCTCCTGCT TCCTTAGCTG TATCTCTGGG GCAGAGGGCC ACCATCTCAT GCAGGGCCAG CAAAATTGTC AGTACATCTG GCTATAGTTA TATGCACTGG TACCAACAGA AACCAGGACA GCCGCCCAAA CTCCTCATCT ATCTTGCATC CAACCTAGAA TCTGGGGTCC CTGCCAGGTT CAGTGGCAGT GGGTCTGGGA CAGACTTCAC CCTCAACATC CATCCTGTGG AGGAGGAGGA TGCTGCAACC TATTACTGTC AGCACAGTAG GGAGCTTCCT CCCACGTTCG GCTCGGGGAC AAAGTTGGAA ATAAAACGGG CTGATGCTGC CACAACTGTA TCCATCTTCC CACCATCCAG TGAGCAGTTA ACATCTGGAG GT |
| 103 | 1.815 heavy chain variable region polynucleotide sequence | TCTGACAGAG GAGCCAAGCC CTGGATTCCC AGGTCCTCAC ATTCAGTGAT CAGCACTGAA CACAGACCAC TCACCATGGA CTCCAGGCTC AATTTAGTTT TCCTTGTCCT TATTTTAAAA GGTGTCCAGT GTGATGTGCA ACTGCTGGAA TCTGGGGGAG GCTTAGTGCA GCCTGGAGGG TCCCGGAAAC TCTCCTGTGC AGCCTCTGGA TTCACTTTCA GTGACTTTGG AATGCACTGG GTTCGTCAGG CTCCAGAGAA GGGGCTGGAG TGGGTCGCAT ACAGTAGTAG TGGCGGTACT ACCGTCTACT ATGCAGACAC GGTGAAGGGC CGACTCACCC TCTCCAGAGA CAATTCCAAG AACACCCTGT TCCTGGAAAT GACCAGTCTA AGGTCTGAGG ACACGGCCAT GTATTACTGT GCAAGAGCGT CCTATGATGG AGGGTACTTT GACTGCTGGG GCCAAGGCAC CTCTCTCACA GTCTCCTCAG CCAAAACGAC ACCCCCATCT GTCTATCCAC TGGCCCCTGG ATCTGCTGCC CAAACTAACT CCATGGTGAC CCTGGGATGC |
| 104 | 1.815 light chain variable region polynucleotide sequence | ATCCTCTCTT CCAGCTCTCA GAGATGGAGA CAGACACACT CCTGTTATGG GTACTGCTGC TCTGGGTTCC AGGTTCCACT GGTGACATTG TGCTGACACA GTCTCCTGCT TCCTTAGCTG TATCTCTGGG GCAGAGGGCC ACCATCTCAT GCAGGGCCAG CAAAAGTGTC AGTACATCTG GCTATAGTTA TATACACTGG TACCAACAGA AACCAGGACA GCCACCCAAA CTCCTCATCT ATCTTGCATC CGACCTAGAA TCTGGGGTCC CTGCCAGGTT CAGTGGCAGT GGATCTGGGG CAGCCTTCAC CCTCAACATC CATCCTGTGG AGGAGGAGGA TGCTGCAACC TATTACTGTC ACCACAGTAG GGAGCTTCCA TTCACGTTCG GCTCGGGGAC AAAGTTGGAA ATAAAACGGG CTGATGCTGC CACAACTGTA TCCATCTTCC CACCATCCAG TGAGCAGTTA ACATCTGGAG GTGCCTCAGT CGTGTGC |
| 105 | 1.846 heavy chain variable region polynucleotide sequence | AGAGGAGCCA AACCCTGGAT TCCCAGGTCC TCACATTCAG TGATCAGCAC TGAACACAGA CCACTCACCA TGGACTCCAG GCTCAATTTA GTTTTCCTTG TCCTTATTTT AAAAGGTGTC CAGTGTGAGG TGCAGCTGGT GGAGTCTGGG GGAGACTTAG TGAAGCCTGG AGGGTCCCTG AAACTCTCCT GTGCAGCCTC TGGATTCACT TTCAGTGACT ATGGAATGCA CTGGCTTCGT CAGGCTCCAG AGAAGGGGCT GGAGTGGGTT GCATATATTA GTAGTGGCAG TACTACCCTC TCCTATGCAA ACACAATGAA GGGCCGATTC ACCATCTCCA GAGACAATGC CAAGAAAACC CTGTCCCTGC AAATGACCAG TCTGAGGTCT GAGGACACGG CCATTTATTA CTGTGCGCGG AAAAATTACA ACGGTGGTTA CTTCGATGTC TGGGGCACAG GGACCACGGT CACCGTCTCC TCAGCCAAAA CAACACCCCC |

| SEQ ID NO | Description | Sequence |
|---|---|---|
| | | ATCAGTCTAT CCACTGGCCC CTGGGTGTGG AGATACAACT GGTTCCTCTG<br>TGACTCTGGG ATGCCTGGTC AAGGG |
| 106 | 1.846 light chain variable region polynucleotide sequence | ATCCTCTCTT CCAGCTCTCA GAGATGGAGA CAGACACACT CCTGTTATGG<br>GTACTGCTGC TCTGGGTTCC AGGTTCCACT GGTGACATTG TGCTGACACA<br>GTCTCCTGCT TCCTTAGTTG TATCTCTGGG GCAGAGGGCC ACCATCTCAT<br>GCAGGGCCAG CAAAAGTGTC AGTGAATCTG GCTATAGTTA TATGCACTGG<br>TACCAACAGA AACCAGGACA GCCACCCAAA CTCCTCATCT ATCTTGCATC<br>CAACCTAGAG TCTGGGGTCC CTGCCAGGTT CAGTGGCAGT GGGTCTGGGA<br>CAGACTTCAC CCTCAACATC CATCCTGTGG AGGAGGGGGA TGCTACAACC<br>TATTACTGTC AGCACAGTAG GGTCCTTCCT CCCACGTTCG GCTCGGGGAC<br>AAAGTTGGAA ATAAAACGGG CTGATGCTGC ACCAACTGTA TCCATCTTCC<br>CACCATCCAG TGAGCAGTTA ACATCTGGAG GTGC |
| 107 | 2.78 heavy chain variable region polynucleotide | GACAGAGGAG CCAAGCCCTG GATTCCCAGG TCCTCACATT CAGTGATCAG<br>CACTGAACAC AGACCACTCA CCATGGACTC CAGGCTCAAT TTAGTTTTCC<br>TTGTCCTTAT TTTAAAAGGT GTCCAGTGTG ATGTGCAGCT GGTGGAGTCT<br>GGGGGAGGCT TAGTGCAGCC TGGAGGGTCC CGGAAACTCT CCTGTGCAGC<br>CTCTGGATTC ACTTTCAGTA GCTTTGGCAT GCACTGGGTT CGTCAGGCTC<br>CAGAGAAGGG ACTGGAGTGG GTCGCATACA TTACTAGTGG CAGTGGTGCC<br>ATCTACTATG CAGACACAGT GAGGGGCCGA TTCACCATCT CCAGAGACAC<br>TCCCAAGAAC ACCCTGTTCC TGCAGATGAC CAGTCTAAGG TCTGAGGACA<br>CGGCCATGTA TTACTGTGCA AGATCGGCTG ATGGTTTGGA CTACTGGGGT<br>CAAGGAACCT CAGTCACCGT CTCCTCAGCC AAAACAACAC CCCCATCAGT<br>CTATCCACTG GCCCCTGGGT GTGGAGATAC AACTG |
| 108 | 2.78 light chain variable region polynucleotide sequence | CAGCCTCACA CTGATCACAC ACAGACATGA GTGTGGCCAC TCAGGTCCTG<br>GGGTTGCTGC TGCTGTGGCT TACAGATGCC AGATGTGACA TCCAGATGAC<br>TCAGTCTCCA GCCTCCCTAT ATGTATCTGT GGGAGAAACT GTCACCATCA<br>CATGTCGAGC AAGTGAGAAT ATTTACAGTA ATTTAGCATG GTATCAGCAG<br>AAACAGGGAA AATCTCCTCA GCTCCTGGTC TATGGTGCAA CAAACTTAGC<br>AGATGGTGTG CCATCAAGGT TCAGTGGCAG TGGATCAGGC ACACAGTATT<br>CCCTCAAGAT CAACAGCCTG AAGTCTGAAG ATTTTGGGAG TTATTACTGT<br>CAACATTTTT GGGGTACTCC ATTCACGTTC GGCTCGGGGA CAAAGTTGGA<br>AATAAAACGG GCTGATGCTG CACCAACTGT ATCCATCTTC CCACCATCCA<br>GTGAGCAGTT AACATCTGGA GGTGCCTCAG TCGTGTGC |
| 109 | 2.1029 heavy chain variable region polynucleotide sequence | ATCTCCTCAC TAGAGCCCCC ATCAGAGCAT GGCTGTCCTG GTGCTGTTCC<br>TCTGCCTGGT TGCATTTCCA AGCTGTGTCC TGTCCCAGGT GCAGCTGAAG<br>GAGTCAGGAC CTGGCCTGGT GGCGCCCTCA CAGAGCCTGT CCATCACTTG<br>CACTGTCTCT GGGTTTTCAT TAACCAGCTA TGGTGTACAC TGGGTTCGCC<br>AGCCTCCAGG AAAGGGTCTG GAGTGGCTGG GAGTAATATG GGCTGGTGGA<br>AGCACAAATT ATAATTCGGC TCTCATGTCC AGACTGAGCA TCAGCAAAGA<br>CAACTCCAAG AGCCAAGTTT TCTTAAAAAT GAACAGTCTG CAAACTGATG<br>ACACAGCCAT CTACTTCTGT GCCAGAGATG GCGACTACGG TACTATCTAC<br>GCTATGGACT ACTGGGGTCA AGGAACCTCA GTCACCGTCT CCTCAGCCAA<br>AACAACAGCC CCATCGGTCT ATCCACTGGC CCCTGTGTGT GGAGATACAA<br>CTGGCTCCTC GGTGACTCTA GGATGCCTGG TCAAGG |
| 110 | 2.1029 light chain variable region polynucleotide sequence | ATTGAAGTCA AGACTCAGCC TGGACATGAT GTCCTCTGCT CAGTTCCTTG<br>GTCTCCTGTT GCTCTGTTTT CAAGGTACCA GATGTGATAT CCAGATGACA<br>CAGACTACAT CCTCCCTGTC TGCCTCTCTG GGAGACAGAG TCACCATCAG<br>TTGCAGGGCA AGTCAGGACA TTAGCAATTA TTTAAACTGG TATCAGCAGA<br>AACCAGATGG AACTGTTAAA CTCCTGATCT ACTACACATC AAGATTACAC<br>TCAGGAGTCC CATCAAGGTT CACTGGCAGT GGGTCTGGAA CAGATTATTC<br>TCTCACCATT AGCAACCTGG AGCAAGAAGA TATTGCCACT TACTTTTGCC<br>AACAGGGTAA AACGCTTCCT CGGACGTTCG GTGGAGGCAC CATGCTGGAA<br>ATCAAACGGG CTGATGCTGC ACCAACTGTA TCCATCTTCC CACCATCCAG<br>TGAGCAGTTA ACATCTGGAG GTGCCTCAGT CGTGTGC |
| 111 | Humanized Ab (HumAb) 2.78 heavy chain variable region polynucleotide sequence | gaggtgcagc tggtggagag cggcggcggc ctggtgcagc ccggcggcag<br>cctgagactg agctgcgccg ccagcggctt caccttcagc agcttcggca<br>tgcactgggt gagacaggcc cccggcaagg gcctggagtg ggtgagctac<br>atcaccagcg gcagcggcgc catctactac gccgacagcg tgaagggcag<br>attcaccatc agcagagaca acgccaagaa cagcctgtac ctgcagatga<br>acagcctgag agccgaggac accgccgtgt actactgcgc cagaagcgcc<br>gacggcctgg actactgggg ccagggcacc accgtgaccg tgagcagc |
| 112 | HumAb 2.78 heavy chain polynucleotide sequence | ATGCGTACTC TGGCTATCCT TGCAGCTATT CTGCTTGTTG CACTGCAGGC<br>TCAAGCGGAG GTGCAGCTGG TGGAGAGCGG CGGCGGCCTG GTGCAGCCCG<br>GCGGCAGCCT GAGACTGAGC TGCGCCGCCA GCGGCTTCAC CTTCAGCAGC<br>TTCGGCATGC ACTGGGTGAG ACAGGCCCCC GGCAAGGGCC TGGAGTGGGT<br>GAGCTACATC ACCAGCGGCA GCGGCGCCAT CTACTACGCC GACAGCGTGA<br>AGGGCAGATT CACCATCAGC AGAGACAACG CCAAGAACAG CCTGTACCTG<br>CAGATGAACA GCCTGAGAGC CGAGGACACC GCCGTGTACT ACTGCGCCAG |

Table of Sequences

| SEQ ID NO | Description | Sequence |
|---|---|---|
| | | AAGCGCCGAC GGCCTGGACT ACTGGGGCCA GGGCACCACC GTGACCGTGA<br>GCAGCGATGT GTGGGGCCAG GGCACCACCG TGACCGTGAG CAGCGCGTCG<br>ACCAAGGGCC CATCGGTCTT CCCCCTGGCG CCCTGCTCCA GGAGCACCTC<br>CGAGAGCACA GCGGCCCTGG GCTGCCTGGT CAAGGACTAC TTCCCCGAAC<br>CGGTGACGGT GTCGTGGAAC TCAGGCGCTC TGACCAGCGG CGTGCACACC<br>TTCCCGGCTG TCCTACAGTC CTCAGGACTC TACTCCCTCA GCAGCGTGGT<br>GACCGTGACC TCCAGCAACT TCGGCACCCA GACCTACACC TGCAACGTAG<br>ATCACAAGCC CAGCAACACC AAGGTGGACA AGACAGTTGA GCGCAAATGT<br>TGTGTCGAGT GCCCACCGTG CCCAGCACCA CCTGTGGCAG GACCGTCAGT<br>CTTCCTCTTC CCCCCAAAAC CAAGGACAC CCTCATGATC TCCCGGACCC<br>CTGAGGTCAC GTGCGTGGTG GTGGACGTGA GCCACGAAGA CCCCGAGGTC<br>CAGTTCAACT GGTACGTGGA CGGCATGGAG GTGCATAATG CCAAGACAAA<br>GCCGCGGGAG GAGCAGTTCA ACAGCACGTT CCGTGTGGTC AGCGTCCTCA<br>CCGTCGTGCA CCAGGACTGG CTGAACGGCA AGGAGTACAA GTGCAAGGTC<br>TCCAACAAAG GCCTCCCAGC CCCCATCGAG AAAACCATCT CCAAAACCAA<br>AGGGCAGCCC CGAGAACCAC AGGTGTACAC CCTGCCCCCA TCCCGGGAGG<br>AGATGACCAA GAACCAGGTC AGCCTGACCT GCCTGGTCAA AGGCTTCTAC<br>CCCAGCGACA TCGCCGTGGA GTGGGAGAGC AATGGGCAGC CGGAGAACAA<br>CTACAAGACC ACACCTCCCA TGCTGGACTC CGACGGCTCC TTCTTCCTCT<br>ACAGCAAGCT CACCGTGGAC AAGAGCAGGT GGCAGCAGGG GAACGTCTTC<br>TCATGCTCCG TGATGCATGA GGCTCTGCAC AACCACTACA CACAGAAGAG<br>CCTCTCCCTG TCTCCGGGTA AATGA |
| 113 | HumAb 2.78 light chain variable region polynucleotide sequence | gacatccaga tgacccagag ccccagcagc ctgagcgcca gcgtgggcga<br>cagagtgacc atcacctgca gccagcgca gaacatctac agcaacctgg<br>cctggtacca gcagaagccc ggcaaggccc ccaagctgct gatctacgc<br>gccaccaacc tggccgacgg cgtgccagc agattcagcg gcagcggcag<br>cggcaccgac ttcaccctga ccatcagcag cctgcagccc gaggacttcg<br>ccacctacta ctgccagcac ttctggggca ccccccttcac cttcggccag<br>ggcaccaagg tggagatc |
| 114 | HumAb 2.78 light chain polynucleotide sequence | ATGAAAATCC TGATTCTCGG TATCTTCCTG TTTCTCTGTT CTACTCCAGC<br>TTGGGCAGAC ATCCAGATGA CCCAGAGCCC CAGCAGCCTG AGCGCCAGCG<br>TGGGCGACAG AGTGACCATC ACCTGCAGCC CCAGCAGAA CATCTACGAC<br>AACCTGGCCT GGTACCAGCA GAAGCCCGGC AAGGCCCCCA AGCTGCTGAT<br>CTACGGCGCC ACCAACCTGG CCGACGGCGT GCCCAGCAGA TTCAGCGGCA<br>GCGGCAGCGG CACCGACTTC ACCCTGACCA TCAGCAGCCT GCAGCCCGAG<br>GACTTCGCCA CCTACTACTG CCAGCACTTC TGGGGCACCC CCTTCACCTT<br>CGGCCAGGGC ACCAAGGTGG AGATCAAACG TACGGTGGCT GCACCATCTG<br>TCTTCATCTT CCCGCCATCT GATGAGCAGT TGAAATCTGG AACTGCCTCT<br>GTTGTGTGCC TGCTGAATAA CTTCTATCCC AGAGAGGCCA AAGTACAGTG<br>GAAGGTGGAT AACGCCCTCC AATCGGGTAA CTCCCAGGAG AGTGTCACAG<br>AGCAGGACAG CAAGGACAGC ACCTACAGCC TCAGCAGCAC CCTGACGCTG<br>AGCAAAGCAG ACTACGAGAA ACACAAAGTC TACGCCTGCG AAGTCACCCA<br>TCAGGGCCTG AGCTCGCCCG TCACAAAGAG CTTCAACAGG GGAGAGTGTT<br>GA |
| 115 | HumAb 2.1029 heavy chain variable region polynucleotide sequence | caggtgcagc tgcaggagag cggccccggc ctggtgaagc ccagcgagac<br>cctgagcctg acctgcaccg tgagcggctt cagcctgacc agctacggcg<br>tgcactggat cagacagccc cccggcaagg gcctggagtg gatcggcgtg<br>atctgggccg gcggcagcac caactacaac cccagcctga agagcagagt<br>gaccatcagc gtgaccacca gcaagaacca gttcagcctg aagctgagca<br>gcgtgaccgc cgccgacacc gccgtgtact actgcgccag agacggcgac<br>tacggcacca tctacgccat ggactactgg ggccagggca ccctggtgac<br>cgtgagcagc |
| 116 | HumAb 2.1029 heavy chain polynucleotide sequence | ATGCGTACTC TGGCTATCCT TGCAGCTATT CTGCTTGTTG CACTGCAGGC<br>TCAAGCGCAG GTGCAGCTGC AGGAGAGCGG CCCCGGCCTG GTGAAGCCCA<br>GCGAGACCCT GAGCCTGACC TGCACCGTGA GCGGCTTCAG CCTGACCAGC<br>TACGGCGTGC ACTGGATCAG ACAGCCCCCC GGCAAGGGCC TGGAGTGGAT<br>CGGCGTGATC TGGGCCGGCG GCAGCACCAA CTACAACCCC AGCCTGAAGA<br>GCAGAGTGAC CATCAGCGTG ACCACCAGCA AGAACCAGTT CAGCCTGAAG<br>CTGAGCAGCG TGACCGCCGC CGACACCGCC GTGTACTACT GCGCCAGAGA<br>CGGCGACTAC GGCACCATCT ACGCCATGGA CTACTGGGGC CAGGGCACCC<br>TGGTGACCGT GAGCAGCGAT GTGTGGGGCC AGGGCACCAC CGTGACCGTG<br>AGCAGCGCGT CGACCAAGGG CCCATCGGTC TTCCCCCTGG CGCCCTGCTC<br>CAGGAGCACC TCCGAGAGCA CAGCGGCCCT GGGCTGCCTG GTCAAGGACT<br>ACTTCCCCGA ACCGGTGACG GTGTCGTGGA ACTCAGGCGC TCTGACCAGC<br>GGCGTGCACA CCTTCCCGGC TGTCCTACAG TCCTCAGGAC TCTACTCCCT<br>CAGCAGCGTG GTGACCGTGA CCTCCAGCAA CTTCGGCACC CAGACCTACA<br>CCTGCAACGT AGATCACAAG CCCAGCAACA CCAAGGTGGA CAAGACAGTT<br>GAGCGCAAAT GTTGTGTCGA GTGCCCACCG TGCCCAGCAC CACCTGTGGC<br>AGGACCGTCA GTCTTCCTCT TCCCCCCAAA ACCCAAGGAC ACCCTCATGA<br>TCTCCCGGAC CCCTGAGGTC ACGTGCGTGG TGGTGGACGT GAGCCACGAA<br>GACCCCGAGG TCCAGTTCAA CTGGTACGTG GACGGCATGG AGGTGCATAA |

| SEQ ID NO | Description | Sequence |
|---|---|---|
| | | TGCCAAGACA AAGCCGCGGG AGGAGCAGTT CAACAGCACG TTCCGTGTGG<br>TCAGCGTCCT CACCGTCGTG CACCAGGACT GGCTGAACGG CAAGGAGTAC<br>AAGTGCAAGG TCTCCAACAA AGGCCTCCCA GCCCCCATCG AGAAAACCAT<br>CTCCAAAACC AAAGGGCAGC CCCGAGAACC ACAGGTGTAC ACCCTGCCCC<br>CATCCCGGGA GGAGATGACC AAGAACCAGG TCAGCCTGAC CTGCCTGGTC<br>AAAGGCTTCT ACCCCAGCGA CATCGCCGTG GAGTGGGAGA GCAATGGGCA<br>GCCGGAGAAC AACTACAAGA CCACACCTCC CATGCTGGAC TCCGACGGCT<br>CCTTCTTCCT CTACAGCAAG CTCACCGTGG ACAAGAGCAG GTGGCAGCAG<br>GGGAACGTCT TCTCATGCTC CGTGATGCAT GAGGCTCTGC ACAACCACTA<br>CACACAGAAG AGCCTCTCCC TGTCTCCGGG TAAATGA |
| 117 | HumAb 2.1029 light chain variable region polynucleotide sequence | gacatccaga tgacccagag ccccagcagc ctgagcgcca gcgtgggcga<br>cagagtgacc atcacctgca gagccagcca ggacatcagc aactacctga<br>actggtacca gcagaagccc ggcaaggccc ccaagctgct gatctactac<br>accagcagac tgcacagcgg cgtgcccagc agattcagcg gcagcggcag<br>cggcaccgac ttcaccttca ccatcagcag cctgcagccc gaggacatcg<br>ccacctacta ctgccagcag ggcaagaccc tgcccagaac cttcggcggc<br>ggcaccaagg tggagatc |
| 118 | HumAb 2.1029 light chain polynucleotide sequence | ATGAAAATCC TGATTCTCGG TATCTTCCTG TTTCTCTGTT CTACTCCAGC<br>TTGGGCAGAC ATCCAGATGA CCCAGAGCCC CAGCAGCCTG AGCGCCAGCG<br>TGGGCGACAG AGTGACCATC ACCTGCAGAG CCAGCCAGGA CATCAGCAAC<br>TACCTGAACT GGTACCAGCA GAAGCCCGGC AAGGCCCCCA AGCTGCTGAT<br>CTACTACACC AGCAGACTGC ACAGCGGCGT GCCCAGCAGA TTCAGCGGCA<br>GCGGCAGCGG CACCGACTTC ACCTTCACCA TCAGCAGCCT GCAGCCCGAG<br>GACATCGCCA CCTACTACTG CCAGCAGGGC AAGACCCTGC CCAGAACCTT<br>CGGCGGCGGC ACCAAGGTGG AGATCAAACG TACGGTGGCT GCACCATCTG<br>TCTTCATCTT CCCGCCATCT GATGAGCAGT TGAAATCTGG AACTGCCTCT<br>GTTGTGTGCC TGCTGAATAA CTTCTATCCC AGAGAGGCCA AAGTACAGTG<br>GAAGGTGGAT AACGCCCTCC AATCGGGTAA CTCCCAGGAG AGTGTCACAG<br>AGCAGGACAG CAAGGACAGC ACCTACAGCC TCAGCAGCAC CCTGACGCTG<br>AGCAAAGCAG ACTACGAGAA ACACAAAGTC TACGCCTGCG AAGTCACCCA<br>TCAGGGCCTG AGCTCGCCCG TCACAAAGAG CTTCAACAGG GGAGAGTGTT<br>GA |
| 119 | HumAb 1.802 heavy chain variable region polynucleotide sequence | gaggtgcagc tggtggagag cggcggcggc ctggtgcagc ccggcggcag<br>cctgagactg agctgcgccg ccagcggctt caccttcagc gactacggca<br>tgcactgggt gagacaggcc cccggcaagg gcctggagtg ggtgagctac<br>atcagcagcg gcagcagaac cgtgtactac gccgacagcg tgaagggcag<br>attcaccatc agcagagaca cgccaagaa cagcctgtac ctgcagatga<br>acagcctgag agacgaggac accgccgtgt actactgcgc cagaaagcac<br>tacaacggcg gctacttcga cgtgtggggc cagggcaccc tggtgaccgt<br>gagcagc |
| 120 | HumAb 1.802 heavy chain polynucleotide sequence | ATGCGTACTC TGGCTATCCT TGCAGCTATT CTGCTTGTTG CACTGCAGGC<br>TCAAGCGGAG GTGCAGCTGG TGGAGAGCGG CGGCGGCCTG GTGCAGCCCG<br>GCGGCAGCCT GAGACTGAGC TGCGCCGCCA GCGGCTTCAC CTTCAGCGAC<br>TACGGCATGC ACTGGGTGAG ACAGGCCCCC GGCAAGGGCC TGGAGTGGGT<br>GAGCTACATC AGCAGCGGCA GCAGAACCGT GTACTACGCC GACAGCGTGA<br>AGGGCAGATT CACCATCAGC AGAGACAACG CCAAGAACAG CCTGTACCTG<br>CAGATGAACA GCCTGAGAGA CGAGGACACC GCCGTGTACT ACTGCGCCAG<br>AAAGCACTAC AACGGCGGCT ACTTCGACGT GTGGGGCCAG GGCACCCTGG<br>TGACCGTGAG CAGCGATGTG TGGGGCCAGG GCACCACCGT GACCGTGAGC<br>AGCGCGTCGA CCAAGGGCCC ATCGGTCTTC CCCCTGGCGC CCTGCTCCAG<br>GAGCACCTCC GAGAGCACAG CGGCCCTGGG CTGCCTGGTC AAGGACTACT<br>TCCCCGAACC GGTGACGGTG TCGTGGAACT CAGGCGCTCT GACCAGCGGC<br>GTGCACACCT TCCCGGCTGT CCTACAGTCC TCAGGACTCT ACTCCCTCAG<br>CAGCGTGGTG ACCGTGACCT CCAGCAACTT CGGCACCCAG ACCTACACCT<br>GCAACGTAGA TCACAAGCCC AGCAACACCA AGGTGGACAA GACAGTTGAG<br>CGCAAATGTT GTGTCGAGTG CCCACCGTGC CCAGCACCAC CTGTGGCAGG<br>ACCGTCAGTC TTCCTCTTCC CCCCAAAACC CAAGGACACC CTCATGATCT<br>CCCGGACCCC TGAGGTCACG TGCGTGGTGG TGGACGTGAG CCACGAAGAC<br>CCCGAGGTCC AGTTCAACTG GTACGTGGAC GGCATGGAGG TGCATAATGC<br>CAAGACAAAG CCGCGGGAGG AGCAGTTCAA CAGCACGTTC CGTGTGGTCA<br>GCGTCCTCAC CGTCGTGCAC CAGGACTGGC TGAACGGCAA GGAGTACAAG<br>TGCAAGGTCT CCAACAAAGG CCTCCCAGCC CCCATCGAGA AACCATCTC<br>CAAAACCAAA GGGCAGCCCC GAGAACCACA GGTGTACACC CTGCCCCCAT<br>CCCGGGAGGA GATGACCAAG AACCAGGTCA GCCTGACCTG CCTGGTCAAA<br>GGCTTCTACC CCAGCGACAT CGCCGTGGAG TGGGAGAGCA ATGGGCAGCC<br>GGAGAACAAC TACAAGACCA CACCTCCCAT GCTGGACTCC GACGGCTCCT<br>TCTTCCTCTA CAGCAAGCTC ACCGTGGACA AGAGCAGGTG GCAGCAGGGG<br>AACGTCTTCT CATGCTCCGT GATGCATGAG GCTCTGCACA ACCACTACAC<br>ACAGAAGAGC CTCTCCCTGT CTCCGGGTAA ATGA |

| SEQ ID NO | Description | Sequence |
|---|---|---|
| 121 | HumAb 1.802 light chain variable region polynucleotide sequence | gacatcgtga tgacccagag ccccgacagc ctggccgtga gcctgggcga gagagccacc atcaactgca gagccagcaa gatcgtgagc accagcggct acagctacat gcactggtac cagcagaagc ccgccagcc ccccaagctg ctgatctacc tggccagcaa cctggagagc ggcgtgcccg acagattcag cggcagcggc agcggcaccg acttcaccct gaccatcagc agcctgcagg ccgaggacgt ggccgtgtac tactgccagc acagcagaga gctgccccc accttcggcc agggcaccaa gctggagatc |
| 122 | HumAb 1.802 light chain polynucleotide sequence | ATGAAAATCC TGATTCTCGG TATCTTCCTG TTTCTCTGTT CTACTCCAGC TTGGGCAGAC ATCGTGATGA CCCAGAGCCC CGACAGCCTG GCCGTGAGCC TGGGCGAGAG AGCCACCATC AACTGCAGAG CCAGCAAGAT CGTGAGCACC AGCGGCTACA GCTACATGCA CTGGTACCAG CAGAAGCCCG CCCAGCCCCC CAAGCTGCTG ATCTACCTGG CCAGCAACCT GGAGAGCGGC GTGCCCGACA GATTCAGCGG CAGCGGCAGC GGCACCGACT TCACCCTGAC CATCAGCAGC CTGCAGGCCG AGGACGTGGC CGTGTACTAC TGCCAGCACA GCAGAGAGCT GCCCCCCACC TTCGGCCAGG GCACCAAGCT GGAGATCAAA CGTACGGTGG CTGCACCATC TGTCTTCATC TTCCCGCCAT CTGATGAGCA GTTGAAATCT GGAACTGCCT CTGTTGTGTG CCTGCTGAAT AACTTCTATC CCAGAGAGGC CAAAGTACAG TGGAAGGTGG ATAACGCCCT CCAATCGGGT AACTCCCAGG AGAGTGTCAC AGAGCAGGAC AGCAAGGACA GCACCTACAG CCTCAGCAGC ACCCTGACGC TGAGCAAAGC AGACTACGAG AAACACAAAG TCTACGCCTG CGAAGTCACC CATCAGGGCC TGAGCTCGCC CGTCACAAAG AGCTTCAACA GGGGAGAGTG TTGA |
| 123 | HumAb 1.815 heavy chain variable region polynucleotide sequence | caggtgcagc tggtggagag cggcggcggc ctggtgaagc ccggcggcag cctgagactg agctgcgccg ccagcggctt caccttcagc gacttcggca tgcactggat cagacaggcc cccggcaagg gcctggagtg ggtgagctac agcagcagcg gcggcaccac cgtgtactac gccgacagcg tgaagggcag attcaccatc agcagagaca acgccaagaa cagcctgtac ctgcagatga cagcctgag agccgaggac accgccgtgt actactgcgc cagagccagc tacgacggcg gctacttcga ctgctggggc cagggcacca ccgtgaccgt gagcagc |
| 124 | HumAb 1.815 heavy chain polynucleotide sequence | ATGCGTACTC TGGCTATCCT TGCAGCTATT CTGCTTGTTG CACTGCAGGC TCAAGCGCAG GTGCAGCTGG TGGAGAGCGG CGGCGGCCTG GTGAAGCCCG GCGGCAGCCT GAGACTGAGC TGCGCCGCCA GCGGCTTCAC CTTCAGCGAC TTCGGCATGC ACTGGATCAG ACAGGCCCCC GGCAAGGGCC TGGAGTGGGT GAGCTACAGC AGCAGCGGCG GCACCACCGT GTACTACGCC GACAGCGTGA AGGGCAGATT CACCATCAGC AGAGACAACG CCAAGAACAG CCTGTACCTG CAGATGAACA GCCTGAGAGC CGAGGACACC GCCGTGTACT ACTGCGCCAG AGCCAGCTAC GACGGCGGCT ACTTCGACTG CTGGGGCCAG GGCACCACCG TGACCGTGAG CAGCGATGTG TGGGGCCAGG GCACCACCGT GACCGTGAGC AGCGCGTCGA CCAAGGGCCC ATCGGTCTTC CCCCTGGCGC CCTGCTCCAG GAGCACCTCC GAGAGCACAG CGGCCCTGGG CTGCCTGGTC AAGGACTACT TCCCCGAACC GGTGACGGTG TCGTGGAACT CAGGCGCTCT GACCAGCGGC GTGCACACCT TCCCGGCTGT CCTACAGTCC TCAGGACTCT ACTCCCTCAG CAGCGTGGTG ACCGTGACCT CCAGCAACTT CGGCACCCAG ACCTACACCT GCAACGTAGA TCACAAGCCC AGCAACACCA AGGTGGACAA GACAGTTGAG CGCAAATGTT GTGTCGAGTG CCCACCGTGC CCAGCACCAC CTGTGGCAGG ACCGTCAGTC TTCCTCTTCC CCCCAAAACC CAAGGACACC CTCATGATCT CCCGGACCCC TGAGGTCACG TGCGTGGTGG TGGACGTGAG CCACGAAGAC CCCGAGGTCC AGTTCAACTG GTACGTGGAC GGCATGGAGG TGCATAATGC CAAGACAAAG CCGCGGGAGG AGCAGTTCAA CAGCACGTTC CGTGTGGTCA GCGTCCTCAC CGTCGTGCAC CAGGACTGGC TGAACGGCAA GGAGTACAAG TGCAAGGTCT CCAACAAAGG CCTCCCAGCC CCCATCGAGA AAACCATCTC CAAAACCAAA GGGCAGCCCC GAGAACCACA GGTGTACACC CTGCCCCCAT CCCGGGAGGA GATGACCAAG AACCAGGTCA GCCTGACCTG CCTGGTCAAA GGCTTCTACC CCAGCGACAT CGCCGTGGAG TGGGAGAGCA ATGGGCAGCC GGAGAACAAC TACAAGACCA CACCTCCCAT GCTGGACTCC GACGGCTCCT TCTTCCTCTA CAGCAAGCTC ACCGTGGACA AGAGCAGGTG GCAGCAGGGG AACGTCTTCT CATGCTCCGT GATGCATGAG GCTCTGCACA ACCACTACAC ACAGAAGAGC CTCTCCCTGT CTCCGGGTAA ATGA |
| 125 | HumAb 1.815 light chain variable region polynucleotide sequence | gacatcgtga tgacccagag ccccgacagc ctggccgtga gcctgggcga gagagccacc atcaactgca gagccagcaa gagcgtgagc accagcggct acagctacat ccactggtac cagcagaagc ccgccagcc ccccaagctg ctgatctacc tggccagcga cctggagagc ggcgtgcccg acagattcag cggcagcggc agcggcaccg acttcaccct gaccatcagc agcctgcagg ccgaggacgt ggccgtgtac tactgccacc acagcagaga gctgcccttc accttcggcc agggcaccaa gctggagatc |
| 126 | HumAb 1.815 light chain polynucleotide | ATGAAAATCC TGATTCTCGG TATCTTCCTG TTTCTCTGTT CTACTCCAGC TTGGGCAGAC ATCGTGATGA CCCAGAGCCC CGACAGCCTG GCCGTGAGCC TGGGCGAGAG AGCCACCATC AACTGCAGAG CCAGCAAGAG CGTGAGCACC |

| SEQ ID NO | Description | Sequence |
|---|---|---|
| | sequence | AGCGGCTACA GCTACATCCA CTGGTACCAG CAGAAGCCCG GCCAGCCCCC<br>CAAGCTGCTG ATCTACCTGG CCAGCGACCT GGAGAGCGGC GTGCCCGACA<br>GATTCAGCGG CAGCGGCAGC GGCACCGACT TCACCCTGAC CATCAGCAGC<br>CTGCAGGCCG AGGACGTGGC CGTGTACTAC TGCCACCACA GCAGAGAGCT<br>GCCCTTCACC TTCGGCCAGG GCACCAAGCT GGAGATCAAA CGTACGGTGG<br>CTGCACCATC TGTCTTCATC TTCCCGCCAT CTGATGAGCA GTTGAAATCT<br>GGAACTGCCT CTGTTGTGTG CCTGCTGAAT AACTTCTATC CCAGAGAGGC<br>CAAAGTACAG TGGAAGGTGG ATAACGCCCT CCAATCGGGT AACTCCCAGG<br>AGAGTGTCAC AGAGCAGGAC AGCAAGGACA GCACCTACAG CCTCAGCAGC<br>ACCCTGACGC TGAGCAAAGC AGACTACGAG AAACACAAAG TCTACGCCTG<br>CGAAGTCACC CATCAGGGCC TGAGCTCGCC CGTCACAAAG AGCTTCAACA<br>GGGGAGAGTG TTGA |
| 127 | HumAb 1.846 heavy chain variable region polynucleotide sequence | gaggtgcagc tggtggagag cggcggcggc ctggtgcagc ccggcggcag<br>cctgagactg agctgcgccg ccagcggctt caccttcagc gactacggca<br>tgcactgggt gagacaggcc cccggcaagg gcctggagtg ggtgagctac<br>atcagcagcg gcagcaccac cctgagctac gccgacagcg tgaagggcag<br>attccaccatc agcagagaca acgccaagaa cagcctgtac ctgcagatga<br>acagcctgag agacgaggac accgccgtgt actactgcgc cagaaagaac<br>tacaacgcg gctacttcga cgtgtggggc cagggcaccc tggtgaccgt<br>gagcagc |
| 128 | HumAb 1.846 heavy chain polynucleotide sequence | ATGCGTACTC TGGCTATCCT TGCAGCTATT CTGCTTGTTG CACTGCAGGC<br>TCAAGCGGAG GTGCAGCTGG TGGAGAGCGG CGGCGGCCTG GTGCAGCCCG<br>GCGGCAGCCT GAGACTGAGC TGCGCCGCCA GCGGCTTCAC CTTCAGCGAC<br>TACGGCATGC ACTGGGTGAG ACAGGCCCCC GGCAAGGGCC TGGAGTGGGT<br>GAGCTACATC AGCAGCGGCA GCACCACCCT GAGCTACGCC GACAGCGTGA<br>AGGGCAGATT CACCATCAGC AGAGACAACG CCAAGAACAG CCTGTACCTG<br>CAGATGAACA GCCTGAGAGA CGAGGACACC GCCGTGTACT ACTGCGCCAG<br>AAAGAACTAC AACGCGGCT ACTTCGACGT GTGGGGCCAG GGCACCCTGG<br>TGACCGTGAG CAGCGATGTG TGGGGCCAGG GCACCACCGT GACCGTGAGC<br>AGCGCGTCGA CCAAGGGCCC ATCGGTCTTC CCCCTGGCGC CCTGCTCCAG<br>GAGCACCTCC GAGAGCACAG CGGCCCTGGG CTGCCTGGTC AAGGACTACT<br>TCCCCGAACC GGTGACGGTG TCGTGGAACT CAGGCGCTCT GACCAGCGGC<br>GTGCACACCT TCCCGGCTGT CCTACAGTCC TCAGGACTCT ACTCCCTCAG<br>CAGCGTGGTG ACCGTGACCT CCAGCAACTT CGGCACCCAG ACCTACACCT<br>GCAACGTAGA TCACAAGCCC AGCAACACCA AGGTGGACAA GACAGTTGAG<br>CGCAAATGTT GTGTCGAGTG CCCACCGTGC CCAGCACCAC CTGTGGCAGG<br>ACCGTCAGTC TTCCTCTTCC CCCCAAAACC CAAGGACACC CTCATGATCT<br>CCCGGACCCC TGAGGTCACG TGCGTGGTGG TGGACGTGAG CCACGAAGAC<br>CCCGAGGTCC AGTTCAACTG GTACGTGGAC GGCATGGAGG TGCATAATGC<br>CAAGACAAAG CCGCGGGAGG AGCAGTTCAA CAGCACGTTC CGTGTGGTCA<br>GCGTCCTCAC CGTCGTGCAC CAGGACTGGC TGAACGGCAA GGAGTACAAG<br>TGCAAGGTCT CCAACAAAGG CCTCCCAGCC CCCATCGAGA AAACCATCTC<br>CAAAACCAAA GGGCAGCCCC GAGAACCACA GGTGTACACC CTGCCCCCAT<br>CCCGGGAGGA GATGACCAAG AACCAGGTCA GCCTGACCTG CCTGGTCAAA<br>GGCTTCTACC CCAGCGACAT CGCCGTGGAG TGGGAGAGCA ATGGGCAGCC<br>GGAGAACAAC TACAAGACCA CACCTCCCAT GCTGGACTCC GACGGCTCCT<br>TCTTCCTCTA CAGCAAGCTC ACCGTGGACA AGAGCAGGTG GCAGCAGGGG<br>AACGTCTTCT CATGCTCCGT GATGCATGAG GCTCTGCACA ACCACTACAC<br>ACAGAAGAGC CTCTCCCTGT CTCCGGGTAA ATGA |
| 129 | HumAb 1.846 light chain variable region polynucleotide sequence | gacatcgtga tgacccagag ccccgacagc ctggccgtga gcctgggcga<br>gagagccacc atcaactgca gagccagcaa gagcgtgagc gagagcggct<br>acagctacat gcactggtac cagcagaagc ccggccagcc ccccaagctg<br>ctgatctacc tggccagcaa cctggagagc ggcgtgcccg acagattcag<br>cggcagcggc agcggcaccg acttcaccct gaccatcagc agcctgcagg<br>ccgaggacgt ggccgtgtac tactgccagc acagcagagt gctgcccccc<br>accttcggcc agggcaccaa gctggagatc |
| 130 | HumAb 1.846 light chain polynucleotide sequence | ATGAAAATCC TGATTCTCGG TATCTTCCTG TTTCTCTGTT CTACTCCAGC<br>TTGGGCAGAC ATCGTGATGA CCCAGAGCCC CGACAGCCTG GCCGTGAGCC<br>TGGGCGAGAG AGCCACCATC AACTGCAGAG CCAGCAAGAG CGTGAGCGAG<br>AGCGGCTACA GCTACATGCA CTGGTACCAG CAGAAGCCCG GCCAGCCCCC<br>CAAGCTGCTG ATCTACCTGG CCAGCAACCT GGAGAGCGGC GTGCCCGACA<br>GATTCAGCGG CAGCGGCAGC GGCACCGACT TCACCCTGAC CATCAGCAGC<br>CTGCAGGCCG AGGACGTGGC CGTGTACTAC TGCCAGCACA GCAGAGTGCT<br>GCCCCCCACC TTCGGCCAGG GCACCAAGCT GGAGATCAAA CGTACGGTGG<br>CTGCACCATC TGTCTTCATC TTCCCGCCAT CTGATGAGCA GTTGAAATCT<br>GGAACTGCCT CTGTTGTGTG CCTGCTGAAT AACTTCTATC CCAGAGAGGC<br>CAAAGTACAG TGGAAGGTGG ATAACGCCCT CCAATCGGGT AACTCCCAGG |

| Table of Sequences | | |
|---|---|---|
| SEQ ID NO | Description | Sequence |
| | | AGAGTGTCAC AGAGCAGGAC AGCAAGGACA GCACCTACAG CCTCAGCAGC ACCCTGACGC TGAGCAAAGC AGACTACGAG AAACACAAAG TCTACGCCTG CGAAGTCACC CATCAGGGCC TGAGCTCGCC CGTCACAAAG AGCTTCAACA GGGGAGAGTG TTGA |

---

What is claimed is:

1. A method of stimulating endocortical bone formation in a patient in need thereof, comprising administering an effective amount of a pharmaceutical composition comprising a monoclonal antibody that binds to human notum pectinacetylesterase (NOTUM) and neutralizes at least one activity of NOTUM, wherein the antibody binds to a region of NOTUM from amino acids 47 to 177 of SEQ ID NO: 1, and wherein the antibody reduces NOTUM activity in a trisodium 8-octanoyloxypyrene-1,3,6-trisulfonate (OPTS) assay in vitro and reduces NOTUM activity in a Wnt signaling assay in vitro, wherein the antibody comprises a heavy chain variable region and a light chain variable region, wherein:

a) the heavy chain variable region comprises a CDR1 having the amino acid sequence of SEQ ID NO: 17, a CDR2 having the amino acid sequence of SEQ ID NO: 18, and a CDR3 having the amino acid sequence of SEQ ID NO: 19, and the light chain variable region comprises a CDR1 having the amino acid sequence of SEQ ID NO: 20, a CDR2 having the amino acid sequence of SEQ ID NO: 21, and a CDR3 having the amino acid sequence of SEQ ID NO: 22;

b) the heavy chain variable region comprises a CDR1 having the amino acid sequence of SEQ ID NO: 25, a CDR2 having the amino acid sequence of SEQ ID NO: 26, and a CDR3 having the amino acid sequence of SEQ ID NO: 27, and wherein the light chain variable region comprises a CDR1 having the amino acid sequence of SEQ ID NO: 28, a CDR2 having the amino acid sequence of SEQ ID NO: 29, and a CDR3 having the amino acid sequence of SEQ ID NO: 30;

c) the heavy chain variable region comprises a CDR1 having the amino acid sequence of SEQ ID NO: 33, a CDR2 having the amino acid sequence of SEQ ID NO: 34, and a CDR3 having the amino acid sequence of SEQ ID NO: 35, and the light chain variable region comprises a CDR1 having the amino acid sequence of SEQ ID NO: 36, a CDR2 having the amino acid sequence of SEQ ID NO: 37, and a CDR3 having the amino acid sequence of SEQ ID NO: 38; or d) the heavy chain variable region comprises a CDR1 having the amino acid sequence of SEQ ID NO: 57, a CDR2 having the amino acid sequence of SEQ ID NO: 58, and a CDR3 having the amino acid sequence of SEQ ID NO: 59, and wherein the light chain variable region comprises a CDR1 having the amino acid sequence of SEQ ID NO: 60, a CDR2 having the amino acid sequence of SEQ ID NO: 61, and a CDR3 having the amino acid sequence of SEQ ID NO: 62.

2. The method of claim 1, wherein the antibody increases serum Procollagen I N-terminal Propeptide (PINP) levels in vivo, increases bone mineral density in vivo, increases midshaft femur cortical thickness in vivo, increases midshaft femur bone area in vivo, increases midshaft humerus cortical thickness in vivo, increases endocortical bone formation in vivo, increases the proportion of cortical bone volume in the LV5 vertebral body in vivo, and/or increases the proportion of femoral neck bone volume to femoral neck total volume in vivo.

3. The method of claim 1, wherein the antibody is selected from a chimeric antibody, a humanized antibody, and a human antibody.

4. The antibody of claim 1, wherein the heavy chain variable region comprises an amino acid sequence selected from SEQ ID NOs: 15, 23, 31, 55, 63, 71, 75, and 79.

5. The antibody of claim 1, wherein the light chain variable region comprises an amino acid sequence selected from SEQ ID NOs: 16, 24, 32, 56, 65, 73, 77, and 81.

6. The antibody of claim 1, wherein:
a) the heavy chain variable region comprises the amino acid sequence of SEQ ID NO: 15 and the light chain variable region comprises the amino acid sequence of SEQ ID NO: 16;
b) the heavy chain variable region comprises the amino acid sequence of SEQ ID NO: 71 and the light chain variable region comprises the amino acid sequence of SEQ ID NO: 73;
c) the heavy chain comprises the amino acid sequence of SEQ ID NO: 72 and the light chain comprises the amino acid sequence of SEQ ID NO: 74;
d) the heavy chain variable region comprises the amino acid sequence of SEQ ID NO: 23 and the light chain variable region comprises the amino acid sequence of SEQ ID NO: 24;
e) the heavy chain variable region comprises the amino acid sequence of SEQ ID NO: 75 and the light chain variable region comprises the amino acid sequence of SEQ ID NO: 77;
f) the heavy chain comprises the amino acid sequence of SEQ ID NO: 76 and the light chain comprises the amino acid sequence of SEQ ID NO: 78;
g) the heavy chain variable region comprises the amino acid sequence of SEQ ID NO: 31 and the light chain variable region comprises the amino acid sequence of SEQ ID NO: 32;
h) the heavy chain variable region comprises the amino acid sequence of SEQ ID NO: 79 and the light chain variable region comprises the amino acid sequence of SEQ ID NO: 81;
i) the heavy chain comprises the amino acid sequence of SEQ ID NO: 80 and the light chain comprises the amino acid sequence of SEQ ID NO: 82;
j) the heavy chain variable region comprises the amino acid sequence of SEQ ID NO: 55 and the light chain variable region comprises the amino acid sequence of SEQ ID NO: 56;
k) the heavy chain variable region comprises the amino acid sequence of SEQ ID NO: 63 and the light chain variable region comprises the amino acid sequence of SEQ ID NO: 65; or
l) the heavy chain comprises the amino acid sequence of SEQ ID NO: 64 and the light chain comprises the amino acid sequence of SEQ ID NO: 66.

7. A method of treating, managing, or preventing a disease or disorder characterized by bone loss in a patient, comprising administering an effective amount of a pharmaceutical composition comprising a monoclonal antibody that binds to human notum pectinacetylesterase (NOTUM) and neutralizes at least one activity of NOTUM, wherein the antibody binds to a region of NOTUM from amino acids 47 to 177 of SEQ ID NO: 1, and wherein the antibody reduces NOTUM activity in a trisodium 8-octanoyloxypyrene-1,3,6-trisulfonate (OPTS) assay in vitro and reduces NOTUM activity in a Wnt signaling assay in vitro, wherein the antibody comprises a heavy chain variable region and a light chain variable region, wherein:
a) the heavy chain variable region comprises a CDR1 having the amino acid sequence of SEQ ID NO: 17, a CDR2 having the amino acid sequence of SEQ ID NO: 18, and a CDR3 having the amino acid sequence of SEQ ID NO: 19, and the light chain variable region comprises a CDR1 having the amino acid sequence of SEQ ID NO: 20, a CDR2 having the amino acid sequence of SEQ ID NO: 21, and a CDR3 having the amino acid sequence of SEQ ID NO: 22;
b) the heavy chain variable region comprises a CDR1 having the amino acid sequence of SEQ ID NO: 25, a CDR2 having the amino acid sequence of SEQ ID NO: 26, and a CDR3 having the amino acid sequence of SEQ ID NO: 27, and wherein the light chain variable region comprises a CDR1 having the amino acid sequence of SEQ ID NO: 28, a CDR2 having the amino acid sequence of SEQ ID NO: 29, and a CDR3 having the amino acid sequence of SEQ ID NO: 30;
c) the heavy chain variable region comprises a CDR1 having the amino acid sequence of SEQ ID NO: 33, a CDR2 having the amino acid sequence of SEQ ID NO: 34, and a CDR3 having the amino acid sequence of SEQ ID NO: 35, and the light chain variable region comprises a CDR1 having the amino acid sequence of SEQ ID NO: 36, a CDR2 having the amino acid sequence of SEQ ID NO: 37, and a CDR3 having the amino acid sequence of SEQ ID NO: 38; or
d) the heavy chain variable region comprises a CDR1 having the amino acid sequence of SEQ ID NO: 57, a CDR2 having the amino acid sequence of SEQ ID NO: 58, and a CDR3 having the amino acid sequence of SEQ ID NO: 59, and wherein the light chain variable region comprises a CDR1 having the amino acid sequence of SEQ ID NO: 60, a CDR2 having the amino acid sequence of SEQ ID NO: 61, and a CDR3 having the amino acid sequence of SEQ ID NO: 62.

8. The method of claim 7, wherein the disease or disorder is osteoporosis.

9. The method of claim 7, wherein the antibody increases serum Procollagen I N-terminal Propeptide (PINP) levels in vivo, increases bone mineral density in vivo, increases midshaft femur cortical thickness in vivo, increases midshaft femur bone area in vivo, increases midshaft humerus cortical thickness in vivo, increases endocortical bone formation in vivo, increases the proportion of cortical bone volume in the LV5 vertebral body in vivo, and/or increases the proportion of femoral neck bone volume to femoral neck total volume in vivo.

10. The method of claim 7, wherein the antibody is selected from a chimeric antibody, a humanized antibody, and a human antibody.

11. The antibody of claim 7, wherein the heavy chain variable region comprises an amino acid sequence selected from SEQ ID NOs: 15, 23, 31, 55, 63, 71, 75, and 79.

12. The antibody of claim 7, wherein the light chain variable region comprises an amino acid sequence selected from SEQ ID NOs: 16, 24, 32, 56, 65, 73, 77, and 81.

13. The antibody of claim 7, wherein:
- a) the heavy chain variable region comprises the amino acid sequence of SEQ ID NO: 15 and the light chain variable region comprises the amino acid sequence of SEQ ID NO: 16;
- b) the heavy chain variable region comprises the amino acid sequence of SEQ ID NO: 71 and the light chain variable region comprises the amino acid sequence of SEQ ID NO: 73;
- c) the heavy chain comprises the amino acid sequence of SEQ ID NO: 72 and the light chain comprises the amino acid sequence of SEQ ID NO: 74;
- d) the heavy chain variable region comprises the amino acid sequence of SEQ ID NO: 23 and the light chain variable region comprises the amino acid sequence of SEQ ID NO: 24;
- e) the heavy chain variable region comprises the amino acid sequence of SEQ ID NO: 75 and the light chain variable region comprises the amino acid sequence of SEQ ID NO: 77;
- f) the heavy chain comprises the amino acid sequence of SEQ ID NO: 76 and the light chain comprises the amino acid sequence of SEQ ID NO: 78;
- g) the heavy chain variable region comprises the amino acid sequence of SEQ ID NO: 31 and the light chain variable region comprises the amino acid sequence of SEQ ID NO: 32;
- h) the heavy chain variable region comprises the amino acid sequence of SEQ ID NO: 79 and the light chain variable region comprises the amino acid sequence of SEQ ID NO: 81;
- i) the heavy chain comprises the amino acid sequence of SEQ ID NO: 80 and the light chain comprises the amino acid sequence of SEQ ID NO: 82;
- j) the heavy chain variable region comprises the amino acid sequence of SEQ ID NO: 55 and the light chain variable region comprises the amino acid sequence of SEQ ID NO: 56;
- k) the heavy chain variable region comprises the amino acid sequence of SEQ ID NO: 63 and the light chain variable region comprises the amino acid sequence of SEQ ID NO: 65; or
- l) the heavy chain comprises the amino acid sequence of SEQ ID NO: 64 and the light chain comprises the amino acid sequence of SEQ ID NO: 66.

* * * * *

UNITED STATES PATENT AND TRADEMARK OFFICE
CERTIFICATE OF CORRECTION

PATENT NO. : 11,059,907 B2  
APPLICATION NO. : 16/277466  
DATED : July 13, 2021  
INVENTOR(S) : Robert Joseph Brommage, Jr. et al.

Page 1 of 1

It is certified that error appears in the above-identified patent and that said Letters Patent is hereby corrected as shown below:

In the Claims

Claim 4, Column 215, Line 20, delete "antibody" and insert --method--  
Claim 5, Column 215, Line 23, delete "antibody" and insert --method--  
Claim 6, Column 215, Line 26, delete "antibody" and insert --method--  
Claim 11, Column 217, Line 1, delete "antibody" and insert --method--  
Claim 12, Column 217, Line 4, delete "antibody" and insert --method--  
Claim 13, Column 217, Line 7, delete "antibody" and insert --method--

Signed and Sealed this  
Ninth Day of November, 2021

Drew Hirshfeld  
*Performing the Functions and Duties of the*  
*Under Secretary of Commerce for Intellectual Property and*  
*Director of the United States Patent and Trademark Office*